US011833164B2

(12) United States Patent
Benjamin et al.

(10) Patent No.: US 11,833,164 B2
(45) Date of Patent: Dec. 5, 2023

(54) METHODS OF TREATING FABRY DISEASE IN PATIENTS HAVING A MUTATION IN THE GLA GENE

(71) Applicant: Amicus Therapeutics, Inc., Cranbury, NJ (US)

(72) Inventors: Elfrida Benjamin, Millstone Township, NJ (US); Xiaoyang Wu, Edison, NJ (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 522 days.

(21) Appl. No.: 16/987,884

(22) Filed: Aug. 7, 2020

(65) Prior Publication Data

US 2021/0038625 A1 Feb. 11, 2021

Related U.S. Application Data

(60) Provisional application No. 62/986,297, filed on Mar. 6, 2020, provisional application No. 62/883,756, filed on Aug. 7, 2019.

(51) Int. Cl.

| | |
|---|---|
| ***A61K 31/7008*** | (2006.01) |
| ***G16H 50/20*** | (2018.01) |
| ***G16B 20/20*** | (2019.01) |
| ***C12Q 1/6883*** | (2018.01) |

(52) U.S. Cl.

CPC ........ *A61K 31/7008* (2013.01); *C12Q 1/6883* (2013.01); *G16B 20/20* (2019.02); *G16H 50/20* (2018.01); *C12Q 2600/106* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 7,851,143 | B2 | 12/2010 | Kaneski et al. |
| 7,973,157 | B2 | 7/2011 | Major et al. |
| 8,321,148 | B2 | 11/2012 | Lockhart et al. |
| 8,592,362 | B2 | 11/2013 | Benjamin et al. |
| 9,000,011 | B2 | 4/2015 | Lockhart et al. |
| 9,056,101 | B2 | 6/2015 | Lockhart |
| 9,066,939 | B2 | 6/2015 | Schiffmann et al. |
| 9,095,584 | B2 | 8/2015 | Benjamin et al. |
| 9,206,457 | B2 | 12/2015 | Do |
| 9,480,682 | B2 | 11/2016 | Lockhart et al. |
| 9,545,397 | B2 | 1/2017 | Benjamin et al. |
| 9,694,056 | B2 | 7/2017 | Khanna et al. |
| 9,750,732 | B2 | 9/2017 | Schiffmann et al. |
| 9,987,263 | B2 | 6/2018 | Lockhart et al. |
| 9,999,618 | B2 | 6/2018 | Castelli et al. |
| 10,076,514 | B2 | 9/2018 | Benjamin |
| 10,155,027 | B2 | 12/2018 | Khanna et al. |
| D843,850 | S | 3/2019 | Loprete et al. |
| 10,251,873 | B2 | 4/2019 | Castelli et al. |
| 10,357,548 | B2 | 7/2019 | Khanna |
| 10,383,864 | B2 | 8/2019 | Lockhart et al. |
| 10,406,143 | B2 | 9/2019 | Lockhart et al. |
| D867,162 | S | 11/2019 | Loprete et al. |
| 10,471,053 | B2 | 11/2019 | Castelli et al. |
| 10,525,045 | B2 | 1/2020 | Castelli et al. |
| D877,625 | S | 3/2020 | Loprete et al. |
| 10,537,564 | B2 | 6/2020 | Benjamin |
| 10,792,278 | B2 | 10/2020 | Castelli et al. |
| 10,792,279 | B2 | 10/2020 | Castelli et al. |
| 10,799,491 | B2 | 10/2020 | Castelli et al. |
| 10,806,727 | B2 | 10/2020 | Castelli et al. |
| 10,813,921 | B2 | 10/2020 | Benjamin et al. |
| 10,849,889 | B2 | 12/2020 | Castelli et al. |
| 10,849,890 | B2 | 12/2020 | Castelli et al. |
| 10,857,141 | B2 | 12/2020 | Castelli et al. |
| 10,857,142 | B2 | 12/2020 | Castelli et al. |
| 10,874,655 | B2 | 12/2020 | Castelli et al. |
| 10,874,656 | B2 | 12/2020 | Castelli et al. |
| 10,874,657 | B2 | 12/2020 | Castelli et al. |
| 10,925,866 | B2 | 2/2021 | Castelli et al. |
| RE48,608 | E | 6/2021 | Benjamin et al. |
| 11,033,538 | B2 | 6/2021 | Castelli et al. |

(Continued)

FOREIGN PATENT DOCUMENTS

| | | | |
|---|---|---|---|
| OA | 2012125402 | A3 | 9/2012 |
| WO | 2007137072 | A2 | 11/2007 |

(Continued)

OTHER PUBLICATIONS

Saito, Seiji , et al., "Comparative Study of Structural Changes Caused by Different Substitutions at the Same Residue on a-Galactosidase A", PLoS ONE 8(12): e84267. doi:10.1371/journal.pone.0084267.

Sakac, Dejan , et al., "Fabry disease, do we think enough about this multisystemic disorder?—A presentation of three cases in a Serbial family", Vojnosanit Pregl 2012; 69(7): 620-622.

Savostyanov, K.V. , et al., "The New Genome Variants in Russian Children with Genetically Determined Cardiomyopathies Revealed with Massive Parallel Sequencing", Annals of the Russian Academy of Medical Sciences. 2017;72 (4):242-253.

Schiffmann, R , et al., "Cardiac Outcomes With Long-term Migalastat Treatment in Patients With Fabry Disease: Results From Phase 3 Trials", 2018.

(Continued)

*Primary Examiner* — John S Brusca
*Assistant Examiner* — Steven W. Bailey
(74) *Attorney, Agent, or Firm* — Servilla Whitney LLC

(57) ABSTRACT

Provided are methods of treating a patient diagnosed with Fabry disease and methods of enhancing α-galactosidase A in a patient diagnosed with or suspected of having Fabry disease. Certain methods comprise administering to a patient a therapeutically effective dose of a pharmacological chaperone for α-galactosidase A, wherein the patient has a mutation in the nucleic acid sequence encoding α-galactosidase A. Also described are uses of pharmacological chaperones for the treatment of Fabry disease and compositions for use in the treatment of Fabry disease.

33 Claims, 11 Drawing Sheets

Specification includes a Sequence Listing.

(56) References Cited

U.S. PATENT DOCUMENTS

| | | | |
|---|---|---|---|
| 11,234,972 | B2 | 2/2022 | Benjamin |
| 11,241,422 | B2 | 2/2022 | Lockhart et al. |
| 11,278,536 | B2 | 3/2022 | Castelli et al. |
| 11,278,537 | B2 | 3/2022 | Castelli et al. |
| 11,278,538 | B2 | 3/2022 | Castelli et al. |
| 11,278,539 | B2 | 3/2022 | Castelli et al. |
| 11,278,540 | B2 | 3/2022 | Castelli et al. |
| 11,304,940 | B2 | 4/2022 | Castelli et al. |
| 11,357,761 | B2 | 6/2022 | Castelli et al. |
| 11,357,762 | B2 | 6/2022 | Castelli et al. |
| 11,357,763 | B2 | 6/2022 | Castelli et al. |
| 11,357,764 | B1 | 6/2022 | Castelli et al. |
| 11,357,765 | B1 | 6/2022 | Castelli et al. |
| 11,357,784 | B2 | 6/2022 | Barth |
| 11,376,244 | B2 | 7/2022 | Castelli et al. |
| 11,389,436 | B2 | 7/2022 | Castelli et al. |
| 11,389,437 | B2 | 7/2022 | Castelli et al. |
| 11,426,396 | B2 | 8/2022 | Castelli et al. |
| 11,458,128 | B2 | 10/2022 | Castelli et al. |
| 11,612,593 | B2 | 3/2023 | Castelli et al. |
| 11,612,594 | B2 | 3/2023 | Castelli et al. |
| 11,622,962 | B2 | 4/2023 | Castelli et al. |
| 11,623,916 | B2 | 4/2023 | Sheth et al. |
| 11,633,387 | B2 | 4/2023 | Castelli et al. |
| 11,633,388 | B2 | 4/2023 | Castelli et al. |
| 11,642,334 | B2 | 5/2023 | Castelli et al. |
| 11,666,564 | B2 | 6/2023 | Castelli et al. |
| 11,685,718 | B2 | 6/2023 | Sheth et al. |
| 2011/0152319 | A1 | 6/2011 | Banjamin et al. |
| 2014/0219986 | A1 | 8/2014 | Greene et al. |
| 2017/0051267 | A1 | 2/2017 | Calhoun |
| 2018/0153999 | A1 | 6/2018 | Greene et al. |
| 2018/0360812 | A1 | 12/2018 | Castelli et al. |
| 2018/0360814 | A1 | 12/2018 | Castelli et al. |
| 2019/0000818 | A1 | 1/2019 | Benjamin et al. |
| 2019/0183869 | A1 | 6/2019 | Castelli |
| 2019/0358302 | A1 | 11/2019 | Gotcschall |
| 2019/0388409 | A1 | 12/2019 | Lockhart et al. |
| 2020/0215043 | A1 | 7/2020 | Benjamin |
| 2020/0222377 | A1 | 7/2020 | Castelli et al. |
| 2020/0268890 | A1 | 8/2020 | Greene et al. |
| 2021/0030730 | A1 | 2/2021 | Castelli et al. |
| 2021/0038579 | A1 | 2/2021 | Barth et al. |
| 2021/0038581 | A1 | 2/2021 | Castelli et al. |
| 2021/0038582 | A1 | 2/2021 | Castelli et al. |
| 2021/0038583 | A1 | 2/2021 | Castelli et al. |
| 2021/0038624 | A1 | 2/2021 | Barth |
| 2021/0038625 | A1 | 2/2021 | Benjamin et al. |
| 2021/0069161 | A1 | 3/2021 | Castelli et al. |
| 2021/0069162 | A1 | 3/2021 | Castelli |
| 2021/0085660 | A1 | 3/2021 | Castelli et al. |
| 2021/0085661 | A1 | 3/2021 | Castelli et al. |
| 2021/0220344 | A1 | 7/2021 | Castelli et al. |
| 2021/0251971 | A1 | 8/2021 | Benjamin et al. |
| 2021/0251972 | A1 | 8/2021 | Skuban |
| 2021/0315875 | A1 | 10/2021 | Benjamin |
| 2022/0087993 | A1 | 3/2022 | Skuban et al. |
| 2022/0142998 | A1 | 5/2022 | Benjamin |
| 2022/0160690 | A1 | 5/2022 | Lockhart et al. |
| 2022/0313670 | A1 | 10/2022 | Johnson |
| 2022/0387462 | A1 | 12/2022 | Barth |
| 2023/0136297 | A1 | 5/2023 | Benjamin et al. |
| 2023/0201180 | A1 | 6/2023 | Castelli et al. |
| 2023/0218598 | A1 | 7/2023 | Castelli et al. |
| 2023/0218599 | A1 | 7/2023 | Castelli et al. |

FOREIGN PATENT DOCUMENTS

| | | | |
|---|---|---|---|
| WO | 2008045015 | A1 | 4/2008 |
| WO | 2008134628 | A3 | 11/2008 |
| WO | 2009102895 | A3 | 8/2009 |
| WO | 2010048532 | A1 | 4/2010 |
| WO | 2010138608 | A1 | 12/2010 |
| WO | 2011063048 | A2 | 5/2011 |
| WO | 2012071451 | A2 | 5/2012 |
| WO | 2012/154681 | A1 | 11/2012 |
| WO | 2013/091897 | A1 | 6/2013 |
| WO | 2014014938 | A1 | 1/2014 |
| WO | 2017165164 | A1 | 9/2017 |
| WO | 2018017721 | A1 | 1/2018 |
| WO | 2018132471 | A1 | 7/2018 |
| WO | 2018222655 | A1 | 12/2018 |
| WO | 2019017938 | A1 | 1/2019 |
| WO | 2019046244 | A1 | 3/2019 |
| WO | 2019157047 | A1 | 8/2019 |
| WO | 2019157056 | A1 | 8/2019 |
| WO | 2020040806 | A1 | 2/2020 |
| WO | 2020252129 | A1 | 12/2020 |
| WO | 2023288210 | A1 | 1/2023 |

OTHER PUBLICATIONS

Schiffmann, R. , et al., "Long-Term Migalastat Treatment Stabilizes Renal Function in Patients With Fabry Disease: Results from a Phase 3 Clinical Study (AT1001-041)", Presented at the 54th European Renal Association-European Dialysis and Transplant Association Congress; Jun. 3-6, 2017; Madrid, Spain, 1 page.

Scott, C. Ronald, et al., "Identification of infants at risk for developing Fabry, Pompe or Mucopolysaccharidosis-I from newborn blood spots by tandem mass spectrome", Pediatr. Aug. 2013 ; 163(2): 498-503. doi:10.1016/j.jpeds.2013.01.031.

Serebrinsky, G. , "Late onset variants in Fabry disease: Results in high risk population screenings in Argentina", Molecular Genetics and Metabolism Reports 4 (2015) 19-24.

Sheng, Sen , et al., "Fabry's disease and stroke: Effectiveness of enzyme replacement therapy (ERT) in stroke prevention, a review with meta-analysis", Journal of Clinical Neuroscience 65 (2019) 83-86.

Shin, Sang H., "Prediction of Response of Mutated a-Galactosidase A To a Pharmacological Chaperone", Pharmacogenetics and Genomics, Lippincott Williams & Wilkins, Philadelphia, PA, US, vol. 18, No. 9, Sep. 1, 2008, pp. 773-780.

Sirrs, S. , et al., "Baseline characteristics of patients enrolled in the Canadian Fabry Disease Initiative", Molecular Genetics and Metabolism 99 (2010) 367-373.

Skuban, Nina , et al., "Clinical Outcomes with Migalastat in Patients with Fabry Disease Based on Degree of Renal Impairment: Results from Phase 3 Trials", Nephrology Dialysis Transplantation, vol. 33, 2018 (Supplement 1): i346.

Spada, Marco , et al., "High Incidence of Later-Onset Fabry Disease Revealed by Newborn Screening", The American Journal of Human Genetics, vol. 79, Jul. 2006.

Sunder-Plassmann, Gere , et al., "Migalastat for the treatment of Fabry disease", Expert Opinion on Orphan Drugs, 2018, vol. 6, No. 5, pp. 301-309.

Takahashi, Naoki , "A heterozygous female with Fabry disease due to a novel α-galactosidase A mutation exhibits a unique synaptopodin distribution in vacuolated podocytes", Clin Nephrol. May 2015;83(5):301-8. doi: 10.5414/CN108317. PMID: 25295576., Oct. 8, 2014.

Thomas, Alison Sian Buchanan, "Vascular Events in Fabry and Gaucher Disease", Thesis submitted to Cancer Institute for the degree of MD (Res) (2014).

Tsukimura, Takahiro , et al., "Plasma mutant α-galactosidase A protein and globotriaosylsphingosine level in Fabry disease", Molecular Genetics and Metabolism Reports 1 (2014) 288-298.

Tuttolomondo, Antonino , et al., "Novel alpha-galactosidase A mutation in a female with recurrent strokes", Clinical Biochemistry 45 (2012) 1525-1530.

Umeda, Toshiko , et al., "Identification of a novel GLA mutation (F69 L) in a Japanese patient with late-onset Fabry disease", Human Genome Variation (2015) 2, 15044; doi:10.1038/hgv.2015.44.

Van Der Tol, Linda , et al., "In Patients with an a-Galactosidase A Variant, Small Nerve Fibre Assessment Cannot Confirm a Diagnosis of Fabry Disease", JIMD Reports DOI 10.1007/8904_2015_503, Nov. 14, 2015.

(56) References Cited

OTHER PUBLICATIONS

Vedder, Anouk C., et al., "Treatment of Fabry Disease: Outcome of a Comparative Trial with Agalsidase Alfa or Beta at a Dose of 0.2 mg/kg", PLoS ONE 2(7): e598. doi:10.1371/journal.pone.0000598 (2007).
Williams, Hadis , et al., "Effects of Long-Term Migalastat Treatment on Renal Function by Baseline Proteinuria in Patients (PTS) with Fabry Disease", Nephrology Dialysis Transplantation, vol. 33, 2018 (Supplement 1): i346-i348.
Wu, Yi Shuan, et al., "Migalastat Tissue Distribution: Extrapolation From Mice to Humans Using Pharmacokinetic Modeling and Comparison With Agalsidase Beta Tissue Distribution in Mice", Clinical Pharmacology in Drug Development 2021, 10(9) 1075-1088.
Feldt-Rasmussen, U., et al., "Response of Patients With Fabry Disease With the Amenable GLA Mutation p. N215S to Treatment With Migalastat", Presented at the 13th International Congress of Inborn Errors of Metabolism; Sep. 5-8, 2017; Rio de Janeiro, Brazil.
Flanagan, John J., et al., "The pharmacological chaperone 1-deoxynojirimycin increases the activity and lysosomal trafficking of multiple mutant forms of acid alpha-glucosidase", Human Mutation, vol. 30, Issue 12, 1683-1692.
Froissart, Roseline , et al., "Fabry disease: D313Y is an a-galactosidase A sequence variant that causes pseudodeficient activity in plasma", Molecular Genetics and Metabolism 80 (2003) 307-314.
Fukutomi, Motoki , et al., "Japanese patients with Fabry disease predominantly showing cardiac and neurological manifestation with novel missense mutation: R220P", Journal of Cardiology 62 (2013) 63-69.
Garman, Scott C., et al., "Structural basis of Fabry disease", Molecular Genetics and Metabolism 77 (2002) 3-11.
Garman, Scott C., et al., "The Molecular Defect Leading to Fabry Disease: Structure of Human a-Galactosidase", J. Mol. Biol. (2004) 337, 319-335.
Germain, Dominique P., et al., "Efficacy of the pharmacologic chaperone migalastat in a subset of male patients with the classic phenotype of Fabry disease and migalastat-amenable variants: data from the phase 3 randomized, multicenter, double-blind clinical trial and extension study", Genetics in Medicine, vol. 21, No. 9, Feb. 6, 2019, 1987-1997.
Germain, Dominique P., et al., "Safety and pharmacodynamic effects of a pharmacological chaperone on !-galactosidase A activity and globotriaosylceramide clearance in Fabry disease: report from two phase 2 clinical studies", Orphanet Journal of Rare Diseases 2012, 7:91, 1-11.
Germain, D.P. , et al., "Treatment of Fabry's Disease with the Pharmacologic Chaperone Migalastat", The New England Journal of Medicine 375;6, Aug. 11, 2016, 545-555.
Giugliani, R. , et al., "A Phase 2 study of migalastat hydrochloride in females with Fabry disease: Selection of population, safety and pharmacodynamic effects", Molecular Genetics and Metabolism 109, 2013, 86-92.
Havndrup, Ole , et al., "Fabry disease mimicking hypertrophic cardiomyopathy: genetic screening needed for establishing the diagnosis in women", European Journal of Heart Failure (2010) 12, 535-540.
Hughes, Derralynn A., et al., "Oral pharmacological chaperone migalastat compared with enzyme replacement therapy in Fabry disease: 18-month results from the randomised phase III Attract study", J Med Genet 2017; 54, Nov. 10, 2016, 288-296.
Hughes, D. , et al., "Phenotype of Fabry Disease in Patients with Mutations Amenable to Migalastat", Posters at WORLDSymposium™ 2016, Mar. 1, 2016.
Hughes, D. A., et al., "Response of Patients With Fabry Disease With the Amenable GLA Mutation p.N215S to Treatment With Migalastat (ATTRACT Study)", Presented at the 13th Annual WORLDSymposium, Feb. 13-17, 2017, San Diego, CA, 1 page.
Ichinose, Mayuri , et al., "Significance of screening for Fabry disease among male dialysis patients", Clin Exp Nephrol (2005) 9:228-232.
Ishii, Satoshi , et al., "Role of Ser-65 in the activity of a-galactosidase A: characterization of a point mutation (S65T) detected in a patient with Fabry disease", Archives of biochemistry and biophysics, 377(2), May 15, 2000 (May 15, 2000), 228-233.
Iwafuchi, Yoichi , et al., "Enzyme replacement therapy in a patient of heterozygous Fabry disease: clinical and pathological evaluations by repeat kidney biopsy and a successful pregnancy", CEN Case Rep (2017) 6:210-214.
Johnson, Franklin K., et al., "An Open-Label Study to Determine the Pharmacokinetics and Safety of Migalastat HCl in Subjects with Impaired Renal Function and Healthy Subjects with Normal Renal Function", American College of Clinical Pharmacology, Clinical Pharmacology in Drug Development 2015, 4(4) 256-261.
Johnson, Britt , et al., "Analysis of Lyso-Globotriaosylsphingosine in Dried Blood Spots", Ann Lab Med 2013;33:274-278.
Johnson, F. K., et al., "Comparison of Integrated White Blood Cell Alpha-Galactosidase A Activity Exposure Between Every-Other-Day Orally Administered Migalastat and Biweekly Infusions of Agalsidase Beta or Agalsidase Alfa", Posters at WORLDSymposium™ 2016, Mar. 1, 2016.
Johnson, F. K., et al., "Pharmacokinetic Simulation of a 150-mg Every Other Day Dose Regimen for the Pharmacological Chaperone Migalastat HCl in Fabry Disease", Presented at the 2017 College of Clinical Pharmacology Annual Meeting, Sep. 17-19, 2017, San Diego, CA, 1 page.
Kawano, Makoto , et al., "Significance of Asymmetric Basal Posterior Wall Thinning in Patients With Cardiac Fabry's Disease", The American Journal of Cardiology (2007).
Khanna, Richie , et al., "Co-Administration of the Pharmacological Chaperone AT2221 with A Proprietary Recombinant Human Acid Alpha-Glucosidase Leads to Greater Plasma Exposure and Substrate Reduction Compared to Alglucosidase Alfa", Posters at WORLDSymposium™ 2016, Mar. 1, 2016.
Kobayashi, H. , et al., "A retrospective ESI-MS/MS analysis of newborn blood spots from 18 symptomatic patients with organic acid and fatty acid oxidation disorders diagnosed either in infancy or in childhood", J Inherit Metab Dis Short Report #065 (2007).
Koulousios, Konstantinos , et al., "Fabry disease due to D313Y and novel GLA mutations", BMJ Open 2017;7: e017098. doi:10.1136/bmjopen-2017-017098.
Kroepfl, TH. , et al., "A novel 6 bp insertion in exon 7 associated with an unusual phenotype in a family with Fabry disease", J. Inherit. Metab. Dis. 25 (2002) 695-696.
Lee, Sheng-Hung , et al., "High-throughput detection of common sequence variations of Fabry disease in Taiwan using DNA mass spectrometry", Molecular Genetics and Metabolism 111 (2014) 507-512.
Liao, Hsuan-Chieh , et al., "Detecting multiple lysosomal storage diseases by tandem mass spectrometry—A national newborn screening program in Taiwan", Clinica Chimica Acta 431 (2014) 80-86.
Liao, Hsuan-Chieh , et al., "Functional and biological studies of α-galactosidase A variants with uncertain significance from newborn screening in Taiwan", Molecular Genetics and Metabolism 123 (2018) 140-147.
Lin, Hsiang-Yu , et al., "Clinical observations on enzyme replacement therapy in patients with Fabry disease and the switch from agalsidase beta to agalsidase alfa", Journal of the Chinese Medical Association xx (2013) 1-8.
Lin, Hsiang-Yu , et al., "High Incidence of the Cardiac Variant of Fabry Disease Revealed by Newborn Screening in the Taiwan Chinese Population", Circ Cardiovasc Genet, Oct. 2009, pp. pp. 450-456.
Linthorst, Gabor E., et al., "a-Galactosidase A deficiency in Dutch patients on dialysis: a critical appraisal of screening for Fabry disease", Nephrol Dial Transplant (2003) 18: 1581-1584.
Lukas, Jan , et al., "Functional and Clinical Consequences of Novel Alpha-Galactosidase A Mutations in Fabry Disease", Human Mutation, vol. 0, No. 0, Sep. 29, 2015, 1-9.
Lukas, Jan , et al., "Functional Characterisation of Alpha-Galactosidase A Mutations as a Basis for a New Classification System in Fabry Disease", PLoS Genet 9(8): e1003632. doi:10.1371/journal.pgen.1003632.

(56) References Cited

OTHER PUBLICATIONS

Matsuda, Mitsuhiro , et al., "Novel G144D mutation of the GLA gene in a Chinese patient with Fabry disease", The Journal of Dermatology 2014.
Matsuzawa, Fumiko , et al., "Fabry disease: correlation between structural changes in [alpha] -galactosidase, and clinical and biochemical phenotypes",, Human Genetics, Springer, Berlin, DE, vol. 117, No. 4, Aug. 1, 2005, 317-328.
Mehta, A, et al., "Enzyme replacement therapy with agalsidase alfa in patients with Fabry's disease: an analysis of registry data", Lavet 2009, vol. 374: 1986-96.
Mignani, Renzo , et al., "Agalsidase therapy in patients with Fabry disease on renal replacement therapy: a nationwide study in Italy", Nephrol Dial Transplant (2008) 23: 1628-1635, Dec. 5, 2007.
Mills, K. , et al., "Measurement of urinary CDH and CTH by tandem mass spectrometry in patients hemizygous and heterozygous for Fabry disease", J. Inherit. Metab.Dis. 28 (2005) 35/\48.
Najafian, B. , et al., "Six months of Migalastat Treatment Reduces Podocyte Globotriaosylceramide Content in Adult Male Patients with Fabry Disease", Posters at WORLDSymposium™ 2016, Mar. 1, 2016.
Nakagawa, Naoki , et al., "Clinical and Genetic Investigation of a Japanese Family With Cardiac Fabry Disease", Int Heart J, vol. 52, No. 5, Sep. 2011.
Namazova-Baranova, Leyla Seymurovna, et al., "Fabry disease in children: a federal screening programme in Russia", Eur J Pediatr (2017) 176:1385-1391.
Narita, Ichiei , et al., "Efficacy and safety of migalastat in a Japanese population: a subgroup analysis of the ATT RAC T study", Clinical and Experimental Nephrology (2020) 24, Dec. 30, 2019, 157-166.
Nicholls, K., et al., "Renal Outcomes With Up to 9 Years of Migalastat in Patients With Fabry Disease: Results From an Open-label Extension Study", Presented at the 14th Annual WORLDSymposium, Feb. 5-9, 2018, San Diego, CA, 1 page.
Okumiya, Toshika , et al., "Galactose Stabilizes Various Missense Mutants Of «-Galactosidase in Fabry Disease", Biochemical and Biophysical Research Communications, vol. 214, No. 3, Sep. 25, 1995, pp. 1219-1224.
Okur, Ilyas , et al., "Screening for Fabry disease in patients undergoing dialysis for chronic renal failure in Turkey: identification of new case with novel mutation", Gene 527(2013)42-47.
Pan, Xiaoxia , et al., "Genotype: A Crucial but Not Unique Factor Affecting the Clinical Phenotypes in Fabry Disease", PLoS ONE 11(8): e0161330.
Pereira, F.S. , et al., "Genomic analysis of Brazilian patients with Fabry disease", Brazilian Journal of Medical and Biological Research (2007) 40: ISSN 0100-879X.
Prabakaran, Thaneas , et al., "Long-term enzyme replacement therapy is associated with reduced proteinuria and preserved proximal tubular function in women with Fabry disease", Nephrol Dial Transplant (2014) 29: 619-625.
Ranieri, Michela , et al., "Fabry Disease: Recognition, Diagnosis, and Treatment of Neurological Features", Curr Treat Options Neurol (2016) IS: 33.
J Inherit Metab Dis (2007) 30 (Supple 1).
"A Phase 2, Open-Label, Multicenter, Ascending-Dose, 12-Week Study to Evaluate the Safety, Tolerability, Pharmacokinetics, and Pharmacodynamics of AT1001 in Patients with Fabry Disease", ClinicalTrials.gov Archive, Sep. 21, 2005.
"A Phase 2, Open-Label, Multiple Dose Level, 12-Week Study to Evaluate the Safety, Tolerability, and Pharmacodynamics of AT1001 in Female Patients With Fabry Disease", ClinicalTrials.gov Archive, Mar. 17, 2006.
"A Phase 2, Open-Label, Multiple Dose Level, 12-Week Study to Evaluate the Safety, Tolerability, and Pharmacodynamics of AT1001 in Female Patients with Fabry Disease", EU Clinical Trials Register, Feb. 13, 2013.
"A Phase 2, Open-Label, Single Dose Level, 12-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients with Fabry Disease", EU Clinical Trials Register, Oct. 17, 2005.
"Amicus Therapeutics Announces Positive Phase 3 Data From Fabry Monotherapy Study 012", Amicus Therapeutics Press Release, Aug. 20, 2014.
"Amicus Therapeutics Announces Presentations and Posters at 12th Annual WORLDSymposium™ 2016", Amicus Therapeutics Press Release, Feb. 10, 2016.
"Amicus Therapeutics, Current Report Pursuant to Section 13 or 15(d) of the Securities Exchange Act of 1934 (Form 8-K) (Mar. 3, 2016)".
"Fabry mutants list", http://fabry-database.org/mutants/, accessed Jan. 24, 2023.
"Galafold EP Label Summary of Product Characteristics", Feb. 2021, 59 pgs.
"Galafold EP Label Summary of Product Characteristics", May 2022, 59 pages.
"GALAFOLD Product Information", Dec. 2021, 28 pages.
"GALAFOLD Product Information (original version), May 30, 2016, 45 pages".
"GALAFOLD Summary of Product Characteristics", Aug. 14, 2018, 49 pages.
"Galafold Summary of Product Characteristics", Feb. 2021, 28 pages.
"Galafold U.S. Label, Revised Aug. 10, 2018, 24 pages".
"Long-Term Migalastat Treatment Stabilizes Renal Function in Patients With Fabry Disease: Results From a Phase 3 Clinical Study (AT1001-041)", Presented at the 13th International Congress of Inborn Errors of Metabolism; Sep. 5-8, 2017; Rio de Janeiro, Brazil, 1 page.
"Lukas 2013 Supplementary Table".
"MSDS—Deoxygalactonojirimycin (hydrochloride)", according to Regulation (EC) No. 1907/2006 as amended by (EC) No. 2015/830 and US OSHA HCS 2015, 1-5.
"PCT International Search Report and Written Opinion in PCT/US2020/045392 dated Jan. 20, 2021, 20 pages".
"Study of the Effects of Oral AT1001 (Migalastat Hydrochloride) in Patients With Fabry Disease", ClinicalTrials.gov Archive.
"Table S3. List of mutations and their reference.".
"U.S. Appl. No. 18/199,120, filed May 18, 2023, 75 pages".
"U.S. Appl. No. 18/199,125, filed May 18, 2023, 71 pages".
"U.S. Appl. No. 18/214,002, filed Jun. 26, 2023, 211 pages".
"U.S. Appl. No. 18/315,928, filed May 11, 2023, 73 pages".
"U.S. Appl. No. 18/326,274, filed May 31, 2023, 64 pages".
"U.S. Appl. No. 18/326,279, filed May 31, 2023, 64 pages".
"U.S. Appl. No. 18/326,281, filed May 31, 2023, 64 pages".
Ashley, Grace Ann, "a-Galactosidase A: Mutation analysis in patients with Fabry disease and expression and regulation in transgenic mice", A dissertation submitted to the Graduate Faculty of the Mount Sinai Graduate School of Biological Sciences, Biomedical Sciences Doctoral Program (2001).
Ataides, Thiago Lacerda, et al., "Clinical Nephrology, Primary and Secondary Glomerulonephritis-1", Nephrology Dialysis Transplantation 30 (Supplement 3): iii104-iii124, 2015 doi:10.1093/ndt/gfv171.55.
Benjamin, E. R., et al., "The pharmacological eliaperone 1-deoxygalactonojirimycin Increases a-galactosidase A levels in Fabry patient cell lines", J Inherit Metab Dis (2009 ) 32:424-440 DOT I(U007/sl0545-009-1 077-0.
Benjamin , et al., "The Validation of Pharmacogenetics for the Identification of Fabry Patients for Treatment with Migalastat", Supplementary Information (2017).

(56) References Cited

OTHER PUBLICATIONS

Benjamin, Elfrida R., et al., "The validation of pharmacogenetics for the identification of Fabry patients to be treated with migalastat", Genetics in Medicine, vol. 19, No. 4, Sep. 22, 2016 (Sep. 22, 2016), pp. 430-438, XP055582063, US ISSN: 1098-3600, DOI: 10. 1038/ gim.2016. 122 table 11SA.
Benjamin, Elfrida R., et al., "The validation of pharmacogenetics for the identification of Fabry patients to be treated with migalastat", Genetics in Medicine, vol. 19, No. 4, Sep. 22, 2016, 430-438.
Benjamin, E. R., et al., "The Validation of Pharmacogenetics in the Identification of Target Fabry Patients for Treatment with Migalastat", Posters at WORLDSymposium™ 2016, Mar. 1, 2016.
Bichet, D. G., et al., "Persistence of Positive Renal and Cardiac Effects of Migalastat in Fabry Patients with Amenable Mutations Following 30 Months of Treatment in the ATTRACT Study", Posters at WORLDSymposium™ 2016, Mar. 1, 2016.
Brennan, Paul , et al., "Case-finding in Fabry disease: experience from the North of England", J Inherit Metab Dis (2014) 37:103-107 DOI 10.1007/s10545-013-9629-8.
Brennan, P. , et al., "Case-finding in Fabry disease: experience from the North of England", Supplementary Online Material (2014).
Citro, Valentina, et al., "The Large Phenotypic Spectrum of Fabry Disease Requires Graduated Diagnosis and Personalized Therapy: A Meta-Analysis Can Help to Differentiate Missense Mutations", Int. J. Mol. Sci. 2016, 17, 2010.
Csányi, Beáta , et al., "Identification of a Novel GLA Gene Mutation, p.Ile239Met, in Fabry Disease With a Predominant Cardiac Phenotype", Novel P.ILE239MET GLA Mutation in Fabry Disease, vol. 158, No. 3, May 2017.
Desnick , et al., "Posters Metabolic Disorders", The American Society of Human Genetics (2015).
Dobrovolny, Robert , et al., "Relationship between X-inactivation and clinical Involvement In Fabry heterozygotes, Eleven novel mutations in the a-galactosidase A gene in the Czech and Slovak population", J Mol Med (2005) 83: 647-654 DOI 10. 1007/s00109-005-0656-2.
Doi, Kent , et al., "High-throughput screening identified disease-causing mutants and functional variants of a-galactosidase A gene in Japanese male hemodialysis patients", Journal of Human Genetics (2012) 57, 575-579.
Ebrahim, Hatim Y., et al., "Functional analysis of variant lysosomal acid glycosidases of Anderson-Fabry and Pompe disease in a human embryonic kidney epithelial cell line (HEK 293 T)", J Inherit Metab Dis (2012) 35:325-334.
Echevarria, L. , et al., "X-chromosome inactivation in female patients with Fabry disease", Clinical Genetics 2016: 89: 44-54.
Fan, Jian-Qiang , et al., "Accelerated transport and maturation of lysosomal alpha-galactosidase A in Fabry lymphoblasts by an enzyme inhibitor", Nat. Med. vol. 5 No. 1, 1999, 112-115.
Favalli, Valentina , et al., "Genetic Screening of Anderson-Fabry Disease in Probands Referred From Multispecialty Clinics", Journal of the American College of Cardiology, vol. 68, No. 10, 2016.

ccccttctgtaggggcagagaggttctacttcattactgcgtctcctgggaaggccatcag 60
gactgctggctaaagtgggaaccaggactctttgtgagttaagaatttgtgtatttatat 120
gtgtgttatacacatttttaaaaaactgtaacgacatcaggttgagcagtcgtctccgg 180
gtggtgaattatgtgtatttttaaattttatactatattgttatttttcaaatgttcgaa 240
attgaatatgtagattgttgttatcagcagaaaaataaacattattcaaatactctattc 300
agtaaagtaatttattgggcgcctttgtcaagcacgcatttgcctagatgtgactctaca 360
gataaaattcacttggggcctccccttacagacaatcaggcagtggagactgagtgcctg 420
aatggatagaccagcactcagaccactattttcagtatctgtttttcttaactcagggcc 480
gtggttttcaaacgtttttcgccttacggtcacccttagggtcccccgagaccggcccag 540
acagacagatatacaaaaacacatacacagtcatgagcgtccaccatttccccaccaggc 600
gcagcacaggcggcttcccggcactgagatgggggggaggagggagagagcgcgaggggg 660
gaggggaaagcagagaacgaaagaggcggaggcggcccccgaaccccgctctggtcttca 720
tcatcaccacccctgggtccccagttcccacccacacaccaacctctaacgataccgggt 780
aattttcctccttcttccctcaaacggctatagcgagacggtagacgacgaccagaacta 840
cttctgctcacgtaagcgagtaatcacgtgagcgcctacgtcatgtgagatctcggtcac 900
gtgagcaactctcggcttaaactcgggatcactaaggtgccgcacttccttctggtatgg 960
aaatagggcgggtcaatatcaagaaaggaagagggtgattggttagcggaacgtcttacg 1020
tgactgattattggtctacctctggggataaccgtcccagttgccagagaaacaataacg 1080
tcattatttaataagtcatcggtgattggtccgcccctgaggttaatcttaaaagcccag 1140
gttacccgcggaaatttatgctgtccggtcaccgtgacaatgcagctgaggaacccagaa 1200
ctacatctgggctgcgcgcttgcgcttcgcttcctggccctcgtttcctgggacatccct 1260
ggggctagagcactggacaatggattggcaaggacgcctaccatgggctggctgcactgg 1320
gagcgcttcatgtgcaaccttgactgccaggaagagccagattcctgcatcaggtatcag 1380
atattgggtactcccttccctttgcttttccatgtgtttgggtgtgtttggggaactgga 1440
gagtctcaacgggaacagttgagcccgagggagagctcccccacccgactctgctgctgc 1500
tttttatccccagcaaactgtcccgaatcaggactagccctaaactttctctgtgtgac 1560
ctttcctgggatgggagtccggccagcggcccctgtttctttctctctctctctctctct 1620
cgttctccttctctttctctttctcttctttcctctctctttctctctctccctgcccgg 1680
ttctctttttcactgctccttgcagagcagggccaccccataggcagtgtgcccaaagt 1740
agccctgcccggttctattcagacccttcttgtgaacttctgctcttcctctgccgggtg 1800
ctaaccgttagaacatctagggtgggtaggaggaatggggaactaagattcgtgccattt 1860
tttctccttttggggtcgtggatttctcggcagtatctcgagggagttagagagaccata 1920
aggtcgctgagatctctcccacctcgcccatgagcgtggcatcaggctggaaggttgaca 1980
tggaggaactttatacatttacacctttgcgtgagggttgaggctggattagataggtat 2040
tgaacatatctgaccctcacaatccttatctgtaaattgggattacaaccttttaatttc 2100
agggagctgacaaaaaaaatctgaaaaatagttcttatctcacacaggtgagttttcaag 2160
gagataacctatttaaagtacatagcacagcgcttgaccattcaactgcgcttacagagc 2220
aaatgttcaatgggaaaatgaatgtaaatctacaaatctgaatgaatatgtgtattttc 2280
tggagagaggatatttacctttcttcaaattctcaaagggctctgtgatttaaaaaaggt 2340
taggaatcactgatagatgttggtaaaaggtggcagtcacagtacatttctgtgtccata 2400
agttattcctatgaatatctttatagataaagtcaggatgttggtcagacatcacagaag 2460
aaattggccttgtaagtttcatgtgaccctgtggtacagtatgtgtggcaattttgccca 2520
tcacggatttttttttattggtatttgcatctgattataaaactaatgcatgatcattgc 2580
aaaaaatgtagataaagaagagcaaaatgaaaataaagatttccccccaccgttccacca 2640
cccagaaataatcatggtttaaatgttaatatacaaccttacaattgttttctatataaa 2700
tgaaaacatagatttctttatttcattattttccataaaaaatggatcatgtttatgtca 2760
tgtttggctaatggcaagaccctggcacccagtctgggctcaaattctgcctcattgtta 2820
cttagccctgtgacattgggtaaattacacttttttttttttttttttttgagacgggg 2880

FIG. 1A

```
tctcgctctgtcgcccaggctggagtgcagtggcacgatctcggctcactgcaagtccgc    2940
ctcctgggttcacgccattcttctgcctcagcctcccgagtagctgggactacaggcgcc    3000
tgccaccacgcctggctcttttttttttttttttttttttagtacagacggggtttcac    3060
catgttagccagggtggtctcaatctcctgacctcgtgattcgcccgcctcagcctccca    3120
aagtgctggtgtgagccaccgtgcccagccttacttttttttttttgagaggggtctcact    3180
ctgtcacccaggttggagtgcagtggcgcgatctctgctcagtgcaaactccacctcccg    3240
ggtttaagcagttctcctgtcgtagtctcctgagtagctgggattacaggcacaccacca    3300
cggccagctaatttttgtattttcagtagagacgggtttcaccatgttgcccaagctggt    3360
ctcgaactcctggcctcaagtgatctgcccgccttggcctcccagagtgctgggattaca    3420
ggtgtgagccaccgcacccggcctctttttttcttttttagtctatcataccttgcaaata    3480
cagtggttcttcctatgtgttggttttgatatttatgtaatcaaacacatcagtttttcc    3540
tttctgatttctgactttggggtcatgctgagaaagtcctttcctacctgaagataatac    3600
agtatatacgtttcttactagtattttttgtggattttaaaatatttaaatctttagtcc    3660
atctgaacttgttcttctatcagaaatgccacatttaataaataataagtcccatggtat    3720
cagatggctggaaggacctctttcgaaactttgtttaattccattaatctgtgtattctt    3780
attctaatgctaatagttccacactagcttcctttatcttttttttctttttttttttttt    3840
ttttgagctggagtttcgctcttgttgcccaggctggagtacaatgtcacgatctcggtt    3900
caccgcaacctccgcctcccaggttcaagcaattctcctgcctcatcctcgcgagtagct    3960
ggaattacaggcatgcgccaccacgcctagctattttgtatttttagtagagatggggtt    4020
tctccatgttggtcaggctggtctcaaactcccagcctcaggtgatctgcctgcctcggc    4080
ctcccaaaatgctgttattacaggcgtgagccaccacgcccagccttcatcttttaatga    4140
atgtacatgtatgtaatcttttaggtgaactttttgtaatgttgtgccaagttccttaaa    4200
aagcccttttggaagctgggcaggtggccacgcctgtaatcccagcattttgggagtctg    4260
aggcaggtggatcacttgaggccaggagttcaagactagcctagccaaaatgcaaaaccc    4320
tgtctctactaaagatacaaaaattagccggatgcgatggcacatgcctgtaatctcagc    4380
tactcgggaggctgaggtagaagaatcgcttgaaccggggaggcagaggttgcagtgagc    4440
aagatggcgccactgcactccagcctgggtgacagagggagactccatctcaaaaaaaaa    4500
aaaaaaaaaaaaagataaaaggaaacctaagtactcttgggctttgttaaggattttgtt    4560
aaatatacaaaggattgcagggaaaattaacttatttttaatattgagtatgcttatcca    4620
agagcaaaataatatttctccatttattcaaatcatttaggagcatcatagttttaacat    4680
atgggccttgcacgtatcttaaatttatctctaggcattttaggttgttcagttgttctt    4740
gtgaatgggatctttttctccaaataggattattgttgatatctgttgattatgttaact    4800
ttgtagtttctgactttactgaactgtcttcttagatctaatactcttttcaatttcatc    4860
atatatttctcattcctatttttgtttggggttttagggcgggaatattaacgggataag    4920
agagacaaaagaaaatctggaaaaacaattcattttaccttacattgcttgtgattacta    4980
ccacactattactgggttggaaaaaattgtgaaatcccaaggtgcctaataaatgggagg    5040
tacctaagtgttcatttaatgaattgtaatgattattggaatttctctttcagtgagaag    5100
ctcttcatggagatggcagagctcatggtctcagaaggctggaaggatgcaggttatgag    5160
tacctctgcattgatgactgttggatggctccccaaagagattcagaaggcagacttcag    5220
gcagaccctcagcgctttcctcatgggattcgccagctagctaattatgtgagtttatag    5280
ataatgttcttgttcattcagaggactgtaagcacttctgtacagaagcttgtttagaaa    5340
cagccctcatggccgggcgtggtggctcacgctgtaatcccaacactttgggaggccgag    5400
gcgggtggatcacctgaggtcaagagttcaagaccagcctggccaacatggtgaaacccc    5460
aactctattaaaagtacaaaaaattagctgggcatggtggtgaacgcctgtaaccccagc    5520
tacttgggaggctgaggcaggagaatcgcttgaacccaggaggtggaagtttcagtgagc    5580
tgagatcacgccattgcactctagcctgggcaacaaagagaaactccatctcaaaaaaaa    5640
aaaacaaggaaaaaaagaaacagccctcatgacacttagaaagtagaatagctggctgtt    5700
atctgaacattgaattgtaaggcttatcaggtggactttgcattccatcagcagacaatt    5760
```

FIG. 1B

```
tttttttttttttttttttgagatggagtctcattctgtctcccaggctggagggcagtg      5820
gtgcgatctcggctcactgcaagctccacctcctgggttcatgccattctcctgcctcag      5880
cctcccaagtagctgggaccacaggcacccgccaccatgcccagttaatttttgtattt      5940
ttagtagagacggggtttcaccatgttagccaagatggtctcgatctcctgacctcgtga      6000
tccgcccacctcggcctcccaaagtgctgggattacaggcatgagccaccgcgcctagcc      6060
tacaaatgttttgtaatagctcttgaggcccatcttggagttctccttttgctaaaacca      6120
ctgaactctctaggaggaaaaaggaacttggttcttgacatatgtgtgcatgtatttcca      6180
tataacctttaggaagctattgcaatggtactataaactagaattttagaagatagaagg      6240
aaaatattctggagatcattgaagagaaatggagtccaacactagttaaagatgatgaag      6300
acagattttttttttgacggagtctcgctctgtcgcccaggctggagtgcagtggcaca      6360
atctcagctcactgcaaccctccacctcttgggttcaagtgattctcctgcctcagcctc      6420
ccaagtagctgggactacaggcgcacaccaccacgcccggctaattttgtatttttagt      6480
agagacaaggtttcaccatattcgccaggctggtctcgaactcctgaccttgtaatccgc      6540
ccaccttggcctcccaaagtgctgggattacaggcatgagccaccacgcccggccgatga      6600
agacagattttattcagtactaccacagtagaggaaagagccaagttcaattccaaatac      6660
aacaaagacaggtggagatttatagccaatgagcagattgagggggtcagtggatggaat      6720
atttaagaagacatcaagggtagggagcttcttgctaaagcttcatgtacttaaacaaga      6780
agggtgggggatgagggaaattgatcagatatcaatggtggcagtattgacttagcagga      6840
ttcttgctaagaggtcttgctaggacagacataggaagccaaggtggaggtctagtcgaa      6900
aagaaggctcatcagagaagtctaactaaagtttggtcaagaagagtctttgtcaaggta      6960
aatctatcatttccctcaaaaggtaattttcaggatcccatcaggaagattagcatggct      7020
gctagctttctcctcagttctgggctatagctcacatgcctagtttgaactagctcagca      7080
gaactggggatttattctttgtcttccaacaaactcatctggatgattttgggggtttg      7140
tggggaaaagcccccaatacctggtgaagtaaccttgtctcttcccccagcctggaatgg      7200
ttctctctttctgctacctcacgattgtgcttctacaatggtgactcttttcctccctct      7260
catttcaggttcacagcaaaggactgaagctagggatttatgcagatgttggaaataaaa      7320
cctgcgcaggcttccctgggagttttggatactacgacattgatgcccagacctttgctg      7380
actggggagtagatctgctaaaatttgatggttgttactgtgacagtttggaaaatttgg      7440
cagatggtaatgtttcattccagagatttagccacaaaggaaagaactttgaggccatgg      7500
tagctgagccaaagaaccaatcttcagaattttaaataccctgtcacaatactggaaata      7560
attattctccatgtgccagagctcccatctcttctctttcagttcattaattaattaatt      7620
aattcatgtaaaatccatgcatacctaaccatagctaatattgtgcacttataattcaag      7680
agggctctaagagttaattagtaattgtaactctctataacatcatttaggggagtccag      7740
gttgtcaatcggtcacagagaaagaagcatcttcattcctgcctttcctcaatatacaca      7800
ccatctctgcactacttcctcagaacaatcccagcagtctgggaggtactttacacaatt      7860
taagcacagagcaactgcctgtccctgctgctagtttaaacatgaaccttccaggtagcc      7920
tcttcttaaaatatacagccccagctgggcatgatggctcatgcctgtaatcctagcact      7980
ttgggaggctgaggcgggtggattacttgaggtcaggagttcgagaccaccctggccaac      8040
atggtgaaaccccatctctagtaaaaatacaaaaattagctgactttggtggcacatgcc      8100
tgtaatcccagctacttgggaagctgagacagaagagtcacttgaacctgggaaacagag      8160
gttgcagtgagccaagatcgcaccactgcactccaccctggatgacagactgaaccccat      8220
ctcaaaaaattaaaataaaataaaataaaataactatatatatagccccagctggaaatt      8280
catttctttcccttattttacccattgttttctcatacaggttataagcacatgtccttg      8340
gccctgaataggactggcagaagcattgtgtactcctgtgagtggcctctttatatgtgg      8400
ccctttcaaaaggtgagatagtgagcccagaatccaatagaactgtactgatagatagaa      8460
cttgacaacaaaggaaaccaaggtctccttcaaagtccaacgttacttactatcatccta      8520
ccatctctcccaggttccaaccacttctcaccatccccactgctgtaattatagcctaag      8580
ctaccatcacctggaaagtcatccttgtgtcttcccctttatttcaccattcatgtcctg      8640
```

FIG. 1C tctatcaacagtccttccaccagtatctctaaaatatctcctgaatcagcccacttcctt 8700
ccatcttcactacatgcaccctggccttccaagctactatcggctctcaaccagactgct 8760
gggaccacctgatctctctgcttccactctgtctcaacccccatctattttccaagcagc 8820
actagagttatcatattaaaatgtaaatatcagttttttttttaaagaaaaaaaccctga 8880
gacttaacagagttataaaaaatataaatgtcatcatcagttccctgcttaaaaccctta 8940
actcgcttccaattgcacttggaatgaaaccaaactgcactgatccagcccttgcctgcc 9000
tccccaaagtccaaggggtcatggctctttccctggctacactggtttctttctgtccc 9060
tcaacactgcaagcctattgctgccccagggcctttacacttgctttttttctgcctaga 9120
acagttcttccccaaagattttaaagggccgggctccttaacattgaagtcgcagacca 9180
aacgccacatatgcagacagttcttctctaactactttaaaatagccctctgtccattca 9240
ttcttcatcacattaacctgtttaattttcttctcagagctccacactatttggaagtat 9300
ttgttgacttgttaccatgtctccccactagagtgtaagtttcatgagggcagggacctt 9360
gtctgactttgactgtatctctcgcatatggttaagtgttaaatagttatttatggaatg 9420
aatccctattattccctcattatctctgcaaaatagtctttttttctcaacatcttaaacc 9480
tgatatcccacctgcctatctacaaacttttttttgcgacagagtctcactgtcaccca 9540
ggctagagtgcagtggcgccatctcggctcactgcaacctccgcctcccgggtttaagcg 9600
attctcttgcctcagcctcccagtagctgggattataggcgtgcgctaccacatctggct 9660
aatttttgtatttttagtagagatggtttcaccatgttggccaggcttgtctcgaactcc 9720
tgacctcagatgatccacctgcctcggcctcccaaagtgctgggattacaggcatgagcc 9780
accgtgcccagcctctacaaacttttattccattaacaaactatatgctgggatttaag 9840
ttttcttaatacttgatggagtcctatgtaattttcgagcttttaattttactaagacca 9900
ttttagttctgattatagaagtaaattaactttaagggatttcaagttatatggcctact 9960
tctgaagcaaacttcttacagtgaaaattcattataagggtttagacctccttatggaga 10020
cgttcaatctgtaaactcaagagaaggctacaagtgcctcctttaaactgttttcatctc 10080
acaaggatgttagtagaaagtaaacagaagagtcatatctgttttcacagcccaattata 10140
cagaaatccgacagtactgcaatcactggcgaaattttgctgacattgatgattcctgga 10200
aaagtataaagagtatcttggactggacatcttttaaccaggagagaattgttgatgttg 10260
ctggaccaggggggttggaatgacccagatatggtaaaaacttgagccctccttgttcaag 10320
accctgcggtaggcttgtttcctattttgacattcaaggtaaatacaggtaaagttcctg 10380
ggaggaggctttatgtgagagtacttagagcaggatgctgtggaaagtggtttctccata 10440
tgggtcatctaggtaactttaagaatgtttcctcctctcttgtttgaattatttcattct 10500
ttttctcagttagtgattggcaactttggcctcagctggaatcagcaagtaactcagatg 10560
gccctctgggctatcatggctgctcctttattcatgtctaatgacctccgacacatcagc 10620
cctcaagccaaagctctccttcaggataaggacgtaattgccatcaatcaggaccccttg 10680
ggcaagcaagggtaccagcttagacaggtaaataagagtatatattttaagatggcttta 10740
tatacccaataccaactttgtcttgggcctaaatctattttttttcccttgctcttgatgt 10800
tactatcagtaataaagcttcttgctagaaacattactttatttccaaaataatgctaca 10860
ggatcattttaatttttcctacaagtgcttgatagttctgacattaagaatgaatgccaa 10920
actaacagggccacttatcactagttgctaagcaaccacactttcttggtttttcaggga 10980
gacaactttgaagtgtgggaacgacctctctcaggcttagcctgggctgtagctatgata 11040
aaccggcaggagattggtggacctcgctcttataccatcgcagttgcttccctgggtaaa 11100
ggagtggcctgtaatcctgcctgcttcatcacacagctcctccctgtgaaaaggaagcta 11160
gggttctatgaatggacttcaaggttaagaagtcacataaatcccacaggcactgttttg 11220
cttcagctagaaaatacaatgcagatgtcattaaaagacttactttaaaatgtttatttt 11280
attgccaactactacttcctgtccaccttttctccattcactttaaaagctcaaggcta 11340
ggtggctcatgcctgtaatcccagcactttgggaggctgaggcgggcagatcacctgagg 11400
tcgggactttgagacccgcctggacaacatggtgaaaccccatttctaataaaaatataa 11460
aaattagccaggtgtggtggcgcacctgtggtcccagctactctgggggctgaggcatga 11520

FIG. 1D gaatcgcttgaacccgggagtggaggttgcattgagctgagatcatgccacctcactcca 11580
gcctgggcaacaaagattccatctcaaaaaaaaaaaaaaagccaggcacagtggctcatg 11640
cctggaatcccagcacttttggaagctgaggcaggcagatcacttgaggttaggatttca 11700
agaccagcctggctaacatagtaaagccctgtctctactaaaaatacaaaaattagccag 11760
gtatggtggcgagcttctgtagccccagctactcaggagactgaggcaggagaatcactt 11820
gaacccggaagtggggggggtgcagtgacccaagatcacgccactgcattccagcctggg 11880
caacagagcaagactccatctcaaaaaaaaaaagttctatttccttgaataaattttccg 11940
aagtttaaactttaggaataaaactattaaacccgtatttactcatccagatacccaccc 12000
cccttgttgagattctctcccaattatcaaaatgtgtagcatatttaactaccaagagct 12060
aaacatcattaagactgaaatgtattaagaaggatgtataggccaggcacggtgtctcac 12120
gcctgtaatcccaacactttgggaggccaagtcgggcggatcacgaggtcaggagatgga 12180
gaccatcctggccaacatggtgaaacccctctctactaaaaatacaaaaattagccagg 12240
caggtggcaggcacctgtaatcccagctactccagaggctgaggcaggacaatcacttga 12300
acctgggaggcagaggctgcagtgagctgaggttgtaccaattgcactccagcctaggta 12360
acgagcaacactccatctcaaaaaaagaaaaaaaaaaagatgtataatttggaactgtta 12420
agaggcattttaaaga 12436

FIG. 1E

```
MQLRNPELHL GCALALRFLA LVSWDIPGAR ALDNGLARTP TMGWLHWERF MCNLDCQEEP   60
DSCISEKLFM EMAELMVSEG WKDAGYEYLC IDDCWMAPQR DSEGRLQADP QRFPHGIRQL  120
ANYVHSKGLK LGIYADVGNK TCAGFPGSFG YYDIDAQTFA DWGVDLLKFD GCYCDSLENL  180
ADGYKHMSLA LNRTGRSIVY SCEWPLYMWP FQKPNYTEIR QYCNHWRNFA DIDDSWKSIK  240
SILDWTSFNQ ERIVDVAGPG GWNDPDMLVI GNFGLSWNQQ VTQMALWAIM AAPLFMSNDL  300
RHISPQAKAL LQDKDVIAIN QDPLGKQGYQ LRQGDNFEVW ERPLSGLAWA VAMINRQEIG  360
GPRSYTIAVA SLGKGVACNP ACFITQLLPV KRKLGFYEWT SRLRSHINPT GTVLLQLENT  420
MQMSLKDLL                                                          429
```

FIG. 2

```
atgcagctgaggaatcccgagctccacctgggctgtgctctggctctgcggttcctggccctc
gtgtcctgggacatccctggcgctagggccctcgataacggactggcccggacccccacaatg
ggatggctccactgggaaaggttcatgtgcaatctggactgtcaggaggaacccgactcctgc
atcagcgaaaagctcttcatggagatggccgagctgatggtgagcgagggctggaaggacgcc
ggctacgagtatctgtgcatcgatgactgctggatggcccctcaaagggactccgaaggcagg
ctgcaggctgatccccaaaggtttccccacggaatccggcagctcgccaactacgtgcattcc
aagggcctcaagctcggcatctacgccgacgtgggcaacaaaacatgcgccggattccccggc
agcttcggctactacgacatcgacgcccagacattcgctgattggggagtggacctgctgaag
ttcgacggctgttactgcgattccctggaaaacctggccgacggctacaaacacatgtccctc
gccctgaaccggacaggcaggtccatcgtgtacagctgcgagtggcccctgtacatgtggcct
ttccagaagcccaactacacagagatcaggcagtactgcaaccactggaggaacttcgctgac
atcgacgactcctggaagagcatcaagagcatcctggactggaccagcttcaaccaggagagg
atcgtggacgtggctggacccggaggctggaacgaccccgatatgctggtgattggcaacttc
ggactgagctggaaccagcaggtgacccagatggccctgtgggccattatggccgctcccctg
ttcatgtccaacgacctgaggcacatcagcccccaggccaaggctctgctgcaggacaaggat
gtgatcgccatcaaccaggacccccctgggcaagcagggctaccagctgaggcaaggagataac
ttcgaggtgtgggagaggcccctgtccggactggcttgggccgtggccatgatcaatcggcag
gagatcggcggaccccggtcctacaccattgctgtggccagcctgggaaaggagtcgcctgc
aaccccgcctgcttcattacccagctgctccccgtgaagcggaagctgggcttctatgagtgg
accagcaggctgaggtcccatatcaatcctaccggcaccgtcctcctccagctcgagaatacc
atgcagatgagcctcaaggatctgctgtga
```

FIG. 3

| Nucleotide Change | Nucleotide Change | Protein Sequence Change |
|---|---|---|
| c.167G>T | c.G167T | C56F |
| c.170A>G | c.A170G | Q57R |
| c.170A>T | c.A170T | Q57L |
| c.175G>A | c.G175A | E59K |
| c.178C>A | c.C178A | P60T |
| c.178C>T | c.C178T | P60S |
| c.179C>T | c.C179T | P60L |

METHODS OF TREATING FABRY DISEASE IN PATIENTS HAVING A MUTATION IN THE GLA GENE

TECHNICAL FIELD

Principles and embodiments of the present invention relate generally to the use of pharmacological chaperones for the treatment of Fabry disease, particularly in patients with mutations or variants in the α-galactosidase (GLA) gene.

BACKGROUND

Many human diseases result from mutations that cause changes in the amino acid sequence of a protein which reduce its stability and may prevent it from folding properly. Proteins generally fold in a specific region of the cell known as the endoplasmic reticulum, or ER. The cell has quality control mechanisms that ensure that proteins are folded into their correct three-dimensional shape before they can move from the ER to the appropriate destination in the cell, a process generally referred to as protein trafficking. Misfolded proteins are often eliminated by the quality control mechanisms after initially being retained in the ER. In certain instances, misfolded proteins can accumulate in the ER before being eliminated. The retention of misfolded proteins in the ER interrupts their proper trafficking, and the resulting reduced biological activity can lead to impaired cellular function and ultimately to disease. In addition, the accumulation of misfolded proteins in the ER may lead to various types of stress on cells, which may also contribute to cellular dysfunction and disease.

Such mutations can lead to lysosomal storage disorders (LSDs), which are characterized by deficiencies of lysosomal enzymes due to mutations in the genes encoding the lysosomal enzymes. The resultant disease causes the pathologic accumulation of substrates of those enzymes, which include lipids, carbohydrates, and polysaccharides. Although there are many different mutant genotypes associated with each LSD, many of the mutations are missense mutations which can lead to the production of a less stable enzyme. These less stable enzymes are sometimes prematurely degraded by the ER-associated degradation pathway. This results in the enzyme deficiency in the lysosome, and the pathologic accumulation of substrate. Such mutant enzymes are sometimes referred to in the pertinent art as "folding mutants" or "conformational mutants."

Fabry Disease is a LSD caused by a mutation to the GLA gene, which encodes the enzyme α-galactosidase A (α-Gal A). α-Gal A is required for glycosphingolipid metabolism. The mutation causes the substrate globotriaosylceramide (GL-3) to accumulate in various tissues and organs. Males with Fabry disease are hemizygotes because the disease genes are encoded on the X chromosome. Fabry disease is estimated to affect 1 in 40,000 and 60,000 males, and occurs less frequently in females.

There have been several approaches to treatment of Fabry disease. One approved therapy for treating Fabry disease is enzyme replacement therapy (ERT), which typically involves intravenous, infusion of a purified form of the corresponding wild-type protein. Two α-Gal A products are currently available for the treatment of Fabry disease: agalsidase alfa (Replagal®, Shire Human Genetic Therapies) and agalsidase beta (Fabrazyme®; Sanofi Genzyme Corporation). ERT has several drawbacks, however. One of the main complications with ERT is rapid degradation of the infused protein, which leads to the need for numerous costly high dose infusions. ERT has several additional caveats, such as difficulties with large-scale generation, purification, and storage of properly folded protein; obtaining glycosylated native protein; generation of an anti-protein immune response; and inability of protein to cross the blood-brain barrier to mitigate central nervous system pathologies (i.e., low bioavailability). In addition, replacement enzyme cannot penetrate the heart or kidney in sufficient amounts to reduce substrate accumulation in the renal podocytes or cardiac myocytes, which figure prominently in Fabry pathology.

Another approach to treating some enzyme deficiencies involves the use of small molecule inhibitors to reduce production of the natural substrate of deficient enzyme proteins, thereby ameliorating the pathology. This "substrate reduction" approach has been specifically described for a class of about 40 LSDs that include glycosphingolipid storage disorders. The small molecule inhibitors proposed for use as therapy are specific for inhibiting the enzymes involved in synthesis of glycolipids, reducing the amount of cellular glycolipid that needs to be broken down by the deficient enzyme.

A third approach to treating Fabry disease has been treatment with what are called pharmacological chaperones (PCs). Such PCs include small molecule inhibitors of α-Gal A, which can bind to the α-Gal A to increase the stability of both mutant enzyme and the corresponding wild type. However, patients for PC therapy should have an amenable mutation or variant which results in the production of an enzyme that has the potential to be stabilized and folded into a conformation that permits trafficking out of the ER.

Thus, even when Fabry disease is diagnosed by detecting deficient α-Gal A activity in plasma or peripheral leukocytes (WBCs), it is very difficult, if not impossible, to predict whether a particular Fabry patient will respond to treatment with a PC. Thus, there remains a need to identify new GLA mutations or variants that will be responsive to a PC and make available new methods of treatment to Fabry patients with these mutations or variants.

SUMMARY

One aspect of the invention pertains to a method of treating a patient diagnosed with Fabry disease. The method comprises administering to the patient a therapeutically effective dose of a pharmacological chaperone for α-Gal A, wherein the patient has a missense mutation of the nucleic acid sequence encoding α-Gal A. In one or more embodiments, the mutation is N5D, N5K, P6L, P6Q, P6R, P6S, P6T, E7D, E7K, E7V, L8I, L8P, L8Q, H9L, H9Q, H9R, H9Y, L10M, L10P, L10Q, L10R, L10V, G11C, G11D, G11R, G11S, G11V, C12G, C12R, C125, C12Y, A13E, A13G, L14F, L14H, L14V, R17C, R17G, R17H, R17P, R175, F18I, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, 565C, 565G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G805, W8I L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, 191S, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G1045, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, I117M, I117T, A121V, Y123D, Y123F, Y123N, Y123S, V124I, H125D, H125N, H125R, S126C, S126I, K127E, G128A, L129V, K130M, K130N, K130Q, L131V, I133L, I133T, I133V, A135E, A135G, A135S, A135T, D136A, D136N, D136V, V137A, V137D, V137G, V137I, V137L, G138A, N139H, N139I, N139K, N139Y, K140E, K140I, K140N, K140Q, K140R, T141S, A143E, A143G, G144A, G144C, G144R, G144S, F145C, F145L, F145V, F145Y, P146A, P146H, P146L, P146T, G147A, S148C, S148G, S148T, F149C, G150E, G150V, Y151C, Y151D, Y151S, Y152F, Y152S, D153A, D153H, D153N, D153V, D153Y, A156G, Q157E, Q157K, Q157L, Q157P, T158A, T158I, T158N, T158S, F159I, F159L, F159V, F159Y, A160G, A160S, A160T, A160V, D161H, D161N, D161V, D161Y, W162S, V164A, V164I, V164L, D165A, D165E, L166M, L166Q, L167I, F169C, F169L, F169V, F169Y, G171A, G171V, Y173C, Y173F, Y173H, Y173S, D175G, D175H, D175V, D175Y, S176C, S176R, L177F, L177M, L177S, L177V, L177W, E178A, E178G, E178K, E178Q, L180M, L180S, A181P, A181T, A181V, D182A, D182E, D182V, D182Y, Y184F, Y184H, Y184S, K185M, K185N, K185Q, K185T, H186D, H186L, H186N, H186Q, H186Y, M187L, S188A, S188C, S188F, S188P, S188T, S188Y, L189S, L189V, A190D, A190G, A190S, A190T, A190V, L191M, L191V, N192D, N192H, N192K, N192S, N192T, R193G, R193M, R193T, R193W, T194N, T194P, T194S, G195C, G195R, G195S, R196I, R196K, S197C, S197G, S197I, S197N, S197T, I198M, I198S, V199E, V199L, Y200N, Y200S, S201A, S201C, S201T, E203A, E203G, E203Q, W204S, L206F, L206H, L2061, L206R, L206V, Y207F, M208K, W209C, W209G, P210H, P210T, F211C, F211L, F211S, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T217S, E218A, E218D, E218G, E218K, E218Q, E218V, I219F, I219M, I219S, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, D264H, D264N, P265A, P265Q, M267L, M267V, L268F, L268I, V269L, I270L, I270S, I270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, I317L, I317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, I407L, I407M, I407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N, or L429R. In various embodiments, these mutations are relative to SEQ ID NO: 2. An additional aspect of the invention pertains to a medicament for treating a patient diagnosed with Fabry disease who has a missense mutation of the nucleic acid sequence encoding α-Gal A. In one or more embodiments, the mutation is provided above. In various embodiments, these mutations are relative to SEQ ID NO: 2.

In some embodiments, the pharmacological chaperone or medicament comprises migalastat or salt thereof. In one or more embodiments, the dose of migalastat or salt thereof is from about 100 mg to about 150 mg free base equivalent (FBE). In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, suitable PCs and dosages, formulations and routes of administration thereof.

Another aspect of the invention pertains to a method of enhancing α-Gal A in a patient diagnosed with or suspected of having Fabry disease. The method comprises administering to a patient a therapeutically effective dose of a pharmacological chaperone for α-Gal A, wherein the patient has a missense mutation in the nucleic acid sequence encoding α-Gal A. Accordingly, an additional aspect of the invention pertains to a medicament for enhancing α-Gal A in a patient diagnosed with or suspected of having Fabry disease who has a missense mutation of the nucleic acid sequence encoding α-Gal A. In one or more embodiments, the mutation is provided below.

In one or more embodiments, the mutation is N5D, N5K, P6L, P6Q, P6R, P6S, P6T, E7D, E7K, E7V, L8I, L8P, L8Q, H9L, H9Q, H9R, H9Y, L10M, L10P, L10Q, L10R, L10V, G11C, G11D, G11R, G11S, G11V, C12G, C12R, C12S, C12Y, A13E, A13G, L14F, L14H, L14V, R17C, R17G, R17H, R17P, R17S, F181, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, S65C, S65G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G80S, W81L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, I91S, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G104S, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, I117M, I117T, A121V, Y123D, Y123F, Y123N, Y123S, V124I, H125D, H125N, H125R, S126C, S126I, K127E, G128A, L129V, K130M, K130N, K130Q, L131V, I133L, I133T, I133V, A135E, A135G, A135S, A135T, D136A, D136N, D136V, V137A, V137D, V137G, V137I, V137L, G138A, N139H, N139I, N139K, N139Y, K140E, K140I, K140N, K140Q, K140R, T141S, A143E, A143G, G144A, G144C, G144R, G144S, F145C, F145L, F145V, F145Y, P146A, P146H, P146L, P146T, G147A, S148C, S148G, S148T, F149C, G150E, G150V, Y151C, Y151D, Y151S, Y152F, Y152S, D153A, D153H, D153N, D153V, D153Y, A156G, Q157E, Q157K, Q157L, Q157P, T158A, T158I, T158N, T158S, F159I, F159L, F159V, F159Y, A160G, A160S, A160T, A160V, D161H, D161N, D161V, D161Y, W162S, V164A, V164I, V164L, D165A, D165E, L166M, L166Q, L167I, F169C, F169L, F169V, F169Y, G171A, G171V, Y173C, Y173F, Y173H, Y173S, D175G, D175H, D175V, D175Y, S176C, S176R, L177F, L177M, L177S, L177V, L177W, E178A, E178G, E178K, E178Q, L180M, L180S, A181P, A181T, A181V, D182A, D182E, D182V, D182Y, Y184F, Y184H, Y184S, K185M, K185N, K185Q, K185T, H186D, H186L, H186N, H186Q, H186Y, M187L, S188A, S188C, S188F, S188P, S188T, S188Y, L189S, L189V, A190D, A190G, A190S, A190T, A190V, L191M, L191V, N192D, N192H, N192K, N192S, N192T, R193G, R193M, R193T, R193W, T194N, T194P, T194S, G195C, G195R, G195S, R196I, R196K, S197C, S197G, S197I, S197N, S197T, I198M, I198S, V199E, V199L, Y200N, Y200S, S201A, S201C, S201T, E203A, E203G, E203Q, W204S, L206F, L206H, L2061, L206R, L206V, Y207F, M208K, W209C, W209G, P210H, P210T, F211C, F211L, F211S, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T217S, E218A, E218D, E218G, E218K, E218Q, E218V, I219F, I219M, I219S, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, D264H, D264N, P265A, P265Q, M267L, M267V, L268F, L268I, V269L, I270L, I270S, I270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, I317L, I317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, I407L, I407M, I407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N, or L429R. In various embodiments, these mutations are relative to SEQ ID NO: 2.

In some embodiments, the pharmacological chaperone comprises migalastat or salt thereof. In one or more embodiments, the dose of migalastat or salt thereof is from about 100 mg to about 150 mg FBE. In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of treating a patient with Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, suitable PCs and dosages, formulations and routes of administration thereof.

Another aspect of the invention pertains to use of a pharmacological chaperone for α-Gal A for the manufacture of a medicament for treating a patient diagnosed with Fabry disease, wherein the patient has a missense mutation in the nucleic acid sequence encoding α-Gal A. In one or more embodiments, the mutation is N5D, N5K, P6L, P6Q, P6R, P6S, P6T, E7D, E7K, E7V, L8I, L8P, L8Q, H9L, H9Q, H9R, H9Y, L10M, L10P, L10Q, L10R, L10V, G11C, G11D, G11R, G11S, G11V, C12G, C12R, C12S, C12Y, A13E, A13G, L14F, L14H, L14V, R17C, R17G, R17H, R17P, R17S, F18I, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, S65C, S65G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G80S, W81L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, I91S, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G104S, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, I117M, I117T, A121V, Y123D, Y123F, Y123N, Y123S, V124I, H125D, H125N, H125R, S126C, S126I, K127E, G128A, L129V, K130M, K130N, K130Q, L131V, I133L, I133T, I133V, A135E, A135G, A135S, A135T, D136A, D136N, D136V, V137A, V137D, V137G, V137I, V137L, G138A, N139H, N139I, N139K, N139Y, K140E, K140I, K140N, K140Q, K140R, T141S, A143E, A143G, G144A, G144C, G144R, G144S, F145C, F145L, F145V, F145Y, P146A, P146H, P146L, P146T, G147A, S148C, S148G, S148T, F149C, G150E, G150V, Y151C, Y151D, Y151S, Y152F, Y152S, D153A, D153H, D153N, D153V, D153Y, A156G, Q157E, Q157K, Q157L, Q157P, T158A, T158I, T158N, T158S, F159I, F159L, F159V, F159Y, A160G, A160S, A160T, A160V, D161H, D161N, D161V, D161Y, W162S, V164A, V164I, V164L, D165A, D165E, L166M, L166Q, L167I, F169C, F169L, F169V, F169Y, G171A, G171V, Y173C, Y173F, Y173H, Y173S, D175G, D175H, D175V, D175Y, S176C, S176R, L177F, L177M, L177S, L177V, L177W, E178A, E178G, E178K, E178Q, L180M, L180S, A181P, A181T, A181V, D182A, D182E, D182V, D182Y, Y184F, Y184H, Y184S, K185M, K185N, K185Q, K185T, H186D, H186L, H186N, H186Q, H186Y, M187L, S188A, S188C, S188F, S188P, S188T, S188Y, L189S, L189V, A190D, A190G, A190S, A190T, A190V, L191M, L191V, N192D, N192H, N192K, N192S, N192T, R193G, R193M, R193T, R193W, T194N, T194P, T194S, G195C, G195R, G195S, R196I, R196K, S197C, S197G, S197I, S197N, S197T, I198M, I198S, V199E, V199L, Y200N, Y200S, S201A, S201C, S201T, E203A, E203G, E203Q, W204S, L206F, L206H, L2061, L206R, L206V, Y207F, M208K, W209C, W209G, P210H, P210T, F211C, F211L, F211S, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T217S, E218A, E218D, E218G, E218K, E218Q, E218V, I219F, I219M, I219S, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, D264H, D264N, P265A, P265Q, M267L, M267V, L268F, L268I, V269L, I270L, I270S, I270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, I317L, I317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, I407L, I407M, I407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N, or L429R. In various embodiments, these mutations are relative to SEQ ID NO: 2.

In some embodiments, the pharmacological chaperone comprises migalastat or salt thereof. In one or more embodiments, the dose of migalastat or salt thereof is from about 100 mg to about 150 mg FBE. In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of treating a patient with Fabry disease, a method of enhancing α-Gal A in a patient diagnosed with or suspected of having Fabry disease, or to a pharmacological chaperone for α-Gal A for use in treating a patient diagnosed with Fabry disease as well as embodiments relating to amenable mutations, suitable PCs and dosages, formulations and routes of administration thereof.

Another aspect of the invention pertains to a pharmacological chaperone for α-Gal A for use in treating a patient diagnosed with Fabry disease, wherein the patient has a missense mutation in the nucleic acid sequence encoding α-Gal A. In one or more embodiments, the mutation is N5D, N5K, P6L, P6Q, P6R, P6S, P6T, E7D, E7K, E7V, L8I, L8P, L8Q, H9L, H9Q, H9R, H9Y, L10M, L10P, L10Q, L10R, L10V, G11C, G11D, G11R, G11S, G11V, C12G, C12R, C12S, C12Y, A13E, A13G, L14F, L14H, L14V, R17C, R17G, R17H, R17P, R17S, F18I, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, S65C, S65G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G80S, W81L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, I91S, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G104S, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, I117M, I117T, A121V, Y123D, Y123F, Y123N, Y123S, V124I, H125D, H125N, H125R, S126C, S126I, K127E, G128A, L129V, K130M, K130N, K130Q, L131V, I133L, I133T, I133V, A135E, A135G, A135S, A135T, D136A, D136N, D136V, V137A, V137D, V137G, V137I, V137L, G138A, N139H, N139I, N139K, N139Y, K140E, K140I, K140N, K140Q, K140R, T141S, A143E, A143G, G144A, G144C, G144R, G144S, F145C, F145L, F145V, F145Y, P146A, P146H, P146L, P146T, G147A, S148C, S148G, S148T, F149C, G150E, G150V, Y151C, Y151D, Y151S, Y152F, Y152S, D153A, D153H, D153N, D153V, D153Y, A156G, Q157E, Q157K, Q157L, Q157P, T158A, T158I, T158N, T158S, F159I, F159L, F159V, F159Y, A160G, A160S, A160T, A160V, D161H, D161N, D161V, D161Y, W162S, V164A, V164I, V164L, D165A, D165E, L166M, L166Q, L167I, F169C, F169L, F169V, F169Y, G171A, G171V, Y173C, Y173F, Y173H, Y173S, D175G, D175H, D175V, D175Y, S176C, S176R, L177F, L177M, L177S, L177V, L177W, E178A, E178G, E178K, E178Q, L180M, L180S, A181P, A181T, A181V, D182A, D182E, D182V, D182Y, Y184F, Y184H, Y184S, K185M, K185N, K185Q, K185T, H186D, H186L, H186N, H186Q, H186Y, M187L, S188A, S188C, S188F, S188P, S188T, S188Y, L189S, L189V, A190D, A190G, A190S, A190T, A190V, L191M, L191V, N192D, N192H, N192K, N192S, N192T, R193G, R193M, R193T, R193W, T194N, T194P, T194S, G195C, G195R, G195S, R196I, R196K, S197C, S197G, S197I, S197N, S197T, I198M, I198S, V199E, V199L, Y200N, Y200S, S201A, S201C, S201T, E203A, E203G, E203Q, W204S, L206F, L206H, L2061, L206R, L206V, Y207F, M208K, W209C, W209G, P210H, P210T, F211C, F211L, F211S, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T217S, E218A, E218D, E218G, E218K, E218Q, E218V, I219F, I219M, I219S, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, D264H, D264N, P265A, P265Q, M267L, M267V, L268F, L268I, V269L, I270L, I270S, I270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, I317L, I317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, I407L, I407M, I407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N, or L429R. In various embodiments, these mutations are relative to SEQ ID NO: 2.

In some embodiments, the pharmacological chaperone comprises migalastat or salt thereof. In one or more embodiments, the dose of migalastat or salt thereof is from about 100 mg to about 150 mg FBE. In some embodiments, the salt of migalastat is migalastat hydrochloride. In one or more embodiments, the dose is about 150 mg every other day of migalastat hydrochloride or an equivalent dose of migalastat or a salt thereof other than the hydrochloride salt. In some embodiments, the migalastat or salt thereof is administered orally or by injection. These embodiments may be combined with one another or with other embodiments of the invention, for example embodiments relating to a method of treating a patient with Fabry disease, a method of enhancing α-Gal A in a patient diagnosed with or suspected of having Fabry disease or use of a pharmacological chaperone for α-Gal A for the manufacture of a medicament for treating a patient diagnosed with Fabry disease as well as embodiments relating to amenable mutations, suitable PCs and dosages, formulations and routs of administration thereof.

Another aspect of the invention pertains to migalastat or a salt thereof for use in a method for treatment of Fabry disease in a human patient in, wherein the patient has an α-galactosidase A mutation selected from the group consisting of those mutations provided in Table 2.

Another aspect of the invention pertains to a method of treating a patient diagnosed with Fabry disease, wherein the patient has a HEK assay amenable mutation in α-galactosidase A disclosed in a pharmacological reference table as disclosed herein. This aspect can have any of the features described in the other aspects as disclosed herein.

Another aspect of the invention pertains to a method of enhancing α-galactosidase A in a patient diagnosed with or suspected of having Fabry disease, wherein the patient has a HEK assay amenable mutation in α-galactosidase A disclosed in a pharmacological reference table as disclosed herein. This aspect can have any of the features described in the other aspects as disclosed herein.

Some embodiments relate to a method of treating Fabry disease in a subject. Mutation information corresponding to the subject is accessed. The mutation information identifies one or more α-galactosidase A mutations. Based on the mutation information, it is determined that the subject has at least one mutation as identified in Table 2 and/or at least one mutation of: N5D, N5K, P6L, P6Q, P6R, P6S, P6T, E7D, E7K, E7V, L8I, L8P, L8Q, H9L, H9Q, H9R, H9Y, L10M, L10P, L10Q, L10R, L10V, G11C, G11D, G11R, G11S, G11V, C12G, C12R, C12S, C12Y, A13E, A13G, L14F, L14H, L14V, R17C, R17G, R17H, R17P, R17S, F18I, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, S65C, S65G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G80S, W81L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, I91S, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G104S, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, I117M, I117T, A121V, Y123D, Y123F, Y123N, Y123S, V124I, H125D, H125N, H125R, S126C, S126I, K127E, G128A, L129V, K130M, K130N, K130Q, L131V, I133L, I133T, I133V, A135E, A135G, A135S, A135T, D136A, D136N, D136V, V137A, V137D, V137G, V137I, V137L, G138A, N139H, N139I, N139K, N139Y, K140E, K140I, K140N, K140Q, K140R, T141S, A143E, A143G, G144A, G144C, G144R, G144S, F145C, F145L, F145V, F145Y, P146A, P146H, P146L, P146T, G147A, S148C, S148G, S148T, F149C, G150E, G150V, Y151C, Y151D, Y151S, Y152F, Y152S, D153A, D153H, D153N, D153V, D153Y, A156G, Q157E, Q157K, Q157L, Q157P, T158A, T158I, T158N, T158S, F159I, F159L, F159V, F159Y, A160G, A160S, A160T, A160V, D161H, D161N, D161V, D161Y, W162S, V164A, V164I, V164L, D165A, D165E, L166M, L166Q, L167I, F169C, F169L, F169V, F169Y, G171A, G171V, Y173C, Y173F, Y173H, Y173S, D175G, D175H, D175V, D175Y, S176C, S176R, L177F, L177M, L177S, L177V, L177W, E178A, E178G, E178K, E178Q, L180M, L180S, A181P, A181T, A181V, D182A, D182E, D182V, D182Y, Y184F, Y184H, Y184S, K185M, K185N, K185Q, K185T, H186D, H186L, H186N, H186Q, H186Y, M187L, S188A, S188C, S188F, S188P, S188T, S188Y, L189S, L189V, A190D, A190G, A190S, A190T, A190V, L191M, L191V, N192D, N192H, N192K, N192S, N192T, R193G, R193M, R193T, R193W, T194N, T194P, T194S, G195C, G195R, G195S, R196I, R196K, S197C, S197G, S197I, S197N, S197T, I198M, I198S, V199E, V199L, Y200N, Y200S, S201A, S201C, S201T, E203A, E203G, E203Q, W204S, L206F, L206H, L2061, L206R, L206V, Y207F, M208K, W209C, W209G, P210H, P210T, F211C, F211L, F211S, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T217S, E218A, E218D, E218G, E218K, E218Q, E218V, I219F, I219M, I219S, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, D264H, D264N, P265A, P265Q, M267L, M267V, L268F, L268I, V269L, I270L, I270S, I270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, I317L, I317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, I407L, I407M, I407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N, or L429R. In response to the determination, migalastat or a salt thereof is administered to the subject.

The at least one mutation can include one or more mutations of α-galactosidase A at amino acid residues 5-14, 17-18, 20-30, 32-33, 36-39, 41, 43, 45-46, 48, 50-51, 53-56, 58-62, 64-89, 91, 96-99, 101-102, 104-110, 113-117, 121, 123-131, 133, 135-141, 143-153, 156-162, 164-167, 169, 171, 173, 175-178, 180-182, 184-201, 203, 204, 206-222, 224, 227-230, 232-233, 235, 237-261, 263-265, 267-270, 272-273, 275, 277-278, 280-286, 288-289, 291-292, 294-295, 297-300, 302-304, 306-322, 324-327, 329-339, 341, 343-344, 346-357, 359, 362-371, 373-377, 379-381, 383-388, 391-425, 427, or 429, or any combination thereof, wherein the residues are numbered relative to SEQ ID NO:2

Determining that the subject has at least one mutation as identified in Table 2 can include initiating a query of a data store that identifies two or more mutations from a set of mutations identified in Table 2 and receiving a query result that identifies the at least one mutation is represented in the mutation information and also in Table 2. The data store may further identify two or more mutations from another set of mutations (e.g., identified in Table 2). The data store may identify at least 10%, 25%, 50%, 75%, 90% or 95% of the mutations as included in Table 1 and/or at least 10%, 25%, 50%, 75%, 90% or 95% of the mutations as included in Table 2. The query may be initiated by accessing a particular webpage hosted by a web server that controls a data store identifying at least some of the mutations in Table 2. The query may be initiated by accessing a particular webpage on a website; providing input at the particular webpage that identifies at least part of the mutation information; and selecting an option at the webpage to submit, to a web server, an electronic request to perform the query, the electronic request including a representation of the input. The query result may be received from the web server in response to the query and may be displayed at the particular webpage or another webpage on the website.

The migalastat or salt thereof may be administered to the subject every other day. Administering the migalastat or salt thereof can include administering the migalastat or salt thereof in a dose of about 100 to about 150 mg free base equivalent of the migalastat of salt thereof; or administering about 123 mg free base equivalent of the migalastat of salt thereof. The migalastat or salt thereof may enhance α-galactosidase A activity in the subject. The at least one mutation can include an HEK assay amenable mutation in α-galactosidase A. The migalastat or salt thereof may be administered orally or by injection.

In some embodiments, a computer-implemented method is provided. An electronic communication is received. The electronic communication corresponds to an identification of a particular mutation. A data store is queried using the identification of the particular mutation. The data store includes an identification of each of a set of amenable mutations. Each of the set of amenable mutations corresponds to a mutation listed in Table 2. A result of the query is detected, the result being indicative of whether the particular mutation is represented in the set of amenable mutations. Based on the response, an output is generated that is indicative of a suitability of treating a patient with the particular mutation with migalastat or a migalastat salt. The output is transmitted.

The electronic communication can include the identification of the particular mutation in a first format, and the method can further include determining that the first format differs from a second format used by the data store; extracting one or more components from the identification; generating a second identification based on the components, the second identification being in the second format; transmitting the second identification; and receiving a second electronic communication that indicates that the second identification corresponds to the first identification. The data store may be queried in response to receiving the second electronic communication. The data store may further include an identification of another set of amenable mutations. Each of the second set of amenable mutations corresponds to a mutation listed in Table 1, and the result may be further indicative of whether the particular mutation is represented in the second set of amenable mutations. The result may include a binary indication as to whether migalastat or migalastat salt is a suitable treatment for a condition attributed to the particular mutation. The identification of the particular mutation may correspond to input detected at a webpage (generated at least in part based on webpage data transmitted to a user device from which the electronic device is received). The data store may identify at least 10%, at least 25%, at least 50%, at least 75% or at least 90% of the mutations listed in Table 2.

In some embodiments, a computer-implemented method is provided. A data set unit storing a data set is accessed that identifies, for each mutation of a set of mutations, a degree to which α-Gal A activity is responsive to migalastat or a migalastat salt when the mutation is present. The set of mutations includes one or more mutations listed in Table 2. A communication is received that identifies one or more particular mutations. The data set unit is queried using a representation of the one or more particular mutations. A result of the query is detected. The result indicates, for each particular mutation of the one or more particular mutations, the degree to which α-Gal A activity is responsive to migalastat or a migalastat salt when the particular mutation is present. A metric is determined that corresponds to a predicted efficacy of treating a patient having the one or more particular mutations with migalastat or a migalastat salt. The metric is output.

The one or more particular mutations may include a plurality of particular mutations, and determining the metric includes identifying a minimum or maximum of the degrees to which α-Gal A activity is responsive to migalastat or a migalastat salt across the plurality of particular mutations. The metric can be a binary indication as to whether a condition associated with the one or more particular mutations are amenable to treatment with migalastat or a migalastat salt. the metric may include a number, category or descriptor indicating a predicted extent to which a condition associated with the one or more particular mutations is amenable to treatment with migalastat or a migalastat salt. The result of the query may indicate, for a particular mutation of the one or more particular mutations and as a result of the particular mutation not being detected within the data set, that the α-Gal A activity corresponding to the particular mutation is not responsive to migalastat or a migalastat salt. The set of mutations may further include one or more mutations listed in Table 1. The one or more particular mutations may include a plurality of particular mutations, and determining the metric may include identifying a minimum or maximum of the degrees to which α-Gal A activity is responsive to migalastat or a migalastat salt across the plurality of particular mutations.

In some instances, a method of treating Fabry disease in a subject is provided. Mutation information is accessed that corresponds to the subject. The mutation information identifies one or more α-galactosidase A mutations. It is determined, based on the mutation information, that the subject has a mutation for which □-Gal A activity in lysates prepared from HEK-293 cells transiently transfected with a mutant form of α-Gal A and incubated for 5 days in the presence of 10 □M migalastat is greater than a reference α-Gal A activity in other lysates prepared from other HEK-293 cells transiently transfected with the mutant form of α-Gal A and incubated for 5 days in the absence of 10 μM migalastat, the mutant form of α-Gal A corresponding to the mutation. In response to the determination, migalastat or a salt thereof is administered to the subject.

The α-Gal A activity may be defined as the nmoles of free 4-MU released per milligram of protein per hour. The determination can include determining that the subject has a mutation for which α-Gal A activity is at least 1%, at least 5%, at least 10%, at least 25%, at least 50% or at least 100% greater than the reference α-Gal A activity. The determination can include querying a data store with an identification of the one or more α-galactosidase A mutations and receiving a result of the query. The result can indicate that representation of the mutation is included in the data store. The result can include one or more values associated with a representation of the mutation in the data store, and the method can further include comparing the one or more values or a processed version thereof to a predefined threshold.

In some instances, a method is provided. Mutation information corresponding to a subject is access. The mutation information identifies one or more α-galactosidase A mutations. It is determined, based on the mutation information, that the subject has a mutation for which α-Gal A activity in lysates prepared from HEK-293 cells transiently transfected with a mutant form of α-Gal A and incubated for 5 days in the presence of 10 μM migalastat is greater than a reference α-Gal A activity in other lysates prepared from other HEK-293 cells transiently transfected with the mutant form of α-Gal A and incubated for 5 days in the absence of 10 μM migalastat, the mutant form of α-Gal A corresponding to the mutation. In response to the determination, an indication is output that the mutation is amenable to treatment with migalastat or a salt thereof.

The α-Gal A activity can be defined as the nmoles of free 4-MU released per milligram of protein per hour. The determination can include determining that the subject has a mutation for which α-Gal A activity is at least 1%, at least 5%, at least 10%, at least 25%, at least 50% or at least 100% greater than the reference α-Gal A activity. The determination can include querying a data store with an identification of the one or more α-galactosidase A mutations and receiving a result of the query. The result can indicate that representation of the mutation is included in the data store. The result can include one or more values associated with a representation of the mutation in the data store, and the method can further include comparing the one or more values or a processed version thereof to a predefined threshold. The method can include receiving, from a user device, a first communication that includes the mutation information, and outputting the indication can include, transmitting a second communication to the user device, the second communication including the indication.

In some instances, a system is provided. The system includes one or more data processors and a non-transitory computer readable storage medium containing instructions which, when executed on the one or more data processors, cause the one or more data processors to perform part or all of one or more methods disclosed herein. In some instances, computer-program product is provided that is tangibly embodied in a non-transitory machine-readable storage medium. The computer-program product can include instructions configured to cause one or more data processors to perform part or all of one or more methods disclosed herein.

Another aspect of the invention pertains to a method for diagnosing in a subject Fabry disease which is amenable to treatment with migalastat or a salt thereof, the method comprising determining whether α-Gal A in a sample from the subject has an amino acid sequence comprising at least one mutation as identified in Table 2; wherein if the α-Gal A in the sample from the subject has an amino acid sequence comprising such a mutation, the subject has, or is at risk of developing, Fabry disease which is amenable to treatment with migalastat or a salt thereof. In one or more embodiments, the subject has one or more symptoms of Fabry disease. In other embodiments, the subject does not have any symptoms of Fabry disease. In one or more embodiments, the subject is an infant. In one or more embodiments, the subject is a male. In one or more embodiments, the subject is a female. In one or more embodiments, the subject has a family history of Fabry disease. In one or more embodiments, the subject is the daughter of a classically affect male Fabry patient.

Another aspect of the invention pertains to a method for identifying a subject with Fabry disease which is amenable to treatment with migalastat or a salt thereof, the method comprising determining whether α-Gal A in a sample from the subject has an amino acid sequence comprising at least one mutation as identified in Table 2; wherein if the α-Gal A in the sample from the subject has an amino acid sequence comprising such a mutation, the subject has, or is at risk of developing, Fabry disease which is amenable to treatment with migalastat or a salt thereof. In one or more embodiments, the subject has one or more symptoms of Fabry disease. In other embodiments, the subject does not have any symptoms of Fabry disease. In one or more embodiments, the subject is an infant. In one or more embodiments, the subject is a male. In one or more embodiments, the subject is a female. In one or more embodiments, the subject has a family history of Fabry disease. In one or more embodiments, the subject is the daughter of a classically affect male Fabry patient.

Another aspect of the invention pertains to a method for diagnosing in a subject Fabry disease which is amenable to treatment with migalastat or a salt thereof, the method comprising determining whether the GLA gene in a sample from a subject comprises a point mutation compared to the nucleic acid sequence of SEQ ID NO: 1; if the GLA gene in the sample comprises such a point mutation, determining whether the point mutation results in an amino acid mutation of α-Gal A as identified in Table 2; wherein the point mutation results in an amino acid mutation of α-Gal A as identified in Table 2, the subject has, or is at risk of developing, Fabry disease which is amenable to treatment with migalastat or a salt thereof. In other embodiments, the subject does not have any symptoms of Fabry disease. In one or more embodiments, the subject is an embryo. In one or more embodiments, the subject is an infant. In one or more embodiments, the subject is a male. In one or more embodiments, the subject is a female. In one or more embodiments, the subject has a family history of Fabry disease. In one or more embodiments, the subject is the daughter of a classically affect male Fabry patient.

Another aspect of the invention pertains to a method for identifying a subject with Fabry disease which is amenable to treatment with migalastat or a salt thereof, the method comprising determining whether the GLA gene in a sample from a subject comprises a point mutation compared to the nucleic acid sequence of SEQ ID NO: 1; if the GLA gene in the sample comprises such a point mutation, determining whether the point mutation results in an amino acid mutation of α-Gal A as identified in Table 2; wherein the point mutation results in an amino acid mutation of α-Gal A as identified in Table 2, the subject has, or is at risk of developing, Fabry disease which is amenable to treatment with migalastat or a salt thereof. In other embodiments, the subject does not have any symptoms of Fabry disease. In one or more embodiments, the subject is an embryo. In one or more embodiments, the subject is an infant. In one or more embodiments, the subject is a male. In one or more embodiments, the subject is a female. In one or more embodiments, the subject has a family history of Fabry disease. In one or more embodiments, the subject is the daughter of a classically affect male Fabry patient.

Various embodiments are listed below. It will be understood that the embodiments listed below may be combined not only as listed below, but in other suitable combinations in accordance with the scope of the invention.

BRIEF DESCRIPTION OF THE DRAWINGS

FIGS. 1A-E shows the full DNA sequence of human wild type GLA gene (SEQ ID NO: 1);

FIG. 2 shows the wild-type α-Gal A protein (SEQ ID NO: 2); and

FIG. 3 shows the nucleic acid sequence encoding the wild-type α-Gal A protein (SEQ ID NO: 3).

DETAILED DESCRIPTION

Figure 4A:
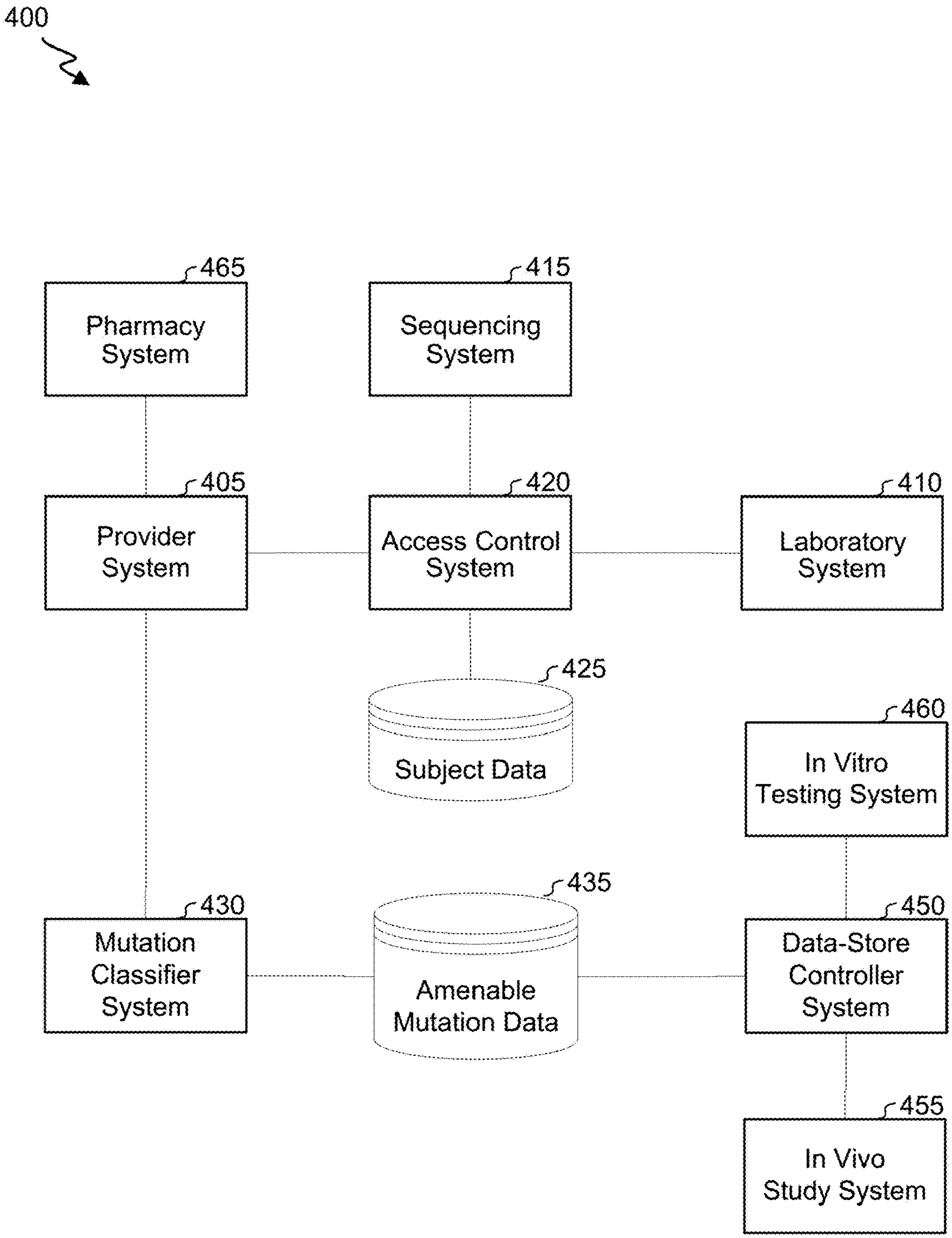
FIG. 4A shows an exemplary interaction system to generate treatment classifications based on mutation data.

Before describing several exemplary embodiments of the invention, it is to be understood that the invention is not limited to the details of construction or process steps set forth in the following description. The invention is capable of other embodiments and of being practiced or being carried out in various ways.

As described above, it is very difficult, if not impossible, to predict whether a particular Fabry patient will respond to treatment with a PC. Currently, when a patient is assessed, it is necessary first to determine the particular mutation in α-Gal A, then to test the patient's specific mutated form of α-Gal A in an assay to determine whether or not the mutation is amenable to treatment with migalastat. The migalastat amenability testing is typically performed by someone other than the clinician that is assessing the patient for treatment. This testing takes time and delays the start of treatment.

Accordingly, various aspects of the invention pertain to identification of new GLA mutations in Fabry patients who will respond to treatment with pharmacological chaperones. Other aspects of the invention pertain to the treatment of these Fabry patients, as well. For example, it has been unexpectedly discovered that the low α-Gal A activity resulting from the missense mutations in α-Gal A shown in Table 2 can be increased when exposed to pharmacological chaperones, even though no patients have previously been identified with these particular mutations. By extension, patients with these mutations are expected to be responsive to treatment with pharmacological chaperones.

Use of the information in Table 2 prevents the delay of starting treatment, as further testing of the PC amenability of the patient's α-Gal A is no longer necessary. Instead, after determining the patient's particular mutation, the clinician can consult a list of α-Gal A mutations (e.g. including one or more mutations listed in Table 2) and, if the patient's mutation is in the list, can begin treatment immediately.

The identification of these new mutations can also be used to determine whether a subject, including an embryo or a neonatal infant, is at risk of developing Fabry disease before the appearance of symptoms. In one or more embodiments, the subject can be at risk for developing Fabry disease, such as having a family history of Fabry disease.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Fabry disease" refers to an X-linked inborn error of glycosphingolipid catabolism due to deficient lysosomal α-Gal A activity. This defect causes accumulation of the substrate globotriaosylceramide (("GL-3", also known as $Gb_3$ or ceramide trihexoside) and related glycosphingolipids in vascular endothelial lysosomes of the heart, kidneys, skin, and other tissues. Another substrate of the enzyme is plasma globotriaosylsphingosine ("plasma lyso-$Gb_3$").

A "carrier" is a female who has one X chromosome with a defective α-Gal A gene and one X chromosome with the normal gene and in whom X chromosome inactivation of the normal allele is present in one or more cell types. A carrier is often diagnosed with Fabry disease.

A "patient" refers to a subject who has been diagnosed with or is suspected of having a particular disease. The patient may be human or animal.

A "Fabry patient" refers to an individual who has been diagnosed with or suspected of having Fabry disease and has a mutated α-Gal A as defined further below. Characteristic markers of Fabry disease can occur in male hemizygotes and female carriers with the same prevalence, although females typically are less severely affected.

Human α-galactosidase A (α-Gal A) refers to an enzyme encoded by the human GLA gene. The full DNA sequence of α-Gal A, including introns and exons, is available in GenBank Accession No. X14448.1 and shown in FIGS. 1A-E (SEQ ID NO: 1). The human α-Gal A enzyme consists of 429 amino acids and is available in GenBank Accession Nos. X14448.1 and U78027 and shown in FIG. 2 (SEQ ID NO: 2). The nucleic acid sequence that only includes the coding regions (i.e. exons) of SEQ ID NO: 1 is shown in FIG. 3 (SEQ ID NO: 3).

The term "mutant protein" includes a protein which has a mutation in the gene encoding the protein which results in the inability of the protein to achieve a stable conformation under the conditions normally present in the ER. The failure to achieve a stable conformation results in a substantial amount of the enzyme being degraded, rather than being transported to the lysosome. Such a mutation is sometimes called a "conformational mutant." Such mutations include, but are not limited to, missense mutations, and in-frame small deletions and insertions.

As used herein in one embodiment, the term “mutant α-Gal A” includes an α-Gal A which has a mutation in the gene encoding α-Gal A which results in the inability of the enzyme to achieve a stable conformation under the conditions normally present in the ER. The failure to achieve a stable conformation results in a substantial amount of the enzyme being degraded, rather than being transported to the lysosome.

As used herein, the term “specific pharmacological chaperone” (“SPC”) or “pharmacological chaperone” (“PC”) refers to any molecule including a small molecule, protein, peptide, nucleic acid, carbohydrate, etc. that specifically binds to a protein and has one or more of the following effects: (i) enhances the formation of a stable molecular conformation of the protein; (ii) induces trafficking of the protein from the ER to another cellular location, preferably a native cellular location, i.e., prevents ER-associated degradation of the protein; (iii) prevents aggregation of misfolded proteins; and/or (iv) restores or enhances at least partial wild-type function and/or activity to the protein. A compound that specifically binds to e.g., α-Gal A, means that it binds to and exerts a chaperone effect on the enzyme and not a generic group of related or unrelated enzymes. More specifically, this term does not refer to endogenous chaperones, such as BiP, or to non-specific agents which have demonstrated non-specific chaperone activity against various proteins, such as glycerol, DMSO or deuterated water, i.e., chemical chaperones. In one or more embodiments of the present invention, the PC may be a reversible competitive inhibitor. In one embodiment, the PC is migalastat or a salt thereof. In another embodiment, the PC is migalastat free base (e.g., 123 mg of migalastat free base). In yet another embodiment, the PC is a salt of migalastat (e.g., 150 mg of migalastat HCl).

A “competitive inhibitor” of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

As used herein, the term “specifically binds” refers to the interaction of a pharmacological chaperone with a protein such as α-Gal A, specifically, an interaction with amino acid residues of the protein that directly participate in contacting the pharmacological chaperone. A pharmacological chaperone specifically binds a target protein, e.g., α-Gal A, to exert a chaperone effect on the protein and not a generic group of related or unrelated proteins. The amino acid residues of a protein that interact with any given pharmacological chaperone may or may not be within the protein’s “active site.” Specific binding can be evaluated through routine binding assays or through structural studies, e.g., co-crystallization, NMR, and the like. The active site for α-Gal A is the substrate binding site.

“Deficient α-Gal A activity” refers to α-Gal A activity in cells from a patient which is below the normal range as compared (using the same methods) to the activity in normal individuals not having or suspected of having Fabry or any other disease (especially a blood disease).

As used herein, the terms “enhance α-Gal A activity” or “increase α-Gal A activity” refer to increasing the amount of α-Gal A that adopts a stable conformation in a cell contacted with a pharmacological chaperone specific for the α-Gal A, relative to the amount in a cell (preferably of the same cell-type or the same cell, e.g., at an earlier time) not contacted with the pharmacological chaperone specific for the α-Gal A. This term also refers to increasing the trafficking of α-Gal A to the lysosome in a cell contacted with a pharmacological chaperone specific for the α-Gal A, relative to the trafficking of α-Gal A not contacted with the pharmacological chaperone specific for the protein. These terms refer to both wild-type and mutant α-Gal A. In one embodiment, the increase in the amount of α-Gal A in the cell is measured by measuring the hydrolysis of an artificial substrate in lysates from cells that have been treated with the PC. An increase in hydrolysis is indicative of increased α-Gal A activity.

The term “α-Gal A activity” refers to the normal physiological function of a wild-type α-Gal A in a cell. For example, α-Gal A activity includes hydrolysis of GL-3.

A “responder” is an individual diagnosed with or suspected of having a lysosomal storage disorder, such, for example Fabry disease, whose cells exhibit sufficiently increased α-Gal A activity, respectively, and/or amelioration of symptoms or enhancement in surrogate markers, in response to contact with a PC. Non-limiting examples of enhancements in surrogate markers for Fabry are lyso-GB3 and those disclosed in US Patent Application Publication No. US 2010-0113517, which is hereby incorporated by reference in its entirety.

Non-limiting examples of improvements in surrogate markers for Fabry disease disclosed in US 2010/0113517 include increases in α-Gal A levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in plasma lyso-Gb3; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin; the absence of laminated inclusion bodies (Zebra bodies) in glomerular epithelial cells; improvements in renal function; mitigation of hypohidrosis; the absence of angiokeratomas; and improvements in hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities). Another type of clinical marker that can be assessed for Fabry disease is the prevalence of deleterious cardiovascular manifestations. Common cardiac-related signs and symptoms of Fabry disease include left ventricular hypertrophy, valvular disease (especially mitral valve prolapse and/or regurgitation), premature coronary artery disease, angina, myocardial infarction, conduction abnormalities, arrhythmias, congestive heart failure.

The dose that achieves one or more of the aforementioned responses is a “therapeutically effective dose.”

The phrase “pharmaceutically acceptable” refers to molecular entities and compositions that are physiologically tolerable and do not typically produce untoward reactions when administered to a human. In some embodiments, as used herein, the term “pharmaceutically acceptable” means approved by a regulatory agency of the Federal or a state government or listed in the U.S. Pharmacopoeia or other generally recognized pharmacopoeia for use in animals, and more particularly in humans. The term "carrier" in reference to a pharmaceutical carrier refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

The term "enzyme replacement therapy" or "ERT" refers to the introduction of a non-native, purified enzyme into an individual having a deficiency in such enzyme. The administered protein can be obtained from natural sources or by recombinant expression (as described in greater detail below). The term also refers to the introduction of a purified enzyme in an individual otherwise requiring or benefiting from administration of a purified enzyme, e.g., suffering from enzyme insufficiency. The introduced enzyme may be a purified, recombinant enzyme produced in vitro, or protein purified from isolated tissue or fluid, such as, e.g., placenta or animal milk, or from plants.

As used herein, the term "free base equivalent" or "FBE" refers to the amount of migalastat present in the migalastat or salt thereof. In other words, the term "FBE" means either an amount of migalastat free base, or the equivalent amount of migalastat free base that is provided by a salt of migalastat. For example, due to the weight of the hydrochloride salt, 150 mg of migalastat hydrochloride only provides as much migalastat as 123 mg of the free base form of migalastat. Other salts are expected to have different conversion factors, depending on the molecular weight of the salt.

The term "migalastat" encompasses migalastat free base or a pharmaceutically acceptable salt thereof (e.g., migalastat HCl), unless specifically indicated to the contrary.

The terms "mutation" and "variant" (e.g., as in "amenable mutation or variant") refer to a change in the nucleotide sequence of a gene or a chromosome. The two terms referred herein are typically used together—e.g., as in "mutation or variant"— referring to the change in nucleotide sequence stated in the previous sentence. If only one of the two terms is recited for some reason, the missing term was intended to be included and one should understand as such. Furthermore, the terms "amenable mutation" and "amenable variant" refer to a mutation or variant that is amenable to PC therapy, e.g. a mutation that is amenable to migalastat therapy. A particular type of amenable mutation or variant is a "HEK assay amenable mutation or variant", which is a mutation or variant that is determined to be amenable to migalastat therapy according to the criteria in the in vitro HEK assay described herein.

Fabry Disease

Fabry disease is a rare, progressive and devastating X-linked lysosomal storage disorder. Mutations in the GLA gene result in a deficiency of the lysosomal enzyme, α-Gal A, which is required for glycosphingolipid metabolism. Beginning early in life, the reduction in α-Gal A activity results in an accumulation of glycosphingolipids, including GL-3 and plasma lyso-Gb3, and leads to the symptoms and life-limiting sequelae of Fabry disease, including pain, gastrointestinal symptoms, renal failure, cardiomyopathy, cerebrovascular events, and early mortality. Early initiation of therapy and lifelong treatment provide an opportunity to slow disease progression and prolong life expectancy.

Fabry disease encompasses a spectrum of disease severity and age of onset, although it has traditionally been divided into 2 main phenotypes, "classic" and "late-onset". The classic phenotype has been ascribed primarily to males with undetectable to low α-Gal A activity and earlier onset of renal, cardiac and/or cerebrovascular manifestations. The late-onset phenotype has been ascribed primarily to males with higher residual α-Gal A activity and later onset of these disease manifestations. Heterozygous female carriers typically express the late-onset phenotype but depending on the pattern of X-chromosome inactivation may also display the classic phenotype.

More than 1,000 Fabry disease-causing GLA mutations have been identified. Approximately 60% are missense mutations, resulting in single amino acid substitutions in the α-Gal A enzyme. Missense GLA mutations often result in the production of abnormally folded and unstable forms of α-Gal A and the majority are associated with the classic phenotype. Normal cellular quality control mechanisms in the endoplasmic reticulum block the transit of these abnormal proteins to lysosomes and target them for premature degradation and elimination. Many missense mutant forms are targets for migalastat, an α-Gal A-specific pharmacological chaperone.

The clinical manifestations of Fabry disease span a broad spectrum of severity and roughly correlate with a patient's residual α-GAL levels. The majority of currently treated patients are referred to as classic Fabry disease patients, most of whom are males. These patients experience disease of various organs, including the kidneys, heart and brain, with disease symptoms first appearing in adolescence and typically progressing in severity until death in the fourth or fifth decade of life. A number of recent studies suggest that there are a large number of undiagnosed males and females that have a range of Fabry disease symptoms, such as impaired cardiac or renal function and strokes, that usually first appear in adulthood. Individuals with this type of Fabry disease, referred to as late-onset Fabry disease, tend to have higher residual α-GAL levels than classic Fabry disease patients. Individuals with late-onset Fabry disease typically first experience disease symptoms in adulthood, and often have disease symptoms focused on a single organ, such as enlargement of the left ventricle or progressive kidney failure. In addition, late-onset Fabry disease may also present in the form of strokes of unknown cause.

Fabry patients have progressive kidney impairment, and untreated patients exhibit end-stage renal impairment by the fifth decade of life. Deficiency in α-Gal A activity leads to accumulation of GL-3 and related glycosphingolipids in many cell types including cells in the kidney. GL-3 accumulates in podocytes, epithelial cells and the tubular cells of the distal tubule and loop of Henle. Impairment in kidney function can manifest as proteinuria and reduced glomerular filtration rate.

Because Fabry disease is rare, involves multiple organs, has a wide age range of onset, and is heterogeneous, proper diagnosis is a challenge. Awareness is low among health care professionals and misdiagnoses are frequent. Diagnosis of Fabry disease is most often confirmed on the basis of decreased α-Gal A activity in plasma or peripheral leukocytes (WBCs) once a patient is symptomatic, coupled with mutational analysis. In females, diagnosis is even more challenging since the enzymatic identification of carrier females is less reliable due to random X-chromosomal inactivation in some cells of carriers. For example, some obligate carriers (daughters of classically affected males) have α-Gal A enzyme activities ranging from normal to very low activities. Since carriers can have normal α-Gal A enzyme activity in leukocytes, only the identification of an α-Gal A mutation by genetic testing provides precise carrier identification and/or diagnosis.

Also, as described above, the age of onset, progression, and severity of Fabry disease is at least partly dependent on the rate of substrate accumulation, which correlates to the enzymatic activity in lysosomes. Thus, a complete lack of residual activity can correspond to rapid substrate accumulation, and therefore a more severe form of the disease (having early onset and rapid progression). However, even small quantities of residual activity may be enough to degrade a large amounts of substrate. This in turn would lead to milder disease with later onset and slower progression because of the slowed substrate accumulation. Considering these factors, it is thought that even modest increases in enzymatic activity can reduce the effect of a severe clinical phenotype. Data suggests that for most LSDs, just 1% to 6% of normal activity has been estimated as sufficient to delay or prevent disease onset or yield a more mild form of the disease. That is, just small increases in activity could have a significant impact on substrate levels, and hence disease severity and the rate of disease progression. Conversely, it is expected that a mutant lysosomal enzyme that shows no response in vitro would also not respond in vivo.

In one or more embodiments, mutant or variant forms of α-Gal A considered to be amenable to migalastat are defined as showing a relative increase (+10 μM migalastat) of ≥1.20-fold and an absolute increase (+10 μM migalastat) of ≥3.0% wild-type when the mutant form of α-Gal A is expressed in HEK-293 cells (referred to as the "HEK assay") according to Good Laboratory Practice (GLP)-validated in vitro assay (GLP HEK or Migalastat Amenability Assay). Such mutations or variants are also referred to herein as "HEK assay amenable" mutations or variants.

Previous screening methods have been provided that assess enzyme enhancement prior to the initiation of treatment. For example, an assay using HEK-293 cells has been utilized in clinical trials to predict whether a given mutation will be responsive to pharmacological chaperone (e.g., migalastat) treatment. In this assay, cDNA constructs are created. The corresponding α-Gal A mutant forms are transiently expressed in HEK-293 cells. Cells are then incubated±migalastat (17 nM to 1 mM) for 4 to 5 days. After, α-Gal A levels are measured in cell lysates using a synthetic fluorogenic substrate (4-MU-α-Gal) or by western blot. This has been done for known disease-causing missense or small in-frame insertion/deletion mutations. Mutations that have previously been identified as responsive to a PC (e.g. migalastat) using these methods are listed in U.S. Pat. No. 8,592,362, which is hereby incorporated by reference in its entirety.

HEK assay amenable mutations include at least those mutations listed in a pharmacological reference table (e.g., the ones recited in the U.S. or International Product labels for a migalastat product such as GALAFOLD®). As used herein, "pharmacological reference table" refers to any publicly accessible written or electronic record, included in either the product label within the packaging of a migalastat product (e.g., GALAFOLD®) or in a website accessible by health care providers, that conveys whether a particular mutation or variant is responsive to migalastat (e.g., GALAFOLD®) PC therapy, and is not necessarily limited to written records presented in tabular form. In one embodiment of the present invention, a "pharmacological reference table" thus refers to any depository of information that includes one or more amenable mutations or variants. In another embodiment, a "pharmacological reference table" refers to an updated depository of amenable mutations or variants that includes the novel mutations or variants disclosed herein (i.e., mutations presented in Table 2). An exemplary pharmacological reference table for HEK assay amenable mutations can be found in the summary of product characteristics and/or prescribing information for GALAFOLD® in various countries in which GALAFOLD® is approved for use, or at a website such as www.galafoldamenabilitytable.com or www.fabrygenevariantsearch.com, each of which is hereby incorporated by reference in its entirety.

An exemplary pharmacological reference table for HEK assay amenable mutations is provided in Table 1 below. In one or more embodiments, if a double mutation is present on the same chromosome (males and females), that patient is considered HEK assay amenable if the double mutation is present in one entry in Table 1 (e.g., D55V/Q57L). In some embodiments, if a double mutation is present on different chromosomes (only in females) that patient is considered HEK assay amenable if either one of the individual mutations is present in Table 1.

TABLE 1

| Nucleotide change | Nucleotide change | Protein sequence change |
|---|---|---|
| c.7C > G | c.C7G | L3V |
| c.8T > C | c.T8C | L3P |
| c.[11G > T; 620A > C] | c.G11T/A620C | R4M/Y207S |
| c.37G > A | c.G37A | A13T |
| c.37G > C | c.G37C | A13P |
| c.43G > A | c.G43A | A15T |
| c.44C > G | c.C44G | A15G |
| c.53T > G | c.T53G | F18C |
| c.58G > C | c.G58C | A20P |
| c.59C > A | c.C59A | A20D |
| c.65T > G | c.T65G | V22G |
| c.70T > C or c.70T > A | c.T70C or c.T70A | W24R |
| c.70T > G | c.T70G | W24G |
| c.72G > C or c.72G > T | c.G72C or c.G72T | W24C |
| c.95T > C | c.T95C | L32P |
| c.97G > C | c.G97C | D33H |
| c.97G > T | c.G97T | D33Y |
| c.98A > G | c.A98G | D33G |
| c.100A > G | c.A100G | N34D |
| c.100A > C | c.A100C | N34H |
| c.101A > C | c.A101C | N34T |
| c.101A > G | c.A101G | N34S |
| c.102T > G or c.102T > A | c.T102G or c.T102A | N34K |
| c.103G > C or c.103G > A | c.G103C or c.G103A | G35R |
| c.104G > A | c.G104A | G35E |
| c.104G > C | c.G104C | G35A |
| c.104G > T | c.G104T | G35V |
| c.107T > C | c.T107C | L36S |
| c.107T > G | c.T107G | L36W |
| c.108G > C or c.108G > T | c.G108C or c.G108T | L36F |
| c.109G > A | c.G109A | A37T |
| c.110C > T | c.C110T | A37V |
| c.122C > T | c.C122T | T41I |
| c.124A > C or c.124A > T | c.A124C or c.A124T | M42L |
| c.124A > G | c.A124G | M42V |
| c.125T > A | c.T125A | M42K |
| c.125T > C | c.T125C | M42T |
| c.125T > G | c.T125G | M42R |
| c.126G > A or c.126G > C or c.126G > T | c.G126A or c.G126C or c.G126T | M42I |
| c.137A > C | c.A137C | H46P |
| c.142G > C | c.G142C | E48Q |
| c.152T > A | c.T152A | M51K |
| c.153G > A or c.153G > T or c.153G > C | c.G153A or c.G153T or c.G153C | M51I |
| c.159C > G or c.159C > A | c.C159G or c.C159A | N53K |
| c.157A > G | c.A157G | N53D |
| c.[157A > C; 158A > T] | c.A157C/A158T | N53L |
| c.160C > T | c.C160T | L54F |
| c.161T > C | c.T161C | L54P |
| c.164A > G | c.A164G | D55G |
| c.164A > T | c.A164T | D55V |
| c.[164A > T; 170A > T] | c.A164T/A170T | D55V/Q57L |
| c.167G > T | c.G167T | C56F |
| c.167G > A | c.G167A | C56Y |
| c.170A > G | c.A170G | Q57R |
| c.170A > T | c.A170T | Q57L |
| c.175G > A | c.G175A | E59K |
| c.178C > A | c.C178A | P60T |
| c.178C > T | c.C178T | P60S |
| c.179C > T | c.C179T | P60L |
| c.184_185insTAG | c.184_185insTAG | S62delinsLA |
| c.196G > A | c.G196A | E66K |
| c.197A > G | c.A197G | E66G |
| c.207C > A or c.207C > G | c.C207A or c.C207G | F69L |
| c.214A > G | c.A214G | M72V |
| c.216G > A or c.216G > T or c.216G > C | c.G216A or c.G216T or c.G216C | M72I |
| c.218C > T | c.C218T | A73V |
| c.227T > C | c.T227C | M76T |
| c.239G > A | c.G239A | G80D |
| c.239G > T | c.G239T | G80V |
| c.247G > A | c.G247A | D83N |
| c.253G > A | c.G253A | G85S |
| c.254G > A | c.G254A | G85D |
| c.[253G > A; 254G > A] | c.G253A/G254A | G85N |
| c.[253G > A; 254G > T; 255T > G] | c.G253A/G254T/T255G | G85M |
| c.261G > C or c.261G > T | c.G261C or c.G261T | E87D |

TABLE 1-continued

| Nucleotide change | Nucleotide change | Protein sequence change |
|---|---|---|
| c.263A > C | c.A263C | Y88S |
| c.265C > T | c.C265T | L89F |
| c.272T > C | c.T272C | I91T |
| c.288G > A or c.288G > T or c.288G > C | c.G288A or c.G288T or c.G288C | M96I |
| c.286A > G | c.A286G | M96V |
| c.289G > C | c.G289C | A97P |
| c.290C > T | c.C290T | A97V |
| c.305C > T | c.C305T | S102L |
| c.311G > T | c.G311T | G104V |
| c.316C > T | c.C316T | L106F |
| c.320A > G | c.A320G | Q107R |
| c.322G > A | c.G322A | A108T |
| c.326A > G | c.A326G | D109G |
| c.334C > G | c.C334G | R112G |
| c.335G > A | c.G335A | R112H |
| c.335G > T | c.G335T | R112L |
| c.337T > A | c.T337A | F113I |
| c.337T > C or c.339T > A or c.339T > G | c.T337C or c.T339A or c.T339G | F113L |
| c.352C > T | c.C352T | R118C |
| c.361G > A | c.G361A | A121T |
| c.368A > G | c.A368G | Y123C |
| c.373C > T | c.C373T | H125Y |
| c.374A > T | c.A374T | H125L |
| c.376A > G | c.A376G | S126G |
| c.383G > A | c.G383A | G128E |
| c.399T > G | c.T399G | I133M |
| c.404C > T | c.C404T | A135V |
| c.408T > A or c.408T > G | c.T408A or c.T408G | D136E |
| c.416A > G | c.A416G | N139S |
| c.419A > C | c.A419C | K140T |
| c.427G > A | c.G427A | A143T |
| c.431G > A | c.G431A | G144D |
| c.431G > T | c.G431T | G144V |
| c.434T > C | c.T434C | F145S |
| c.436C > T | c.C436T | P146S |
| c.437C > G | c.C437G | P146R |
| c.454T > G | c.T454G | Y152D |
| c.454T > C | c.T454C | Y152H |
| c.455A > G | c.A455G | Y152C |
| c.465T > A or c.465T > G | c.T465A or c.T465G | D155E |
| c.466G > T | c.G466T | A156S |
| c.466G > A | c.G466A | A156T |
| c.467C > T | c.C467T | A156V |
| c.471G > C or c.471G > T | c.G471C or c.G471T | Q157H |
| c.484T > G | c.T484G | W162G |
| c.493G > C | c.G493C | D165H |
| c.494A > G | c.A494G | D165G |
| c.[496C > G; 497T > G] | c.C496G/T497G | L166G |
| c.496C > G | c.C496G | L166V |
| c.496_497delinsTC | c.496_497delinsTC | L166S |
| c.499C > G | c.C499G | L167V |
| c.506T > C | c.T506C | F169S |
| c.511G > A | c.G511A | G171S |
| c.520T > C | c.T520C | C174R |
| c.520T > G | c.T520G | C174G |
| c.525C > G or c.525C > A | c.C525G or c.C525A | D175E |
| c.539T > G | c.T539G | L180W |
| c.540G > C | c.G540C | L180F |
| c.548G > C | c.G548C | G183A |
| c.548G > A | c.G548A | G183D |
| c.550T > A | c.T550A | Y184N |
| c.551A > G | c.A551G | Y184C |
| c.553A > G | c.A553G | K185E |
| c.559A > G | c.A559G | M187V |
| c.559_564dup | c.559_564dup | p.M187_S188dup |
| c.560T > C | c.T560C | M187T |
| c.561G > T or c.561G > A or c.561G > C | c.G561T or c.G561A or c.G561C | M187I |
| c.567G > C or c.567G > T | c.G567C or c.G567T | L189F |
| c.572T > A | c.T572A | L191Q |
| c.580A > G | c.A580G | T194A |
| c.581C > T | c.C581T | T194I |
| c.584G > T | c.G584T | G195V |
| c.586A > G | c.A586G | R196G |
| c.593T > C | c.T593C | I198T |
| c.595G > A | c.G595A | V199M |

TABLE 1-continued

| Nucleotide change | Nucleotide change | Protein sequence change |
|---|---|---|
| c.596T > C | c.T596C | V199A |
| c.596T > G | c.T596G | V199G |
| c.599A > G | c.A599G | Y200C |
| c.602C > T | c.C602T | S201F |
| c.602C > A | c.C602A | S201Y |
| c.608A > T | c.A608T | E203V |
| c.609G > C or c.609G > T | c.G609C or c.G609T | E203D |
| c.610T > G | c.T610G | W204G |
| c.611G > T | c.G611T | W204L |
| c.613C > A | c.C613A | P205T |
| c.613C > T | c.C613T | P205S |
| c.614C > T | c.C614T | P205L |
| c.619T > C | c.T619C | Y207H |
| c.620A > C | c.A620C | Y207S |
| c.623T > G | c.T623G | M208R |
| c.628C > T | c.C628T | P210S |
| c.629C > T | c.C629T | P210L |
| c.638A > G | c.A638G | K213R |
| c.638A > T | c.A638T | K213M |
| c.640C > T | c.C640T | P214S |
| c.641C > T | c.C641T | P214L |
| c.643A > G | c.A643G | N215D |
| c.644A > G | c.A644G | N215S |
| c.644A > T | c.A644T | N215I |
| c.[644A > G; 937G > T] | c.A644G/G937T | N215S/D313Y |
| c.646T > G | c.T646G | Y216D |
| c.647A > C | c.A647C | Y216S |
| c.647A > G | c.A647G | Y216C |
| c.655A > C | c.A655C | I219L |
| c.656T > A | c.T656A | I219N |
| c.656T > C | c.T656C | I219T |
| c.659G > A | c.G659A | R220Q |
| c.659G > C | c.G659C | R220P |
| c.662A > C | c.A662C | Q221P |
| c.671A > C | c.A671C | N224T |
| c.671A > G | c.A671G | N224S |
| c.673C > G | c.C673G | H225D |
| c.682A > G | c.A682G | N228D |
| c.683A > G | c.A683G | N228S |
| c.687T > A or c.687T > G | c.T687A or c.T687G | F229L |
| c.695T > C | c.T695C | I232T |
| c.712A > G | c.A712G | S238G |
| c.713G > A | c.G713A | S238N |
| c.716T > C | c.T716C | I239T |
| c.717A > G | c.A717G | I239M |
| c.720G > C or c.720G > T | c.G720C or c.G720T | K240N |
| c.724A > G | c.A724G | I242V |
| c.724A > T | c.A724T | I242F |
| c.725T > A | c.T725A | I242N |
| c.725T > C | c.T725C | I242T |
| c.728T > G | c.T728G | L243W |
| c.729G > C or c.729G > T | c.G729C or c.G729T | L243F |
| c.730G > A | c.G730A | D244N |
| c.730G > C | c.G730C | D244H |
| c.733T > G | c.T733G | W245G |
| c.740C > G | c.C740G | S247C |
| c.747C > G or c.747C > A | c.C747G or c.C747A | N249K |
| c.748C > A | c.C748A | Q250K |
| c.749A > C | c.A749C | Q250P |
| c.749A > G | c.A749G | Q250R |
| c.750G > C | c.G750C | Q250H |
| c.758T > C | c.T758C | I253T |
| c.758T > G | c.T758G | I253S |
| c.760-762delGTT | c.760_762delGTT | p.V254del |
| c.769G > C | c.G769C | A257P |
| c.770C > T | c.C770T | A257V |
| c.770C > G | c.C770G | A257G |
| c.772G > C or c.772G > A | c.G772C or c.G772A | G258R |
| c.773G > T | c.G773T | G258V |
| c.776C > A | c.C776A | P259Q |
| c.776C > G | c.C776G | P259R |
| c.776C > T | c.C776T | P259L |
| c.779G > A | c.G779A | G260E |
| c.779G > C | c.G779C | G260A |
| c.781G > A | c.G781A | G261S |
| c.781G > C | c.G781C | G261R |
| c.781G > T | c.G781T | G261C |
| c.788A > G | c.A788G | N263S |

TABLE 1-continued

| Nucleotide change | Nucleotide change | Protein sequence change |
|---|---|---|
| c.790G > T | c.G790T | D264Y |
| c.794C > T | c.C794T | P265L |
| c.800T > C | c.T800C | M267T |
| c.805G > A | c.G805A | V269M |
| c.806T > C | c.T806C | V269A |
| c.809T > C | c.T809C | I270T |
| c.810T > G | c.T810G | I270M |
| c.811G > A | c.G811A | G271S |
| c.[811G > A; 937G > T] | c.G811A/G937T | G271S/D313Y |
| c.812G > A | c.G812A | G271D |
| c.823C > G | c.C823G | L275V |
| c.827G > A | c.G827A | S276N |
| c.829T > G | c.T829G | W277G |
| c.831G > T or c.831G > C | c.G831T or c.G831C | W277C |
| c.832A > T | c.A832T | N278Y |
| c.835C > G | c.C835G | Q279E |
| c.838C > A | c.C838A | Q280K |
| c.840A > T or c.840A > C | c.A840T or c.A840C | Q280H |
| c.844A > G | c.A844G | T282A |
| c.845C > T | c.C845T | T282I |
| c.850A > G | c.A850G | M284V |
| c.851T > C | c.T851C | M284T |
| c.860G > T | c.G860T | W287L |
| c.862G > C | c.G862C | A288P |
| c.866T > G | c.T866G | I289S |
| c.868A > C or c.868A > T | c.A868C or c.A868T | M290L |
| c.869T > C | c.T869C | M290T |
| c.870G > A or c.870G > C or c.870G > T | c.G870A or c.G870C or c.G870T | M290I |
| c.871G > A | c.G871A | A291T |
| c.877C > A | c.C877A | P293T |
| c.881T > C | c.T881C | L294S |
| c.884T > G | c.T884G | F295C |
| c.886A > G | c.A886G | M296V |
| c.886A > T or c.886A > C | c.A886T or c.A886C | M296L |
| c.887T > C | c.T887C | M296T |
| c.888G > A or c.888G > T or c.888G > C | c.G888A or c.G888T or c.G888C | M296I |
| c.893A > G | c.A893G | N298S |
| c.897C > G or c.897C > A | c.C897G or c.C897A | D299E |
| c.898C > T | c.C898T | L300F |
| c.899T > C | c.T899C | L300P |
| c.901C > G | c.C901G | R301G |
| c.902G > C | c.G902C | R301P |
| c.902G > A | c.G902A | R301Q |
| c.902G > T | c.G902T | R301L |
| c.907A > T | c.A907T | I303F |
| c.908T > A | c.T908A | I303N |
| c.911G > A | c.G911A | S304N |
| c.911G > C | c.G911C | S304T |
| c.919G > A | c.G919A | A307T |
| c.922A > G | c.A922G | K308E |
| c.924A > T or c.924A > C | c.A924T or c.A924C | K308N |
| c.925G > C | c.G925C | A309P |
| c.926C > T | c.C926T | A309V |
| c.928C > T | c.C928T | L310F |
| c.931C > G | c.C931G | L311V |
| c.935A > G | c.A935G | Q312R |
| c.936G > T or c.936G > C | c.G936T or c.G936C | Q312H |
| c.937G > T | c.G937T | D313Y |
| c.[937G > T; 1232G > A] | c.G937T/G1232A | D313Y/G411D |
| c.938A > G | c.A938G | D313G |
| c.946G > A | c.G946A | V316I |
| c.947T > G | c.T947G | V316G |
| c.950T > C | c.T950C | I317T |
| c.955A > T | c.A955T | I319F |
| c.956T > C | c.T956C | I319T |
| c.958A > C | c.A958C | N320H |
| c.959A > T | c.A959T | N320I |
| c.962A > G | c.A962G | Q321R |
| c.962A > T | c.A962T | Q321L |
| c.963G > C or c.963G > T | c.G963C or c.G963T | Q321H |
| c.964G > A | c.G964A | D322N |
| c.964G > C | c.G964C | D322H |
| c.966C > A or c.966C > G | c.C966A or c.C966G | D322E |
| c.967C > A | c.C967A | P323T |
| c.968C > G | c.C968G | P323R |
| c.973G > A | c.G973A | G325S |

TABLE 1-continued

| Nucleotide change | Nucleotide change | Protein sequence change |
|---|---|---|
| c.973G > C | c.G973C | G325R |
| c.978G > C or c.978G > T | c.G978C or c.G978T | K326N |
| c.979C > G | c.C979G | Q327E |
| c.980A > T | c.A980T | Q327L |
| c.983G > C | c.G983C | G328A |
| c.989A > C | c.A989C | Q330P |
| c.989A > G | c.A989G | Q330R |
| c.1001G > A | c.G1001A | G334E |
| c.1010T > C | c.T1010C | F337S |
| c.1012G > A | c.G1012A | E338K |
| c.1013A > T | c.A1013T | E338V |
| c.1016T > C | c.T1016C | V339A |
| c.1016T > A | c.T1016A | V339E |
| c.1027C > A | c.C1027A | P343T |
| c.1028C > T | c.C1028T | P343L |
| c.1033T > C | c.T1033C | S345P |
| c.1046G > C | c.G1046C | W349S |
| c.1055C > G | c.C1055G | A352G |
| c.1055C > T | c.C1055T | A352V |
| c.1061T > A | c.T1061A | I354K |
| c.1066C > G | c.C1066G | R356G |
| c.1066C > T | c.C1066T | R356W |
| c.1067G > A | c.G1067A | R356Q |
| c.1067G > C | c.G1067C | R356P |
| c.1072G > C | c.G1072C | E358Q |
| c.1073A > C | c.A1073C | E358A |
| c.1073A > G | c.A1073G | E358G |
| c.1074G > T or c.1074G > C | c.G1074T or c.G1074C | E358D |
| c.1076T > C | c.T1076C | I359T |
| c.1078G > A | c.G1078A | G360S |
| c.1078G > T | c.G1078T | G360C |
| c.1079G > A | c.G1079A | G360D |
| c.1082G > A | c.G1082A | G361E |
| c.1082G > C | c.G1082C | G361A |
| c.1084C > A | c.C1084A | P362T |
| c.1085C > T | c.C1085T | P362L |
| c.1087C > T | c.C1087T | R363C |
| c.1088G > A | c.G1088A | R363H |
| c.1102G > A | c.G1102A | A368T |
| c.1117G > A | c.G1117A | G373S |
| c.1124G > A | c.G1124A | G375E |
| c.1139C > T | c.C1139T | P380L |
| c.1153A > G | c.A1153G | T385A |
| c.1168G > A | c.G1168A | V390M |
| c.1171A > G | c.A1171G | K391E |
| c.1172A > C | c.A1172C | K391T |
| c.1175G > C | c.G1175C | R392T |
| c.1184G > A | c.G1184A | G395E |
| c.1184G > C | c.G1184C | G395A |
| c.1192G > A | c.G1192A | E398K |
| c.1202_1203insGACTTC | c.1202_1203insGACTTC | p.T400_S401dup |
| c.1208T > C | c.T1208C | L403S |
| c.1222A > T | c.A1222T | N408Y |
| c.1225C > G | c.C1225G | P409A |
| c.1225C > T | c.C1225T | P409S |
| c.1225C > A | c.C1225A | P409T |
| c.1228A > G | c.A1228G | T410A |
| c.1229C > T | c.C1229T | T410I |
| c.1232G > A | c.G1232A | G411D |
| c.1234A > C | c.A1234C | T412P |
| c.1235C > A | c.C1235A | T412N |
| c.1253A > G | c.A1253G | E418G |
| c.1261A > G | c.A1261G | M421V |

However, as only certain mutations are amenable to treatment with migalastat, there is a need to identify new mutations and determine whether such mutations are amenable to migalastat therapy. As described in the Example below, several new mutations have been identified and determined to be mutations that are amenable to migalastat therapy.

As described above, α-Gal A refers to an enzyme encoded by the human GLA gene. The coding sequence of the GLA gene consists of 1287 nucleotides. The human α-Gal A enzyme consists of 429 amino acid residues. To create a list of all possible non-synonymous missense mutations for GLA, each nucleotide on the coding sequence was individually replaced on the coding sequence with the other 3 nucleotides, and the effect of each substitution on the protein sequence was examined.

If the codon change led to a change in the protein sequence by a single amino acid residue substitution and that amino acid substitution had not been identified previously, the mutation was recorded and tested with a HEK assay. Those mutations which were found to be HEK assay amenable were labelled as prophetic amenable mutations. When multiple different nucleotide changes within a single codon lead to the same amino acid residue substitution on that position, the protein sequence change was listed as a single entry with alternative nucleotide changes.

The prophetic amenable mutations identified include N5D, N5K, P6L, P6Q, P6R, P6S, P6T, E7D, E7K, E7V, L8I, L8P, L8Q, H9L, H9Q, H9R, H9Y, L10M, L10P, L10Q, L10R, L10V, G11C, G11D, G11R, G11S, G11V, C12G, C12R, C12S, C12Y, A13E, A13G, L14F, L14H, L14V, R17C, R17G, R17H, R17P, R17S, F18I, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, S65C, S65G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G80S, W81L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, I91S, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G104S, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, I117M, I117T, A121V, Y123D, Y123F, Y123N, Y123S, V124I, H125D, H125N, H125R, S126C, S126I, K127E, G128A, L129V, K130M, K130N, K130Q, L131V, I133L, I133T, I133V, A135E, A135G, A135S, A135T, D136A, D136N, D136V, V137A, V137D, V137G, V137I, V137L, G138A, N139H, N139I, N139K, N139Y, K140E, K140I, K140N, K140Q, K140R, T141S, A143E, A143G, G144A, G144C, G144R, G144S, F145C, F145L, F145V, F145Y, P146A, P146H, P146L, P146T, G147A, S148C, S148G, S148T, F149C, G150E, G150V, Y151C, Y151D, Y151S, Y152F, Y152S, D153A, D153H, D153N, D153V, D153Y, A156G, Q157E, Q157K, Q157L, Q157P, T158A, T158I, T158N, T158S, F159I, F159L, F159V, F159Y, A160G, A160S, A160T, A160V, D161H, D161N, D161V, D161Y, W162S, V164A, V164I, V164L, D165A, D165E, L166M, L166Q, L167I, F169C, F169L, F169V, F169Y, G171A, G171V, Y173C, Y173F, Y173H, Y173S, D175G, D175H, D175V, D175Y, S176C, S176R, L177F, L177M, L177S, L177V, L177W, E178A, E178G, E178K, E178Q, L180M, L180S, A181P, A181T, A181V, D182A, D182E, D182V, D182Y, Y184F, Y184H, Y184S, K185M, K185N, K185Q, K185T, H186D, H186L, H186N, H186Q, H186Y, M187L, S188A, S188C, S188F, S188P, S188T, S188Y, L189S, L189V, A190D, A190G, A190S, A190T, A190V, L191M, L191V, N192D, N192H, N192K, N192S, N192T, R193G, R193M, R193T, R193W, T194N, T194P, T194S, G195C, G195R, G195S, R196I, R196K, S197C, S197G, S197I, S197N, S197T, I198M, I198S, V199E, V199L, Y200N, Y200S, S201A, S201C, S201T, E203A, E203G, E203Q, W204S, L206F, L206H, L2061, L206R, L206V, Y207F, M208K, W209C, W209G, P210H, P210T, F211C, F211L, F211S, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T217S, E218A, E218D, E218G, E218K, E218Q, E218V, I219F, I219M, I219S, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, D264H, D264N, P265A, P265Q, M267L, M267V, L268F, L268I, V269L, I270L, I270S, I270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, I317L, I317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, I407L, I407M, I407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N, and L429R. These mutations are also presented in Table 2 with their corresponding nucleotide changes.

Accordingly, in one or more embodiments, migalastat is used to treat Fabry disease and/or enhance α-Gal A activity in a patient having an α-Gal A mutation selected from the group consisting of the mutations presented in Table 2. In various embodiments, these α-Gal A mutations are relative to the amino acid sequence shown in SEQ ID NO: 2.

Exemplary nucleotide changes associated with these novel mutations are shown in Table 2 below:

TABLE 2

| Nucleotide change | Nucleotide change | Protein change (1 Letter) | Protein Change (3 Letter) |
|---|---|---|---|
| c.13A > G | c.A13G | N5D | p.(Asn5Asp) |
| c.15C > G | c.C15G | N5K | p.(Asn5Lys) |
| c.17C > T | c.C17T | P6L | p.(Pro6Leu) |
| c.17C > A | c.C17A | P6Q | p.(Pro6Gln) |
| c.17C > G | c.C17G | P6R | p.(Pro6Arg) |
| c.16C > T | c.C16T | P6S | p.(Pro6Ser) |
| c.16C > A | c.C16A | P6T | p.(Pro6Thr) |
| c.21A > T | c.A21T | E7D | p.(Glu7Asp) |
| c.19G > A | c.G19A | E7K | p.(Glu7Lys) |
| c.20A > T | c.A20T | E7V | p.(Glu7Val) |
| c.22C > A | c.C22A | L8I | p.(Leu8Ile) |
| c.23T > C | c.T23C | L8P | p.(Leu8Pro) |
| c.23T > A | c.T23A | L8Q | p.(Leu8Gln) |
| c.26A > T | c.A26T | H9L | p.(His9Leu) |
| c.27T > A | c.T27A | H9Q | p.(His9Gln) |
| c.26A > G | c.A26G | H9R | p.(His9Arg) |
| c.25C > T | c.C25T | H9Y | p.(His9Tyr) |
| c.28C > A | c.C28A | L10M | p.(Leu10Met) |
| c.29T > C | c.T29C | L10P | p.(Leu10Pro) |
| c.29T > A | c.T29A | L10Q | p.(Leu10Gln) |
| c.29T > G | c.T29G | L10R | p.(Leu10Arg) |
| c.28C > G | c.C28G | L10V | p.(Leu10Val) |
| c.31G > T | c.G31T | G11C | p.(Gly11Cys) |
| c.32G > A | c.G32A | G11D | p.(Gly11Asp) |
| c.31G > C | c.G31C | G11R | p.(Gly11Arg) |
| c.31G > A | c.G31A | G11S | p.(Gly11Ser) |
| c.32G > T | c.G32T | G11V | p.(Gly11Val) |
| c.34T > G | c.T34G | C12G | p.(Cys12Gly) |
| c.34T > C | c.T34C | C12R | p.(Cys12Arg) |
| c.34T > A | c.T34A | C12S | p.(Cys12Ser) |
| c.35G > A | c.G35A | C12Y | p.(Cys12Tyr) |
| c.38C > A | c.C38A | A13E | p.(Ala13Glu) |
| c.38C > G | c.C38G | A13G | p.(Ala13Gly) |
| c.40C > T | c.C40T | L14F | p.(Leu14Phe) |
| c.41T > A | c.T41A | L14H | p.(Leu14His) |
| c.40C > G | c.C40G | L14V | p.(Leu14Val) |
| c.49C > T | c.C49T | R17C | p.(Arg17Cys) |
| c.49C > G | c.C49G | R17G | p.(Arg17Gly) |
| c.50G > A | c.G50A | R17H | p.(Arg17His) |
| c.50G > C | c.G50C | R17P | p.(Arg17Pro) |
| c.49C > A | c.C49A | R17S | p.(Arg17Ser) |
| c.52T > A | c.T52A | F18I | p.(Phe18Ile) |
| c.54C > G | c.C54G | F18L | p.(Phe18Leu) |
| c.59C > G | c.C59G | A20G | p.(Ala20Gly) |
| c.62T > A | c.T62A | L21H | p.(Leu21His) |
| c.65T > C | c.T65C | V22A | p.(Val22Ala) |
| c.64G > T | c.G64T | V22F | p.(Val22Phe) |
| c.64G > A | c.G64A | V22I | p.(Val22Ile) |
| c.64G > C | c.G64C | V22L | p.(Val22Leu) |
| c.67T > C | c.T67C | S23P | p.(Ser23Pro) |
| c.67T > A | c.T67A | S23T | p.(Ser23Thr) |
| c.71G > C | c.G71C | W24S | p.(Trp24Ser) |
| c.73G > C | c.G73C | D25H | p.(Asp25His) |
| c.77T > A | c.T77A | I26N | p.(Ile26Asn) |
| c.79C > G | c.C79G | P27A | p.(Pro27Ala) |
| c.80C > T | c.C80T | P27L | p.(Pro27Leu) |
| c.79C > T | c.C79T | P27S | p.(Pro27Ser) |
| c.79C > A | c.C79A | P27T | p.(Pro27Thr) |
| c.83G > A | c.G83A | G28E | p.(Gly28Glu) |
| c.82G > C | c.G82C | G28R | p.(Gly28Arg) |
| c.82G > T | c.G82T | G28W | p.(Gly28Trp) |
| c.86C > G | c.C86G | A29G | p.(Ala29Gly) |
| c.85G > C | c.G85C | A29P | p.(Ala29Pro) |
| c.86C > T | c.C86T | A29V | p.(Ala29Val) |
| c.88A > G | c.A88G | R30G | p.(Arg30Gly) |

TABLE 2-continued

| Nucleotide change | Nucleotide change | Protein change (1 Letter) | Protein Change (3 Letter) |
|---|---|---|---|
| c.94C > A | c.C94A | L32M | p.(Leu32Met) |
| c.95T > A | c.T95A | L32Q | p.(Leu32Gln) |
| c.95T > G | c.T95G | L32R | p.(Leu32Arg) |
| c.94C > G | c.C94G | L32V | p.(Leu32Val) |
| c.98A > C | c.A98C | D33A | p.(Asp33Ala) |
| c.99C > G | c.C99G | D33E | p.(Asp33Glu) |
| c.98A > T | c.A98T | D33V | p.(Asp33Val) |
| c.106T > A | c.T106A | L36M | p.(Leu36Met) |
| c.106T > G | c.T106G | L36V | p.(Leu36Val) |
| c.110C > A | c.C110A | A37E | p.(Ala37Glu) |
| c.110C > G | c.C110G | A37G | p.(Ala37Gly) |
| c.109G > T | c.G109T | A37S | p.(Ala37Ser) |
| c.112A > G | c.A112G | R38G | p.(Arg38Gly) |
| c.113G > T | c.G113T | R38M | p.(Arg38Met) |
| c.112A > T | c.A112T | R38W | p.(Arg38Trp) |
| c.115A > G | c.A115G | T39A | p.(Thr39Ala) |
| c.116C > A | c.C116A | T39K | p.(Thr39Lys) |
| c.116C > T | c.C116T | T39M | p.(Thr39Met) |
| c.116C > G | c.C116G | T39R | p.(Thr39Arg) |
| c.115A > T | c.A115T | T39S | p.(Thr39Ser) |
| c.121A > G | c.A121G | T41A | p.(Thr41Ala) |
| c.122C > A | c.C122A | T41N | p.(Thr41Asn) |
| c.121A > T | c.A121T | T41S | p.(Thr41Ser) |
| c.128G > C | c.G128C | G43A | p.(Gly43Ala) |
| c.133C > A | c.C133A | L45M | p.(Leu45Met) |
| c.133C > G | c.C133G | L45V | p.(Leu45Val) |
| c.136C > G | c.C136G | H46D | p.(His46Asp) |
| c.136C > A | c.C136A | H46N | p.(His46Asn) |
| c.138C > G | c.C138G | H46Q | p.(His46Gln) |
| c.143A > C | c.A143C | E48A | p.(Glu48Ala) |
| c.149T > A | c.T149A | F50Y | p.(Phe50Tyr) |
| c.152T > G | c.T152G | M51R | p.(Met51Arg) |
| c.152T > C | c.T152C | M51T | p.(Met51Thr) |
| c.151A > G | c.A151G | M51V | p.(Met51Val) |
| c.157A > C | c.A157C | N53H | p.(Asn53His) |
| c.158A > T | c.A158T | N53I | p.(Asn53Ile) |
| c.158A > G | c.A158G | N53S | p.(Asn53Ser) |
| c.158A > C | c.A158C | N53T | p.(Asn53Thr) |
| c.161T > A | c.T161A | L54H | p.(Leu54His) |
| c.161T > G | c.T161G | L54R | p.(Leu54Arg) |
| c.160C > G | c.C160G | L54V | p.(Leu54Val) |
| c.164A > C | c.A164C | D55A | p.(Asp55Ala) |
| c.165C > G | c.C165G | D55E | p.(Asp55Glu) |
| c.163G > C | c.G163C | D55H | p.(Asp55His) |
| c.163G > T | c.G163T | D55Y | p.(Asp55Tyr) |
| c.168C > G | c.C168G | C56W | p.(Cys56Trp) |
| c.172G > A | c.G172A | E58K | p.(Glu58Lys) |
| c.176A > C | c.A176C | E59A | p.(Glu59Ala) |
| c.177G > C | c.G177C | E59D | p.(Glu59Asp) |
| c.176A > G | c.A176G | E59G | p.(Glu59Gly) |
| c.175G > C | c.G175C | E59Q | p.(Glu59Gln) |
| c.176A > T | c.A176T | E59V | p.(Glu59Val) |
| c.178C > G | c.C178G | P60A | p.(Pro60Ala) |
| c.179C > A | c.C179A | P60Q | p.(Pro60Gln) |
| c.179C > G | c.C179G | P60R | p.(Pro60Arg) |
| c.183T > A | c.T183A | D61E | p.(Asp61Glu) |
| c.182A > T | c.A182T | D61V | p.(Asp61Val) |
| c.184T > G | c.T184G | S62A | p.(Ser62Ala) |
| c.185C > G | c.C185G | S62C | p.(Ser62Cys) |
| c.185C > T | c.C185T | S62F | p.(Ser62Phe) |
| c.184T > C | c.T184C | S62P | p.(Ser62Pro) |
| c.185C > A | c.C185A | S62Y | p.(Ser62Tyr) |
| c.190A > C | c.A190C | I64L | p.(Ile64Leu) |
| c.190A > G | c.A190G | I64V | p.(Ile64Val) |
| c.193A > T | c.A193T | S65C | p.(Ser65Cys) |
| c.193A > G | c.A193G | S65G | p.(Ser65Gly) |
| c.195T > A | c.T195A | S65R | p.(Ser65Arg) |
| c.198G > C | c.G198C | E66D | p.(Glu66Asp) |
| c.197A > T | c.A197T | E66V | p.(Glu66Val) |
| c.199A > G | c.A199G | K67E | p.(Lys67Glu) |
| c.200A > T | c.A200T | K67M | p.(Lys67Met) |
| c.201G > C | c.G201C | K67N | p.(Lys67Asn) |
| c.199A > C | c.A199C | K67Q | p.(Lys67Gln) |
| c.200A > C | c.A200C | K67T | p.(Lys67Thr) |
| c.202C > A | c.C202A | L68I | p.(Leu68Ile) |
| c.205T > A | c.T205A | F69I | p.(Phe69Ile) |
| c.206T > A | c.T206A | F69Y | p.(Phe69Tyr) |

TABLE 2-continued

| Nucleotide change | Nucleotide change | Protein change (1 Letter) | Protein Change (3 Letter) |
|---|---|---|---|
| c.210G > C | c.G210C | M70I | p.(Met70Ile) |
| c.209T > A | c.T209A | M70K | p.(Met70Lys) |
| c.208A > T | c.A208T | M70L | p.(Met70Leu) |
| c.209T > G | c.T209G | M70R | p.(Met70Arg) |
| c.212A > C | c.A212C | E71A | p.(Glu71Ala) |
| c.213G > C | c.G213C | E71D | p.(Glu71Asp) |
| c.212A > G | c.A212G | E71G | p.(Glu71Gly) |
| c.211G > C | c.G211C | E71Q | p.(Glu71Gln) |
| c.212A > T | c.A212T | E71V | p.(Glu71Val) |
| c.214A > T | c.A214T | M72L | p.(Met72Leu) |
| c.215T > C | c.T215C | M72T | p.(Met72Thr) |
| c.217G > T | c.G217T | A73S | p.(Ala73Ser) |
| c.217G > A | c.G217A | A73T | p.(Ala73Thr) |
| c.222G > C | c.G222C | E74D | p.(Glu74Asp) |
| c.221A > G | c.A221G | E74G | p.(Glu74Gly) |
| c.220G > A | c.G220A | E74K | p.(Glu74Lys) |
| c.221A > T | c.A221T | E74V | p.(Glu74Val) |
| c.223C > T | c.C223T | L75F | p.(Leu75Phe) |
| c.224T > C | c.T224C | L75P | p.(Leu75Pro) |
| c.226A > G | c.A226G | M76V | p.(Met76Val) |
| c.229G > A | c.G229A | V77I | p.(Val77Ile) |
| c.229G > C | c.G229C | V77L | p.(Val77Leu) |
| c.233C > T | c.C233T | S78L | p.(Ser78Leu) |
| c.232T > C | c.T232C | S78P | p.(Ser78Pro) |
| c.236A > C | c.A236C | E79A | p.(Glu79Ala) |
| c.237A > T | c.A237T | E79D | p.(Glu79Asp) |
| c.236A > G | c.A236G | E79G | p.(Glu79Gly) |
| c.235G > A | c.G235A | E79K | p.(Glu79Lys) |
| c.235G > C | c.G235C | E79Q | p.(Glu79Gln) |
| c.236A > T | c.A236T | E79V | p.(Glu79Val) |
| c.239G > C | c.G239C | G80A | p.(Gly80Ala) |
| c.238G > T | c.G238T | G80C | p.(Gly80Cys) |
| c.238G > A | c.G238A | G80S | p.(Gly80Ser) |
| c.242G > T | c.G242T | W81L | p.(Trp81Leu) |
| c.244A > G | c.A244G | K82E | p.(Lys82Glu) |
| c.245A > T | c.A245T | K82M | p.(Lys82Met) |
| c.246G > C | c.G246C | K82N | p.(Lys82Asn) |
| c.245A > G | c.A245G | K82R | p.(Lys82Arg) |
| c.245A > C | c.A245C | K82T | p.(Lys82Thr) |
| c.248A > C | c.A248C | D83A | p.(Asp83Ala) |
| c.249T > A | c.T249A | D83E | p.(Asp83Glu) |
| c.248A > G | c.A248G | D83G | p.(Asp83Gly) |
| c.248A > T | c.A248T | D83V | p.(Asp83Val) |
| c.251C > A | c.C251A | A84E | p.(Ala84Glu) |
| c.251C > G | c.C251G | A84G | p.(Ala84Gly) |
| c.250G > C | c.G250C | A84P | p.(Ala84Pro) |
| c.250G > T | c.G250T | A84S | p.(Ala84Ser) |
| c.250G > A | c.G250A | A84T | p.(Ala84Thr) |
| c.251C > T | c.C251T | A84V | p.(Ala84Val) |
| c.254G > C | c.G254C | G85A | p.(Gly85Ala) |
| c.253G > T | c.G253T | G85C | p.(Gly85Cys) |
| c.253G > C | c.G253C | G85R | p.(Gly85Arg) |
| c.257A > T | c.A257T | Y86F | p.(Tyr86Phe) |
| c.260A > G | c.A260G | E87G | p.(Glu87Gly) |
| c.262T > C | c.T262C | Y88H | p.(Tyr88His) |
| c.262T > A | c.T262A | Y88N | p.(Tyr88Asn) |
| c.265C > G | c.C265G | L89V | p.(Leu89Val) |
| c.271A > T | c.A271T | I91F | p.(Ile91Phe) |
| c.271A > C | c.A271C | I91L | p.(Ile91Leu) |
| c.273T > G | c.T273G | I91M | p.(Ile91Met) |
| c.272T > G | c.T272G | I91S | p.(Ile91Ser) |
| c.286A > T | c.A286T | M96L | p.(Met96Leu) |
| c.287T > C | c.T287C | M96T | p.(Met96Thr) |
| c.290C > A | c.C290A | A97D | p.(Ala97Asp) |
| c.289G > T | c.G289T | A97S | p.(Ala97Ser) |
| c.289G > A | c.G289A | A97T | p.(Ala97Thr) |
| c.293C > A | c.C293A | P98H | p.(Pro98His) |
| c.293C > T | c.C293T | P98L | p.(Pro98Leu) |
| c.293C > G | c.C293G | P98R | p.(Pro98Arg) |
| c.295C > G | c.C295G | Q99E | p.(Gln99Glu) |
| c.296A > T | c.A296T | Q99L | p.(Gln99Leu) |
| c.296A > C | c.A296C | Q99P | p.(Gln99Pro) |
| c.296A > G | c.A296G | Q99R | p.(Gln99Arg) |
| c.302A > C | c.A302C | D101A | p.(Asp101Ala) |
| c.303T > A | c.T303A | D101E | p.(Asp101Glu) |
| c.302A > G | c.A302G | D101G | p.(Asp101Gly) |
| c.301G > C | c.G301C | D101H | p.(Asp101His) |

TABLE 2-continued

| Nucleotide change | Nucleotide change | Protein change (1 Letter) | Protein Change (3 Letter) |
|---|---|---|---|
| c.302A > T | c.A302T | D101V | p.(Asp101Val) |
| c.304T > G | c.T304G | S102A | p.(Ser102Ala) |
| c.304T > C | c.T304C | S102P | p.(Ser102Pro) |
| c.304T > A | c.T304A | S102T | p.(Ser102Thr) |
| c.311G > C | c.G311C | G104A | p.(Gly104Ala) |
| c.311G > A | c.G311A | G104D | p.(Gly104Asp) |
| c.310G > A | c.G310A | G104S | p.(Gly104Ser) |
| c.313A > G | c.A313G | R105G | p.(Arg105Gly) |
| c.314G > T | c.G314T | R105I | p.(Arg105Ile) |
| c.314G > A | c.G314A | R105K | p.(Arg105Lys) |
| c.314G > C | c.G314C | R105T | p.(Arg105Thr) |
| c.317T > A | c.T317A | L106H | p.(Leu106His) |
| c.316C > A | c.C316A | L106I | p.(Leu106Ile) |
| c.317T > C | c.T317C | L106P | p.(Leu106Pro) |
| c.316C > G | c.C316G | L106V | p.(Leu106Val) |
| c.319C > G | c.C319G | Q107E | p.(Gln107Glu) |
| c.321G > C | c.G321C | Q107H | p.(Gln107His) |
| c.319C > A | c.C319A | Q107K | p.(Gln107Lys) |
| c.323C > A | c.C323A | A108E | p.(Ala108Glu) |
| c.323C > T | c.C323T | A108V | p.(Ala108Val) |
| c.326A > C | c.A326C | D109A | p.(Asp109Ala) |
| c.327C > G | c.C327G | D109E | p.(Asp109Glu) |
| c.325G > C | c.G325C | D109H | p.(Asp109His) |
| c.325G > A | c.G325A | D109N | p.(Asp109Asn) |
| c.325G > T | c.G325T | D109Y | p.(Asp109Tyr) |
| c.328C > A | c.C328A | P110T | p.(Pro110Thr) |
| c.337T > G | c.T337G | F113V | p.(Phe113Val) |
| c.338T > A | c.T338A | F113Y | p.(Phe113Tyr) |
| c.341C > T | c.C341T | P114L | p.(Pro114Leu) |
| c.343C > G | c.C343G | H115D | p.(His115Asp) |
| c.343C > A | c.C343A | H115N | p.(His115Asn) |
| c.346G > C | c.G346C | G116R | p.(Gly116Arg) |
| c.351T > G | c.T351G | I117M | p.(Ile117Met) |
| c.350T > C | c.T350C | I117T | p.(Ile117Thr) |
| c.362C > T | c.C362T | A121V | p.(Ala121Val) |
| c.367T > G | c.T367G | Y123D | p.(Tyr123Asp) |
| c.368A > T | c.A368T | Y123F | p.(Tyr123Phe) |
| c.367T > A | c.T367A | Y123N | p.(Tyr123Asn) |
| c.368A > C | c.A368C | Y123S | p.(Tyr123Ser) |
| c.370G > A | c.G370A | V124I | p.(Val124Ile) |
| c.373C > G | c.C373G | H125D | p.(His125Asp) |
| c.373C > A | c.C373A | H125N | p.(His125Asn) |
| c.374A > G | c.A374G | H125R | p.(His125Arg) |
| c.376A > T | c.A376T | S126C | p.(Ser126Cys) |
| c.377G > T | c.G377T | S126I | p.(Ser126Ile) |
| c.379A > G | c.A379G | K127E | p.(Lys127Glu) |
| c.383G > C | c.G383C | G128A | p.(Gly128Ala) |
| c.385C > G | c.C385G | L129V | p.(Leu129Val) |
| c.389A > T | c.A389T | K130M | p.(Lys130Met) |
| c.390G > C | c.G390C | K130N | p.(Lys130Asn) |
| c.388A > C | c.A388C | K130Q | p.(Lys130Gln) |
| c.391C > G | c.C391G | L131V | p.(Leu131Val) |
| c.397A > C | c.A397C | I133L | p.(Ile133Leu) |
| c.398T > C | c.T398C | I133T | p.(Ile133Thr) |
| c.397A > G | c.A397G | I133V | p.(Ile133Val) |
| c.404C > A | c.C404A | A135E | p.(Ala135Glu) |
| c.404C > G | c.C404G | A135G | p.(Ala135Gly) |
| c.403G > T | c.G403T | A135S | p.(Ala135Ser) |
| c.403G > A | c.G403A | A135T | p.(Ala135Thr) |
| c.407A > C | c.A407C | D136A | p.(Asp136Ala) |
| c.406G > A | c.G406A | D136N | p.(Asp136Asn) |
| c.407A > T | c.A407T | D136V | p.(Asp136Val) |
| c.410T > C | c.T410C | V137A | p.(Val137Ala) |
| c.410T > A | c.T410A | V137D | p.(Val137Asp) |
| c.410T > G | c.T410G | V137G | p.(Val137Gly) |
| c.409G > A | c.G409A | V137I | p.(Val137Ile) |
| c.409G > C | c.G409C | V137L | p.(Val137Leu) |
| c.413G > C | c.G413C | G138A | p.(Gly138Ala) |
| c.415A > C | c.A415C | N139H | p.(Asn139His) |
| c.416A > T | c.A416T | N139I | p.(Asn139Ile) |
| c.417T > A | c.T417A | N139K | p.(Asn139Lys) |
| c.415A > T | c.A415T | N139Y | p.(Asn139Tyr) |
| c.418A > G | c.A418G | K140E | p.(Lys140Glu) |
| c.419A > T | c.A419T | K140I | p.(Lys140Ile) |
| c.420A > T | c.A420T | K140N | p.(Lys140Asn) |
| c.418A > C | c.A418C | K140Q | p.(Lys140Gln) |
| c.419A > G | c.A419G | K140R | p.(Lys140Arg) |

TABLE 2-continued

| Nucleotide change | Nucleotide change | Protein change (1 Letter) | Protein Change (3 Letter) |
|---|---|---|---|
| c.421A > T | c.A421T | T141S | p.(Thr141Ser) |
| c.428C > A | c.C428A | A143E | p.(Ala143Glu) |
| c.428C > G | c.C428G | A143G | p.(Ala143Gly) |
| c.431G > C | c.G431C | G144A | p.(Gly144Ala) |
| c.430G > T | c.G430T | G144C | p.(Gly144Cys) |
| c.430G > C | c.G430C | G144R | p.(Gly144Arg) |
| c.430G > A | c.G430A | G144S | p.(Gly144Ser) |
| c.434T > G | c.T434G | F145C | p.(Phe145Cys) |
| c.435C > G | c.C435G | F145L | p.(Phe145Leu) |
| c.433T > G | c.T433G | F145V | p.(Phe145Val) |
| c.434T > A | c.T434A | F145Y | p.(Phe145Tyr) |
| c.436C > G | c.C436G | P146A | p.(Pro146Ala) |
| c.437C > A | c.C437A | P146H | p.(Pro146His) |
| c.437C > T | c.C437T | P146L | p.(Pro146Leu) |
| c.436C > A | c.C436A | P146T | p.(Pro146Thr) |
| c.440G > C | c.G440C | G147A | p.(Gly147Ala) |
| c.442A > T | c.A442T | S148C | p.(Ser148Cys) |
| c.442A > G | c.A442G | S148G | p.(Ser148Gly) |
| c.443G > C | c.G443C | S148T | p.(Ser148Thr) |
| c.446T > G | c.T446G | F149C | p.(Phe149Cys) |
| c.449G > A | c.G449A | G150E | p.(Gly150Glu) |
| c.449G > T | c.G449T | G150V | p.(Gly150Val) |
| c.452A > G | c.A452G | Y151C | p.(Tyr151Cys) |
| c.451T > G | c.T451G | Y151D | p.(Tyr151Asp) |
| c.452A > C | c.A452C | Y151S | p.(Tyr151Ser) |
| c.455A > T | c.A455T | Y152F | p.(Tyr152Phe) |
| c.455A > C | c.A455C | Y152S | p.(Tyr152Ser) |
| c.458A > C | c.A458C | D153A | p.(Asp153Ala) |
| c.457G > C | c.G457C | D153H | p.(Asp153His) |
| c.457G > A | c.G457A | D153N | p.(Asp153Asn) |
| c.458A > T | c.A458T | D153V | p.(Asp153Val) |
| c.457G > T | c.G457T | D153Y | p.(Asp153Tyr) |
| c.467C > G | c.C467G | A156G | p.(Ala156Gly) |
| c.469C > G | c.C469G | Q157E | p.(Gln157Glu) |
| c.469C > A | c.C469A | Q157K | p.(Gln157Lys) |
| c.470A > T | c.A470T | Q157L | p.(Gln157Leu) |
| c.470A > C | c.A470C | Q157P | p.(Gln157Pro) |
| c.472A > G | c.A472G | T158A | p.(Thr158Ala) |
| c.473C > T | c.C473T | T158I | p.(Thr158Ile) |
| c.473C > A | c.C473A | T158N | p.(Thr158Asn) |
| c.472A > T | c.A472T | T158S | p.(Thr158Ser) |
| c.475T > A | c.T475A | F159I | p.(Phe159Ile) |
| c.477T > A | c.T477A | F159L | p.(Phe159Leu) |
| c.475T > G | c.T475G | F159V | p.(Phe159Val) |
| c.476T > A | c.T476A | F159Y | p.(Phe159Tyr) |
| c.479C > G | c.C479G | A160G | p.(Ala160Gly) |
| c.478G > T | c.G478T | A160S | p.(Ala160Ser) |
| c.478G > A | c.G478A | A160T | p.(Ala160Thr) |
| c.479C > T | c.C479T | A160V | p.(Ala160Val) |
| c.481G > C | c.G481C | D161H | p.(Asp161His) |
| c.481G > A | c.G481A | D161N | p.(Asp161Asn) |
| c.482A > T | c.A482T | D161V | p.(Asp161Val) |
| c.481G > T | c.G481T | D161Y | p.(Asp161Tyr) |
| c.485G > C | c.G485C | W162S | p.(Trp162Ser) |
| c.491T > C | c.T491C | V164A | p.(Val164Ala) |
| c.490G > A | c.G490A | V164I | p.(Val164Ile) |
| c.490G > C | c.G490C | V164L | p.(Val164Leu) |
| c.494A > C | c.A494C | D165A | p.(Asp165Ala) |
| c.495T > A | c.T495A | D165E | p.(Asp165Glu) |
| c.496C > A | c.C496A | L166M | p.(Leu166Met) |
| c.497T > A | c.T497A | L166Q | p.(Leu166Gln) |
| c.499C > A | c.C499A | L167I | p.(Leu167Ile) |
| c.506T > G | c.T506G | F169C | p.(Phe169Cys) |
| c.507T > A | c.T507A | F169L | p.(Phe169Leu) |
| c.505T > G | c.T505G | F169V | p.(Phe169Val) |
| c.506T > A | c.T506A | F169Y | p.(Phe169Tyr) |
| c.512G > C | c.G512C | G171A | p.(Gly171Ala) |
| c.512G > T | c.G512T | G171V | p.(Gly171Val) |
| c.518A > G | c.A518G | Y173C | p.(Tyr173Cys) |
| c.518A > T | c.A518T | Y173F | p.(Tyr173Phe) |
| c.517T > C | c.T517C | Y173H | p.(Tyr173His) |
| c.518A > C | c.A518C | Y173S | p.(Tyr173Ser) |
| c.524A > G | c.A524G | D175G | p.(Asp175Gly) |
| c.523G > C | c.G523C | D175H | p.(Asp175His) |
| c.524A > T | c.A524T | D175V | p.(Asp175Val) |
| c.523G > T | c.G523T | D175Y | p.(Asp175Tyr) |
| c.526A > T | c.A526T | S176C | p.(Ser176Cys) |

TABLE 2-continued

| Nucleotide change | Nucleotide change | Protein change (1 Letter) | Protein Change (3 Letter) |
|---|---|---|---|
| c.528T > A or c.528T > G | c.T528A or c.T528G | S176R | p.(Ser176Arg) |
| c.531G > C | c.G531C | L177F | p.(Leu177Phe) |
| c.529T > A | c.T529A | L177M | p.(Leu177Met) |
| c.530T > C | c.T530C | L177S | p.(Leu177Ser) |
| c.529T > G | c.T529G | L177V | p.(Leu177Val) |
| c.530T > G | c.T530G | L177W | p.(Leu177Trp) |
| c.533A > C | c.A533C | E178A | p.(Glu178Ala) |
| c.533A > G | c.A533G | E178G | p.(Glu178Gly) |
| c.532G > A | c.G532A | E178K | p.(Glu178Lys) |
| c.532G > C | c.G532C | E178Q | p.(Glu178Gln) |
| c.538T > A | c.T538A | L180M | p.(Leu180Met) |
| c.539T > C | c.T539C | L180S | p.(Leu180Ser) |
| c.541G > C | c.G541C | A181P | p.(Ala181Pro) |
| c.541G > A | c.G541A | A181T | p.(Ala181Thr) |
| c.542C > T | c.C542T | A181V | p.(Ala181Val) |
| c.545A > C | c.A545C | D182A | p.(Asp182Ala) |
| c.546T > A | c.T546A | D182E | p.(Asp182Glu) |
| c.545A > T | c.A545T | D182V | p.(Asp182Val) |
| c.544G > T | c.G544T | D182Y | p.(Asp182Tyr) |
| c.551A > T | c.A551T | Y184F | p.(Tyr184Phe) |
| c.550T > C | c.T550C | Y184H | p.(Tyr184His) |
| c.551A > C | c.A551C | Y184S | p.(Tyr184Ser) |
| c.554A > T | c.A554T | K185M | p.(Lys185Met) |
| c.555G > C | c.G555C | K185N | p.(Lys185Asn) |
| c.553A > C | c.A553C | K185Q | p.(Lys185Gln) |
| c.554A > C | c.A554C | K185T | p.(Lys185Thr) |
| c.556C > G | c.C556G | H186D | p.(His186Asp) |
| c.557A > T | c.A557T | H186L | p.(His186Leu) |
| c.556C > A | c.C556A | H186N | p.(His186Asn) |
| c.558C > G | c.C558G | H186Q | p.(His186Gln) |
| c.556C > T | c.C556T | H186Y | p.(His186Tyr) |
| c.559A > T | c.A559T | M187L | p.(Met187Leu) |
| c.562T > G | c.T562G | S188A | p.(Ser188Ala) |
| c.563C > G | c.C563G | S188C | p.(Ser188Cys) |
| c.563C > T | c.C563T | S188F | p.(Ser188Phe) |
| c.562T > C | c.T562C | S188P | p.(Ser188Pro) |
| c.562T > A | c.T562A | S188T | p.(Ser188Thr) |
| c.563C > A | c.C563A | S188Y | p.(Ser188Tyr) |
| c.566T > C | c.T566C | L189S | p.(Leu189Ser) |
| c.565T > G | c.T565G | L189V | p.(Leu189Val) |
| c.569C > A | c.C569A | A190D | p.(Ala190Asp) |
| c.569C > G | c.C569G | A190G | p.(Ala190Gly) |
| c.568G > T | c.G568T | A190S | p.(Ala190Ser) |
| c.568G > A | c.G568A | A190T | p.(Ala190Thr) |
| c.569C > T | c.C569T | A190V | p.(Ala190Val) |
| c.571C > A | c.C571A | L191M | p.(Leu191Met) |
| c.571C > G | c.C571G | L191V | p.(Leu191Val) |
| c.574A > G | c.A574G | N192D | p.(Asn192Asp) |
| c.574A > C | c.A574C | N192H | p.(Asn192His) |
| c.576T > A | c.T576A | N192K | p.(Asn192Lys) |
| c.575A > G | c.A575G | N192S | p.(Asn192Ser) |
| c.575A > C | c.A575C | N192T | p.(Asn192Thr) |
| c.577A > G | c.A577G | R193G | p.(Arg193Gly) |
| c.578G > T | c.G578T | R193M | p.(Arg193Met) |
| c.578G > C | c.G578C | R193T | p.(Arg193Thr) |
| c.577A > T | c.A577T | R193W | p.(Arg193Trp) |
| c.581C > A | c.C581A | T194N | p.(Thr194Asn) |
| c.580A > C | c.A580C | T194P | p.(Thr194Pro) |
| c.580A > T | c.A580T | T194S | p.(Thr194Ser) |
| c.583G > T | c.G583T | G195C | p.(Gly195Cys) |
| c.583G > C | c.G583C | G195R | p.(Gly195Arg) |
| c.583G > A | c.G583A | G195S | p.(Gly195Ser) |
| c.587G > T | c.G587T | R196I | p.(Arg196Ile) |
| c.587G > A | c.G587A | R196K | p.(Arg196Lys) |
| c.589A > T | c.A589T | S197C | p.(Ser197Cys) |
| c.589A > G | c.A589G | S197G | p.(Ser197Gly) |
| c.590G > T | c.G590T | S197I | p.(Ser197Ile) |
| c.590G > A | c.G590A | S197N | p.(Ser197Asn) |
| c.590G > C | c.G590C | S197T | p.(Ser197Thr) |
| c.594T > G | c.T594G | I198M | p.(Ile198Met) |
| c.593T > G | c.T593G | I198S | p.(Ile198Ser) |
| c.596T > A | c.T596A | V199E | p.(Val199Glu) |
| c.595G > C | c.G595C | V199L | p.(Val199Leu) |
| c.598T > A | c.T598A | Y200N | p.(Tyr200Asn) |
| c.599A > C | c.A599C | Y200S | p.(Tyr200Ser) |
| c.601T > G | c.T601G | S201A | p.(Ser201Ala) |
| c.602C > G | c.C602G | S201C | p.(Ser201Cys) |

TABLE 2-continued

| Nucleotide change | Nucleotide change | Protein change (1 Letter) | Protein Change (3 Letter) |
|---|---|---|---|
| c.601T > A | c.T601A | S201T | p.(Ser201Thr) |
| c.608A > C | c.A608C | E203A | p.(Glu203Ala) |
| c.608A > G | c.A608G | E203G | p.(Glu203Gly) |
| c.607G > C | c.G607C | E203Q | p.(Glu203Gln) |
| c.611G > C | c.G611C | W204S | p.(Trp204Ser) |
| c.616C > T | c.C616T | L206F | p.(Leu206Phe) |
| c.617T > A | c.T617A | L206H | p.(Leu206His) |
| c.616C > A | c.C616A | L206I | p.(Leu206Ile) |
| c.617T > G | c.T617G | L206R | p.(Leu206Arg) |
| c.616C > G | c.C616G | L206V | p.(Leu206Val) |
| c.620A > T | c.A620T | Y207F | p.(Tyr207Phe) |
| c.623T > G | c.T623G | M208K | p.(Met208Lys) |
| c.627G > C | c.G627C | W209C | p.(Trp209Cys) |
| c.625T > G | c.T625G | W209G | p.(Trp209Gly) |
| c.629C > A | c.C629A | P210H | p.(Pro210His) |
| c.628C > A | c.C628A | P210T | p.(Pro210Thr) |
| c.632T > G | c.T632G | F211C | p.(Phe211Cys) |
| c.633T > A | c.T633A | F211L | p.(Phe211Leu) |
| c.632T > C | c.T632C | F211S | p.(Phe211Ser) |
| c.631T > G | c.T631G | F211V | p.(Phe211Val) |
| c.632T > A | c.T632A | F211Y | p.(Phe211Tyr) |
| c.636A > T | c.A636T | Q212H | p.(Gln212His) |
| c.635A > C | c.A635C | Q212P | p.(Gln212Pro) |
| c.637A > G | c.A637G | K213E | p.(Lys213Glu) |
| c.637A > C | c.A637C | K213Q | p.(Lys213Gln) |
| c.640C > G | c.C640G | P214A | p.(Pro214Ala) |
| c.641C > A | c.C641A | P214H | p.(Pro214His) |
| c.641C > G | c.C641G | P214R | p.(Pro214Arg) |
| c.640C > A | c.C640A | P214T | p.(Pro214Thr) |
| c.643A > C | c.A643C | N215H | p.(Asn215His) |
| c.645T > A | c.T645A | N215K | p.(Asn215Lys) |
| c.644A > C | c.A644C | N215T | p.(Asn215Thr) |
| c.643A > T | c.A643T | N215Y | p.(Asn215Tyr) |
| c.647A > T | c.A647T | Y216F | p.(Tyr216Phe) |
| c.646T > C | c.T646C | Y216H | p.(Tyr216His) |
| c.646T > A | c.T646A | Y216N | p.(Tyr216Asn) |
| c.649A > G | c.A649G | T217A | p.(Thr217Ala) |
| c.650C > T | c.C650T | T217I | p.(Thr217Ile) |
| c.650C > A | c.C650A | T217K | p.(Thr217Lys) |
| c.649A > C | c.A649C | T217P | p.(Thr217Pro) |
| c.650C > G | c.C650G | T217R | p.(Thr217Arg) |
| c.649A > T | c.A649T | T217S | p.(Thr217Ser) |
| c.653A > C | c.A653C | E218A | p.(Glu218Ala) |
| c.654A > T | c.A654T | E218D | p.(Glu218Asp) |
| c.653A > G | c.A653G | E218G | p.(Glu218Gly) |
| c.652G > A | c.G652A | E218K | p.(Glu218Lys) |
| c.652G > C | c.G652C | E218Q | p.(Glu218Gln) |
| c.653A > T | c.A653T | E218V | p.(Glu218Val) |
| c.655A > T | c.A655T | I219F | p.(Ile219Phe) |
| c.657C > G | c.C657G | I219M | p.(Ile219Met) |
| c.656T > G | c.T656G | I219S | p.(Ile219Ser) |
| c.659G > T | c.G659T | R220L | p.(Arg220Leu) |
| c.661C > G | c.C661G | Q221E | p.(Gln221Glu) |
| c.663G > C | c.G663C | Q221H | p.(Gln221His) |
| c.661C > A | c.C661A | Q221K | p.(Gln221Lys) |
| c.662A > T | c.A662T | Q221L | p.(Gln221Leu) |
| c.662A > G | c.A662G | Q221R | p.(Gln221Arg) |
| c.665A > G | c.A665G | Y222C | p.(Tyr222Cys) |
| c.664T > G | c.T664G | Y222D | p.(Tyr222Asp) |
| c.664T > C | c.T664C | Y222H | p.(Tyr222His) |
| c.664T > A | c.T664A | Y222N | p.(Tyr222Asn) |
| c.665A > C | c.A665C | Y222S | p.(Tyr222Ser) |
| c.670A > C | c.A670C | N224H | p.(Asn224His) |
| c.679C > G | c.C679G | R227G | p.(Arg227Gly) |
| c.682A > C | c.A682C | N228H | p.(Asn228His) |
| c.683A > T | c.A683T | N228I | p.(Asn228Ile) |
| c.683A > C | c.A683C | N228T | p.(Asn228Thr) |
| c.685T > A | c.T685A | F229I | p.(Phe229Ile) |
| c.686T > C | c.T686C | F229S | p.(Phe229Ser) |
| c.686T > A | c.T686A | F229Y | p.(Phe229Tyr) |
| c.689C > A | c.C689A | A230D | p.(Ala230Asp) |
| c.689C > G | c.C689G | A230G | p.(Ala230Gly) |
| c.688G > C | c.G688C | A230P | p.(Ala230Pro) |
| c.689C > T | c.C689T | A230V | p.(Ala230Val) |
| c.694A > C | c.A694C | I232L | p.(Ile232Leu) |
| c.696T > G | c.T696G | I232M | p.(Ile232Met) |
| c.694A > G | c.A694G | I232V | p.(Ile232Val) |

TABLE 2-continued

| Nucleotide change | Nucleotide change | Protein change (1 Letter) | Protein Change (3 Letter) |
|---|---|---|---|
| c.698A > C | c.A698C | D233A | p.(Asp233Ala) |
| c.699T > A | c.T699A | D233E | p.(Asp233Glu) |
| c.698A > G | c.A698G | D233G | p.(Asp233Gly) |
| c.698A > T | c.A698T | D233V | p.(Asp233Val) |
| c.703T > G | c.T703G | S235A | p.(Ser235Ala) |
| c.703T > A | c.T703A | S235T | p.(Ser235Thr) |
| c.710A > T | c.A710T | K237I | p.(Lys237Ile) |
| c.712A > T | c.A712T | S238C | p.(Ser238Cys) |
| c.713G > T | c.G713T | S238I | p.(Ser238Ile) |
| c.713G > C | c.G713C | S238T | p.(Ser238Thr) |
| c.715A > T | c.A715T | I239L | p.(Ile239Leu) |
| c.718A > G | c.A718G | K240E | p.(Lys240Glu) |
| c.719A > T | c.A719T | K240M | p.(Lys240Met) |
| c.719A > G | c.A719G | K240R | p.(Lys240Arg) |
| c.721A > T | c.A721T | S241C | p.(Ser241Cys) |
| c.722G > T | c.G722T | S241I | p.(Ser241Ile) |
| c.722G > C | c.G722C | S241T | p.(Ser241Thr) |
| c.724A > C | c.A724C | I242L | p.(Ile242Leu) |
| c.726C > G | c.C726G | I242M | p.(Ile242Met) |
| c.725T > G | c.T725G | I242S | p.(Ile242Ser) |
| c.727T > A | c.T727A | L243M | p.(Leu243Met) |
| c.728T > C | c.T728C | L243S | p.(Leu243Ser) |
| c.727T > G | c.T727G | L243V | p.(Leu243Val) |
| c.731A > C | c.A731C | D244A | p.(Asp244Ala) |
| c.732C > G | c.C732G | D244E | p.(Asp244Glu) |
| c.731A > G | c.A731G | D244G | p.(Asp244Gly) |
| c.731A > T | c.A731T | D244V | p.(Asp244Val) |
| c.730G > T | c.G730T | D244Y | p.(Asp244Tyr) |
| c.735G > C | c.G735C | W245C | p.(Trp245Cys) |
| c.736A > G | c.A736G | T246A | p.(Thr246Ala) |
| c.737C > T | c.C737T | T246I | p.(Thr246Ile) |
| c.737C > A | c.C737A | T246K | p.(Thr246Lys) |
| c.737C > G | c.C737G | T246R | p.(Thr246Arg) |
| c.739T > G | c.T739G | S247A | p.(Ser247Ala) |
| c.740C > T | c.C740T | S247F | p.(Ser247Phe) |
| c.739T > A | c.T739A | S247T | p.(Ser247Thr) |
| c.740C > A | c.C740A | S247Y | p.(Ser247Tyr) |
| c.743T > G | c.T743G | F248C | p.(Phe248Cys) |
| c.744T > A | c.T744A | F248L | p.(Phe248Leu) |
| c.742T > G | c.T742G | F248V | p.(Phe248Val) |
| c.743T > A | c.T743A | F248Y | p.(Phe248Tyr) |
| c.745A > G | c.A745G | N249D | p.(Asn249Asp) |
| c.745A > C | c.A745C | N249H | p.(Asn249His) |
| c.746A > T | c.A746T | N249I | p.(Asn249Ile) |
| c.746A > G | c.A746G | N249S | p.(Asn249Ser) |
| c.746A > C | c.A746C | N249T | p.(Asn249Thr) |
| c.745A > T | c.A745T | N249Y | p.(Asn249Tyr) |
| c.748C > G | c.C748G | Q250E | p.(Gln250Glu) |
| c.749A > T | c.A749T | Q250L | p.(Gln250Leu) |
| c.752A > G | c.A752G | E251G | p.(Glu251Gly) |
| c.751G > A | c.G751A | E251K | p.(Glu251Lys) |
| c.751G > C | c.G751C | E251Q | p.(Glu251Gln) |
| c.752A > T | c.A752T | E251V | p.(Glu251Val) |
| c.754A > G | c.A754G | R252G | p.(Arg252Gly) |
| c.757A > T | c.A757T | I253F | p.(Ile253Phe) |
| c.758T > A | c.T758A | I253N | p.(Ile253Asn) |
| c.757A > G | c.A757G | I253V | p.(Ile253Val) |
| c.761T > C | c.T761C | V254A | p.(Val254Ala) |
| c.761T > A | c.T761A | V254D | p.(Val254Asp) |
| c.760G > T | c.G760T | V254F | p.(Val254Phe) |
| c.761T > G | c.T761G | V254G | p.(Val254Gly) |
| c.764A > C | c.A764C | D255A | p.(Asp255Ala) |
| c.765T > A | c.T765A | D255E | p.(Asp255Glu) |
| c.763G > C | c.G763C | D255H | p.(Asp255His) |
| c.763G > A | c.G763A | D255N | p.(Asp255Asn) |
| c.764A > T | c.A764T | D255V | p.(Asp255Val) |
| c.763G > T | c.G763T | D255Y | p.(Asp255Tyr) |
| c.767T > A | c.T767A | V256D | p.(Val256Asp) |
| c.767T > G | c.T767G | V256G | p.(Val256Gly) |
| c.766G > C | c.G766C | V256L | p.(Val256Leu) |
| c.769G > T | c.G769T | A257S | p.(Ala257Ser) |
| c.773G > A | c.G773A | G258E | p.(Gly258Glu) |
| c.775C > G | c.C775G | P259A | p.(Pro259Ala) |
| c.775C > A | c.C775A | P259T | p.(Pro259Thr) |
| c.778G > T | c.G778T | G260W | p.(Gly260Trp) |
| c.782G > C | c.G782C | G261A | p.(Gly261Ala) |
| c.787A > C | c.A787C | N263H | p.(Asn263His) |

TABLE 2-continued

| Nucleotide change | Nucleotide change | Protein change (1 Letter) | Protein Change (3 Letter) |
|---|---|---|---|
| c.788A > C | c.A788C | N263T | p.(Asn263Thr) |
| c.790G > C | c.G790C | D264H | p.(Asp264His) |
| c.790G > A | c.G790A | D264N | p.(Asp264Asn) |
| c.793C > G | c.C793G | P265A | p.(Pro265Ala) |
| c.794C > A | c.C794A | P265Q | p.(Pro265Gln) |
| c.799A > T | c.A799T | M267L | p.(Met267Leu) |
| c.799A > G | c.A799G | M267V | p.(Met267Val) |
| c.804A > T | c.A804T | L268F | p.(Leu268Phe) |
| c.802T > A | c.T802A | L268I | p.(Leu268Ile) |
| c.805G > C | c.G805C | V269L | p.(Val269Leu) |
| c.808A > C | c.A808C | I270L | p.(Ile270Leu) |
| c.809T > G | c.T809G | I270S | p.(Ile270Ser) |
| c.808A > G | c.A808G | I270V | p.(Ile270Val) |
| c.814A > G | c.A814G | N272D | p.(Asn272Asp) |
| c.818T > A | c.T818A | F273Y | p.(Phe273Tyr) |
| c.823C > A | c.C823A | L275I | p.(Leu275Ile) |
| c.830G > T | c.G830T | W277L | p.(Trp277Leu) |
| c.833A > T | c.A833T | N278I | p.(Asn278Ile) |
| c.839A > T | c.A839T | Q280L | p.(Gln280Leu) |
| c.839A > G | c.A839G | Q280R | p.(Gln280Arg) |
| c.842T > C | c.T842C | V281A | p.(Val281Ala) |
| c.842T > A | c.T842A | V281E | p.(Val281Glu) |
| c.842T > G | c.T842G | V281G | p.(Val281Gly) |
| c.841G > C | c.G841C | V281L | p.(Val281Leu) |
| c.844A > T | c.A844T | T282S | p.(Thr282Ser) |
| c.847C > G | c.C847G | Q283E | p.(Gln283Glu) |
| c.849G > C | c.G849C | Q283H | p.(Gln283His) |
| c.848A > T | c.A848T | Q283L | p.(Gln283Leu) |
| c.852G > C | c.G852C | M284I | p.(Met284Ile) |
| c.850A > T | c.A850T | M284L | p.(Met284Leu) |
| c.854C > G | c.C854G | A285G | p.(Ala285Gly) |
| c.853G > A | c.G853A | A285T | p.(Ala285Thr) |
| c.854C > T | c.C854T | A285V | p.(Ala285Val) |
| c.856C > T | c.C856T | L286F | p.(Leu286Phe) |
| c.857T > A | c.T857A | L286H | p.(Leu286His) |
| c.856C > G | c.C856G | L286V | p.(Leu286Val) |
| c.863C > G | c.C863G | A288G | p.(Ala288Gly) |
| c.862G > T | c.G862T | A288S | p.(Ala288Ser) |
| c.863C > T | c.C863T | A288V | p.(Ala288Val) |
| c.865A > C | c.A865C | I289L | p.(Ile289Leu) |
| c.866T > C | c.T866C | I289T | p.(Ile289Thr) |
| c.865A > G | c.A865G | I289V | p.(Ile289Val) |
| c.872C > G | c.C872G | A291G | p.(Ala291Gly) |
| c.875C > G | c.C875G | A292G | p.(Ala292Gly) |
| c.874G > T | c.G874T | A292S | p.(Ala292Ser) |
| c.882A > T | c.A882T | L294F | p.(Leu294Phe) |
| c.880T > A | c.T880A | L294I | p.(Leu294Ile) |
| c.880T > G | c.T880G | L294V | p.(Leu294Val) |
| c.883T > A | c.T883A | F295I | p.(Phe295Ile) |
| c.884T > C | c.T884C | F295S | p.(Phe295Ser) |
| c.883T > G | c.T883G | F295V | p.(Phe295Val) |
| c.884T > A | c.T884A | F295Y | p.(Phe295Tyr) |
| c.889T > A | c.T889A | S297T | p.(Ser297Thr) |
| c.892A > G | c.A892G | N298D | p.(Asn298Asp) |
| c.893A > T | c.A893T | N298I | p.(Asn298Ile) |
| c.893A > C | c.A893C | N298T | p.(Asn298Thr) |
| c.895G > C | c.G895C | D299H | p.(Asp299His) |
| c.895G > A | c.G895A | D299N | p.(Asp299Asn) |
| c.898C > A | c.C898A | L300I | p.(Leu300Ile) |
| c.898C > G | c.C898G | L300V | p.(Leu300Val) |
| c.904C > G | c.C904G | H302D | p.(His302Asp) |
| c.905A > T | c.A905T | H302L | p.(His302Leu) |
| c.904C > A | c.C904A | H302N | p.(His302Asn) |
| c.904C > T | c.C904T | H302Y | p.(His302Tyr) |
| c.908T > G | c.T908G | I303S | p.(Ile303Ser) |
| c.911G > T | c.G911T | S304I | p.(Ser304Ile) |
| c.916C > G | c.C916G | Q306E | p.(Gln306Glu) |
| c.917A > T | c.A917T | Q306L | p.(Gln306Leu) |
| c.917A > C | c.A917C | Q306P | p.(Gln306Pro) |
| c.920C > A | c.C920A | A307D | p.(Ala307Asp) |
| c.920C > G | c.C920G | A307G | p.(Ala307Gly) |
| c.919G > C | c.G919C | A307P | p.(Ala307Pro) |
| c.919G > T | c.G919T | A307S | p.(Ala307Ser) |
| c.920C > T | c.C920T | A307V | p.(Ala307Val) |
| c.923A > T | c.A923T | K308I | p.(Lys308Ile) |
| c.922A > C | c.A922C | K308Q | p.(Lys308Gln) |
| c.923A > G | c.A923G | K308R | p.(Lys308Arg) |

TABLE 2-continued

| Nucleotide change | Nucleotide change | Protein change (1 Letter) | Protein Change (3 Letter) |
|---|---|---|---|
| c.926C > A | c.C926A | A309D | p.(Ala309Asp) |
| c.925G > A | c.G925A | A309T | p.(Ala309Thr) |
| c.928C > A | c.C928A | L310I | p.(Leu310Ile) |
| c.931C > A | c.C931A | L311I | p.(Leu311Ile) |
| c.934C > G | c.C934G | Q312E | p.(Gln312Glu) |
| c.934C > A | c.C934A | Q312K | p.(Gln312Lys) |
| c.935A > T | c.A935T | Q312L | p.(Gln312Leu) |
| c.939T > A | c.T939A | D313E | p.(Asp313Glu) |
| c.938A > T | c.A938T | D313V | p.(Asp313Val) |
| c.940A > G | c.A940G | K314E | p.(Lys314Glu) |
| c.941A > T | c.A941T | K314M | p.(Lys314Met) |
| c.942G > C | c.G942C | K314N | p.(Lys314Asn) |
| c.941A > C | c.A941C | K314T | p.(Lys314Thr) |
| c.944A > C | c.A944C | D315A | p.(Asp315Ala) |
| c.944A > G | c.A944G | D315G | p.(Asp315Gly) |
| c.943G > C | c.G943C | D315H | p.(Asp315His) |
| c.943G > A | c.G943A | D315N | p.(Asp315Asn) |
| c.944A > T | c.A944T | D315V | p.(Asp315Val) |
| c.943G > T | c.G943T | D315Y | p.(Asp315Tyr) |
| c.947T > C | c.T947C | V316A | p.(Val316Ala) |
| c.946G > C | c.G946C | V316L | p.(Val316Leu) |
| c.949A > C | c.A949C | I317L | p.(Ile317Leu) |
| c.951T > G | c.T951G | I317M | p.(Ile317Met) |
| c.949A > G | c.A949G | I317V | p.(Ile317Val) |
| c.953C > A | c.C953A | A318D | p.(Ala318Asp) |
| c.952G > C | c.G952C | A318P | p.(Ala318Pro) |
| c.952G > A | c.G952A | A318T | p.(Ala318Thr) |
| c.953C > T | c.C953T | A318V | p.(Ala318Val) |
| c.957C > G | c.C957G | I319M | p.(Ile319Met) |
| c.959A > G | c.A959G | N320S | p.(Asn320Ser) |
| c.959A > C | c.A959C | N320T | p.(Asn320Thr) |
| c.961C > A | c.C961A | Q321K | p.(Gln321Lys) |
| c.965A > C | c.A965C | D322A | p.(Asp322Ala) |
| c.965A > T | c.A965T | D322V | p.(Asp322Val) |
| c.970T > G | c.T970G | L324V | p.(Leu324Val) |
| c.971T > G | c.T971G | L324W | p.(Leu324Trp) |
| c.974G > C | c.G974C | G325A | p.(Gly325Ala) |
| c.973G > T | c.G973T | G325C | p.(Gly325Cys) |
| c.974G > T | c.G974T | G325V | p.(Gly325Val) |
| c.976A > G | c.A976G | K326E | p.(Lys326Glu) |
| c.977A > T | c.A977T | K326M | p.(Lys326Met) |
| c.976A > C | c.A976C | K326Q | p.(Lys326Gln) |
| c.977A > G | c.A977G | K326R | p.(Lys326Arg) |
| c.977A > C | c.A977C | K326T | p.(Lys326Thr) |
| c.981A > T | c.A981T | Q327H | p.(Gln327His) |
| c.980A > C | c.A980C | Q327P | p.(Gln327Pro) |
| c.986A > G | c.A986G | Y329C | p.(Tyr329Cys) |
| c.985T > G | c.T985G | Y329D | p.(Tyr329Asp) |
| c.986A > T | c.A986T | Y329F | p.(Tyr329Phe) |
| c.985T > C | c.T985C | Y329H | p.(Tyr329His) |
| c.985T > A | c.T985A | Y329N | p.(Tyr329Asn) |
| c.988C > G | c.C988G | Q330E | p.(Gln330Glu) |
| c.990G > C | c.G990C | Q330H | p.(Gln330His) |
| c.988C > A | c.C988A | Q330K | p.(Gln330Lys) |
| c.992T > A | c.T992A | L331H | p.(Leu331His) |
| c.992T > C | c.T992C | L331P | p.(Leu331Pro) |
| c.992T > G | c.T992G | L331R | p.(Leu331Arg) |
| c.991C > G | c.C991G | L331V | p.(Leu331Val) |
| c.994A > G | c.A994G | R332G | p.(Arg332Gly) |
| c.995G > T | c.G995T | R332I | p.(Arg332Ile) |
| c.996A > T | c.A996T | R332S | p.(Arg332Ser) |
| c.995G > C | c.G995C | R332T | p.(Arg332Thr) |
| c.997C > G | c.C997G | Q333E | p.(Gln333Glu) |
| c.998A > T | c.A998T | Q333L | p.(Gln333Leu) |
| c.998A > C | c.A998C | Q333P | p.(Gln333Pro) |
| c.1000G > C | c.G1000C | G334R | p.(Gly334Arg) |
| c.1001G > T | c.G1001T | G334V | p.(Gly334Val) |
| c.1004A > C | c.A1004C | D335A | p.(Asp335Ala) |
| c.1005C > G | c.C1005G | D335E | p.(Asp335Glu) |
| c.1004A > G | c.A1004G | D335G | p.(Asp335Gly) |
| c.1004A > T | c.A1004T | D335V | p.(Asp335Val) |
| c.1003G > T | c.G1003T | D335Y | p.(Asp335Tyr) |
| c.1006A > G | c.A1006G | N336D | p.(Asn336Asp) |
| c.1007A > T | c.A1007T | N336I | p.(Asn336Ile) |
| c.1007A > G | c.A1007G | N336S | p.(Asn336Ser) |
| c.1007A > C | c.A1007C | N336T | p.(Asn336Thr) |
| c.1006A > T | c.A1006T | N336Y | p.(Asn336Tyr) |

TABLE 2-continued

| Nucleotide change | Nucleotide change | Protein change (1 Letter) | Protein Change (3 Letter) |
|---|---|---|---|
| c.1010T > G | c.T1010G | F337C | p.(Phe337Cys) |
| c.1011T > A | c.T1011A | F337L | p.(Phe337Leu) |
| c.1009T > G | c.T1009G | F337V | p.(Phe337Val) |
| c.1010T > A | c.T1010A | F337Y | p.(Phe337Tyr) |
| c.1013A > C | c.A1013C | E338A | p.(Glu338Ala) |
| c.1014A > T | c.A1014T | E338D | p.(Glu338Asp) |
| c.1013A > G | c.A1013G | E338G | p.(Glu338Gly) |
| c.1015G > A | c.G1015A | V339M | p.(Val339Met) |
| c.1022A > C | c.A1022C | E341A | p.(Glu341Ala) |
| c.1021G > C | c.G1021C | E341Q | p.(Glu341Gln) |
| c.1027C > G | c.C1027G | P343A | p.(Pro343Ala) |
| c.1027C > T | c.C1027T | P343S | p.(Pro343Ser) |
| c.1030C > T | c.C1030T | L344F | p.(Leu344Phe) |
| c.1031T > G | c.T1031G | L344R | p.(Leu344Arg) |
| c.1030C > G | c.C1030G | L344V | p.(Leu344Val) |
| c.1037G > C | c.G1037C | G346A | p.(Gly346Ala) |
| c.1036G > T | c.G1036T | G346C | p.(Gly346Cys) |
| c.1037G > A | c.G1037A | G346D | p.(Gly346Asp) |
| c.1037G > T | c.G1037T | G346V | p.(Gly346Val) |
| c.1039T > A | c.T1039A | L347I | p.(Leu347Ile) |
| c.1043C > A | c.C1043A | A348D | p.(Ala348Asp) |
| c.1047G > C | c.G1047C | W349C | p.(Trp349Cys) |
| c.1046G > T | c.G1046T | W349L | p.(Trp349Leu) |
| c.1049C > G | c.C1049G | A350G | p.(Ala350Gly) |
| c.1048G > T | c.G1048T | A350S | p.(Ala350Ser) |
| c.1048G > A | c.G1048A | A350T | p.(Ala350Thr) |
| c.1049C > T | c.C1049T | A350V | p.(Ala350Val) |
| c.1052T > C | c.T1052C | V351A | p.(Val351Ala) |
| c.1052T > A | c.T1052A | V351E | p.(Val351Glu) |
| c.1054G > T | c.G1054T | A352S | p.(Ala352Ser) |
| c.1054G > A | c.G1054A | A352T | p.(Ala352Thr) |
| c.1058T > A | c.T1058A | M353K | p.(Met353Lys) |
| c.1057A > T | c.A1057T | M353L | p.(Met353Leu) |
| c.1058T > C | c.T1058C | M353T | p.(Met353Thr) |
| c.1061T > G | c.T1061G | I354R | p.(Ile354Arg) |
| c.1063A > G | c.A1063G | N355D | p.(Asn355Asp) |
| c.1063A > C | c.A1063C | N355H | p.(Asn355His) |
| c.1064A > G | c.A1064G | N355S | p.(Asn355Ser) |
| c.1063A > T | c.A1063T | N355Y | p.(Asn355Tyr) |
| c.1067G > T | c.G1067T | R356L | p.(Arg356Leu) |
| c.1069C > G | c.C1069G | Q357E | p.(Gln357Glu) |
| c.1075A > T | c.A1075T | I359F | p.(Ile359Phe) |
| c.1075A > C | c.A1075C | I359L | p.(Ile359Leu) |
| c.1076T > A | c.T1076A | I359N | p.(Ile359Asn) |
| c.1076T > G | c.T1076G | I359S | p.(Ile359Ser) |
| c.1075A > G | c.A1075G | I359V | p.(Ile359Val) |
| c.1084C > G | c.C1084G | P362A | p.(Pro362Ala) |
| c.1085C > A | c.C1085A | P362H | p.(Pro362His) |
| c.1085C > G | c.C1085G | P362R | p.(Pro362Arg) |
| c.1084C > T | c.C1084T | P362S | p.(Pro362Ser) |
| c.1087C > G | c.C1087G | R363G | p.(Arg363Gly) |
| c.1088G > T | c.G1088T | R363L | p.(Arg363Leu) |
| c.1087C > A | c.C1087A | R363S | p.(Arg363Ser) |
| c.1091C > G | c.C1091G | S364C | p.(Ser364Cys) |
| c.1090T > C | c.T1090C | S364P | p.(Ser364Pro) |
| c.1093T > G | c.T1093G | Y365D | p.(Tyr365Asp) |
| c.1094A > T | c.A1094T | Y365F | p.(Tyr365Phe) |
| c.1093T > A | c.T1093A | Y365N | p.(Tyr365Asn) |
| c.1094A > C | c.A1094C | Y365S | p.(Tyr365Ser) |
| c.1097C > T | c.C1097T | T366I | p.(Thr366Ile) |
| c.1097C > A | c.C1097A | T366N | p.(Thr366Asn) |
| c.1096A > C | c.A1096C | T366P | p.(Thr366Pro) |
| c.1096A > T | c.A1096T | T366S | p.(Thr366Ser) |
| c.1099A > T | c.A1099T | I367F | p.(Ile367Phe) |
| c.1099A > C | c.A1099C | I367L | p.(Ile367Leu) |
| c.1101C > G | c.C1101G | I367M | p.(Ile367Met) |
| c.1103C > G | c.C1103G | A368G | p.(Ala368Gly) |
| c.1102G > C | c.G1102C | A368P | p.(Ala368Pro) |
| c.1106T > C | c.T1106C | V369A | p.(Val369Ala) |
| c.1105G > T | c.G1105T | V369F | p.(Val369Phe) |
| c.1106T > G | c.T1106G | V369G | p.(Val369Gly) |
| c.1105G > A | c.G1105A | V369I | p.(Val369Ile) |
| c.1105G > C | c.G1105C | V369L | p.(Val369Leu) |
| c.1109C > A | c.C1109A | A370D | p.(Ala370Asp) |
| c.1109C > G | c.C1109G | A370G | p.(Ala370Gly) |
| c.1108G > C | c.G1108C | A370P | p.(Ala370Pro) |
| c.1108G > A | c.G1108A | A370T | p.(Ala370Thr) |

TABLE 2-continued

| Nucleotide change | Nucleotide change | Protein change (1 Letter) | Protein Change (3 Letter) |
|---|---|---|---|
| c.1109C > T | c.C1109T | A370V | p.(Ala370Val) |
| c.1112C > G | c.C1112G | S371C | p.(Ser371Cys) |
| c.1111T > A | c.T1111A | S371T | p.(Ser371Thr) |
| c.1118G > C | c.G1118C | G373A | p.(Gly373Ala) |
| c.1117G > T | c.G1117T | G373C | p.(Gly373Cys) |
| c.1120A > G | c.A1120G | K374E | p.(Lys374Glu) |
| c.1121A > T | c.A1121T | K374I | p.(Lys374Ile) |
| c.1121A > G | c.A1121G | K374R | p.(Lys374Arg) |
| c.1121A > C | c.A1121C | K374T | p.(Lys374Thr) |
| c.1123G > C | c.G1123C | G375R | p.(Gly375Arg) |
| c.1127T > A | c.T1127A | V376E | p.(Val376Glu) |
| c.1127T > G | c.T1127G | V376G | p.(Val376Gly) |
| c.1126G > C | c.G1126C | V376L | p.(Val376Leu) |
| c.1126G > A | c.G1126A | V376M | p.(Val376Met) |
| c.1130C > G | c.C1130G | A377G | p.(Ala377Gly) |
| c.1129G > C | c.G1129C | A377P | p.(Ala377Pro) |
| c.1129G > T | c.G1129T | A377S | p.(Ala377Ser) |
| c.1129G > A | c.G1129A | A377T | p.(Ala377Thr) |
| c.1135A > G | c.A1135G | N379D | p.(Asn379Asp) |
| c.1136A > T | c.A1136T | N379I | p.(Asn379Ile) |
| c.1137T > A | c.T1137A | N379K | p.(Asn379Lys) |
| c.1136A > C | c.A1136C | N379T | p.(Asn379Thr) |
| c.1138C > G | c.C1138G | P380A | p.(Pro380Ala) |
| c.1139C > A | c.C1139A | P380H | p.(Pro380His) |
| c.1139C > G | c.C1139G | P380R | p.(Pro380Arg) |
| c.1138C > A | c.C1138A | P380T | p.(Pro380Thr) |
| c.1142C > A | c.C1142A | A381D | p.(Ala381Asp) |
| c.1148T > G | c.T1148G | F383C | p.(Phe383Cys) |
| c.1147T > A | c.T1147A | F383I | p.(Phe383Ile) |
| c.1148T > A | c.T1148A | F383Y | p.(Phe383Tyr) |
| c.1150A > T | c.A1150T | I384F | p.(Ile384Phe) |
| c.1152C > G | c.C1152G | I384M | p.(Ile384Met) |
| c.1151T > C | c.T1151C | I384T | p.(Ile384Thr) |
| c.1154C > T | c.C1154T | T385I | p.(Thr385Ile) |
| c.1158G > C | c.G1158C | Q386H | p.(Gln386His) |
| c.1156C > A | c.C1156A | Q386K | p.(Gln386Lys) |
| c.1157A > T | c.A1157T | Q386L | p.(Gln386Leu) |
| c.1159C > T | c.C1159T | L387F | p.(Leu387Phe) |
| c.1160T > A | c.T1160A | L387H | p.(Leu387His) |
| c.1159C > A | c.C1159A | L387I | p.(Leu387Ile) |
| c.1160T > G | c.T1160G | L387R | p.(Leu387Arg) |
| c.1162C > T | c.C1162T | L388F | p.(Leu388Phe) |
| c.1163T > A | c.T1163A | L388H | p.(Leu388His) |
| c.1162C > A | c.C1162A | L388I | p.(Leu388Ile) |
| c.1163T > G | c.T1163G | L388R | p.(Leu388Arg) |
| c.1162C > G | c.C1162G | L388V | p.(Leu388Val) |
| c.1172A > T | c.A1172T | K391I | p.(Lys391Ile) |
| c.1173A > T | c.A1173T | K391N | p.(Lys391Asn) |
| c.1171A > C | c.A1171C | K391Q | p.(Lys391Gln) |
| c.1172A > G | c.A1172G | K391R | p.(Lys391Arg) |
| c.1174A > G | c.A1174G | R392G | p.(Arg392Gly) |
| c.1175G > A | c.G1175A | R392K | p.(Arg392Lys) |
| c.1175G > T | c.G1175T | R392M | p.(Arg392Met) |
| c.1174A > T | c.A1174T | R392W | p.(Arg392Trp) |
| c.1177A > G | c.A1177G | K393E | p.(Lys393Glu) |
| c.1179G > C | c.G1179C | K393N | p.(Lys393Asn) |
| c.1177A > C | c.A1177C | K393Q | p.(Lys393Gln) |
| c.1178A > C | c.A1178C | K393T | p.(Lys393Thr) |
| c.1180C > A | c.C1180A | L394I | p.(Leu394Ile) |
| c.1181T > A | c.T1181A | L394Q | p.(Leu394Gln) |
| c.1181T > G | c.T1181G | L394R | p.(Leu394Arg) |
| c.1183G > C | c.G1183C | G395R | p.(Gly395Arg) |
| c.1187T > G | c.T1187G | F396C | p.(Phe396Cys) |
| c.1186T > A | c.T1186A | F396I | p.(Phe396Ile) |
| c.1188C > G | c.C1188G | F396L | p.(Phe396Leu) |
| c.1186T > G | c.T1186G | F396V | p.(Phe396Val) |
| c.1190A > G | c.A1190G | Y397C | p.(Tyr397Cys) |
| c.1190A > T | c.A1190T | Y397F | p.(Tyr397Phe) |
| c.1189T > C | c.T1189C | Y397H | p.(Tyr397His) |
| c.1189T > A | c.T1189A | Y397N | p.(Tyr397Asn) |
| c.1190A > C | c.A1190C | Y397S | p.(Tyr397Ser) |
| c.1193A > G | c.A1193G | E398G | p.(Glu398Gly) |
| c.1192G > C | c.G1192C | E398Q | p.(Glu398Gln) |
| c.1195T > G | c.T1195G | W399G | p.(Trp399Gly) |
| c.1195T > A | c.T1195A | W399R | p.(Trp399Arg) |
| c.1198A > G | c.A1198G | T400A | p.(Thr400Ala) |
| c.1199C > T | c.C1199T | T400I | p.(Thr400Ile) |

TABLE 2-continued

| Nucleotide change | Nucleotide change | Protein change (1 Letter) | Protein Change (3 Letter) |
|---|---|---|---|
| c.1199C > A | c.C1199A | T400N | p.(Thr400Asn) |
| c.1198A > C | c.A1198C | T400P | p.(Thr400Pro) |
| c.1198A > T | c.A1198T | T400S | p.(Thr400Ser) |
| c.1201T > G | c.T1201G | S401A | p.(Ser401Ala) |
| c.1202C > T | c.C1202T | S401L | p.(Ser401Leu) |
| c.1201T > A | c.T1201A | S401T | p.(Ser401Thr) |
| c.1204A > G | c.A1204G | R402G | p.(Arg402Gly) |
| c.1205G > T | c.G1205T | R402M | p.(Arg402Met) |
| c.1206G > C | c.G1206C | R402S | p.(Arg402Ser) |
| c.1205G > C | c.G1205C | R402T | p.(Arg402Thr) |
| c.1204A > T | c.A1204T | R402W | p.(Arg402Trp) |
| c.1209A > T | c.A1209T | L403F | p.(Leu403Phe) |
| c.1207T > G | c.T1207G | L403V | p.(Leu403Val) |
| c.1210A > G | c.A1210G | R404G | p.(Arg404Gly) |
| c.1211G > T | c.G1211T | R404I | p.(Arg404Ile) |
| c.1211G > A | c.G1211A | R404K | p.(Arg404Lys) |
| c.1212A > T | c.A1212T | R404S | p.(Arg404Ser) |
| c.1211G > C | c.G1211C | R404T | p.(Arg404Thr) |
| c.1213A > G | c.A1213G | S405G | p.(Ser405Gly) |
| c.1216C > G | c.C1216G | H406D | p.(His406Asp) |
| c.1217A > T | c.A1217T | H406L | p.(His406Leu) |
| c.1218C > G | c.C1218G | H406Q | p.(His406Gln) |
| c.1219A > T | c.A1219T | I407L | p.(Ile407Leu) |
| c.1221A > G | c.A1221G | I407M | p.(Ile407Met) |
| c.1220T > C | c.T1220C | I407T | p.(Ile407Thr) |
| c.1222A > G | c.A1222G | N408D | p.(Asn408Asp) |
| c.1222A > C | c.A1222C | N408H | p.(Asn408His) |
| c.1223A > C | c.A1223C | N408T | p.(Asn408Thr) |
| c.1226C > T | c.C1226T | P409L | p.(Pro409Leu) |
| c.1228A > T | c.A1228T | T410S | p.(Thr410Ser) |
| c.1232G > C | c.G1232C | G411A | p.(Gly411Ala) |
| c.1231G > T | c.G1231T | G411C | p.(Gly411Cys) |
| c.1232G > T | c.G1232T | G411V | p.(Gly411Val) |
| c.1234A > G | c.A1234G | T412A | p.(Thr412Ala) |
| c.1235C > T | c.C1235T | T412I | p.(Thr412Ile) |
| c.1234A > T | c.A1234T | T412S | p.(Thr412Ser) |
| c.1237G > T | c.G1237T | V413F | p.(Val413Phe) |
| c.1238T > G | c.T1238G | V413G | p.(Val413Gly) |
| c.1237G > A | c.G1237A | V413I | p.(Val413Ile) |
| c.1242G > C | c.G1242C | L414F | p.(Leu414Phe) |
| c.1240T > G | c.T1240G | L414V | p.(Leu414Val) |
| c.1244T > A | c.T1244A | L415H | p.(Leu415His) |
| c.1243C > A | c.C1243A | L415I | p.(Leu415Ile) |
| c.1246C > G | c.C1246G | Q416E | p.(Gln416Glu) |
| c.1248G > C | c.G1248C | Q416H | p.(Gln416His) |
| c.1247A > T | c.A1247T | Q416L | p.(Gln416Leu) |
| c.1249C > A | c.C1249A | L417I | p.(Leu417Ile) |
| c.1253A > C | c.A1253C | E418A | p.(Glu418Ala) |
| c.1254A > T | c.A1254T | E418D | p.(Glu418Asp) |
| c.1252G > A | c.G1252A | E418K | p.(Glu418Lys) |
| c.1252G > C | c.G1252C | E418Q | p.(Glu418Gln) |
| c.1256A > T | c.A1256T | N419I | p.(Asn419Ile) |
| c.1256A > G | c.A1256G | N419S | p.(Asn419Ser) |
| c.1256A > C | c.A1256C | N419T | p.(Asn419Thr) |
| c.1255A > T | c.A1255T | N419Y | p.(Asn419Tyr) |
| c.1259C > A | c.C1259A | T420K | p.(Thr420Lys) |
| c.1258A > C | c.A1258C | T420P | p.(Thr420Pro) |
| c.1259C > G | c.C1259G | T420R | p.(Thr420Arg) |
| c.1258A > T | c.A1258T | T420S | p.(Thr420Ser) |
| c.1263G > C | c.G1263C | M421I | p.(Met421Ile) |
| c.1262T > A | c.T1262A | M421K | p.(Met421Lys) |
| c.1261A > T | c.A1261T | M421L | p.(Met421Leu) |
| c.1262T > G | c.T1262G | M421R | p.(Met421Arg) |
| c.1262T > C | c.T1262C | M421T | p.(Met421Thr) |
| c.1265A > C | c.A1265C | Q422P | p.(Gln422Pro) |
| c.1269G > C | c.G1269C | M423I | p.(Met423Ile) |
| c.1268T > A | c.T1268A | M423K | p.(Met423Lys) |
| c.1267A > T | c.A1267T | M423L | p.(Met423Leu) |
| c.1268T > C | c.T1268C | M423T | p.(Met423Thr) |
| c.1271C > T | c.C1271T | S424L | p.(Ser424Leu) |
| c.1275A > T | c.A1275T | L425F | p.(Leu425Phe) |
| c.1279G > A | c.G1279A | D427N | p.(Asp427Asn) |
| c.1286T > G | c.T1286G | L429R | p.(Leu429Arg) |

Accordingly, in various embodiments, migalastat is used to treat Fabry disease and/or enhance α-Gal A activity in a patient having a GLA mutation selected from the group consisting of the nucleotide changes presented in Table 2. In various embodiments, these GLA mutations are relative to the nucleic sequence shown in SEQ ID NO: 3.

Further prophetic amenable mutations identified include V22G, A29D, D33H, N34H, G35A, R38S, N53K, N53Y, Q57R, F69L, G80V, Y88C, Y88S, M96V, Q107R, R112L, V124G, H125Y, I133M, I133F, A143V, Y152D, Y152N, D155E, A156S, Q157H, F159C, A160D, D165N, F169I, G171S, L180V, D182G, L189F, T194A, R196T, W204L, W204G, W209R, N215I, Y216S, I219L, N224T, N228D, S238G, I239M, K240N, Q250K, A257V, A257T, P259Q, P259S, G271A, L275V, S276T, N278Y, M290V, M290T, A291S, I303T, I303V, K308E, L310V, N320H, D322H, P323T, Q330P, F337S, E338V, V339A, P343T, E358Q, G360A, G360R, G375A, P380L, K391E, R392T, L394P, N408Y, G411S, T412P, and N419D. These mutations are also presented in Table 3 with their corresponding nucleotide changes.

Accordingly, in one or more embodiments, migalastat is used to treat Fabry disease and/or enhance α-Gal A activity in a patient having an α-Gal A mutation selected from the group consisting of the mutations presented in Table 3. In various embodiments, these α-Gal A mutations are relative to the amino acid sequence shown in SEQ ID NO: 2.

Exemplary nucleotide changes associated with these novel mutations are shown in Table 3 below:

TABLE 3

| Nucleotide change | Protein change (1 Letter) |
|---|---|
| c.65T > G | V22G |
| c.86C > A | A29D |
| c.97G > C | D33H |
| c.100A > C | N34H |
| c.104G > C | G35A |
| c.114G > C | R38S |
| c.159C > G or c.159C > A | N53K |
| c.157A > T | N53Y |
| c.170A > G | Q57R |
| c.207C > A or c.207C > G | F69L |
| c.239G > T | G80V |
| c.263A > G | Y88C |
| c.263A > C | Y88S |
| c.286A > G | M96V |
| c.320A > G | Q107R |
| c.335G > T | R112L |
| c.371T > G | V124G |
| c.373C > T | H125Y |
| c.399T > G | I133M |
| c.397A > T | I133F |
| c.428C > T | A143V |
| c.454T > G | Y152D |
| c.454T > A | Y152N |
| c.465T > A or c.465T > G | D155E |
| c.466G > T | A156S |
| c.471G > C or c.471G > T | Q157H |
| c.476T > G | F159C |
| c.479C > A | A160D |
| c.493G > A | D165N |
| c.505T > A | F169I |
| c.511G > A | G171S |
| c.538T > G | L180V |
| c.545A > G | D182G |
| c.567G > C or c.567G > T | L189F |
| c.580A > G | T194A |
| c.587G > C | R196T |
| c.611G > T | W204L |
| c.610T > G | W204G |
| c.625T > A | W209R |
| c.644A > T | N215I |
| c.647A > C | Y216S |
| c.655A > C | I219L |
| c.671A > C | N224T |
| c.682A > G | N228D |

TABLE 3-continued

| Nucleotide change | Protein change (1 Letter) |
|---|---|
| c.712A > G | S238G |
| c.717A > G | I239M |
| c.720G > C or c.720G > T | K240N |
| c.748C > A | Q250K |
| c.770C > T | A257V |
| c.769G > A | A257T |
| c.776C > A | P259Q |
| c.775C > T | P259S |
| c.812G > C | G271A |
| c.823C > G | L275V |
| c.827G > C | S276T |
| c.832A > T | N278Y |
| c.868A > G | M290V |
| c.869T > C | M290T |
| c.871G > T | A291S |
| c.908T > C | I303T |
| c.907A > G | I303V |
| c.922A > G | K308E |
| c.928C > G | L310V |
| c.958A > C | N320H |
| c.964G > C | D322H |
| c.967C > A | P323T |
| c.989A > C | Q330P |
| c.1010T > C | F337S |
| c.1013A > T | E338V |
| c.1016T > C | V339A |
| c.1027C > A | P343T |
| c.1072G > C | E358Q |
| c.1079G > C | G360A |
| c.1078G > C | G360R |
| c.1124G > C | G375A |
| c.1139C > T | P380L |
| c.1171A > G | K391E |
| c.1175G > C | R392T |
| c.1181T > C | L394P |
| c.1222A > T | N408Y |
| c.1231G > A | G411S |
| c.1234A > C | T412P |
| c.1255A > G | N419D |

Accordingly, in various embodiments, migalastat is used to treat Fabry disease and/or enhance α-Gal A activity in a patient having a GLA mutation selected from the group consisting of the nucleotide changes presented in Table 3. In various embodiments, these GLA mutations are relative to the nucleic sequence shown in SEQ ID NO: 3.

While the amenable mutations presented in Table 2 and Table 3 were initially prophetic amenable mutations evaluated by HEK assay, later-identified patients have since presented with several of these mutations. Accordingly, the mutations listed in Table 4 are now patient-associated amenable mutations, thus confirming that the prophetic mutations described herein may later present in patients and that such patients can be treated with migalastat.

TABLE 4

| Nucleotide change | Protein change (1 Letter) |
|---|---|
| c.23T > A | L8Q |
| c.65T > G | V22G |
| c.86C > A | A29D |
| c.97G > C | D33H |
| c.100A > C | N34H |
| c.104G > C | G35A |
| c.114G > C | R38S |
| c.159C > G or c.159C > A | N53K |
| c.157A > T | N53Y |
| c.170A > G | Q57R |
| c.207C > A or c.207C > G | F69L |
| c.239G > T | G80V |

TABLE 4-continued

| Nucleotide change | Protein change (1 Letter) |
|---|---|
| c.263A > G | Y88C |
| c.263A > C | Y88S |
| c.286A > G | M96V |
| c.320A > G | Q107R |
| c.335G > T | R112L |
| c.371T > G | V124G |
| c.373C > T | H125Y |
| c.399T > G | I133M |
| c.397A > T | I133F |
| c.428C > T | A143V |
| c.454T > G | Y152D |
| c.454T > A | Y152N |
| c.455A > C | Y152S |
| c.465T > A or c.465T > G | D155E |
| c.466G > T | A156S |
| c.471G > C or c.471G > T | Q157H |
| c.476T > G | F159C |
| c.479C > A | A160D |
| c.493G > A | D165N |
| c.505T > A | F169I |
| c.511G > A | G171S |
| c.538T > G | L180V |
| c.545A > G | D182G |
| c.551A > C | Y184S |
| c.567G > C or c.567G > T | L189F |
| c.580A > G | T194A |
| c.587G > C | R196T |
| c.598T > A | Y200N |
| c.611G > T | W204L |
| c.610T > G | W204G |
| c.625T > A | W209R |
| c.644A > T | N215I |
| c.647A > C | Y216S |
| c.655A > C | I219L |
| c.664T > G | Y222D |
| c.671A > C | N224T |
| c.682A > G | N228D |
| c.712A > G | S238G |
| c.717A > G | I239M |
| c.720G > C or c.720G > T | K240N |
| c.748C > A | Q250K |
| c.770C > T | A257V |
| c.769G > A | A257T |
| c.776C > A | P259Q |
| c.775C > T | P259S |
| c.812G > C | G271A |
| c.823C > G | L275V |
| c.827G > C | S276T |
| c.832A > T | N278Y |
| c.868A > G | M290V |
| c.869T > C | M290T |
| c.871G > T | A291S |
| c.908T > C | I303T |
| c.907A > G | I303V |
| c.922A > G | K308E |
| c.928C > G | L310V |
| c.958A > C | N320H |
| c.964G > C | D322H |
| c.967C > A | P323T |
| c.973G > T | G325C |
| c.989A > C | Q330P |
| c.1010T > C | F337S |
| c.1013A > T | E338V |
| c.1016T > C | V339A |
| c.1027C > A | P343T |
| c.1072G > C | E358Q |
| c.1079G > C | G360A |
| c.1078G > C | G360R |
| c.1093T > A | Y365N |
| c.1124G > C | G375A |
| c.1139C > T | P380L |
| c.1162C > T | L388F |
| c.1171A > G | K391E |
| c.1175G > C | R392T |
| c.1181T > C | L394P |
| c.1181T > G | L394R |
| c.1222A > T | N408Y |

TABLE 4-continued

| Nucleotide change | Protein change (1 Letter) |
|---|---|
| c.1231G > A | G411S |
| c.1234A > C | T412P |
| c.1255A > G | N419D |

In addition to the prophetic amenable mutations identified above in Tables 2 and 3, several new mutations have been identified and determined to be mutations that are not amenable to migalastat therapy.

As described above, those mutations which were not found to be HEK assay amenable were labelled as prophetic non-amenable mutations. When multiple different nucleotide changes within a single codon lead to the same amino acid residue substitution on that position, the protein sequence change was listed as a single entry with alternative nucleotide changes.

The prophetic non-amenable mutations identified include Q2E, Q2K, Q2L, Q2P, Q2R, Q2H, L3M, L3Q, L3R, R4G, R4W, R4K, R4T, R4M, R4S, N5I, N5Y, N5H, N5T, N5S, P6A, E7Q, E7A, E7G, L8R, L8V, H9D, H9P, H9N, G11A, C12F, C12W, A13S, A13V, L14R, L14I, A15V, A15S, L16R, L16I, L16F, R17L, F18V, F18Y, L19M, L19V, L19R, A20S, A20T, L21I, L21V, V22D, S23A, S23C, S23Y, S23F, W24L, D25G, D25Y, D25A, D25E, D25V, D25N, I26F, I26L, I26M, I26S, I26T, I26V, P27H, P27R, G28A, G28V, A29S, A29T, R301, R30K, R30S, R30T, A31T, A31E, A31G, A31P, A31S, D33N, N34I, N34Y, R38K, R38T, T39P, P40T, T41P, G43C, W44G, W44L, W44R, W44S, L45Q, W47S, E48G, E48V, R49H, F50I, F50L, F50S, F50V, M51L, C52F, L54I, D55N, C56R, Q57E, Q57H, Q57K, Q57P, E58A, E58G, E58Q, E58D, E58V, D61A, D61G, D61H, D61N, D61Y, S62T, C63F, C63G, C63W, I64F, I64M, I64N, I64S, I64T, E66A, K67R, L68V, L68H, L68P, L68R, F69V, F69C, F69S, M70V, M70T, E71K, M72K, A73P, A73G, E74Q, E74A, L75V, L75H, L751, L75R, M76K, M76L, M761, V77F, V77A, V77G, V77D, S78T, S78A, G80R, W81G, K82Q, D83Y, D83H, G85V, Y86N, Y86S, E87K, E87A, E87V, E87Q, Y88F, L891, C90F, C90G, C90S, I91V, I91N, D92A, D92E, D93A, D93H, C94R, C94W, W95R, M96K, M96R, A97G, P98A, P98S, P98T, Q99H, Q99K, R100G, R100I, R100S, D101N, D101Y, E103A, E103D, E103G, E103K, E103V, G104C, G104R, R105S, Q107P, A108G, A108P, A108S, D109V, P110H, P110S, Q111E, Q111H, Q111R, Q111K, Q111L, Q111P, R112P, F113C, P114A, P114H, P114S, P114T, P114R, H115L, H115P, H115Q, H115R, H115Y, G116W, G116A, G116E, I117F, I117L, I117N, I117V, R118G, R118P, R118S, R118L, R118H, Q119E, Q119H, Q119K, Q119L, Q119P, L120I, L120Q, L120R, A121S, A121D, A121G, N122D, N122H, N122I, N122K, N122S, N122T, N122Y, Y123H, V124L, V124A, V124F, H125Q, S126T, S126R, S126N, K127Q, K127T, K127R, K1271, K127N, G128R, G128V, L129M, L129Q, L129R, K130E, K130T, L131Q, L131I, L131R, G132W, G132V, I133S, Y134N, Y134C, Y134F, A135P, D136G, V137F, G138V, N139D, T141P, T141A, C142S, C142G, C142F, A143S, F1451, G147W, G147V, S1481, F1491, F149V, F149Y, F149L, F149S, G150A, G150R, Y151H, Y151N, Y151F, D153E, D153G, I154F, I154L, I154M, I154N, I154S, I154T, I154V, D155A, D155G, D155N, D155V, D155Y, A156P, Q157R, T158P, F159S, A160P, D161A, D161E, D161G, G163A, G163E, G163R, V164E, L166P, L166R, L167R, K168Q, K168E, K168I, K168T, D170A, D170E, D170Y, Y173D, Y173N, C174F, C174S, C174W, C174Y, D175A, S176G, S176I, S176N, S176T, E178D, E178V, N179D, N179H, N179I, N179K, N179S, N179T, N179Y, A181S, A181E, A181G, D182N, D182H, Y184D, K185R, H186R, M187K, L189M, L189W, A190P, L191R, N192Y, N192I, R193K, R193S, G195A, G195D, S197R, I198F, I198L, I198N, I198V, Y200D, Y200F, Y200H, C202F, C202G, C202S, P205A, P205H, Y207D, Y207N, M2081, M208L, M208T, M208V, W209L, W209S, P210A, P210R, F211I, Q212E, Q212K, Q212L, Q212R, K213T, I219V, R220G, Y222F, C223S, C223F, C223W, N224K, N224Y, N224I, H225N, H225Y, H225P, H225L, H225Q, W226G, W226S, W226L, R227L, N228Y, N228K, F229V, F229C, A230S, D231H, D231Y, D231A, D231E, I232N, I232F, D233N, D233H, D233Y, D234N, D234H, D234A, D234G, S235P, W236G, W236S, K237E, K237N, K237Q, K237R, K237T, I239K, I239R, I239V, K240Q, K240T, S241G, S241N, S241R, W245R, W245S, T246P, T246S, F2481, F248S, E251A, E251D, R2521, R252K, R252S, I253M, I253L, V2541, V254L, D255G, V256F, V2561, V256A, G258A, G260R, G260V, W262R, W262G, W262S, N263D, N263I, N263K, N263Y, D264E, D264G, P265T, D266G, M267K, L268V, V269G, I270F, I270N, G271R, N272H, N272Y, N272T, N2721, F2731, F273V, F273S, F273C, G274R, G274C, G274D, G274A, L275P, L275R, S276C, S2761, S276R, W277R, W277S, N278H, N278D, N278T, N278S, N278K, Q279L, Q279P, Q280E, Q280P, V2811, T282P, Q283K, M284R, M284K, A285S, L2861, L286R, L286P, W287S, A288T, I289N, I289M, M290R, M290K, A291D, A291V, A292D, P293R, F295L, M296R, M296K, S297P, S297Y, S297A, N298Y, D299A, D299V, D299Y, L300R, H302P, H302Q, H302R, I303L, 1303M, S304G, S304C, S304R, P305A, P305H, P305L, P305R, P305S, P305T, Q306H, Q306K, Q306R, K308T, A309G, A309S, L310H, L310P, L311H, D313H, D313N, D313A, K314Q, K314R, D315E, A318G, A318S, 1319S, I319L, I319V, 1319N, N320D, Q321P, D322Y, D322G, P323A, P323H, P323L, P323S, L324M, L324F, L324S, Q327R, Y329S, Q330L, L3311, L331F, R332K, Q333H, Q333K, G334A, D335H, D335N, N336H, N336K, F3371, E338Q, V339L, W340G, W340L, W340S, W340C, E341V, E341G, P343R, P343H, L3441, L344H, S345L, S345T, S345A, G346S, G346R, L347V, L347S, L347F, A348T, A348S, A348G, A348V, W349G, A350D, V3511, V351L, V351G, M3531, M353V, M353R, I354M, I354L, I354V, I354T, N355I, N355T, Q357L, Q357P, Q357H, Q357R, Q357K, E358V, I359M, G360V, G361V, S364T, S364A, S364Y, S364F, Y365C, Y365H, T366A, I367V, I367N, I367T, I367S, A368S, A368E, A368V, V369D, A370S, S371A, S371F, S371P, S371Y, L372M, L372V, G373V, K374N, K374Q, G375V, V376A, A377V, C378F, C378G, C378W, N379H, N379S, N379Y, P380S, A381P, A381S, A381T, A381G, A381V, C382F, C382G, C382S, F383L, F383S, F383V, I384L, I384S, I384V, T385K, T385R, T385S, Q386E, Q386R, L387P, L387V, P389H, P389S, P389T, V390A, V390E, V390G, V390L, R392S, K393M, K393R, L394V, G395V, G395W, F396S, Y397D, E398D, E398V, W399C, W399L, S401P, R402K, L4031, S405C, S4051, S405N, S405T, H406N, H406P, H406Y, N408I, N408K, N408S, P409H, P409R, T410R, G411R, V413A, V413D, V413L, L414M, L414W, L415R, L415V, Q416K, Q416R, L417Q, L417V, E418V, N419H, N419K, T420A, T4201, Q422E, Q422H, Q422K, Q422L, Q422R, M423R, M423V, S424A, S424P, S424T, L4251, L425S, L425V, K426E, K426Q, K426T, K4261, K426N, K426R, D427A, D427H, D427Y, D427E, D427G, D427V, L428F, L428S, L4281, L428V, L4291, L429V, L429F, L429H, and L429P.

These mutations are also presented in Table 5 with their corresponding nucleotide changes.

Exemplary nucleotide changes associated with these novel mutations are shown in Table 5 below:

TABLE 5

| Nucleotide change | Protein change (1 Letter) |
|---|---|
| c.4C > G | Q2E |
| c.4C > A | Q2K |
| c.5A > T | Q2L |
| c.5A > C | Q2P |
| c.5A > G | Q2R |
| c.6G > C | Q2H |
| c.7C > A | L3M |
| c.8T > A | L3Q |
| c.8T > G | L3R |
| c.10A > G | R4G |
| c.10A > T | R4W |
| c.11G > A | R4K |
| c.11G > C | R4T |
| c.11G > T | R4M |
| c.12G > C | R4S |
| c.14A > T | N5I |
| c.13A > T | N5Y |
| c.13A > C | N5H |
| c.14A > C | N5T |
| c.14A > G | N5S |
| c.16C > G | P6A |
| c.19G > C | E7Q |
| c.20A > C | E7A |
| c.20A > G | E7G |
| c.23T > G | L8R |
| c.22C > G | L8V |
| c.25C > G | H9D |
| c.26A > C | H9P |
| c.25C > A | H9N |
| c.32G > C | G11A |
| c.35G > T | C12F |
| c.36C > G | C12W |
| c.37G > T | A13S |
| c.38C > T | A13V |
| c.41T > G | L14R |
| c.40C > A | L14I |
| c.44C > T | A15V |
| c.43G > T | A15S |
| c.47T > G | L16R |
| c.46C > A | L16I |
| c.46C > T | L16F |
| c.50G > T | R17L |
| c.52T > G | F18V |
| c.53T > A | F18Y |
| c.55C > A | L19M |
| c.55C > G | L19V |
| c.56T > G | L19R |
| c.58G > T | A20S |
| c.58G > A | A20T |
| c.61C > A | L21I |
| c.61C > G | L21V |
| c.65T > A | V22D |
| c.67T > G | S23A |
| c.68C > G | S23C |
| c.68C > A | S23Y |
| c.68C > T | S23F |
| c.71G > T | W24L |
| c.74A > G | D25G |
| c.73G > T | D25Y |
| c.74A > C | D25A |
| c.75C > G | D25E |
| c.74A > T | D25V |
| c.73G > A | D25N |
| c.76A > T | I26F |
| c.76A > C | I26L |
| c.78C > G | I26M |
| c.77T > G | I26S |
| c.77T > C | I26T |
| c.76A > G | I26V |
| c.80C > A | P27H |
| c.80C > G | P27R |

TABLE 5-continued

| Nucleotide change | Protein change (1 Letter) |
|---|---|
| c.83G > C | G28A |
| c.83G > T | G28V |
| c.85G > T | A29S |
| c.85G > A | A29T |
| c.89G > T | R30I |
| c.89G > A | R30K |
| c.90A > T | R30S |
| c.89G > C | R30T |
| c.91G > A | A31T |
| c.92C > A | A31E |
| c.92C > G | A31G |
| c.91G > C | A31P |
| c.91G > T | A31S |
| c.97G > A | D33N |
| c.101A > T | N34I |
| c.100A > T | N34Y |
| c.113G > A | R38K |
| c.113G > C | R38T |
| c.115A > C | T39P |
| c.118C > A | P40T |
| c.121A > C | T41P |
| c.127G > T | G43C |
| c.130T > G | W44G |
| c.131G > T | W44L |
| c.130T > A | W44R |
| c.131G > C | W44S |
| c.134T > A | L45Q |
| c.140G > C | W47S |
| c.143A > G | E48G |
| c.143A > T | E48V |
| c.146G > A | R49H |
| c.148T > A | F50I |
| c.148T > C or c.150C > G or c.150C > A | F50L |
| c.149T > C | F50S |
| c.148T > G | F50V |
| c.151A > T | M51L |
| c.155G > T | C52F |
| c.160C > A | L54I |
| c.163G > A | D55N |
| c.166T > C | C56R |
| c.169C > G | Q57E |
| c.171G > C | Q57H |
| c.169C > A | Q57K |
| c.170A > C | Q57P |
| c.173A > C | E58A |
| c.173A > G | E58G |
| c.172G > C | E58Q |
| c.174A > T | E58D |
| c.173A > T | E58V |
| c.182A > C | D61A |
| c.182A > G | D61G |
| c.181G > C | D61H |
| c.181G > A | D61N |
| c.181G > T | D61Y |
| c.184T > A | S62T |
| c.188G > T | C63F |
| c.187T > G | C63G |
| c.189C > G | C63W |
| c.190A > T | I64F |
| c.192C > G | I64M |
| c.191T > A | I64N |
| c.191T > G | I64S |
| c.191T > C | I64T |
| c.197A > C | E66A |
| c.200A > G | K67R |
| c.202C > G | L68V |
| c.203T > A | L68H |
| c.203T > C | L68P |
| c.203T > G | L68R |
| c.205T > G | F69V |
| c.206T > G | F69C |
| c.206T > C | F69S |
| c.208A > G | M70V |
| c.209T > C | M70T |
| c.211G > A | E71K |
| c.215T > A | M72K |
| c.217G > C | A73P |

TABLE 5-continued

| Nucleotide change | Protein change (1 Letter) |
|---|---|
| c.218C > G | A73G |
| c.220G > C | E74Q |
| c.221A > C | E74A |
| c.223C > G | L75V |
| c.224T > A | L75H |
| c.223C > A | L75I |
| c.224T > G | L75R |
| c.227T > A | M76K |
| c.226A > T | M76L |
| c.228G > C or c.228G > A or c.228G > T | M76I |
| c.229G > T | V77F |
| c.230T > C | V77A |
| c.230T > G | V77G |
| c.230T > A | V77D |
| c.232T > A | S78T |
| c.232T > G | S78A |
| c.238G > C | G80R |
| c.241T > G | W81G |
| c.244A > C | K82Q |
| c.247G > T | D83Y |
| c.247G > C | D83H |
| c.254G > T | G85V |
| c.256T > A | Y86N |
| c.257A > C | Y86S |
| c.259G > A | E87K |
| c.260A > C | E87A |
| c.260A > T | E87V |
| c.259G > C | E87Q |
| c.263A > T | Y88F |
| c.265C > A | L89I |
| c.269G > T | C90F |
| c.268T > G | C90G |
| c.268T > A | C90S |
| c.271A > G | I91V |
| c.272T > A | I91N |
| c.275A > C | D92A |
| c.276T > A | D92E |
| c.278A > C | D93A |
| c.277G > C | D93H |
| c.280T > C | C94R |
| c.282T > G | C94W |
| c.283T > A | W95R |
| c.287T > A | M96K |
| c.287T > G | M96R |
| c.290C > G | A97G |
| c.292C > G | P98A |
| c.292C > T | P98S |
| c.292C > A | P98T |
| c.297A > T | Q99H |
| c.295C > A | Q99K |
| c.298A > G | R100G |
| c.299G > T | R100I |
| c.300A > T | R100S |
| c.301G > A | D101N |
| c.301G > T | D101Y |
| c.308A > C | E103A |
| c.309A > T | E103D |
| c.308A > G | E103G |
| c.307G > A | E103K |
| c.308A > T | E103V |
| c.310G > T | G104C |
| c.310G > C | G104R |
| c.315A > T | R105S |
| c.320A > C | Q107P |
| c.323C > G | A108G |
| c.322G > C | A108P |
| c.322G > T | A108S |
| c.326A > T | D109V |
| c.329C > A | P110H |
| c.328C > T | P110S |
| c.331C > G | Q111E |
| c.333G > C | Q111H |
| c.332A > G | Q111R |
| c.331C > A | Q111K |
| c.332A > T | Q111L |
| c.332A > C | Q111P |
| c.335G > C | R112P |

TABLE 5-continued

| Nucleotide change | Protein change (1 Letter) |
|---|---|
| c.338T > G | F113C |
| c.340C > G | P114A |
| c.341C > A | P114H |
| c.340C > T | P114S |
| c.340C > A | P114T |
| c.341C > G | P114R |
| c.344A > T | H115L |
| c.344A > C | H115P |
| c.345T > A | H115Q |
| c.344A > G | H115R |
| c.343C > T | H115Y |
| c.346G > T | G116W |
| c.347G > C | G116A |
| c.347G > A | G116E |
| c.349A > T | I117F |
| c.349A > C | I117L |
| c.350T > A | I117N |
| c.349A > G | I117V |
| c.352C > G | R118G |
| c.353G > C | R118P |
| c.352C > A | R118S |
| c.353G > T | R118L |
| c.353G > A | R118H |
| c.355C > G | Q119E |
| c.357G > C | Q119H |
| c.355C > A | Q119K |
| c.356A > T | Q119L |
| c.356A > C | Q119P |
| c.358C > A | L120I |
| c.359T > A | L120Q |
| c.359T > G | L120R |
| c.361G > T | A121S |
| c.362C > A | A121D |
| c.362C > G | A121G |
| c.364A > G | N122D |
| c.364A > C | N122H |
| c.365A > T | N122I |
| c.366T > A | N122K |
| c.365A > G | N122S |
| c.365A > C | N122T |
| c.364A > T | N122Y |
| c.367T > C | Y123H |
| c.370G > C | V124L |
| c.371T > C | V124A |
| c.370G > T | V124F |
| c.375C > G | H125Q |
| c.377G > C | S126T |
| c.378C > G | S126R |
| c.377G > A | S126N |
| c.379A > C | K127Q |
| c.380A > C | K127T |
| c.380A > G | K127R |
| c.380A > T | K127I |
| c.381A > T | K127N |
| c.382G > C | G128R |
| c.383G > T | G128V |
| c.385C > A | L129M |
| c.386T > A | L129Q |
| c.386T > G | L129R |
| c.388A > G | K130E |
| c.389A > C | K130T |
| c.392T > A | L131Q |
| c.391C > A | L131I |
| c.392T > G | L131R |
| c.394G > T | G132W |
| c.395G > T | G132V |
| c.398T > G | I133S |
| c.400T > A | Y134N |
| c.401A > G | Y134C |
| c.401A > T | Y134F |
| c.403G > C | A135P |
| c.407A > G | D136G |
| c.409G > T | V137F |
| c.413G > T | G138V |
| c.415A > G | N139D |
| c.421A > C | T141P |
| c.421A > G | T141A |

TABLE 5-continued

| Nucleotide change | Protein change (1 Letter) |
|---|---|
| c.424T > A | C142S |
| c.424T > G | C142G |
| c.425G > T | C142F |
| c.427G > T | A143S |
| c.433T > A | F145I |
| c.439G > T | G147W |
| c.440G > T | G147V |
| c.443G > T | S148I |
| c.445T > A | F149I |
| c.445T > G | F149V |
| c.446T > A | F149Y |
| c.447T > A | F149L |
| c.446T > C | F149S |
| c.449G > C | G150A |
| c.448G > C | G150R |
| c.451T > C | Y151H |
| c.451T > A | Y151N |
| c.452A > T | Y151F |
| c.459C > G | D153E |
| c.458A > G | D153G |
| c.460A > T | I154F |
| c.460A > C | I154L |
| c.462T > G | I154M |
| c.461T > A | I154N |
| c.461T > G | I154S |
| c.461T > C | I154T |
| c.460A > G | I154V |
| c.464A > C | D155A |
| c.464A > G | D155G |
| c.463G > A | D155N |
| c.464A > T | D155V |
| c.463G > T | D155Y |
| c.466G > C | A156P |
| c.470A > G | Q157R |
| c.472A > C | T158P |
| c.476T > C | F159S |
| c.478G > C | A160P |
| c.482A > C | D161A |
| c.483C > G | D161E |
| c.482A > G | D161G |
| c.488G > C | G163A |
| c.488G > A | G163E |
| c.487G > C | G163R |
| c.491T > A | V164E |
| c.497T > C | L166P |
| c.497T > G | L166R |
| c.500T > G | L167R |
| c.502A > C | K168Q |
| c.502A > G | K168E |
| c.503A > T | K168I |
| c.503A > C | K168T |
| c.509A > C | D170A |
| c.510T > A | D170E |
| c.508G > T | D170Y |
| c.517T > G | Y173D |
| c.517T > A | Y173N |
| c.521G > T | C174F |
| c.520T > A | C174S |
| c.522T > G | C174W |
| c.521G > A | C174Y |
| c.524A > C | D175A |
| c.526A > G | S176G |
| c.527G > T | S176I |
| c.527G > A | S176N |
| c.527G > C | S176T |
| c.534A > T | E178D |
| c.533A > T | E178V |
| c.535A > G | N179D |
| c.535A > C | N179H |
| c.536A > T | N179I |
| c.537T > A | N179K |
| c.536A > G | N179S |
| c.536A > C | N179T |
| c.535A > T | N179Y |
| c.541G > T | A181S |
| c.542C > A | A181E |
| c.542C > G | A181G |

TABLE 5-continued

| Nucleotide change | Protein change (1 Letter) |
|---|---|
| c.544G > A | D182N |
| c.544G > C | D182H |
| c.550T > G | Y184D |
| c.554A > G | K185R |
| c.557A > G | H186R |
| c.560T > A | M187K |
| c.565T > A | L189M |
| c.566T > G | L189W |
| c.568G > C | A190P |
| c.572T > G | L191R |
| c.574A > T | N192Y |
| c.575A > T | N192I |
| c.578G > A | R193K |
| c.579G > C | R193S |
| c.584G > C | G195A |
| c.584G > A | G195D |
| c.589A > G or c.591C > G or c.591C > A | S197R |
| c.592A > T | I198F |
| c.592A > C | I198L |
| c.593T > A | I198N |
| c.592A > G | I198V |
| c.598T > G | Y200D |
| c.599A > T | Y200F |
| c.598T > C | Y200H |
| c.605G > T | C202F |
| c.604T > G | C202G |
| c.604T > A | C202S |
| c.613C > G | P205A |
| c.614C > A | P205H |
| c.619T > G | Y207D |
| c.619T > A | Y207N |
| c.624G > C | M208I |
| c.622A > T | M208L |
| c.623T > C | M208T |
| c.622A > G | M208V |
| c.626G > T | W209L |
| c.626G > C | W209S |
| c.628C > G | P210A |
| c.629C > G | P210R |
| c.631T > A | F211I |
| c.634C > G | Q212E |
| c.634C > A | Q212K |
| c.635A > T | Q212L |
| c.635A > G | Q212R |
| c.638A > C | K213T |
| c.655A > G | I219V |
| c.658C > G | R220G |
| c.665A > T | Y222F |
| c.667T > A or c.668G > C | C223S |
| c.668G > T | C223F |
| c.669C > G | C223W |
| c.672T > A | N224K |
| c.670A > T | N224Y |
| c.671A > T | N224I |
| c.673C > A | H225N |
| c.673C > T | H225Y |
| c.674A > C | H225P |
| c.674A > T | H225L |
| c.675C > G | H225Q |
| c.676T > G | W226G |
| c.677G > C | W226S |
| c.677G > T | W226L |
| c.680G > T | R227L |
| c.682A > T | N228Y |
| c.684T > A | N228K |
| c.685T > G | F229V |
| c.686T > G | F229C |
| c.688G > T | A230S |
| c.691G > C | D231H |
| c.691G > T | D231Y |
| c.692A > C | D231A |
| c.693C > G | D231E |
| c.695T > A | I232N |
| c.694A > T | I232F |
| c.697G > A | D233N |
| c.697G > C | D233H |
| c.697G > T | D233Y |

TABLE 5-continued

| Nucleotide change | Protein change (1 Letter) |
|---|---|
| c.700G > A | D234N |
| c.700G > C | D234H |
| c.701A > C | D234A |
| c.701A > G | D234G |
| c.703T > C | S235P |
| c.706T > G | W236G |
| c.707G > C | W236S |
| c.709A > G | K237E |
| c.711A > T | K237N |
| c.709A > C | K237Q |
| c.710A > G | K237R |
| c.710A > C | K237T |
| c.716T > A | I239K |
| c.716T > G | I239R |
| c.715A > G | I239V |
| c.718A > C | K240Q |
| c.719A > C | K240T |
| c.721A > G | S241G |
| c.722G > A | S241N |
| c.723T > A | S241R |
| c.733T > A | W245R |
| c.734G > C | W245S |
| c.736A > C | T246P |
| c.736A > T | T246S |
| c.742T > A | F248I |
| c.743T > C | F248S |
| c.752A > C | E251A |
| c.753G > C | E251D |
| c.755G > T | R252I |
| c.755G > A | R252K |
| c.756A > T | R252S |
| c.759T > G | I253M |
| c.757A > C | I253L |
| c.760G > A | V254I |
| c.760G > C | V254L |
| c.764A > G | D255G |
| c.766G > T | V256F |
| c.766G > A | V256I |
| c.767T > C | V256A |
| c.773G > C | G258A |
| c.778G > C or c.778G > A | G260R |
| c.779G > T | G260V |
| c.784T > A or c.784T > C | W262R |
| c.784T > G | W262G |
| c.785G > C | W262S |
| c.787A > G | N263D |
| c.788A > T | N263I |
| c.789T > A or c.789T > G | N263K |
| c.787A > T | N263Y |
| c.792C > G | D264E |
| c.791A > G | D264G |
| c.793C > A | P265T |
| c.797A > G | D266G |
| c.800T > A | M267K |
| c.802T > G | L268V |
| c.806T > G | V269G |
| c.808A > T | I270F |
| c.809T > A | I270N |
| c.811G > C | G271R |
| c.814A > C | N272H |
| c.814A > T | N272Y |
| c.815A > C | N272T |
| c.815A > T | N272I |
| c.817T > A | F273I |
| c.817T > G | F273V |
| c.818T > C | F273S |
| c.818T > G | F273C |
| c.820G > C | G274R |
| c.820G > T | G274C |
| c.821G > A | G274D |
| c.821G > C | G274A |
| c.824T > C | L275P |
| c.824T > G | L275R |
| c.826A > T | S276C |
| c.827G > T | S276I |
| c.828C > A or c.828C > G | S276R |
| c.829T > A | W277R |

TABLE 5-continued

| Nucleotide change | Protein change (1 Letter) |
|---|---|
| c.830G > C | W277S |
| c.832A > C | N278H |
| c.832A > G | N278D |
| c.833A > C | N278T |
| c.833A > G | N278S |
| c.834T > G or c.834T > A | N278K |
| c.836A > T | Q279L |
| c.836A > C | Q279P |
| c.838C > G | Q280E |
| c.839A > C | Q280P |
| c.841G > A | V281I |
| c.844A > C | T282P |
| c.847C > A | Q283K |
| c.851T > G | M284R |
| c.851T > A | M284K |
| c.853G > T | A285S |
| c.856C > A | L286I |
| c.857T > G | L286R |
| c.857T > C | L286P |
| c.860G > C | W287S |
| c.862G > A | A288T |
| c.866T > A | I289N |
| c.867C > G | I289M |
| c.869T > G | M290R |
| c.869T > A | M290K |
| c.872C > A | A291D |
| c.872C > T | A291V |
| c.875C > A | A292D |
| c.878C > G | P293R |
| c.885C > G | F295L |
| c.887T > G | M296R |
| c.887T > A | M296K |
| c.889T > C | S297P |
| c.890C > A | S297Y |
| c.889T > G | S297A |
| c.892A > T | N298Y |
| c.896A > C | D299A |
| c.896A > T | D299V |
| c.895G > T | D299Y |
| c.899T > G | L300R |
| c.905A > C | H302P |
| c.906C > G | H302Q |
| c.905A > G | H302R |
| c.907A > C | I303L |
| c.909C > G | I303M |
| c.910A > G | S304G |
| c.910A > T | S304C |
| c.912C > G | S304R |
| c.913C > G | P305A |
| c.914C > A | P305H |
| c.914C > T | P305L |
| c.914C > G | P305R |
| c.913C > T | P305S |
| c.913C > A | P305T |
| c.918A > T | Q306H |
| c.916C > A | Q306K |
| c.917A > G | Q306R |
| c.923A > C | K308T |
| c.926C > G | A309G |
| c.925G > T | A309S |
| c.929T > A | L310H |
| c.929T > C | L310P |
| c.932T > A | L311H |
| c.937G > C | D313H |
| c.937G > A | D313N |
| c.938A > C | D313A |
| c.940A > C | K314Q |
| c.941A > G | K314R |
| c.945C > G | D315E |
| c.953C > G | A318G |
| c.952G > T | A318S |
| c.956T > G | I319S |
| c.955A > C | I319L |
| c.955A > G | I319V |
| c.956T > A | I319N |
| c.958A > G | N320D |
| c.962A > C | Q321P |

TABLE 5-continued

| Nucleotide change | Protein change (1 Letter) |
|---|---|
| c.964G > T | D322Y |
| c.965A > G | D322G |
| c.967C > G | P323A |
| c.968C > A | P323H |
| c.968C > T | P323L |
| c.967C > T | P323S |
| c.970T > A | L324M |
| c.972G > C | L324F |
| c.971T > C | L324S |
| c.980A > G | Q327R |
| c.986A > C | Y329S |
| c.989A > T | Q330L |
| c.991C > A | L331I |
| c.991C > T | L331F |
| c.995G > A | R332K |
| c.999G > C | Q333H |
| c.997C > A | Q333K |
| c.1001G > C | G334A |
| c.1003G > C | D335H |
| c.1003G > A | D335N |
| c.1006A > C | N336H |
| c.1008C > G | N336K |
| c.1009T > A | F337I |
| c.1012G > C | E338Q |
| c.1015G > C | V339L |
| c.1018T > G | W340G |
| c.1019G > T | W340L |
| c.1019G > C | W340S |
| c.1020G > C | W340C |
| c.1022A > T | E341V |
| c.1022A > G | E341G |
| c.1028C > G | P343R |
| c.1028C > A | P343H |
| c.1030C > A | L344I |
| c.1031T > A | L344H |
| c.1034C > T | S345L |
| c.1033T > A | S345T |
| c.1033T > G | S345A |
| c.1036G > A | G346S |
| c.1036G > C | G346R |
| c.1039T > G | L347V |
| c.1040T > C | L347S |
| c.1041A > T | L347F |
| c.1042G > A | A348T |
| c.1042G > T | A348S |
| c.1043C > G | A348G |
| c.1043C > T | A348V |
| c.1045T > G | W349G |
| c.1049C > A | A350D |
| c.1051G > A | V351I |
| c.1051G > C | V351L |
| c.1052T > G | V351G |
| c.1059G > C | M353I |
| c.1057A > G | M353V |
| c.1058T > G | M353R |
| c.1062A > G | I354M |
| c.1060A > T | I354L |
| c.1060A > G | I354V |
| c.1061T > C | I354T |
| c.1064A > T | N355I |
| c.1064A > C | N355T |
| c.1070A > T | Q357L |
| c.1070A > C | Q357P |
| c.1071G > C | Q357H |
| c.1070A > G | Q357R |
| c.1069C > A | Q357K |
| c.1073A > T | E358V |
| c.1077T > G | I359M |
| c.1079G > T | G360V |
| c.1082G > T | G361V |
| c.1090T > A | S364T |
| c.1090T > G | S364A |
| c.1091C > A | S364Y |
| c.1091C > T | S364F |
| c.1094A > G | Y365C |
| c.1093T > C | Y365H |
| c.1096A > G | T366A |

TABLE 5-continued

| Nucleotide change | Protein change (1 Letter) |
|---|---|
| c.1099A > G | I367V |
| c.1100T > A | I367N |
| c.1100T > C | I367T |
| c.1100T > G | I367S |
| c.1102G > T | A368S |
| c.1103C > A | A368E |
| c.1103C > T | A368V |
| c.1106T > A | V369D |
| c.1108G > T | A370S |
| c.1111T > G | S371A |
| c.1112C > T | S371F |
| c.1111T > C | S371P |
| c.1112C > A | S371Y |
| c.1114C > A | L372M |
| c.1114C > G | L372V |
| c.1118G > T | G373V |
| c.1122A > T | K374N |
| c.1120A > C | K374Q |
| c.1124G > T | G375V |
| c.1127T > C | V376A |
| c.1130C > T | A377V |
| c.1133G > T | C378F |
| c.1132T > G | C378G |
| c.1134T > G | C378W |
| c.1135A > C | N379H |
| c.1136A > G | N379S |
| c.1135A > T | N379Y |
| c.1138C > T | P380S |
| c.1141G > C | A381P |
| c.1141G > T | A381S |
| c.1141G > A | A381T |
| c.1142C > G | A381G |
| c.1142C > T | A381V |
| c.1145G > T | C382F |
| c.1144T > G | C382G |
| c.1144T > A | C382S |
| c.1147T > C or c.1149C > G or c.1149C > A | F383L |
| c.1148T > C | F383S |
| c.1147T > G | F383V |
| c.1150A > C | I384L |
| c.1151T > G | I384S |
| c.1150A > G | I384V |
| c.1154C > A | T385K |
| c.1154C > G | T385R |
| c.1153A > T | T385S |
| c.1156C > G | Q386E |
| c.1157A > G | Q386R |
| c.1160T > C | L387P |
| c.1159C > G | L387V |
| c.1166C > A | P389H |
| c.1165C > T | P389S |
| c.1165C > A | P389T |
| c.1169T > C | V390A |
| c.1169T > A | V390E |
| c.1169T > G | V390G |
| c.1168G > C | V390L |
| c.1176G > C | R392S |
| c.1178A > T | K393M |
| c.1178A > G | K393R |
| c.1180C > G | L394V |
| c.1184G > T | G395V |
| c.1183G > T | G395W |
| c.1187T > C | F396S |
| c.1189T > G | Y397D |
| c.1194A > T | E398D |
| c.1193A > T | E398V |
| c.1197G > C | W399C |
| c.1196G > T | W399L |
| c.1201T > C | S401P |
| c.1205G > A | R402K |
| c.1207T > A | L403I |
| c.1213A > T | S405C |
| c.1214G > T | S405I |
| c.1214G > A | S405N |
| c.1214G > C | S405T |
| c.1216C > A | H406N |
| c.1217A > C | H406P |

TABLE 5-continued

| Nucleotide change | Protein change (1 Letter) |
|---|---|
| c.1216C > T | H406Y |
| c.1223A > T | N408I |
| c.1224T > A | N408K |
| c.1223A > G | N408S |
| c.1226C > A | P409H |
| c.1226C > G | P409R |
| c.1229C > G | T410R |
| c.1231G > C | G411R |
| c.1238T > C | V413A |
| c.1238T > A | V413D |
| c.1237G > C | V413L |
| c.1240T > A | L4I4M |
| c.1241T > G | L414W |
| c.1244T > G | L415R |
| c.1243C > G | L415V |
| c.1246C > A | Q416K |
| c.1247A > G | Q416R |
| c.1250T > A | L417Q |
| c.1249C > G | L417V |
| c.1253A > T | E418V |
| c.1255A > C | N419H |
| c.1257T > A | N419K |
| c.1258A > G | T420A |
| c.1259C > T | T420I |
| c.1264C > G | Q422E |
| c.1266G > C | Q422H |
| c.1264C > A | Q422K |
| c.1265A > T | Q422L |
| c.1265A > G | Q422R |
| c.1268T > G | M423R |
| c.1267A > G | M423V |
| c.1270T > G | S424A |
| c.1270T > C | S424P |
| c.1270T > A | S424T |
| c.1273T > A | L425I |
| c.1274T > C | L425S |
| c.1273T > G | L425V |
| c.1276A > G | K426E |
| c.1276A > C | K426Q |
| c.1277A > C | K426T |
| c.1277A > T | K426I |
| c.1278A > T | K426N |
| c.1277A > G | K426R |
| c.1280A > C | D427A |
| c.1279G > C | D427H |
| c.1279G > T | D427Y |
| c.1281C > G | D427E |
| c.1280A > G | D427G |
| c.1280A > T | D427V |
| c.1284A > T | L428F |
| c.1283T > C | L428S |
| c.1282T > A | L428I |
| c.1282T > G | L428V |
| c.1285C > A | L429I |
| c.1285C > G | L429V |
| c.1285C > T | L429F |
| c.1286T > A | L429H |
| c.1286T > C | L429P |

While the non-amenable mutations presented in Table 5 were initially prophetic non-amenable mutations evaluated by HEK assay, later-identified patients have since presented with several of these mutations. Accordingly, the mutations listed in Table 6 are now patient-associated amenable mutations, thus confirming that the prophetic mutations described herein may later present in patients.

TABLE 6

| Nucleotide change | Protein change (1 Letter) |
|---|---|
| c.47T > G | L16R |
| c.146G > A | R49H |

TABLE 6-continued

| Nucleotide change | Protein change (1 Letter) |
|---|---|
| c.148T > C or c.150C > G or c.150C > A | F50L |
| c.155G > T | C52F |
| c.188G > T | C63F |
| c.206T > C | F69S |
| c.208A > G | M70V |
| c.228G > C or c.228G > A or c.228G > T | M76I |
| c.241T > G | W81G |
| c.254G > T | G85V |
| c.338T > G | F113C |
| c.346G > T | G116W |
| c.359T > G | L120R |
| c.383G > T | G128V |
| c.386T > G | L129R |
| c.388A > G | K130E |
| c.389A > C | K130T |
| c.392T > A | L131Q |
| c.409G > T | V137F |
| c.421A > G | T141A |
| c.424T > A | C142S |
| c.440G > T | G147V |
| c.443G > T | S148I |
| c.476T > C | F159S |
| c.478G > C | A160P |
| c.487G > C | G163R |
| c.497T > C | L166P |
| c.502A > C | K168Q |
| c.550T > G | Y184D |
| c.574A > T | N192Y |
| c.605G > T | C202F |
| c.613C > G | P205A |
| c.667T > A or c.668G > C | C223S |
| c.668G > T | C223F |
| c.674A > C | H225P |
| c.676T > G | W226G |
| c.680G > T | R227L |
| c.685T > G | F229V |
| c.691G > T | D231Y |
| c.692A > C | D231A |
| c.700G > A | D234N |
| c.701A > G | D234G |
| c.706T > G | W236G |
| c.743T > C | F248S |
| c.778G > C or c.778G > A | G260R |
| c.784T > A or c.784T > C | W262R |
| c.785G > C | W262S |
| c.787A > G | N263D |
| c.789T > A or c.789T > G | N263K |
| c.793C > A | P265T |
| c.797A > G | D266G |
| c.808A > T | I270F |
| c.815A > C | N272T |
| c.815A > T | N272I |
| c.818T > C | F273S |
| c.820G > C | G274R |
| c.820G > T | G274C |
| c.821G > A | G274D |
| c.826A > T | S276C |
| c.827G > T | S276I |
| c.828C > A or c.828C > G | S276R |
| c.834T > G or c.834T > A | N278K |
| c.857T > C | L286P |
| c.887T > A | M296K |
| c.889T > C | S297P |
| c.890C > A | S297Y |
| c.896A > T | D299V |
| c.929T > C | L310P |
| c.980A > G | Q327R |
| c.1019G > C | W340S |
| c.1022A > G | E341G |
| c.1058T > G | M353R |
| c.1124G > T | G375V |
| c.1133G > T | C378F |
| c.1147T > C or c.1149C > G or c.1149C > A | F383L |
| c.1160T > C | L387P |
| c.1165C > T | P389S |

Furthermore, various embodiments of the present invention provide PCs for the treatment of Fabry disease in a patient having a mutation in the gene encoding α-Gal A, wherein the patient is identified as having a missense mutation in a human α-Gal A encoded by a nucleic acid sequence set forth in SEQ ID NO: 1 and/or SEQ ID NO: 3. Another aspect of the invention pertains a method of treating a patient diagnosed with Fabry disease. In one or more embodiments, the method comprises administering to a patient a therapeutically effective dose of a PC of α-Gal A. In further embodiments, the patient has a missense mutation in the nucleic acid sequence encoding α-Gal A. Another aspect of the invention pertains to a method of enhancing α-Gal A in a patient diagnosed with or suspected of having Fabry disease. In one or more embodiments, the method comprises administering to a patient a therapeutically effective dose of a PC of α-Gal A, wherein the patient has a mutant α-Gal A encoded by a nucleic acid sequence having a missense mutation relative to SEQ ID NO: 1 and/or SEQ ID NO: 3. Details and further embodiments of these uses and methods follows below. Any of the embodiments relating a method of treating a patient with Fabry disease, a method of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease wherein the patient is identified as having a missense mutation in a human α-Gal A encoded by a nucleic acid sequence set forth in SEQ ID NO: 1 and/or SEQ ID NO: 3 can be combined with any of the other embodiments of the invention, for example embodiments relating to the PCs and suitable dosages thereof.

In one or more embodiments, the patient may have other mutations in their GLA gene. For example, there may be mutations in the intron region which may or may not affect the resulting α-Gal A enzyme. Thus, in one or more embodiments, the patient has mutant α-Gal A encoded by a nucleic acid sequence having at least 95, 96, 97, 98, 99, 99.1, 99.2, 99.3, 99.4, 99.5, 99.6, 99.7, 99.8 or 99.9% identity to SEQ ID NO: 1. Furthermore, the patient may have one or more additional mutations in the coding region of the GLA gene. Thus, in one or more embodiments, the patient has mutant α-Gal A encoded by a nucleic acid sequence having at least 95, 96, 97, 98, 99, 99.1, 99.2, 99.3, 99.4, 99.5, 99.6, 99.7, 99.8 or 99.9% identity to SEQ ID NO: 3. Moreover, in one or more embodiments, the patient has 1, 2, 3, 4, 5, 6, 7, 8, 9, 10, 15, 20 or 30 mutations relative to SEQ ID NO: 1 or SEQ ID NO: 3. It is also noted that some nucleic acid mutations in SEQ ID NO: 1 or SEQ ID NO: 3 can result in no change in amino acid for the resulting protein, as various amino acids are encoded by multiple nucleic acid sequences. Again, any of these embodiments can be combined with any of the other embodiments of the invention, for example embodiments relating to amenable mutations, the PCs and suitable dosages thereof.

In various embodiments, a pharmacological reference table is provided that includes one or more of the mutations discloses herein. In one or more embodiments, the pharmacological reference table includes one or more of the mutations from Table 2. In one or more embodiments, the pharmacological reference table includes all of the mutations from Table 2. In one or more embodiments, pharmacological reference table includes one or more of the mutations from Table 1. In one or more embodiments, the pharmacological reference table includes all of the mutations from Table 1. In one or more embodiments, the pharmacological reference table includes one or more of the mutations from Table 1 and one or more of the mutations from Table 2. In one or more embodiments, the pharmacological reference table includes all of the mutations from Table 1 and one or more of the mutations from Table 2. In one or more embodiments, the pharmacological reference table includes one or more of the mutations from Table 1 and all of the mutations from Table 2. In one or more embodiments, the pharmacological reference table includes all of the mutations from Table 1 and all of the mutations from Table 2.

As described above, the pharmacological reference table can be any publicly accessible written or electronic record. In one or more embodiments, the pharmacological reference table is a written record. In one or more embodiments, the pharmacological reference table is provided in a product label for a migalastat product, such as a migalastat product approved by a US or other regulatory agency for the treatment of Fabry disease. In one or more embodiments, the pharmacological reference table is provided in a product label for GALAFOLD®. In one or more embodiments, the pharmacological reference table is an electronic record. In one or more embodiments, the pharmacological reference table is provided at a website. In one or more embodiments, the website is associated with a migalastat product, such as a migalastat product approved by a US or other regulatory agency for the treatment of Fabry disease. In one or more embodiments, the pharmacological reference table is provided at www.galafoldamenabilitytable.com. In one or more embodiments, the pharmacological reference table is provided at www.fabrygenevariantsearch.com.

Various embodiments also relate to a data store including a pharmacological reference table as described herein. Such a data store can include an electronic searching function for determining whether a particular mutation is included in the pharmacological reference table. In one or more embodiments, the data store and optional search function is provided at a website. In one or more embodiments, the data store and optional search function is provided in an electronic storage medium. Examples of such electronic storage media include, but are not limited to, compact discs (CDs), digital versatile discs (DVDs) hard drives and flash drives.

Pharmacological Chaperones

The binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the ER (Ishii et al., *Biochem. Biophys. Res. Comm.* 1996; 220: 812-815), the enzyme protein is retarded in the normal transport pathway (ER→Golgi apparatus→endosomes→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to lysosomes.

In one or more embodiments, the pharmacological chaperone comprises migalastat or a salt thereof. The compound migalastat, also known as 1-deoxygalactonojirimycin (1-DGJ) or (2R,3S,4R,5S)-2-(hydroxymethyl) piperdine-3,4,5-triol is a compound having the following chemical formula:

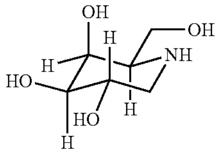

and

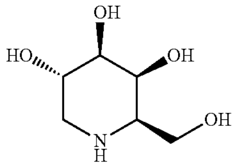

Migalastat free base

As discussed herein, pharmaceutically acceptable salts of migalastat may also be used in the present invention. When a salt of migalastat is used, the dosage of the salt will be adjusted so that the dose of migalastat received by the patient is equivalent to the amount which would have been received had the migalastat free base been used. One example of a pharmaceutically acceptable salt of migalastat is migalastat HCl:

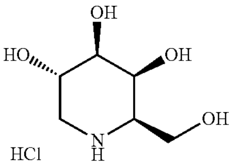

Migalastat HCl

Migalastat is a low molecular weight iminosugar and is an analogue of the terminal galactose of GL-3. In vitro and in vivo pharmacologic studies have demonstrated that migalastat acts as a pharmacological chaperone, selectively and reversibly binding, with high affinity, to the active site of wild-type α-Gal A and specific mutant forms of α-Gal A. Migalastat binding stabilizes these mutant forms of α-Gal A in the endoplasmic reticulum facilitating their proper trafficking to lysosomes where dissociation of migalastat allows α-Gal A to reduce the level of GL-3 and other substrates.

In a specific embodiment, the PC comprises migalastat or salt thereof. In further embodiments, the PC comprises migalastat hydrochloride.

Any of these PCs for α-Gal A may be used in combination with any of the other embodiments of the invention, for example embodiments relating to a method of treating a patient with Fabry disease, a method of enhancing α-Gal A in a patient diagnosed with or suspected of having Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to suitable doses of PCs, amenable mutations and to the treatment of a Fabry patient having certain mutations in the nucleic acid sequence encoding α-Gal A.

Dosing, Formulation and Administration

In one or more embodiments, the Fabry patient is administered migalastat or salt thereof at a frequency of once every other day (also referred to as "QOD"). In various embodiments, the doses described herein pertain to migalastat hydrochloride or an equivalent dose of migalastat or a salt thereof other than the hydrochloride salt. In some embodiments, these doses pertain to the free base of migalastat. In alternate embodiments, these doses pertain to a salt of migalastat. In further embodiments, the salt of migalastat is migalastat hydrochloride. The administration of migalastat or a salt of migalastat is referred to herein as "migalastat therapy".

The effective amount of migalastat or salt thereof can be in the range from about 100 mg FBE to about 150 mg FBE. Exemplary doses include about 100 mg FBE, about 105 mg FBE, about 110 mg FBE, about 115 mg FBE, about 120 mg FBE, about 123 mg FBE, about 125 mg FBE, about 130 mg FBE, about 135 mg FBE, about 140 mg FBE, about 145 mg FBE or about 150 mg FBE.

Again, it is noted that 150 mg of migalastat hydrochloride is equivalent to 123 mg of the free base form of migalastat. Thus, in one or more embodiments, the dose is 150 mg of migalastat hydrochloride or an equivalent dose of migalastat or a salt thereof other than the hydrochloride salt, administered at a frequency of once every other day. As set forth above, this dose is referred to as 123 mg FBE of migalastat. In further embodiments, the dose is 150 mg of migalastat hydrochloride administered at a frequency of once every other day. In other embodiments, the dose is 123 mg of the migalastat free base administered at a frequency of once every other day.

In various embodiments, the effective amount is about 122 mg, about 128 mg, about 134 mg, about 140 mg, about 146 mg, about 150 mg, about 152 mg, about 159 mg, about 165 mg, about 171 mg, about 177 mg or about 183 mg of migalastat hydrochloride.

Accordingly, in various embodiments, migalastat therapy includes administering 123 mg FBE at a frequency of once every other day, such as 150 mg of migalastat hydrochloride every other day.

The administration of migalastat or salt thereof may be for a certain period of time. In one or more embodiments, the migalastat or salt thereof is administered for a duration of at least 28 days, such as at least 30, 60 or 90 days or at least 3, 4, 5, 6, 7, 8, 9, 10, 11, 12, 16, 20, 24, 30 or 36 months or at least 1, 2, 3, 4 or 5 years. In various embodiments, the migalastat therapy is long-term migalastat therapy of at least 6 months, such as at least 6, 7, 8, 9, 10, 11, 12, 16, 20, 24, 30 or 36 months or at least 1, 2, 3, 4 or 5 years.

Administration of migalastat or salt thereof according to the present invention may be in a formulation suitable for any route of administration, but is preferably administered in an oral dosage form such as a tablet, capsule or solution. As one example, the patient is orally administered capsules each containing 150 mg migalastat hydrochloride or an equivalent dose of migalastat or a salt thereof other than the hydrochloride salt.

In some embodiments, the PC (e.g., migalastat or salt thereof) is administered orally. In one or more embodiments, the PC (e.g., migalastat or salt thereof) is administered by injection. The PC may be accompanied by a pharmaceutically acceptable carrier, which may depend on the method of administration.

In one or more embodiments, the PC (e.g., migalastat or salt thereof) is administered as monotherapy, and can be in a form suitable for any route of administration, including e.g., orally in the form tablets or capsules or liquid, or in sterile aqueous solution for injection. In other embodiments, the PC is provided in a dry lyophilized powder to be added to the formulation of the replacement enzyme during or immediately after reconstitution to prevent enzyme aggregation in vitro prior to administration.

When the PC (e.g., migalastat or salt thereof) is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active chaperone compound.

The pharmaceutical formulations of the PC (e.g., migalastat or salt thereof) suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the purified enzyme (if any) and the PC (e.g., migalastat or salt thereof) in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, bicarbonate buffer, amino acids, urea, alcohols, ascorbic acid, and phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The route of administration of the chaperone compound may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the chaperone compound may be by periodic injections of a bolus of the preparation, or may be administered by intravenous or intraperitoneal administration from a reservoir which is external (e.g., an i.v. bag) or internal (e.g., a bioerodable implant).

Embodiments relating to pharmaceutical formulations and administration may be combined with any of the other embodiments of the invention, for example embodiments relating to methods of treating patients with Fabry disease, use of a pharmacological chaperone for α-Gal A for the manufacture of a medicament for treating a patient diagnosed with Fabry disease or to a pharmacological chaperone for α-Gal A for use in treating a patient diagnosed with Fabry disease as well as embodiments relating to amenable mutations, the PCs and suitable dosages thereof.

In one or more embodiments, the PC (e.g., migalastat or salt thereof) is administered in combination with ERT. ERT increases the amount of protein by exogenously introducing wild-type or biologically functional enzyme by way of infusion. This therapy has been developed for many genetic disorders, including LSDs such as Fabry disease, as referenced above. After the infusion, the exogenous enzyme is expected to be taken up by tissues through non-specific or receptor-specific mechanism. In general, the uptake efficiency is not high, and the circulation time of the exogenous protein is short. In addition, the exogenous protein is unstable and subject to rapid intracellular degradation as well as having the potential for adverse immunological reactions with subsequent treatments. In one or more embodiments, the chaperone is administered at the same time as replacement enzyme (e.g., replacement α-Gal A). In some embodiments, the chaperone is co-formulated with the replacement enzyme (e.g., replacement α-Gal A).

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in various embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

Example: Effect of Migalastat on Mutations of α-Gal A

The α-Gal A activity was measured in lysates prepared from HEK-293 cells transiently transfected with the indicated mutant form of α-Gal A and incubated in the absence or presence of 10 μM migalastat for 5 days. The α-Gal A activity is expressed as the nmoles of free 4-MU released per milligram of protein per hour (nmol/mg/hr). Baseline α-Gal A activity and α-Gal A activity after incubation with 10 μM migalastat, were additionally expressed as a percentage of baseline wild-type α-Gal A activity (% WT). The wild-type α-Gal A activity that was used to calculate these percentages was the average activity measured in lysates from wild-type transfected cells, incubated in the absence of migalastat, measured in parallel.

The results of the α-Gal A activity testing for the novel mutations presented in Table 2 is shown in Table 7 below:

TABLE 7

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| N5D | 26578 ± 1944 | 34661 ± 1816 | 0.0017 | 74.9 ± 5.1 | 98.9 ± 5.5 | 24.1 | 1.3 |
| N5K | 22221 ± 753 | 27689 ± 955 | 0.0002 | 58.6 ± 2.6 | 73 ± 3.3 | 14.4 | 1.3 |
| P6L | 18599 ± 1034 | 24229 ± 1870 | 0.0158 | 49.2 ± 3.1 | 63.4 ± 5 | 14.2 | 1.3 |
| P6Q | 17261 ± 825 | 22316 ± 1261 | 0.0013 | 49.4 ± 2.2 | 64.8 ± 4.3 | 15.4 | 1.3 |
| P6R | 24240 ± 1350 | 32919 ± 1593 | 0.0003 | 70.1 ± 4.2 | 94.1 ± 3.6 | 24.0 | 1.4 |
| P6S | 34848 ± 1440 | 43046 ± 1713 | 0.0009 | 82 ± 2.9 | 101.5 ± 3.7 | 19.5 | 1.2 |
| P6T | 30926 ± 1479 | 37354 ± 1577 | 0.0077 | 88.3 ± 3.3 | 108 ± 5.1 | 19.7 | 1.2 |
| E7D | 31325 ± 1280 | 39271 ± 1669 | 0.0005 | 77.6 ± 2.3 | 97.2 ± 3 | 19.6 | 1.3 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| E7K | 18705 ± 801 | 25316 ± 1403 | 0.0001 | 55.2 ± 3.1 | 75.4 ± 5.7 | 20.2 | 1.4 |
| E7V | 25273 ± 1376 | 30825 ± 1805 | 0.0193 | 74.7 ± 2.8 | 91.6 ± 4.3 | 16.9 | 1.2 |
| L8I | 21345 ± 1469 | 26036 ± 1514 | 0.0090 | 67.5 ± 4.2 | 82.4 ± 4.3 | 14.9 | 1.2 |
| L8P | 19934 ± 3444 | 25868 ± 4321 | 0.0028 | 55.1 ± 6.9 | 72.3 ± 8.5 | 17.2 | 1.3 |
| L8Q | 18234 ± 1818 | 22878 ± 1755 | 0.0053 | 57.5 ± 5.4 | 72.3 ± 5.1 | 14.7 | 1.3 |
| H9L | 26490 ± 1295 | 36318 ± 2304 | 0.0003 | 75.9 ± 5.5 | 107.8 ± 11.2 | 31.9 | 1.4 |
| H9Q | 20382 ± 918 | 27072 ± 1062 | 0.0001 | 57.3 ± 2.9 | 78.2 ± 5.6 | 20.9 | 1.3 |
| H9R | 21497 ± 2019 | 27866 ± 1854 | 0.0042 | 56.2 ± 4.2 | 75.2 ± 5.4 | 19.0 | 1.3 |
| H9Y | 27713 ± 2168 | 33834 ± 2369 | 0.0090 | 81.9 ± 8.5 | 101 ± 10 | 19.1 | 1.2 |
| L10M | 19028 ± 958 | 26110 ± 1344 | 0.0001 | 55.1 ± 4.1 | 78.3 ± 6.8 | 23.2 | 1.4 |
| L10P | 21054 ± 1238 | 26571 ± 1812 | 0.0042 | 68.3 ± 3.9 | 85.9 ± 5.5 | 17.5 | 1.3 |
| L10Q | 14594 ± 970 | 20723 ± 1583 | 0.0013 | 47.8 ± 3.3 | 67.3 ± 5.4 | 19.5 | 1.4 |
| L10R | 15760 ± 920 | 24293 ± 2170 | 0.0017 | 51.9 ± 3.3 | 78.9 ± 7.7 | 27.0 | 1.5 |
| L10V | 17475 ± 683 | 23595 ± 1256 | 0.0001 | 49.5 ± 2.6 | 68.8 ± 6.1 | 19.3 | 1.4 |
| G11C | 34393 ± 2207 | 43933 ± 3128 | 0.0049 | 111.9 ± 7.3 | 142.3 ± 10.3 | 30.4 | 1.3 |
| G11D | 13315 ± 1237 | 18851 ± 1704 | 0.0142 | 43.9 ± 4.3 | 61.3 ± 5.8 | 17.3 | 1.4 |
| G11R | 32525 ± 2047 | 41260 ± 3644 | 0.0339 | 105.2 ± 6.1 | 134.3 ± 12.7 | 29.1 | 1.3 |
| G11S | 28169 ± 1641 | 38524 ± 3460 | 0.0072 | 91 ± 4.9 | 122.9 ± 10.8 | 31.9 | 1.4 |
| G11V | 39507 ± 1757 | 49059 ± 1869 | 0.0010 | 121.8 ± 7 | 153 ± 9.2 | 31.3 | 1.2 |
| C12G | 14560 ± 1307 | 21780 ± 2916 | 0.0234 | 44.4 ± 3.1 | 64.7 ± 6.9 | 20.3 | 1.5 |
| C12R | 10869 ± 1110 | 16596 ± 2243 | 0.0128 | 32.9 ± 2.6 | 49.1 ± 5.3 | 16.2 | 1.5 |
| C12S | 15741 ± 1462 | 23071 ± 2829 | 0.0219 | 47.6 ± 3.2 | 68.6 ± 6.4 | 21.0 | 1.5 |
| C12Y | 32218 ± 2218 | 38717 ± 2744 | 0.0339 | 99.8 ± 5.9 | 118.6 ± 7.4 | 18.9 | 1.2 |
| A13E | 16631 ± 1310 | 23633 ± 2424 | 0.0083 | 51.2 ± 3.5 | 71.5 ± 6 | 20.2 | 1.4 |
| A13G | 21739 ± 1693 | 27200 ± 2187 | 0.0360 | 67 ± 4.3 | 83.6 ± 5.5 | 16.6 | 1.3 |
| L14F | 30970 ± 2383 | 38206 ± 2599 | 0.0283 | 97.4 ± 5.3 | 122.1 ± 7.4 | 24.7 | 1.2 |
| L14H | 1316 ± 125 | 3166 ± 428 | 0.0022 | 3.8 ± 0.2 | 8.8 ± 1 | 5.0 | 2.4 |
| L14V | 25550 ± 1778 | 31818 ± 1959 | 0.0249 | 82.5 ± 5.2 | 101.6 ± 5.1 | 19.1 | 1.3 |
| R17C | 33909 ± 1965 | 48618 ± 2267 | 0.0001 | 97.2 ± 5.8 | 140.5 ± 8.4 | 43.3 | 1.4 |
| R17G | 40647 ± 2328 | 50772 ± 2273 | 0.0028 | 117 ± 7.1 | 145.2 ± 6.2 | 28.2 | 1.3 |
| R17H | 32181 ± 2325 | 47769 ± 2358 | 0.0001 | 91.7 ± 6 | 138.1 ± 8.8 | 46.4 | 1.5 |
| R17P | 28074 ± 1526 | 45995 ± 2671 | 0.0001 | 80.6 ± 4.7 | 133.4 ± 9.9 | 52.8 | 1.6 |
| R17S | 28809 ± 1251 | 42089 ± 1807 | 0.0001 | 82.1 ± 3.1 | 121.4 ± 6.6 | 39.4 | 1.5 |
| F18I | 38335 ± 2361 | 49150 ± 2675 | 0.0026 | 113.3 ± 8 | 146.5 ± 10.7 | 33.2 | 1.3 |
| F18L | 22788 ± 1848 | 27677 ± 2429 | 0.0301 | 79.6 ± 3.7 | 97.1 ± 6.6 | 17.5 | 1.2 |
| A20G | 8349 ± 475 | 10555 ± 783 | 0.0067 | 30.2 ± 1.5 | 37.4 ± 2.4 | 7.2 | 1.3 |
| L21H | 17203 ± 1913 | 23891 ± 2271 | 0.0158 | 47.2 ± 4.5 | 66.1 ± 5.8 | 19.0 | 1.4 |
| V22A | 15790 ± 1037 | 22194 ± 2010 | 0.0077 | 43.9 ± 2.5 | 61.2 ± 5.1 | 17.3 | 1.4 |
| V22F | 29970 ± 2021 | 36745 ± 2458 | 0.0339 | 83.5 ± 4.6 | 102.5 ± 5.7 | 19.0 | 1.2 |
| V22I | 27969 ± 1731 | 43104 ± 3250 | 0.0003 | 75.7 ± 4.1 | 116.4 ± 8.5 | 40.7 | 1.5 |
| V22L | 27041 ± 1471 | 38357 ± 3293 | 0.0083 | 74.7 ± 3.6 | 105.8 ± 8.9 | 31.1 | 1.4 |
| S23P | 28512 ± 2197 | 38609 ± 2917 | 0.0067 | 88.2 ± 3.5 | 119.1 ± 5.7 | 31.0 | 1.4 |
| S23T | 32295 ± 2128 | 40230 ± 2181 | 0.0057 | 90.2 ± 5.1 | 112.8 ± 5.4 | 22.6 | 1.3 |
| W24S | 13019 ± 845 | 18420 ± 1212 | 0.0001 | 40 ± 2.5 | 56.7 ± 4 | 16.7 | 1.4 |
| D25H | 30857 ± 1142 | 37503 ± 1794 | 0.0053 | 94.9 ± 3.9 | 115.8 ± 6.5 | 20.9 | 1.2 |
| I26N | 32979 ± 2494 | 44191 ± 5046 | 0.0382 | 75.5 ± 4.2 | 97.3 ± 7.3 | 21.8 | 1.3 |
| P27A | 19346 ± 1192 | 27202 ± 1150 | 0.0001 | 51.9 ± 3.2 | 72.6 ± 2.3 | 20.7 | 1.4 |
| P27L | 26913 ± 1947 | 32775 ± 1415 | 0.0030 | 72.4 ± 5.4 | 90 ± 5.3 | 17.6 | 1.2 |
| P27S | 28366 ± 1590 | 38366 ± 1767 | 0.0003 | 70.4 ± 3.3 | 95.3 ± 3.6 | 24.9 | 1.4 |
| P27T | 26456 ± 954 | 34628 ± 1113 | 0.0001 | 62.4 ± 2.4 | 81.9 ± 3.2 | 19.5 | 1.3 |
| G28E | 27350 ± 1663 | 34034 ± 2028 | 0.0024 | 73.8 ± 4.5 | 91.1 ± 4.6 | 17.2 | 1.2 |
| G28R | 26315 ± 1950 | 32315 ± 1988 | 0.0062 | 71.5 ± 5.7 | 87.6 ± 5.4 | 16.1 | 1.2 |
| G28W | 27378 ± 1600 | 36559 ± 1783 | 0.0003 | 74 ± 4.4 | 97.9 ± 4.2 | 23.9 | 1.3 |
| A29G | 15101 ± 1719 | 18785 ± 1854 | 0.0147 | 44.5 ± 4.2 | 55.1 ± 4.4 | 10.6 | 1.2 |
| A29P | 4738 ± 402 | 6987 ± 388 | 0.0003 | 14 ± 1 | 20.6 ± 0.6 | 6.6 | 1.5 |
| A29V | 18656 ± 1649 | 22884 ± 1713 | 0.0382 | 55.7 ± 4.3 | 68.2 ± 4.4 | 12.5 | 1.2 |
| R30G | 21934 ± 2016 | 27320 ± 1888 | 0.0053 | 65.4 ± 5.2 | 80.7 ± 4 | 15.3 | 1.3 |
| L32M | 23345 ± 1826 | 30767 ± 2014 | 0.0067 | 66.9 ± 3.8 | 89.4 ± 4.5 | 22.5 | 1.3 |
| L32Q | 228 ± 24 | 5733 ± 357 | 0.0001 | 0.7 ± 0.1 | 16.9 ± 1.1 | 16.2 | 25.2 |
| L32R | 15594 ± 1339 | 24030 ± 1883 | 0.0033 | 45.4 ± 3.9 | 70.6 ± 5.6 | 25.2 | 1.5 |
| L32V | 17391 ± 1265 | 25028 ± 1678 | 0.0018 | 51.2 ± 3.7 | 73.7 ± 4.7 | 22.5 | 1.4 |
| D33A | 21613 ± 1926 | 37153 ± 2439 | 0.0001 | 55.1 ± 3.5 | 94.5 ± 3.5 | 39.4 | 1.7 |
| D33E | 32178 ± 2816 | 44926 ± 3037 | 0.0010 | 81.8 ± 5.9 | 116.8 ± 7.1 | 34.9 | 1.4 |
| D33V | 8815 ± 815 | 28371 ± 2762 | 0.0001 | 22.3 ± 1.7 | 71 ± 4.2 | 48.7 | 3.2 |
| L36M | 29476 ± 1787 | 37839 ± 2103 | 0.0030 | 75.8 ± 4.5 | 97.4 ± 5.7 | 21.6 | 1.3 |
| L36V | 32854 ± 2003 | 45155 ± 2152 | 0.0001 | 87.7 ± 8.1 | 118.1 ± 7.7 | 30.4 | 1.4 |
| A37E | 17508 ± 1781 | 22216 ± 922 | 0.0039 | 51.1 ± 3.2 | 68.6 ± 3.1 | 17.5 | 1.3 |
| A37G | 20059 ± 1634 | 26374 ± 1068 | 0.0011 | 59.5 ± 3.1 | 81.2 ± 3.3 | 21.7 | 1.3 |
| A37S | 28548 ± 1621 | 36678 ± 2507 | 0.0090 | 68.2 ± 2.9 | 87.8 ± 5.4 | 19.6 | 1.3 |
| R38G | 20871 ± 1596 | 26474 ± 1182 | 0.0017 | 59.2 ± 3.2 | 76.8 ± 3.1 | 17.5 | 1.3 |
| R38M | 27519 ± 2289 | 33201 ± 1837 | 0.0104 | 82.2 ± 4.6 | 105.3 ± 8.7 | 23.2 | 1.2 |
| R38W | 13728 ± 1660 | 19031 ± 797 | 0.0026 | 39.4 ± 3.1 | 58.3 ± 2 | 18.9 | 1.4 |
| T39A | 14133 ± 599 | 22863 ± 1308 | 0.0001 | 58 ± 2.5 | 92.9 ± 4.5 | 35.0 | 1.6 |
| T39K | 14243 ± 982 | 19261 ± 1065 | 0.0010 | 57.9 ± 3.6 | 78 ± 3.4 | 20.1 | 1.4 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| T39M | 18868 ± 1035 | 29341 ± 1094 | 0.0001 | 42.9 ± 2.6 | 66.7 ± 3.3 | 23.8 | 1.6 |
| T39R | 16386 ± 946 | 19594 ± 1257 | 0.0049 | 66.6 ± 3.3 | 79.3 ± 4.2 | 12.7 | 1.2 |
| T39S | 22746 ± 1704 | 30290 ± 1697 | 0.0010 | 68.8 ± 3.9 | 98.5 ± 10.1 | 29.6 | 1.3 |
| T41A | 23027 ± 1729 | 35730 ± 2325 | 0.0001 | 93.8 ± 6.4 | 144.3 ± 7.5 | 50.5 | 1.6 |
| T41N | 15106 ± 1455 | 27001 ± 1828 | 0.0001 | 61.7 ± 5.7 | 109.4 ± 6.3 | 47.7 | 1.8 |
| T41S | 36978 ± 1637 | 47987 ± 2574 | 0.0001 | 83 ± 3.1 | 108.3 ± 5.2 | 25.2 | 1.3 |
| G43A | 547 ± 39 | 9152 ± 903 | 0.0001 | 2.1 ± 0.2 | 35.6 ± 4.2 | 33.6 | 16.7 |
| L45M | 10167 ± 738 | 15884 ± 1038 | 0.0001 | 35.4 ± 3.2 | 55.3 ± 4.8 | 20.0 | 1.6 |
| L45V | 7728 ± 553 | 12995 ± 870 | 0.0001 | 27 ± 2.4 | 45.5 ± 4.1 | 18.5 | 1.7 |
| H46D | 5064 ± 346 | 12824 ± 844 | 0.0001 | 17.5 ± 1.4 | 44.8 ± 3.9 | 27.3 | 2.5 |
| H46N | 4890 ± 293 | 16015 ± 971 | 0.0001 | 16.9 ± 1.3 | 55.9 ± 4.6 | 39.0 | 3.3 |
| H46Q | 5784 ± 357 | 12138 ± 771 | 0.0001 | 20 ± 1.5 | 42.4 ± 3.6 | 22.4 | 2.1 |
| E48A | 1795 ± 172 | 7438 ± 547 | 0.0001 | 7.4 ± 1 | 29.1 ± 2.7 | 21.7 | 4.1 |
| F50Y | 756 ± 43 | 15051 ± 1103 | 0.0001 | 2.4 ± 0.2 | 46.3 ± 4.9 | 43.9 | 19.9 |
| M51R | 14619 ± 996 | 18178 ± 722 | 0.0039 | 53.3 ± 4 | 65.5 ± 2.8 | 12.1 | 1.2 |
| M51T | 9539 ± 615 | 17742 ± 498 | 0.0001 | 37.8 ± 2.1 | 71.1 ± 2.2 | 33.3 | 1.9 |
| M51V | 8888 ± 629 | 12943 ± 674 | 0.0001 | 34.1 ± 2.8 | 49.2 ± 3.1 | 15.1 | 1.5 |
| N53H | 4889 ± 672 | 10065 ± 346 | 0.0001 | 19.2 ± 2.3 | 40.3 ± 1.4 | 21.1 | 2.1 |
| N53I | 12636 ± 1899 | 20010 ± 2488 | 0.0006 | 35 ± 3 | 57.2 ± 3.8 | 22.2 | 1.6 |
| N53S | 15799 ± 1945 | 25411 ± 2907 | 0.0007 | 47.3 ± 3.7 | 75.3 ± 4.1 | 28.0 | 1.6 |
| N53T | 16203 ± 1515 | 26147 ± 2763 | 0.0001 | 49.4 ± 3.1 | 78.4 ± 4.1 | 29.0 | 1.6 |
| L54H | BLD | 6158 ± 377 | 0.0001 | N/A | 17.5 ± 0.8 | 17.5 | NC |
| L54R | 15536 ± 1823 | 23973 ± 743 | 0.0001 | 44.4 ± 4.6 | 70.1 ± 3.1 | 25.8 | 1.5 |
| L54V | 24595 ± 2022 | 30741 ± 1942 | 0.0045 | 69.6 ± 4 | 87.9 ± 4.5 | 18.4 | 1.3 |
| D55A | 16170 ± 1627 | 21497 ± 801 | 0.0010 | 47 ± 4.6 | 63.3 ± 3.4 | 16.3 | 1.3 |
| D55E | 16212 ± 1607 | 22237 ± 896 | 0.0002 | 47 ± 4.3 | 66.2 ± 4.6 | 19.2 | 1.4 |
| D55H | 9076 ± 1049 | 16638 ± 569 | 0.0001 | 27.3 ± 3 | 50.4 ± 2.9 | 23.1 | 1.8 |
| D55Y | 2268 ± 94 | 9956 ± 562 | 0.0001 | 7.5 ± 0.6 | 32.1 ± 1.9 | 24.5 | 4.4 |
| C56W | BLD | 1854 ± 140 | 0.0001 | N/A | 5.6 ± 0.4 | 5.6 | NC |
| E58K | 11757 ± 839 | 18105 ± 1138 | 0.0001 | 37.2 ± 2.7 | 57.6 ± 4.2 | 20.5 | 1.5 |
| E59A | 17204 ± 1538 | 21575 ± 1115 | 0.0014 | 47 ± 3.9 | 58.9 ± 2.2 | 11.9 | 1.3 |
| E59D | 22266 ± 1484 | 28238 ± 1077 | 0.0005 | 69.7 ± 3.8 | 89.5 ± 3.5 | 19.8 | 1.3 |
| E59G | 4551 ± 506 | 12357 ± 924 | 0.0001 | 12.4 ± 0.9 | 35.1 ± 1.6 | 22.7 | 2.7 |
| E59Q | 13611 ± 1152 | 18673 ± 1404 | 0.0011 | 42.7 ± 3.2 | 58.8 ± 3.9 | 16.0 | 1.4 |
| E59V | 2072 ± 168 | 7546 ± 732 | 0.0001 | 6.7 ± 0.6 | 24.4 ± 2.8 | 17.8 | 3.6 |
| P60A | 19972 ± 1596 | 26820 ± 1669 | 0.0006 | 54.9 ± 4 | 73.2 ± 3 | 18.3 | 1.3 |
| P60Q | 15470 ± 799 | 26238 ± 1132 | 0.0001 | 48.7 ± 2 | 82.7 ± 2.9 | 34.0 | 1.7 |
| P60R | 10622 ± 882 | 17095 ± 698 | 0.0001 | 30 ± 2.1 | 48.8 ± 2 | 18.8 | 1.6 |
| D61E | 29588 ± 1345 | 37109 ± 2077 | 0.0049 | 97.9 ± 6 | 119.2 ± 5 | 21.4 | 1.3 |
| D61V | 15741 ± 668 | 21299 ± 748 | 0.0001 | 54.8 ± 2.9 | 74.8 ± 3.9 | 20.0 | 1.4 |
| S62A | 31726 ± 1779 | 38602 ± 2163 | 0.0030 | 95.2 ± 3.8 | 115.5 ± 4.2 | 20.2 | 1.2 |
| S62C | 12299 ± 669 | 16978 ± 1074 | 0.0006 | 41.3 ± 1.9 | 58.2 ± 4.6 | 16.9 | 1.4 |
| S62F | 10360 ± 706 | 15534 ± 903 | 0.0002 | 34.5 ± 1.7 | 52.6 ± 3 | 18.1 | 1.5 |
| S62P | 245 ± 39 | 6945 ± 844 | 0.0001 | 0.7 ± 0.1 | 19.3 ± 1.6 | 18.6 | 28.3 |
| S62Y | 12108 ± 1047 | 19476 ± 875 | 0.0001 | 40 ± 2.4 | 66.7 ± 3.7 | 26.7 | 1.6 |
| I64L | 229 ± 32 | 8452 ± 484 | 0.0001 | 0.7 ± 0.1 | 24.3 ± 1.2 | 23.6 | 36.9 |
| I64V | 18259 ± 1030 | 27706 ± 637 | 0.0001 | 54.5 ± 3.2 | 82.7 ± 2.6 | 28.2 | 1.5 |
| S65C | 26986 ± 2021 | 35417 ± 2097 | 0.0022 | 61.1 ± 2.3 | 81 ± 1.9 | 19.9 | 1.3 |
| S65G | 19996 ± 2296 | 33127 ± 2448 | 0.0005 | 64 ± 7.4 | 105.3 ± 7.1 | 41.3 | 1.7 |
| S65R | 37555 ± 2042 | 45657 ± 2084 | 0.0053 | 87.1 ± 4 | 105.7 ± 2.4 | 18.5 | 1.2 |
| E66D | 24426 ± 1399 | 30874 ± 1190 | 0.0007 | 56.4 ± 2 | 72.2 ± 2.3 | 15.8 | 1.3 |
| E66V | 10943 ± 1124 | 15435 ± 1251 | 0.0007 | 24.7 ± 1.7 | 35.2 ± 1.7 | 10.5 | 1.4 |
| K67E | 30290 ± 1420 | 46106 ± 1265 | 0.0001 | 70.7 ± 2.7 | 108.2 ± 2.8 | 37.6 | 1.5 |
| K67M | 22374 ± 1366 | 33812 ± 1237 | 0.0001 | 53.3 ± 2.9 | 81.1 ± 2.6 | 27.8 | 1.5 |
| K67N | 30951 ± 2447 | 48271 ± 1855 | 0.0001 | 73.9 ± 5.6 | 115.9 ± 4.1 | 42.0 | 1.6 |
| K67Q | 33571 ± 1439 | 48101 ± 1363 | 0.0001 | 78.2 ± 2.3 | 113.2 ± 3.4 | 35.0 | 1.4 |
| K67T | 29063 ± 2114 | 42744 ± 1271 | 0.0001 | 69.3 ± 4.9 | 102.5 ± 2.6 | 33.2 | 1.5 |
| L68I | 1191 ± 125 | 9012 ± 534 | 0.0001 | 2.8 ± 0.3 | 21.5 ± 1.1 | 18.7 | 7.6 |
| F69I | 376 ± 38 | 10829 ± 488 | 0.0001 | 0.9 ± 0.1 | 25.4 ± 0.8 | 24.5 | 28.8 |
| F69Y | 1500 ± 119 | 18806 ± 1141 | 0.0001 | 3.3 ± 0.2 | 40.7 ± 2.2 | 37.4 | 12.5 |
| M70I | 24534 ± 1064 | 32895 ± 1518 | 0.0001 | 60.7 ± 2.7 | 82.2 ± 4.6 | 21.5 | 1.3 |
| M70K | 25582 ± 1732 | 38457 ± 1757 | 0.0001 | 62.5 ± 3 | 94.9 ± 4.1 | 32.5 | 1.5 |
| M70L | 26515 ± 1172 | 31930 ± 1211 | 0.0024 | 63.9 ± 1.4 | 78.4 ± 3.4 | 14.5 | 1.2 |
| M70R | 27578 ± 2110 | 42595 ± 1951 | 0.0001 | 59.4 ± 4 | 93 ± 5 | 33.6 | 1.5 |
| E71A | 23766 ± 1537 | 32700 ± 1312 | 0.0001 | 59.3 ± 4.5 | 81.1 ± 3.6 | 21.8 | 1.4 |
| E71D | 26962 ± 1987 | 36176 ± 2174 | 0.0009 | 61.1 ± 2.5 | 82.7 ± 3.1 | 21.7 | 1.3 |
| E71G | 22820 ± 1979 | 32128 ± 878 | 0.0001 | 54.7 ± 3 | 80.3 ± 3.4 | 25.6 | 1.4 |
| E71Q | 29109 ± 1574 | 37795 ± 1474 | 0.0003 | 70.8 ± 2.4 | 93.3 ± 3.4 | 22.5 | 1.3 |
| E71V | 25328 ± 994 | 33957 ± 879 | 0.0001 | 62.8 ± 2.8 | 85.3 ± 3.8 | 22.4 | 1.3 |
| M72L | 8208 ± 664 | 23988 ± 1422 | 0.0001 | 18.5 ± 1.1 | 54.9 ± 2.1 | 36.4 | 2.9 |
| M72T | 25205 ± 1791 | 32476 ± 2471 | 0.0206 | 57 ± 2.4 | 73.4 ± 3.3 | 16.5 | 1.3 |
| A73S | 23566 ± 1631 | 31993 ± 1944 | 0.0033 | 53.7 ± 2.9 | 73.3 ± 3 | 19.6 | 1.4 |
| A73T | 23379 ± 1999 | 28403 ± 1642 | 0.0283 | 53.6 ± 3.3 | 66 ± 2.2 | 12.4 | 1.2 |
| E74D | 28411 ± 1782 | 39202 ± 2134 | 0.0003 | 69.6 ± 2.7 | 96.8 ± 2.7 | 27.2 | 1.4 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| E74G | 23718 ± 1447 | 33068 ± 1675 | 0.0002 | 58.8 ± 2.8 | 82.9 ± 3.5 | 24.2 | 1.4 |
| E74K | 23026 ± 2084 | 27539 ± 1592 | 0.0193 | 52.4 ± 4.3 | 63.1 ± 2.4 | 10.6 | 1.2 |
| E74V | 20975 ± 1489 | 25386 ± 1823 | 0.0234 | 51.6 ± 3.1 | 63.2 ± 4.1 | 11.6 | 1.2 |
| L75F | 25253 ± 1313 | 30602 ± 1493 | 0.0042 | 63.5 ± 3.6 | 76.7 ± 3.1 | 13.3 | 1.2 |
| L75P | 4084 ± 434 | 5513 ± 287 | 0.0111 | 9.7 ± 0.9 | 13.6 ± 1 | 3.9 | 1.4 |
| M76V | 11543 ± 644 | 20077 ± 1484 | 0.0001 | 30 ± 1.2 | 51.3 ± 2.6 | 21.3 | 1.7 |
| V77I | 29128 ± 1593 | 36588 ± 2669 | 0.0360 | 72 ± 3.8 | 87.4 ± 2.9 | 15.4 | 1.3 |
| V77L | 29482 ± 1970 | 35834 ± 1940 | 0.0174 | 77 ± 5.5 | 92.8 ± 3.2 | 15.7 | 1.2 |
| S78L | 27575 ± 1856 | 34892 ± 1683 | 0.0024 | 68.9 ± 2.5 | 89.4 ± 3.2 | 20.5 | 1.3 |
| S78P | 2263 ± 319 | 3971 ± 333 | 0.0014 | 5.4 ± 0.7 | 9.7 ± 0.5 | 4.3 | 1.8 |
| E79A | 24732 ± 1717 | 33721 ± 1802 | 0.0011 | 72 ± 4.8 | 100.2 ± 6.9 | 28.3 | 1.4 |
| E79D | 38422 ± 3185 | 51309 ± 3083 | 0.0008 | 112.5 ± 9.3 | 153.4 ± 11.9 | 40.8 | 1.3 |
| E79G | 23729 ± 2129 | 34762 ± 2171 | 0.0005 | 68.9 ± 5.6 | 104.1 ± 8.5 | 35.2 | 1.5 |
| E79K | 12002 ± 931 | 19360 ± 953 | 0.0001 | 29.9 ± 1.3 | 50.5 ± 3 | 20.6 | 1.6 |
| E79Q | 31940 ± 2387 | 44470 ± 3000 | 0.0007 | 92.6 ± 6.2 | 134 ± 11.8 | 41.4 | 1.4 |
| E79V | 3360 ± 551 | 8915 ± 565 | 0.0001 | 9.8 ± 1.5 | 26.3 ± 1.9 | 16.6 | 2.7 |
| G80A | 12723 ± 1236 | 21243 ± 1698 | 0.0001 | 35.3 ± 3.2 | 60.7 ± 5.7 | 25.4 | 1.7 |
| G80C | 4279 ± 732 | 8085 ± 487 | 0.0005 | 12.5 ± 2 | 24 ± 1.6 | 11.5 | 1.9 |
| G80S | 14825 ± 1175 | 24788 ± 1376 | 0.0001 | 43.2 ± 3.3 | 73.8 ± 5.1 | 30.6 | 1.7 |
| W81L | BLD | 1190 ± 99 | 0.0001 | N/A | 4.4 ± 0.3 | 4.4 | NC |
| K82E | 7610 ± 608 | 10952 ± 967 | 0.0100 | 30.7 ± 2.3 | 43.7 ± 3.2 | 12.9 | 1.4 |
| K82M | 19592 ± 1306 | 25993 ± 2122 | 0.0266 | 72.6 ± 4 | 94.8 ± 5.2 | 22.3 | 1.3 |
| K82N | 11724 ± 855 | 17397 ± 1132 | 0.0005 | 43.5 ± 2.6 | 63.9 ± 2.5 | 20.4 | 1.5 |
| K82R | 22252 ± 1312 | 27326 ± 1986 | 0.0455 | 83.6 ± 4.2 | 101.4 ± 5.6 | 17.7 | 1.2 |
| K82T | 13117 ± 769 | 17594 ± 1185 | 0.0026 | 49.2 ± 2.4 | 65.5 ± 3.5 | 16.3 | 1.3 |
| D83A | 19999 ± 1698 | 24545 ± 1346 | 0.0067 | 65.6 ± 3.9 | 81 ± 2.6 | 15.4 | 1.2 |
| D83E | 26423 ± 1478 | 41691 ± 3309 | 0.0007 | 76.3 ± 3.5 | 120.2 ± 9 | 43.9 | 1.6 |
| D83G | 16734 ± 1241 | 21951 ± 1455 | 0.0049 | 54.7 ± 2.5 | 72 ± 3 | 17.3 | 1.3 |
| D83V | 14758 ± 1130 | 25238 ± 1768 | 0.0001 | 45.8 ± 2.2 | 78.5 ± 3.9 | 32.7 | 1.7 |
| A84E | 9978 ± 952 | 16862 ± 1319 | 0.0003 | 27.7 ± 1.8 | 48.6 ± 3.9 | 20.9 | 1.7 |
| A84G | 9870 ± 942 | 18181 ± 1377 | 0.0001 | 28.6 ± 2.3 | 52.4 ± 3.3 | 23.9 | 1.8 |
| A84P | 180 ± 47 | 1255 ± 141 | 0.0001 | 0.6 ± 0.2 | 3.9 ± 0.4 | 3.3 | 7.0 |
| A84S | 27798 ± 2763 | 36913 ± 2263 | 0.0042 | 84.8 ± 5 | 116.1 ± 5.6 | 31.3 | 1.3 |
| A84T | 16960 ± 1350 | 23585 ± 2022 | 0.0072 | 48.8 ± 2.7 | 69.3 ± 6 | 20.5 | 1.4 |
| A84V | 34751 ± 2600 | 41833 ± 2901 | 0.0455 | 94.9 ± 4.5 | 115.4 ± 6 | 20.5 | 1.2 |
| G85A | 3114 ± 442 | 8107 ± 550 | 0.0001 | 7.9 ± 0.9 | 20.8 ± 1.2 | 12.9 | 2.6 |
| G85C | 926 ± 66 | 3079 ± 427 | 0.0001 | 2.4 ± 0.2 | 7.5 ± 0.8 | 5.1 | 3.3 |
| G85R | 9145 ± 1128 | 13622 ± 1053 | 0.0039 | 22.5 ± 2.2 | 33.7 ± 1.5 | 11.2 | 1.5 |
| Y86F | 12275 ± 707 | 16114 ± 468 | 0.0002 | 31 ± 1.7 | 41 ± 1.7 | 10.0 | 1.3 |
| E87G | 16130 ± 877 | 20394 ± 867 | 0.0008 | 41 ± 2.6 | 52 ± 3 | 11.0 | 1.3 |
| Y88H | 11199 ± 689 | 16074 ± 612 | 0.0001 | 28.4 ± 1.3 | 41.5 ± 1.6 | 13.1 | 1.4 |
| Y88N | 5381 ± 557 | 7561 ± 298 | 0.0001 | 13.5 ± 1.1 | 19.5 ± 0.9 | 6.0 | 1.4 |
| E89V | 26558 ± 1501 | 33849 ± 1243 | 0.0005 | 63.4 ± 4.6 | 80.7 ± 4.4 | 17.3 | 1.3 |
| I91F | 353 ± 36 | 3846 ± 338 | 0.0001 | 1 ± 0.1 | 9.7 ± 0.5 | 8.7 | 10.9 |
| I91E | 17057 ± 1308 | 28279 ± 1631 | 0.0001 | 54.3 ± 6 | 91.4 ± 9.9 | 37.0 | 1.7 |
| I91M | 19360 ± 1837 | 32190 ± 1335 | 0.0001 | 47.9 ± 3.4 | 82.4 ± 3.8 | 34.5 | 1.7 |
| I91S | 946 ± 38 | 3966 ± 176 | 0.0001 | 2.5 ± 0.2 | 10.2 ± 0.6 | 7.7 | 4.2 |
| M96L | 24584 ± 1414 | 37462 ± 1866 | 0.0001 | 61.8 ± 2.8 | 93.8 ± 3.1 | 32.0 | 1.5 |
| M96T | 12103 ± 1633 | 18415 ± 1827 | 0.0033 | 30.3 ± 3.3 | 46.7 ± 3.4 | 16.4 | 1.5 |
| A97D | 17634 ± 1789 | 29319 ± 4081 | 0.0039 | 45 ± 3.4 | 74.5 ± 9.5 | 29.5 | 1.7 |
| A97S | 21262 ± 1383 | 27841 ± 2335 | 0.0128 | 55.7 ± 3.7 | 70.9 ± 4.2 | 15.1 | 1.3 |
| A97T | 11157 ± 776 | 19875 ± 1502 | 0.0001 | 29.4 ± 2.2 | 50.9 ± 2.7 | 21.4 | 1.8 |
| P98H | 21896 ± 1232 | 29920 ± 1808 | 0.0013 | 60.8 ± 3.1 | 83.4 ± 4.6 | 22.5 | 1.4 |
| P98L | 24223 ± 1555 | 31835 ± 2399 | 0.0072 | 69 ± 5.5 | 88.5 ± 6.3 | 19.6 | 1.3 |
| P98R | 24969 ± 1730 | 31289 ± 2550 | 0.0405 | 69.4 ± 4 | 85.8 ± 5.8 | 16.4 | 1.3 |
| Q99E | 25264 ± 1668 | 34635 ± 3117 | 0.0104 | 70.3 ± 4.1 | 95.8 ± 7.9 | 25.5 | 1.4 |
| Q99L | 23382 ± 1548 | 33479 ± 2746 | 0.0012 | 65.9 ± 5.1 | 93.4 ± 7.3 | 27.4 | 1.4 |
| Q99P | 3034 ± 340 | 9885 ± 794 | 0.0001 | 8.8 ± 1.2 | 28 ± 2.4 | 19.1 | 3.3 |
| Q99R | 32963 ± 1757 | 41024 ± 3001 | 0.0193 | 93.4 ± 6.3 | 114.8 ± 8 | 21.4 | 1.2 |
| D101A | 10144 ± 1069 | 14707 ± 1289 | 0.0049 | 23.9 ± 3 | 34.1 ± 3.3 | 10.2 | 1.5 |
| D101E | 10465 ± 624 | 14682 ± 993 | 0.0010 | 23.9 ± 1.6 | 34 ± 2.8 | 10.1 | 1.4 |
| D101G | 18091 ± 1103 | 23672 ± 1428 | 0.0033 | 41.8 ± 3.1 | 54.5 ± 3.8 | 12.7 | 1.3 |
| D101H | 7311 ± 556 | 10493 ± 561 | 0.0002 | 16.5 ± 1.2 | 23.8 ± 1.3 | 7.3 | 1.4 |
| D101V | 3368 ± 179 | 7489 ± 936 | 0.0001 | 7.8 ± 0.5 | 18 ± 2.6 | 10.2 | 2.2 |
| S102A | 17330 ± 2084 | 26790 ± 1958 | 0.0018 | 42.6 ± 3.5 | 69.9 ± 5.1 | 27.3 | 1.6 |
| S102P | 27252 ± 1778 | 35885 ± 2754 | 0.0111 | 69.4 ± 3.4 | 91.7 ± 5 | 22.3 | 1.3 |
| S102T | 22123 ± 2319 | 29662 ± 2559 | 0.0339 | 56.4 ± 5.2 | 76.9 ± 6.2 | 20.5 | 1.3 |
| G104A | 5271 ± 397 | 19670 ± 1202 | 0.0001 | 14.8 ± 1 | 55.2 ± 3 | 40.4 | 3.7 |
| G104D | 14123 ± 1096 | 24797 ± 1771 | 0.0001 | 39.3 ± 2.6 | 69.8 ± 4.7 | 30.5 | 1.8 |
| G104S | 5720 ± 464 | 22242 ± 1000 | 0.0001 | 17.9 ± 1.8 | 69.8 ± 5.8 | 52.0 | 3.9 |
| R105G | 16513 ± 681 | 22993 ± 1042 | 0.0001 | 38 ± 2.1 | 53.3 ± 3.5 | 15.3 | 1.4 |
| R105I | 9696 ± 798 | 12128 ± 1157 | 0.0158 | 33.4 ± 2.2 | 41.6 ± 3.1 | 8.2 | 1.3 |
| R105K | 25495 ± 1793 | 31647 ± 2251 | 0.0360 | 76.2 ± 2.9 | 96.7 ± 5.2 | 20.5 | 1.2 |
| R105T | 12553 ± 603 | 17062 ± 1134 | 0.0020 | 44 ± 2.2 | 59.6 ± 3.9 | 15.6 | 1.4 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| L106H | 856 ± 58 | 3009 ± 399 | 0.0001 | 3 ± 0.2 | 10.2 ± 1.1 | 7.3 | 3.5 |
| L106I | 13485 ± 1014 | 20120 ± 1416 | 0.0002 | 46.4 ± 2.7 | 70 ± 4.7 | 23.6 | 1.5 |
| L106P | 8835 ± 878 | 16075 ± 1039 | 0.0001 | 30.7 ± 2.7 | 56.5 ± 3.9 | 25.8 | 1.8 |
| L106V | 15393 ± 1288 | 20991 ± 1611 | 0.0033 | 53.6 ± 4.3 | 73.4 ± 5.9 | 19.8 | 1.4 |
| Q107E | 13148 ± 985 | 16149 ± 1059 | 0.0111 | 45.7 ± 3.1 | 56.2 ± 3.3 | 10.4 | 1.2 |
| Q107H | 12307 ± 487 | 14822 ± 384 | 0.0001 | 41.7 ± 1.5 | 50.8 ± 2 | 9.1 | 1.2 |
| Q107K | 14579 ± 2689 | 20402 ± 3399 | 0.0128 | 38.2 ± 3.9 | 54.6 ± 4.8 | 16.4 | 1.4 |
| A108E | 11629 ± 835 | 15648 ± 1305 | 0.0111 | 38.4 ± 2.6 | 52.6 ± 4.6 | 14.2 | 1.4 |
| A108V | 4914 ± 799 | 17249 ± 2284 | 0.0001 | 13.3 ± 1.7 | 47.7 ± 4.6 | 34.4 | 3.5 |
| D109A | 6345 ± 1034 | 13742 ± 1780 | 0.0002 | 17.5 ± 2.2 | 38 ± 3.7 | 20.4 | 2.2 |
| D109E | 13839 ± 1179 | 16926 ± 1156 | 0.0147 | 41.3 ± 3.4 | 50.6 ± 3.6 | 9.3 | 1.2 |
| D109H | 7540 ± 684 | 16483 ± 1317 | 0.0001 | 24.6 ± 1.7 | 54.6 ± 3.5 | 30.0 | 2.2 |
| D109N | 1475 ± 83 | 12358 ± 973 | 0.0001 | 5 ± 0.3 | 41.5 ± 2.8 | 36.5 | 8.4 |
| D109Y | 212 ± 30 | 2530 ± 415 | 0.0001 | 0.7 ± 0.1 | 8.2 ± 1.1 | 7.5 | 11.9 |
| P110T | 20474 ± 1528 | 26745 ± 1678 | 0.0049 | 62.6 ± 5.9 | 81.2 ± 6.5 | 18.6 | 1.3 |
| F113V | 341 ± 41 | 3614 ± 596 | 0.0001 | 1.1 ± 0.1 | 10.3 ± 1 | 9.2 | 10.6 |
| F113Y | BLD | 1328 ± 79 | 0.0001 | N/A | 4.4 ± 0.3 | 4.4 | NC |
| P114L | 6229 ± 901 | 7973 ± 626 | 0.0062 | 18.3 ± 2.1 | 23.7 ± 1.3 | 5.4 | 1.3 |
| H115D | 10284 ± 1141 | 15258 ± 1412 | 0.0028 | 30.7 ± 2.9 | 44.8 ± 3 | 14.1 | 1.5 |
| H115N | 13745 ± 890 | 23018 ± 1098 | 0.0001 | 44.9 ± 2.5 | 75 ± 2.5 | 30.1 | 1.7 |
| G116R | 1922 ± 143 | 5251 ± 464 | 0.0001 | 5.4 ± 0.3 | 15.4 ± 1.5 | 9.9 | 2.7 |
| I117M | 20226 ± 1373 | 31280 ± 1153 | 0.0001 | 54.2 ± 3.9 | 83.5 ± 3.6 | 29.4 | 1.6 |
| I117T | 1607 ± 54 | 3303 ± 308 | 0.0001 | 4.3 ± 0.2 | 9 ± 0.9 | 4.7 | 2.1 |
| A121V | 7301 ± 253 | 26639 ± 1124 | 0.0001 | 21.5 ± 1.2 | 78.2 ± 4.2 | 56.7 | 3.7 |
| Y123D | 15093 ± 815 | 18723 ± 1237 | 0.0083 | 43.4 ± 1.6 | 53.6 ± 2.7 | 10.2 | 1.2 |
| Y123F | 22066 ± 1408 | 33544 ± 1384 | 0.0001 | 63.6 ± 3.3 | 97.4 ± 3.4 | 33.8 | 1.5 |
| Y123N | 13817 ± 816 | 20466 ± 846 | 0.0001 | 40.9 ± 3.2 | 60.6 ± 4.1 | 19.7 | 1.5 |
| Y123S | 14556 ± 986 | 21255 ± 1484 | 0.0008 | 41.7 ± 2.1 | 61 ± 3.6 | 19.3 | 1.5 |
| V124I | 32074 ± 1858 | 43288 ± 2179 | 0.0003 | 80.7 ± 2 | 111.3 ± 4.5 | 30.6 | 1.4 |
| H125D | 995 ± 106 | 3282 ± 375 | 0.0001 | 2.3 ± 0.2 | 8.8 ± 1.4 | 6.5 | 3.3 |
| H125N | 14162 ± 994 | 20228 ± 1240 | 0.0006 | 33.5 ± 1.8 | 48.4 ± 2.7 | 14.9 | 1.4 |
| H125R | 14738 ± 699 | 24004 ± 987 | 0.0001 | 36 ± 1.2 | 59.1 ± 1.9 | 23.0 | 1.6 |
| S126C | 7046 ± 488 | 10050 ± 554 | 0.0004 | 16.9 ± 1.1 | 24.5 ± 1.5 | 7.5 | 1.4 |
| S126I | 28685 ± 1923 | 35340 ± 2027 | 0.0234 | 69.8 ± 5.1 | 85.9 ± 5.3 | 16.0 | 1.2 |
| K127E | 8968 ± 519 | 11003 ± 768 | 0.0147 | 25.8 ± 1.1 | 32.2 ± 2.3 | 6.4 | 1.2 |
| G128A | 8484 ± 872 | 10204 ± 703 | 0.0319 | 20.8 ± 2 | 25.9 ± 2.3 | 5.1 | 1.2 |
| L129V | 12614 ± 1265 | 19488 ± 1603 | 0.0012 | 31.8 ± 3.3 | 48.1 ± 4.5 | 16.4 | 1.5 |
| K130M | 12335 ± 890 | 16496 ± 921 | 0.0020 | 30.5 ± 2.1 | 41.4 ± 2.6 | 10.9 | 1.3 |
| K130N | 8597 ± 678 | 12595 ± 989 | 0.0017 | 21.5 ± 1.9 | 31.5 ± 3 | 10.1 | 1.5 |
| K130Q | 11880 ± 450 | 16001 ± 701 | 0.0001 | 35.8 ± 2.6 | 47.8 ± 3.1 | 12.0 | 1.4 |
| L131V | 18644 ± 1664 | 24913 ± 3151 | 0.0319 | 40.5 ± 2.8 | 53.2 ± 5.3 | 12.7 | 1.3 |
| I133L | 24431 ± 1181 | 31550 ± 1420 | 0.0004 | 60.7 ± 2.7 | 78.2 ± 3.1 | 17.5 | 1.3 |
| I133T | 4362 ± 397 | 10255 ± 335 | 0.0001 | 10.8 ± 1 | 25.8 ± 1.1 | 15.0 | 2.4 |
| I133V | 38738 ± 1624 | 47299 ± 1885 | 0.0007 | 96.2 ± 3.7 | 118.1 ± 5.1 | 21.9 | 1.2 |
| A135E | 10143 ± 752 | 12954 ± 678 | 0.0045 | 25.1 ± 1.5 | 32.5 ± 1.6 | 7.4 | 1.3 |
| A135G | 29959 ± 2193 | 36552 ± 2309 | 0.0206 | 73.9 ± 3.8 | 90 ± 3.6 | 16.1 | 1.2 |
| A135S | 16777 ± 897 | 21383 ± 1125 | 0.0020 | 45.6 ± 2.9 | 57.9 ± 3.2 | 12.2 | 1.3 |
| A135T | 7906 ± 694 | 18890 ± 2092 | 0.0001 | 17.4 ± 1.3 | 40.5 ± 3.4 | 23.2 | 2.4 |
| D136A | 8054 ± 482 | 12166 ± 927 | 0.0001 | 20.4 ± 1.1 | 29.8 ± 1 | 9.4 | 1.5 |
| D136N | 5079 ± 248 | 9827 ± 630 | 0.0001 | 13 ± 0.8 | 24.2 ± 0.9 | 11.2 | 1.9 |
| D136V | 17164 ± 1203 | 47647 ± 3779 | 0.0001 | 42.2 ± 1.7 | 116.4 ± 5.5 | 74.2 | 2.8 |
| V137A | 22393 ± 1429 | 40016 ± 2785 | 0.0001 | 61.1 ± 4.6 | 106.6 ± 5.9 | 45.4 | 1.8 |
| V137D | 516 ± 80 | 4757 ± 618 | 0.0001 | 1.4 ± 0.2 | 13 ± 1.6 | 11.6 | 9.2 |
| V137G | 16515 ± 1170 | 36258 ± 1701 | 0.0001 | 45.9 ± 4.2 | 98.2 ± 5 | 52.4 | 2.2 |
| V137I | 12148 ± 597 | 21313 ± 987 | 0.0001 | 32.8 ± 1.6 | 57.4 ± 2.5 | 24.7 | 1.8 |
| V137L | 15359 ± 656 | 19794 ± 1475 | 0.0045 | 41.6 ± 2.1 | 53.3 ± 3.7 | 11.7 | 1.3 |
| G138A | 4768 ± 480 | 11112 ± 732 | 0.0001 | 14.4 ± 1.1 | 34.5 ± 1.5 | 20.1 | 2.3 |
| N139H | 29115 ± 2336 | 40678 ± 3158 | 0.0024 | 73.1 ± 5.4 | 101.2 ± 7.1 | 28.1 | 1.4 |
| N139I | 17180 ± 1455 | 26326 ± 1627 | 0.0001 | 51.8 ± 5.1 | 78.3 ± 4.5 | 26.4 | 1.5 |
| N139K | 33797 ± 2244 | 45090 ± 2667 | 0.0022 | 93.6 ± 5.8 | 127.4 ± 8.8 | 33.8 | 1.3 |
| N139Y | 19998 ± 1682 | 24303 ± 2079 | 0.0405 | 52.3 ± 3.8 | 64 ± 5.2 | 11.7 | 1.2 |
| K140E | 26053 ± 1925 | 46670 ± 2685 | 0.0001 | 72.6 ± 5.8 | 132.1 ± 9 | 59.5 | 1.8 |
| K140I | 15415 ± 1294 | 32440 ± 2092 | 0.0001 | 42.7 ± 3.3 | 92.1 ± 7.1 | 49.4 | 2.1 |
| K140N | 40575 ± 2928 | 54681 ± 3030 | 0.0013 | 113.8 ± 9.5 | 154.1 ± 11.1 | 40.3 | 1.4 |
| K140Q | 42995 ± 3236 | 59162 ± 3600 | 0.0009 | 123.2 ± 12.1 | 165.7 ± 9.7 | 42.5 | 1.4 |
| K140R | 50348 ± 3558 | 62820 ± 3401 | 0.0120 | 141.5 ± 12 | 180.9 ± 15 | 39.4 | 1.3 |
| T141S | 22602 ± 2254 | 34806 ± 2770 | 0.0018 | 63.8 ± 7.1 | 98.2 ± 9.1 | 34.4 | 1.5 |
| A143E | 7681 ± 439 | 11458 ± 884 | 0.0015 | 25.9 ± 1.5 | 37.3 ± 1.8 | 11.4 | 1.5 |
| A143G | 20419 ± 1260 | 36821 ± 2997 | 0.0001 | 67.8 ± 3.4 | 119.7 ± 5.9 | 51.9 | 1.8 |
| G144A | 20304 ± 1590 | 27268 ± 1039 | 0.0011 | 44.9 ± 3.6 | 60.4 ± 2.8 | 15.5 | 1.3 |
| G144C | 759 ± 69 | 2988 ± 262 | 0.0001 | 2.5 ± 0.2 | 9.5 ± 0.8 | 7.1 | 3.9 |
| G144R | 10574 ± 838 | 21406 ± 1764 | 0.0001 | 35.7 ± 2.8 | 73.4 ± 6.5 | 37.7 | 2.0 |
| G144S | 14190 ± 967 | 23153 ± 1847 | 0.0003 | 47.6 ± 2.4 | 78 ± 5.6 | 30.4 | 1.6 |
| F145C | 768 ± 54 | 11083 ± 678 | 0.0001 | 2.1 ± 0.2 | 27.8 ± 0.8 | 25.7 | 14.4 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| F145L | 5455 ± 412 | 29794 ± 1799 | 0.0001 | 13.9 ± 0.8 | 75.7 ± 2.9 | 61.8 | 5.5 |
| F145V | BLD | 2359 ± 333 | 0.0001 | N/A | 5.7 ± 0.6 | 5.7 | NC |
| F145Y | 41985 ± 2942 | 51524 ± 2970 | 0.0147 | 108.1 ± 6.2 | 131.7 ± 5.1 | 23.5 | 1.2 |
| P146A | 15393 ± 1271 | 25029 ± 1628 | 0.0002 | 38.7 ± 2.5 | 64.1 ± 4.4 | 25.4 | 1.6 |
| P146H | 3220 ± 211 | 11903 ± 844 | 0.0001 | 8.5 ± 0.7 | 30.2 ± 2.1 | 21.8 | 3.7 |
| P146L | 9940 ± 899 | 14540 ± 903 | 0.0009 | 24.7 ± 1.8 | 37.1 ± 2.2 | 12.4 | 1.5 |
| P146T | 13711 ± 1154 | 24123 ± 2081 | 0.0004 | 33.6 ± 1.5 | 58.6 ± 2.4 | 25.0 | 1.8 |
| G147A | BLD | 1159 ± 74 | 0.0001 | N/A | 3 ± 0.2 | 3.0 | NC |
| S148C | 11927 ± 1020 | 19343 ± 919 | 0.0001 | 30.2 ± 2.2 | 49.5 ± 2 | 19.3 | 1.6 |
| S148G | 435 ± 55 | 4879 ± 263 | 0.0001 | 1.1 ± 0.1 | 12.9 ± 1 | 11.8 | 11.2 |
| S148T | 24827 ± 1221 | 30620 ± 813 | 0.0006 | 66.5 ± 3.8 | 82.4 ± 3.7 | 15.9 | 1.2 |
| F149C | 15198 ± 1188 | 19032 ± 1272 | 0.0301 | 47 ± 4.4 | 60.9 ± 6.4 | 13.9 | 1.3 |
| G150E | 18804 ± 1070 | 22710 ± 1059 | 0.0120 | 61.5 ± 6.6 | 73.8 ± 7 | 12.3 | 1.2 |
| G150V | 1080 ± 63 | 4639 ± 361 | 0.0001 | 2.9 ± 0.1 | 12.1 ± 0.7 | 9.2 | 4.3 |
| Y151C | 11271 ± 579 | 15859 ± 752 | 0.0001 | 32.4 ± 1.5 | 45.6 ± 2 | 13.2 | 1.4 |
| Y151D | 10673 ± 604 | 15196 ± 1025 | 0.0006 | 29.3 ± 1.7 | 40.8 ± 2.2 | 11.5 | 1.4 |
| Y151S | 30047 ± 1943 | 37527 ± 2003 | 0.0067 | 84.8 ± 4.2 | 107 ± 4.9 | 22.2 | 1.3 |
| Y152F | 18675 ± 907 | 23612 ± 1095 | 0.0013 | 45.4 ± 2.6 | 56.8 ± 2.7 | 11.4 | 1.3 |
| Y152S | 9917 ± 917 | 16642 ± 1218 | 0.0002 | 27.1 ± 1.7 | 46.7 ± 2.6 | 19.6 | 1.7 |
| D153A | 22606 ± 1445 | 30854 ± 1997 | 0.0028 | 60.1 ± 2.4 | 81.6 ± 2.3 | 21.6 | 1.4 |
| D153H | 23578 ± 1741 | 31052 ± 1774 | 0.0030 | 60.5 ± 2.2 | 81 ± 2.1 | 20.5 | 1.3 |
| D153N | 29386 ± 1518 | 39338 ± 1551 | 0.0001 | 65.6 ± 2.8 | 89.7 ± 4.4 | 24.1 | 1.3 |
| D153V | 7357 ± 1139 | 16301 ± 766 | 0.0001 | 17.4 ± 2 | 42.4 ± 1.6 | 25.0 | 2.2 |
| D153Y | 12609 ± 1299 | 22535 ± 1174 | 0.0001 | 29.1 ± 3.1 | 52.4 ± 2.8 | 23.3 | 1.8 |
| A156G | 17406 ± 1187 | 23415 ± 1710 | 0.0033 | 46.7 ± 2.7 | 63.6 ± 4.3 | 16.9 | 1.4 |
| Q157E | 28269 ± 1306 | 37204 ± 2126 | 0.0007 | 77.4 ± 4.1 | 101.5 ± 6.1 | 24.1 | 1.3 |
| Q157K | 9815 ± 1083 | 31331 ± 2428 | 0.0001 | 24.1 ± 1.8 | 79.7 ± 5 | 55.6 | 3.2 |
| Q157L | 5734 ± 700 | 28942 ± 2013 | 0.0001 | 14.3 ± 1.5 | 74.4 ± 4.3 | 60.2 | 5.1 |
| Q157P | 3887 ± 487 | 20888 ± 1527 | 0.0001 | 9 ± 1 | 49.6 ± 3.4 | 40.6 | 5.4 |
| T158A | 14835 ± 1107 | 25678 ± 1673 | 0.0001 | 38.6 ± 2.5 | 67.3 ± 3.1 | 28.7 | 1.7 |
| T158I | 17360 ± 1159 | 24097 ± 1695 | 0.0042 | 49 ± 2.7 | 67.8 ± 3.4 | 18.8 | 1.4 |
| T158N | 1906 ± 106 | 5991 ± 499 | 0.0001 | 5.4 ± 0.2 | 18.2 ± 2 | 12.8 | 3.1 |
| T158S | 31043 ± 2073 | 39060 ± 2937 | 0.0169 | 79.3 ± 4 | 99.1 ± 5.6 | 19.8 | 1.3 |
| F159I | 21543 ± 1754 | 29402 ± 1960 | 0.0057 | 64.7 ± 3.5 | 89.3 ± 4.2 | 24.6 | 1.4 |
| F159L | 22840 ± 1245 | 31357 ± 1408 | 0.0001 | 75.6 ± 8.4 | 103.6 ± 10.7 | 28.0 | 1.4 |
| F159V | 16474 ± 1048 | 26241 ± 1907 | 0.0001 | 50.9 ± 2.9 | 80.7 ± 4.8 | 29.8 | 1.6 |
| F159Y | 2573 ± 301 | 10052 ± 825 | 0.0001 | 7.7 ± 0.7 | 30.1 ± 1.7 | 22.4 | 3.9 |
| A160G | 13634 ± 2705 | 19647 ± 3137 | 0.0017 | 35.1 ± 3.7 | 54.1 ± 5.3 | 19.0 | 1.4 |
| A160S | 18308 ± 685 | 27775 ± 1478 | 0.0001 | 56 ± 3.1 | 85.9 ± 6.3 | 29.9 | 1.5 |
| A160T | 20193 ± 1713 | 29082 ± 1980 | 0.0001 | 59.6 ± 3.5 | 90.9 ± 8.1 | 31.3 | 1.4 |
| A160V | 15511 ± 1847 | 22124 ± 1885 | 0.0013 | 44.1 ± 2.7 | 66 ± 4.8 | 21.9 | 1.4 |
| D161H | 21949 ± 2587 | 26457 ± 2512 | 0.0026 | 61.5 ± 2.9 | 77 ± 3.8 | 15.5 | 1.2 |
| D161N | 19553 ± 2838 | 24298 ± 3201 | 0.0062 | 54.5 ± 4.3 | 68.7 ± 4.9 | 14.1 | 1.2 |
| D161V | 13728 ± 1344 | 19117 ± 2241 | 0.0057 | 43.7 ± 1.7 | 59.7 ± 2.7 | 16.0 | 1.4 |
| D161Y | 11060 ± 1571 | 21231 ± 2136 | 0.0001 | 31 ± 2.5 | 63.1 ± 4.6 | 32.1 | 1.9 |
| W162S | 653 ± 38 | 3019 ± 210 | 0.0001 | 2.6 ± 0.2 | 11.8 ± 0.8 | 9.2 | 4.6 |
| V164A | 6491 ± 691 | 8468 ± 832 | 0.0147 | 24.5 ± 1.8 | 32 ± 2.2 | 7.5 | 1.3 |
| V164I | 12164 ± 1271 | 23219 ± 2640 | 0.0003 | 45.1 ± 3.4 | 87.1 ± 8.2 | 41.9 | 1.9 |
| V164L | 22055 ± 1619 | 36486 ± 1952 | 0.0001 | 51.2 ± 3.8 | 86.2 ± 5.2 | 35.0 | 1.7 |
| D165A | 271 ± 30 | 1397 ± 86 | 0.0001 | 1 ± 0.1 | 5.4 ± 0.3 | 4.4 | 5.2 |
| D165E | 1442 ± 43 | 6279 ± 288 | 0.0001 | 5.4 ± 0.2 | 23.8 ± 1.6 | 18.4 | 4.4 |
| L166M | 15603 ± 1630 | 27922 ± 1578 | 0.0001 | 55.2 ± 4.5 | 104 ± 7.3 | 48.8 | 1.8 |
| L166Q | 5656 ± 325 | 14720 ± 616 | 0.0001 | 18.4 ± 1.2 | 47.6 ± 1.9 | 29.2 | 2.6 |
| L167I | 14763 ± 942 | 22948 ± 1321 | 0.0001 | 46.8 ± 2.2 | 72.9 ± 2.7 | 26.1 | 1.6 |
| F169C | 6861 ± 977 | 16396 ± 1516 | 0.0001 | 18.1 ± 2 | 44.9 ± 2.3 | 26.9 | 2.4 |
| F169L | 15588 ± 1463 | 26527 ± 1806 | 0.0001 | 47.8 ± 2.9 | 82.3 ± 3.2 | 34.5 | 1.7 |
| F169V | 2870 ± 239 | 16145 ± 1680 | 0.0001 | 10.2 ± 0.9 | 53 ± 2.1 | 42.8 | 5.6 |
| F169Y | 14358 ± 1768 | 23459 ± 2391 | 0.0003 | 45.3 ± 2.8 | 75.5 ± 3.6 | 30.2 | 1.6 |
| G171A | 19081 ± 1801 | 27514 ± 2486 | 0.0030 | 57.6 ± 2.8 | 84 ± 5.7 | 26.4 | 1.4 |
| G171V | 856 ± 62 | 3111 ± 411 | 0.0001 | 2.8 ± 0.2 | 9.2 ± 0.9 | 6.4 | 3.6 |
| Y173C | 17669 ± 1240 | 27924 ± 1225 | 0.0001 | 51.1 ± 3.6 | 80.5 ± 3.3 | 29.3 | 1.6 |
| Y173F | 26479 ± 1523 | 33158 ± 657 | 0.0004 | 76.5 ± 4.2 | 97.7 ± 4.7 | 21.2 | 1.3 |
| Y173H | 21234 ± 879 | 27455 ± 1147 | 0.0002 | 61.9 ± 3.4 | 80.2 ± 4.6 | 18.3 | 1.3 |
| Y173S | 21751 ± 1625 | 26270 ± 994 | 0.0007 | 61.4 ± 3.3 | 76.2 ± 3.3 | 14.8 | 1.2 |
| D175G | 23065 ± 2315 | 28273 ± 1968 | 0.0128 | 74.7 ± 6.7 | 92.8 ± 6.2 | 18.1 | 1.2 |
| D175H | 18529 ± 1174 | 26201 ± 994 | 0.0001 | 60.7 ± 3.4 | 87.1 ± 3.9 | 26.4 | 1.4 |
| D175V | 10430 ± 915 | 16384 ± 1039 | 0.0001 | 33.7 ± 2.2 | 53.5 ± 2.5 | 19.7 | 1.6 |
| D175Y | 8991 ± 838 | 15923 ± 778 | 0.0001 | 29.4 ± 2.4 | 52.3 ± 1.9 | 22.9 | 1.8 |
| S176C | 20097 ± 1126 | 24777 ± 960 | 0.0067 | 63.3 ± 3.9 | 79.5 ± 5.1 | 16.2 | 1.2 |
| S176R | 22675 ± 886 | 30159 ± 1226 | 0.0001 | 66.3 ± 2 | 88.3 ± 3.3 | 22.0 | 1.3 |
| L177F | 15605 ± 911 | 28893 ± 1210 | 0.0001 | 45.3 ± 2.1 | 84 ± 2.3 | 38.7 | 1.9 |
| L177M | 23730 ± 946 | 33080 ± 829 | 0.0001 | 69.5 ± 2.3 | 97.4 ± 2.7 | 27.9 | 1.4 |
| L177S | 17445 ± 533 | 29868 ± 1909 | 0.0001 | 51.4 ± 1.7 | 87.2 ± 4.5 | 35.9 | 1.7 |
| L177V | 23616 ± 1282 | 31347 ± 1132 | 0.0001 | 68.9 ± 3.2 | 91.8 ± 2.8 | 22.9 | 1.3 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| L177W | 17321 ± 1025 | 30075 ± 867 | 0.0001 | 50.5 ± 2.6 | 88.2 ± 2 | 37.6 | 1.7 |
| E178A | 23910 ± 1511 | 29125 ± 2326 | 0.0481 | 70.3 ± 4.9 | 84.8 ± 6.8 | 14.5 | 1.2 |
| E178G | 17470 ± 2323 | 26566 ± 4263 | 0.0219 | 43.1 ± 4.7 | 61.7 ± 6.4 | 18.6 | 1.5 |
| E178K | 25584 ± 1225 | 31222 ± 1660 | 0.0077 | 74.5 ± 3.4 | 90.9 ± 4.8 | 16.4 | 1.2 |
| E178Q | 23272 ± 1501 | 29671 ± 1733 | 0.0062 | 68.1 ± 4.5 | 86.4 ± 5 | 18.3 | 1.3 |
| L180M | 35987 ± 2266 | 47587 ± 2132 | 0.0002 | 93.4 ± 6.6 | 122.9 ± 5.5 | 29.5 | 1.3 |
| L180S | 5625 ± 604 | 18335 ± 964 | 0.0001 | 15.4 ± 1.5 | 50.9 ± 2.3 | 35.5 | 3.3 |
| A181P | 10948 ± 725 | 21274 ± 1279 | 0.0001 | 31.7 ± 2 | 61.5 ± 3.3 | 29.8 | 1.9 |
| A181T | 17946 ± 1002 | 24490 ± 1576 | 0.0012 | 52.1 ± 2.7 | 71.3 ± 4.6 | 19.2 | 1.4 |
| A181V | 26667 ± 1945 | 32358 ± 2863 | 0.0339 | 79.1 ± 3.5 | 93.2 ± 5.3 | 14.2 | 1.2 |
| D182A | 33673 ± 2886 | 44436 ± 3828 | 0.0096 | 101.5 ± 5.7 | 133.3 ± 8.2 | 31.8 | 1.3 |
| D182E | 28082 ± 2023 | 38956 ± 2806 | 0.0011 | 84.8 ± 4 | 117.1 ± 4.5 | 32.3 | 1.4 |
| D182V | 26881 ± 2166 | 42107 ± 3524 | 0.0005 | 80.2 ± 4.2 | 124.8 ± 6.9 | 44.7 | 1.6 |
| D182Y | 28377 ± 2226 | 39247 ± 3250 | 0.0062 | 84.7 ± 4.1 | 116.5 ± 6.4 | 31.9 | 1.4 |
| Y184F | 26088 ± 1334 | 36815 ± 2009 | 0.0002 | 77.9 ± 4.4 | 109.7 ± 5.8 | 31.8 | 1.4 |
| Y184H | 10980 ± 867 | 17894 ± 1145 | 0.0001 | 30.2 ± 2.9 | 48.6 ± 3.5 | 18.4 | 1.6 |
| Y184S | 5213 ± 371 | 13965 ± 799 | 0.0001 | 15.4 ± 1 | 40.6 ± 1.6 | 25.2 | 2.7 |
| K185M | 33484 ± 2151 | 44387 ± 2696 | 0.0014 | 75.1 ± 4.6 | 102.9 ± 9 | 27.8 | 1.3 |
| K185N | 833 ± 38 | 10540 ± 618 | 0.0001 | 1.9 ± 0.1 | 24.4 ± 1.9 | 22.5 | 12.7 |
| K185Q | 14992 ± 947 | 25543 ± 1463 | 0.0001 | 43.6 ± 2.2 | 74.5 ± 2.9 | 30.9 | 1.7 |
| K185T | 32028 ± 1167 | 39805 ± 2259 | 0.0024 | 73.6 ± 4.4 | 92.6 ± 7.8 | 19.0 | 1.2 |
| H186D | 26924 ± 2047 | 34055 ± 1657 | 0.0067 | 60 ± 4.1 | 78.2 ± 5.2 | 18.2 | 1.3 |
| H186L | 31615 ± 1833 | 42145 ± 2540 | 0.0009 | 70.4 ± 3.4 | 97.5 ± 8.2 | 27.1 | 1.3 |
| H186N | 28175 ± 1462 | 39509 ± 1885 | 0.0001 | 63.5 ± 3.1 | 90.3 ± 5.8 | 26.8 | 1.4 |
| H186Q | 28845 ± 2365 | 38865 ± 2966 | 0.0120 | 76.9 ± 4.3 | 105.3 ± 7 | 28.5 | 1.4 |
| H186Y | 37644 ± 2421 | 53613 ± 2581 | 0.0001 | 83.8 ± 4.5 | 123.6 ± 8.9 | 39.8 | 1.4 |
| M187L | 1924 ± 64 | 12810 ± 929 | 0.0001 | 5.3 ± 0.2 | 34.5 ± 1.9 | 29.2 | 6.7 |
| S188A | 22589 ± 1833 | 32197 ± 2515 | 0.0072 | 60.6 ± 4 | 86.3 ± 4.9 | 25.7 | 1.4 |
| S188C | 18465 ± 1552 | 25569 ± 2083 | 0.0033 | 50.1 ± 3.7 | 68.6 ± 4.3 | 18.5 | 1.4 |
| S188F | 7746 ± 839 | 21273 ± 1477 | 0.0001 | 20.7 ± 2 | 57.1 ± 2.8 | 36.4 | 2.8 |
| S188P | BLD | 1159 ± 61 | 0.0001 | N/A | 3.2 ± 0.2 | 3.2 | NC |
| S188T | 17041 ± 1389 | 26198 ± 2461 | 0.0004 | 45.4 ± 2.5 | 69.5 ± 4.5 | 24.0 | 1.5 |
| S188Y | 12244 ± 1167 | 23849 ± 1725 | 0.0001 | 32.6 ± 2.6 | 64.1 ± 3.5 | 31.5 | 2.0 |
| L189S | 23204 ± 1213 | 29510 ± 1181 | 0.0007 | 72.6 ± 3.1 | 92.7 ± 3.2 | 20.1 | 1.3 |
| L189V | 25544 ± 1758 | 32031 ± 1633 | 0.0049 | 79.9 ± 5.1 | 100.1 ± 3.9 | 20.2 | 1.3 |
| A190D | 7141 ± 423 | 15887 ± 1308 | 0.0001 | 22.1 ± 1 | 49 ± 3.4 | 26.9 | 2.2 |
| A190G | 24299 ± 2173 | 34126 ± 2992 | 0.0030 | 70.5 ± 7.3 | 97.9 ± 9.8 | 27.4 | 1.4 |
| A190S | 27316 ± 1369 | 35787 ± 2235 | 0.0026 | 84.5 ± 3.2 | 110.6 ± 5.5 | 26.1 | 1.3 |
| A190T | 8600 ± 733 | 18373 ± 795 | 0.0001 | 26.3 ± 2 | 57 ± 1.9 | 30.7 | 2.1 |
| A190V | 12542 ± 1642 | 27078 ± 2910 | 0.0001 | 36.8 ± 5.1 | 77.9 ± 9.5 | 41.2 | 2.2 |
| L191M | 19968 ± 2010 | 34977 ± 3072 | 0.0001 | 58.4 ± 6.6 | 100.2 ± 9.8 | 41.7 | 1.8 |
| L191V | 24068 ± 1533 | 37342 ± 2569 | 0.0001 | 71.1 ± 4.7 | 110.2 ± 7.9 | 39.1 | 1.6 |
| N192D | 9035 ± 886 | 28923 ± 1892 | 0.0001 | 25.9 ± 3 | 81.5 ± 6.7 | 55.6 | 3.2 |
| N192H | 3103 ± 402 | 8765 ± 935 | 0.0001 | 8.6 ± 1.1 | 24.9 ± 3 | 16.4 | 2.8 |
| N192K | 8005 ± 776 | 22845 ± 1943 | 0.0001 | 26.3 ± 1.7 | 76.8 ± 5.6 | 50.5 | 2.9 |
| N192S | 2470 ± 217 | 4712 ± 843 | 0.0003 | 8.3 ± 0.6 | 15 ± 1.9 | 6.6 | 1.9 |
| N192T | 3756 ± 319 | 8326 ± 1268 | 0.0001 | 10.1 ± 0.7 | 23.5 ± 4 | 13.4 | 2.2 |
| R193G | 20819 ± 1615 | 32498 ± 2580 | 0.0009 | 64.7 ± 4.1 | 102.7 ± 7.8 | 38.0 | 1.6 |
| R193M | 27533 ± 2087 | 34818 ± 2049 | 0.0077 | 68.2 ± 2.7 | 89.4 ± 5.4 | 21.2 | 1.3 |
| R193T | 27863 ± 1953 | 38519 ± 2880 | 0.0053 | 70.7 ± 3.6 | 99.1 ± 7.6 | 28.4 | 1.4 |
| R193W | 10407 ± 919 | 21063 ± 1562 | 0.0001 | 32 ± 2.4 | 66.6 ± 4.6 | 34.6 | 2.0 |
| T194N | 753 ± 80 | 5923 ± 816 | 0.0001 | 2.2 ± 0.2 | 17.3 ± 2.2 | 15.1 | 7.9 |
| T194P | 951 ± 71 | 8134 ± 602 | 0.0001 | 2.6 ± 0.3 | 21.2 ± 1.6 | 18.6 | 8.6 |
| T194S | 27831 ± 2308 | 44208 ± 2889 | 0.0001 | 69.5 ± 3.9 | 112.1 ± 6.2 | 42.6 | 1.6 |
| G195C | 8165 ± 500 | 13240 ± 568 | 0.0001 | 24.6 ± 2.4 | 39.6 ± 3 | 15.0 | 1.6 |
| G195R | 15572 ± 893 | 30415 ± 1008 | 0.0001 | 46 ± 3.5 | 89.4 ± 4.8 | 43.4 | 2.0 |
| G195S | 20112 ± 883 | 25947 ± 1235 | 0.0001 | 60.5 ± 5 | 78 ± 6.6 | 17.5 | 1.3 |
| R196I | 12764 ± 1241 | 25303 ± 3386 | 0.0003 | 30.6 ± 1.8 | 59.6 ± 5 | 29.0 | 2.0 |
| R196K | 27718 ± 2086 | 38090 ± 2117 | 0.0009 | 69.8 ± 2.9 | 97.6 ± 3.2 | 27.8 | 1.4 |
| S197C | 4181 ± 151 | 7035 ± 598 | 0.0002 | 11.7 ± 0.8 | 18.3 ± 1 | 6.5 | 1.7 |
| S197G | 27255 ± 1639 | 33018 ± 1986 | 0.0249 | 72.3 ± 2.1 | 88.4 ± 3.7 | 16.1 | 1.2 |
| S197I | 9277 ± 581 | 18272 ± 1006 | 0.0001 | 25.2 ± 1.3 | 49.5 ± 2.1 | 24.3 | 2.0 |
| S197N | 23664 ± 1103 | 30051 ± 1440 | 0.0006 | 56.9 ± 2.5 | 72.1 ± 3.3 | 15.2 | 1.3 |
| S197T | 24022 ± 1698 | 33425 ± 1713 | 0.0001 | 57.6 ± 3.9 | 79.9 ± 3.6 | 22.3 | 1.4 |
| I198M | 29416 ± 1526 | 41174 ± 2420 | 0.0002 | 82.3 ± 6.7 | 113.7 ± 8 | 31.4 | 1.4 |
| I198S | 1296 ± 63 | 8455 ± 513 | 0.0001 | 3.6 ± 0.3 | 22.8 ± 1.3 | 19.2 | 6.5 |
| V199E | 5470 ± 293 | 15458 ± 855 | 0.0001 | 15.2 ± 1.1 | 41.5 ± 1.9 | 26.2 | 2.8 |
| V199L | 23090 ± 1117 | 41654 ± 2281 | 0.0001 | 64.4 ± 4.6 | 113.2 ± 6.6 | 48.8 | 1.8 |
| Y200N | 3364 ± 193 | 17117 ± 1368 | 0.0001 | 9.5 ± 0.8 | 46.8 ± 3.5 | 37.3 | 5.1 |
| Y200S | 514 ± 47 | 8573 ± 601 | 0.0001 | 1.4 ± 0.1 | 24.4 ± 1.5 | 22.9 | 16.7 |
| S201A | 37974 ± 2291 | 47325 ± 1754 | 0.0024 | 90.6 ± 5 | 113.1 ± 3.3 | 22.5 | 1.3 |
| S201C | 10947 ± 594 | 23033 ± 1510 | 0.0001 | 33.3 ± 2 | 71.2 ± 6 | 37.9 | 2.1 |
| S201T | 21522 ± 1510 | 43648 ± 2695 | 0.0001 | 60.5 ± 3.4 | 122.5 ± 4.4 | 62.0 | 2.0 |
| E203A | 2061 ± 101 | 4400 ± 185 | 0.0001 | 8.2 ± 0.5 | 17.3 ± 0.8 | 9.1 | 2.1 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| E203G | 12576 ± 575 | 21197 ± 865 | 0.0001 | 48.9 ± 1.9 | 83.7 ± 4.4 | 34.8 | 1.7 |
| E203Q | 612 ± 36 | 2639 ± 161 | 0.0001 | 1.9 ± 0.1 | 8.2 ± 0.7 | 6.3 | 4.3 |
| W204S | 355 ± 31 | 7926 ± 612 | 0.0001 | 1.4 ± 0.1 | 30.8 ± 2.2 | 29.4 | 22.3 |
| L206F | 17666 ± 1621 | 30374 ± 2385 | 0.0001 | 62.9 ± 3.5 | 111.6 ± 7.6 | 48.7 | 1.7 |
| L206H | 8805 ± 1133 | 11278 ± 619 | 0.0011 | 26.9 ± 3.5 | 34.2 ± 1.8 | 7.4 | 1.3 |
| L206I | 7337 ± 1182 | 18864 ± 2437 | 0.0002 | 25 ± 3.2 | 66.7 ± 7.2 | 41.7 | 2.6 |
| L206R | 3629 ± 311 | 4495 ± 188 | 0.0104 | 12.7 ± 1.1 | 15.8 ± 0.8 | 3.1 | 1.2 |
| L206V | 16753 ± 1106 | 30218 ± 1706 | 0.0001 | 61.1 ± 2.7 | 113.7 ± 7.9 | 52.6 | 1.8 |
| Y207F | 1499 ± 68 | 3459 ± 412 | 0.0001 | 4.8 ± 0.2 | 10.2 ± 0.9 | 5.4 | 2.3 |
| M208K | 1899 ± 80 | 14453 ± 1319 | 0.0001 | 6.6 ± 0.3 | 48.4 ± 3.1 | 41.9 | 7.6 |
| W209C | 11982 ± 1623 | 18442 ± 991 | 0.0001 | 33.3 ± 4.1 | 52.8 ± 4.1 | 19.5 | 1.5 |
| W209G | 27639 ± 2262 | 35592 ± 1340 | 0.0005 | 77.9 ± 6.3 | 101.9 ± 6.7 | 24.0 | 1.3 |
| P210H | 20611 ± 1077 | 32983 ± 1037 | 0.0001 | 63.4 ± 2.6 | 102.9 ± 4 | 39.5 | 1.6 |
| P210T | 17748 ± 2301 | 21988 ± 829 | 0.0077 | 53.5 ± 6 | 69.5 ± 3.7 | 16.0 | 1.2 |
| F211C | 15289 ± 1161 | 22737 ± 1182 | 0.0001 | 44.4 ± 3.3 | 65.9 ± 3.1 | 21.4 | 1.5 |
| F211L | 27936 ± 2981 | 44713 ± 1823 | 0.0001 | 65 ± 5.8 | 106.5 ± 3.4 | 41.5 | 1.6 |
| F211S | 22923 ± 1035 | 34359 ± 1783 | 0.0001 | 68 ± 4.4 | 100.9 ± 5.9 | 32.9 | 1.5 |
| F211V | 24843 ± 2001 | 35355 ± 1742 | 0.0003 | 72.7 ± 5.9 | 103.8 ± 5.7 | 31.1 | 1.4 |
| F211Y | 28160 ± 2206 | 35233 ± 1670 | 0.0049 | 83.4 ± 7.5 | 104.3 ± 6.5 | 20.9 | 1.3 |
| Q212H | 32993 ± 2051 | 40381 ± 2380 | 0.0049 | 87.6 ± 4.3 | 108.6 ± 6 | 21.0 | 1.2 |
| Q212P | 14401 ± 1189 | 19918 ± 903 | 0.0003 | 37.1 ± 3.5 | 53.1 ± 3.7 | 15.9 | 1.4 |
| K213E | 16620 ± 1446 | 20792 ± 1647 | 0.0096 | 37.7 ± 1.9 | 48.1 ± 2.8 | 10.4 | 1.3 |
| K213Q | 20448 ± 1811 | 26374 ± 2372 | 0.0033 | 47.1 ± 2.8 | 60.8 ± 4 | 13.7 | 1.3 |
| P214A | 18022 ± 1147 | 36961 ± 1888 | 0.0001 | 54.1 ± 4.3 | 110.2 ± 6.9 | 56.1 | 2.1 |
| P214H | 1652 ± 116 | 16179 ± 1128 | 0.0001 | 4.8 ± 0.4 | 46.9 ± 4 | 42.1 | 9.8 |
| P214R | 25368 ± 1515 | 46719 ± 2717 | 0.0001 | 74.9 ± 4.7 | 137.3 ± 7.8 | 62.4 | 1.8 |
| P214T | 14899 ± 1328 | 36244 ± 2498 | 0.0001 | 43.4 ± 4.5 | 103.9 ± 8.4 | 60.5 | 2.4 |
| N215H | 7453 ± 631 | 18621 ± 1170 | 0.0001 | 22.2 ± 2.2 | 55.6 ± 4.2 | 33.3 | 2.5 |
| N215K | 10660 ± 1166 | 20220 ± 1700 | 0.0001 | 31.6 ± 2.4 | 61.4 ± 3.3 | 29.7 | 1.9 |
| N215T | 5392 ± 425 | 13007 ± 910 | 0.0001 | 16.6 ± 1 | 40 ± 1.7 | 23.4 | 2.4 |
| N215Y | 2599 ± 259 | 12737 ± 1218 | 0.0001 | 7.4 ± 0.6 | 36.2 ± 2.8 | 28.8 | 4.9 |
| Y216F | 30024 ± 2106 | 37273 ± 1708 | 0.0026 | 94.3 ± 6.3 | 118.9 ± 6.6 | 24.6 | 1.2 |
| Y216H | 17014 ± 764 | 27689 ± 1530 | 0.0001 | 53.3 ± 1.9 | 86.7 ± 4.1 | 33.4 | 1.6 |
| Y216N | 2280 ± 162 | 19311 ± 1513 | 0.0001 | 7 ± 0.6 | 56.2 ± 3 | 49.2 | 8.5 |
| T217A | 18943 ± 1372 | 26939 ± 2043 | 0.0026 | 57.8 ± 3.9 | 81.4 ± 5.2 | 23.7 | 1.4 |
| T217I | 16049 ± 1284 | 23470 ± 1933 | 0.0026 | 48.1 ± 3.2 | 70.4 ± 4.8 | 22.3 | 1.5 |
| T217K | 23428 ± 1823 | 33844 ± 2556 | 0.0024 | 71 ± 4.9 | 101.9 ± 6.3 | 30.9 | 1.4 |
| T217P | 16181 ± 1175 | 22379 ± 1763 | 0.0120 | 49.2 ± 3.4 | 67.2 ± 4.1 | 18.0 | 1.4 |
| T217R | 17019 ± 1476 | 25272 ± 1907 | 0.0013 | 51 ± 3.8 | 75.7 ± 4.5 | 24.8 | 1.5 |
| T217S | 22763 ± 1515 | 30767 ± 1213 | 0.0001 | 71.8 ± 4.6 | 98.3 ± 5.3 | 26.5 | 1.4 |
| E218A | 25638 ± 2941 | 39175 ± 3493 | 0.0022 | 76 ± 7.5 | 116.7 ± 8.1 | 40.7 | 1.5 |
| E218D | 33776 ± 2840 | 43841 ± 3581 | 0.0072 | 93.6 ± 8.3 | 122.7 ± 11.5 | 29.1 | 1.3 |
| E218G | 7563 ± 677 | 26769 ± 3204 | 0.0001 | 19.9 ± 1.3 | 68 ± 4.3 | 48.2 | 3.5 |
| E218K | 12974 ± 1017 | 27016 ± 2228 | 0.0001 | 39.3 ± 2.8 | 82.1 ± 6 | 42.8 | 2.1 |
| E218Q | 30758 ± 2592 | 42487 ± 3621 | 0.0169 | 92.7 ± 7 | 128 ± 9.5 | 35.3 | 1.4 |
| E218V | 26041 ± 1888 | 36278 ± 2419 | 0.0013 | 71.4 ± 5.3 | 101.7 ± 8.6 | 30.3 | 1.4 |
| I219F | 5506 ± 561 | 29184 ± 2616 | 0.0001 | 14.9 ± 1.5 | 80.6 ± 7.3 | 65.6 | 5.3 |
| I219M | 8627 ± 769 | 26166 ± 1736 | 0.0001 | 23.6 ± 2.1 | 71.5 ± 4.3 | 47.9 | 3.0 |
| I219S | 154 ± 20 | 3592 ± 274 | 0.0001 | 0.4 ± 0.1 | 10.3 ± 1.1 | 9.8 | 23.3 |
| R220L | 18399 ± 1213 | 27014 ± 1455 | 0.0001 | 49.7 ± 2.9 | 73.7 ± 3.6 | 24.0 | 1.5 |
| Q221E | 30425 ± 2264 | 37571 ± 2598 | 0.0360 | 86.7 ± 6.1 | 109.5 ± 8.8 | 22.8 | 1.2 |
| Q221H | 31494 ± 2714 | 40085 ± 3310 | 0.0111 | 87.8 ± 6.6 | 113.5 ± 8.3 | 25.7 | 1.3 |
| Q221K | 33217 ± 2944 | 42352 ± 3561 | 0.0319 | 93.5 ± 7.4 | 122.5 ± 10.4 | 29.0 | 1.3 |
| Q221L | 31279 ± 2821 | 39379 ± 3245 | 0.0158 | 87.6 ± 7 | 112.4 ± 8.8 | 24.9 | 1.3 |
| Q221R | 29462 ± 2455 | 38738 ± 3284 | 0.0283 | 82.1 ± 5.8 | 110.5 ± 8.7 | 28.4 | 1.3 |
| Y222C | 21231 ± 1470 | 32597 ± 1888 | 0.0001 | 52.6 ± 2.9 | 83.5 ± 6.1 | 30.9 | 1.5 |
| Y222D | 1393 ± 93 | 12177 ± 1005 | 0.0001 | 3.9 ± 0.2 | 34.5 ± 2.5 | 30.6 | 8.7 |
| Y222H | 31229 ± 1985 | 41680 ± 2577 | 0.0020 | 87.2 ± 4.4 | 118.6 ± 6.8 | 31.4 | 1.3 |
| Y222N | 25948 ± 1953 | 37634 ± 2615 | 0.0007 | 72.1 ± 4.4 | 107.8 ± 7.2 | 35.6 | 1.5 |
| Y222S | 22757 ± 1745 | 35534 ± 2237 | 0.0001 | 63.4 ± 4.1 | 101.2 ± 6.1 | 37.9 | 1.6 |
| N224H | 26013 ± 2235 | 42176 ± 3315 | 0.0006 | 64.6 ± 5.1 | 109.2 ± 10.4 | 44.6 | 1.6 |
| R227G | 1392 ± 71 | 5084 ± 651 | 0.0001 | 3.4 ± 0.1 | 11.9 ± 1.3 | 8.5 | 3.7 |
| N228H | 23110 ± 1663 | 37026 ± 2206 | 0.0001 | 56.1 ± 3.7 | 90.8 ± 5.2 | 34.7 | 1.6 |
| N228I | 42680 ± 3934 | 65879 ± 4049 | 0.0002 | 102 ± 7.8 | 158.6 ± 6.1 | 56.6 | 1.5 |
| N228T | 47321 ± 3640 | 57308 ± 3851 | 0.0405 | 122.7 ± 8.2 | 149.8 ± 8.1 | 27.1 | 1.2 |
| F229I | 26139 ± 2203 | 31786 ± 1919 | 0.0301 | 63.2 ± 4.6 | 77.3 ± 3.6 | 14.1 | 1.2 |
| F229S | 55992 ± 4881 | 67601 ± 4129 | 0.0360 | 134 ± 9.1 | 163.4 ± 7.6 | 29.4 | 1.2 |
| F229Y | 45676 ± 3431 | 56301 ± 4108 | 0.0319 | 110.8 ± 6.6 | 135.1 ± 7.9 | 24.3 | 1.2 |
| A230D | 19022 ± 1950 | 25008 ± 2188 | 0.0283 | 62.5 ± 4.5 | 84 ± 4.8 | 21.5 | 1.3 |
| A230G | 34550 ± 3372 | 51722 ± 3294 | 0.0008 | 123.1 ± 9.6 | 189 ± 9.5 | 65.9 | 1.5 |
| A230P | 18686 ± 1606 | 27571 ± 2579 | 0.0072 | 63.2 ± 4.9 | 92.7 ± 7.3 | 29.5 | 1.5 |
| A230V | 30702 ± 2050 | 40168 ± 2422 | 0.0039 | 81.3 ± 4.2 | 106.6 ± 3.6 | 25.3 | 1.3 |
| I232L | 1031 ± 81 | 7224 ± 945 | 0.0001 | 2.7 ± 0.2 | 17.5 ± 1.6 | 14.9 | 7.0 |
| I232M | 15493 ± 1384 | 41190 ± 2297 | 0.0001 | 38.6 ± 2.2 | 109.4 ± 8.9 | 70.8 | 2.7 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| I232V | 44901 ± 3412 | 63373 ± 3592 | 0.0003 | 113.8 ± 5.7 | 162.7 ± 7.7 | 48.9 | 1.4 |
| D233A | 23075 ± 1494 | 33219 ± 2019 | 0.0002 | 59.1 ± 3.1 | 86.1 ± 5.7 | 27.0 | 1.4 |
| D233E | 17676 ± 758 | 23493 ± 924 | 0.0001 | 51 ± 2.4 | 67.3 ± 2.5 | 16.4 | 1.3 |
| D233G | 15091 ± 776 | 21651 ± 773 | 0.0001 | 41.5 ± 1.9 | 60 ± 2.4 | 18.6 | 1.4 |
| D233V | 14655 ± 833 | 22394 ± 944 | 0.0001 | 42.1 ± 2.3 | 64.1 ± 2.5 | 22.0 | 1.5 |
| S235A | 1594 ± 58 | 10500 ± 653 | 0.0001 | 4.4 ± 0.1 | 28.1 ± 1.1 | 23.7 | 6.6 |
| S235T | 630 ± 54 | 4696 ± 235 | 0.0001 | 1.8 ± 0.1 | 13.4 ± 0.7 | 11.6 | 7.5 |
| K237I | 27059 ± 1342 | 40071 ± 1794 | 0.0001 | 79.4 ± 2.6 | 119 ± 5 | 39.6 | 1.5 |
| S238C | 4369 ± 302 | 13891 ± 677 | 0.0001 | 12.6 ± 0.9 | 39 ± 1.3 | 26.4 | 3.2 |
| S238I | 1456 ± 58 | 11704 ± 556 | 0.0001 | 4.3 ± 0.3 | 33.8 ± 1.9 | 29.5 | 8.0 |
| S238T | 22557 ± 1256 | 32589 ± 1426 | 0.0001 | 64.7 ± 4 | 93.7 ± 4.6 | 29.0 | 1.4 |
| I239L | 15008 ± 905 | 26331 ± 1039 | 0.0001 | 42.7 ± 2.5 | 75.4 ± 3.3 | 32.7 | 1.8 |
| K240E | 34180 ± 2424 | 41878 ± 3056 | 0.0455 | 105.2 ± 5.1 | 130.6 ± 7.9 | 25.4 | 1.2 |
| K240M | 20450 ± 2148 | 32367 ± 2715 | 0.0010 | 62.4 ± 5.2 | 99.6 ± 6.2 | 37.2 | 1.6 |
| K240R | 15131 ± 1420 | 22482 ± 1791 | 0.0030 | 46.8 ± 3.7 | 70.8 ± 5.5 | 23.9 | 1.5 |
| S241C | 19490 ± 1584 | 24585 ± 1839 | 0.0283 | 60.5 ± 4.1 | 75.9 ± 4 | 15.5 | 1.3 |
| S241I | 18643 ± 1223 | 39204 ± 2588 | 0.0001 | 53.8 ± 2.4 | 113.8 ± 5.7 | 60.0 | 2.1 |
| S241T | 29172 ± 2586 | 38406 ± 3223 | 0.0057 | 82.6 ± 4.4 | 108.9 ± 5.2 | 26.2 | 1.3 |
| I242L | 20179 ± 1224 | 33317 ± 2686 | 0.0001 | 58.5 ± 2.7 | 96.2 ± 5.7 | 37.7 | 1.7 |
| I242M | 2184 ± 180 | 4826 ± 337 | 0.0001 | 6.4 ± 0.5 | 13.9 ± 0.9 | 7.5 | 2.2 |
| I242S | 1533 ± 62 | 15351 ± 937 | 0.0001 | 4.8 ± 0.5 | 44.9 ± 2.5 | 40.1 | 10.0 |
| L243M | 24772 ± 1493 | 36055 ± 2526 | 0.0004 | 72.7 ± 3.7 | 104.7 ± 5.3 | 31.9 | 1.5 |
| L243S | 7839 ± 489 | 21312 ± 1381 | 0.0001 | 23.6 ± 1.8 | 61.7 ± 2.9 | 38.1 | 2.7 |
| L243V | 23758 ± 1553 | 32500 ± 2227 | 0.0020 | 68.4 ± 2.7 | 94.1 ± 4.9 | 25.7 | 1.4 |
| D244A | 10530 ± 850 | 20925 ± 1168 | 0.0001 | 28.3 ± 1.6 | 57.5 ± 2.6 | 29.2 | 2.0 |
| D244E | 16889 ± 1765 | 31657 ± 1775 | 0.0001 | 45.1 ± 3.7 | 86.8 ± 3.7 | 41.7 | 1.9 |
| D244G | 9983 ± 848 | 23926 ± 1422 | 0.0001 | 26.8 ± 1.6 | 64.6 ± 2.2 | 37.8 | 2.4 |
| D244V | 983 ± 99 | 7446 ± 537 | 0.0001 | 2.8 ± 0.3 | 20.2 ± 1 | 17.4 | 7.6 |
| D244Y | 5983 ± 586 | 15554 ± 1191 | 0.0001 | 15.7 ± 1.2 | 42 ± 2.3 | 26.3 | 2.6 |
| W245C | 23353 ± 1993 | 33826 ± 2561 | 0.0015 | 63.8 ± 4.2 | 93.4 ± 6.6 | 29.7 | 1.5 |
| T246A | 20184 ± 1516 | 26581 ± 909 | 0.0001 | 67.4 ± 5.2 | 89.3 ± 5.1 | 21.9 | 1.3 |
| T246I | 18702 ± 1095 | 29303 ± 1319 | 0.0001 | 61.2 ± 3.1 | 98.8 ± 6.8 | 37.6 | 1.6 |
| T246K | BLD | 4118 ± 265 | 0.0001 | N/A | 14 ± 1.2 | 14.0 | NC |
| T246R | BLD | 1009 ± 64 | 0.0001 | N/A | 3.5 ± 0.4 | 3.5 | NC |
| S247A | 24276 ± 1509 | 29111 ± 1498 | 0.0045 | 80 ± 4.9 | 97.9 ± 7.1 | 18.0 | 1.2 |
| S247F | 7957 ± 848 | 18686 ± 1093 | 0.0001 | 25.3 ± 2.1 | 62.6 ± 4.7 | 37.3 | 2.4 |
| S247T | 16039 ± 1152 | 22511 ± 1461 | 0.0003 | 53.2 ± 3.9 | 74.8 ± 5.2 | 21.6 | 1.4 |
| S247Y | 7433 ± 798 | 18101 ± 1419 | 0.0001 | 23.5 ± 2 | 60.3 ± 4.9 | 36.8 | 2.4 |
| F248C | 20087 ± 2973 | 27351 ± 4250 | 0.0283 | 57.9 ± 3.3 | 77.1 ± 5 | 19.2 | 1.4 |
| F248L | 21360 ± 3675 | 28268 ± 4495 | 0.0072 | 59.8 ± 4.4 | 79.5 ± 5.2 | 19.8 | 1.3 |
| F248V | 20424 ± 2940 | 27075 ± 4121 | 0.0429 | 58.6 ± 3.1 | 76.7 ± 5 | 18.1 | 1.3 |
| F248Y | 25850 ± 2314 | 31204 ± 1758 | 0.0018 | 86.6 ± 4.9 | 107.8 ± 6.1 | 21.2 | 1.2 |
| N249D | 9050 ± 1262 | 19080 ± 2665 | 0.0001 | 26.6 ± 1.7 | 55.7 ± 2.8 | 29.0 | 2.1 |
| N249H | 25157 ± 2681 | 32119 ± 3556 | 0.0028 | 76.1 ± 2.2 | 96.2 ± 2.9 | 20.1 | 1.3 |
| N249I | 1864 ± 80 | 3353 ± 340 | 0.0014 | 7.1 ± 0.4 | 13.1 ± 1.8 | 6.0 | 1.8 |
| N249S | 7395 ± 926 | 12077 ± 977 | 0.0018 | 26.2 ± 2.9 | 45.1 ± 4.6 | 18.9 | 1.6 |
| N249T | 13923 ± 1557 | 21314 ± 2561 | 0.0022 | 42.4 ± 2.8 | 64.4 ± 3.7 | 21.9 | 1.5 |
| N249Y | 16445 ± 2008 | 22166 ± 2504 | 0.0018 | 49.4 ± 3.1 | 66.8 ± 2.5 | 17.3 | 1.4 |
| Q250E | 8159 ± 688 | 14252 ± 1068 | 0.0001 | 30.2 ± 1.6 | 52.9 ± 2.4 | 22.8 | 1.8 |
| Q250L | 2088 ± 234 | 7820 ± 877 | 0.0001 | 7.6 ± 0.6 | 28.9 ± 3 | 21.4 | 3.8 |
| E251G | 11980 ± 1124 | 16458 ± 1113 | 0.0064 | 46.1 ± 3.6 | 64.1 ± 3.3 | 18.0 | 1.4 |
| E251K | 16089 ± 1970 | 21714 ± 2048 | 0.0339 | 58.7 ± 6 | 80.8 ± 6.4 | 22.0 | 1.4 |
| E251Q | 11708 ± 1222 | 16261 ± 1537 | 0.0147 | 43.2 ± 3.6 | 60.8 ± 4.9 | 17.6 | 1.4 |
| E251V | 18585 ± 562 | 24051 ± 593 | 0.0001 | 61.6 ± 2.2 | 81.1 ± 3.9 | 19.5 | 1.3 |
| R252G | 18020 ± 692 | 23372 ± 803 | 0.0001 | 60.5 ± 3.5 | 77.9 ± 3.4 | 17.4 | 1.3 |
| I253F | 21127 ± 1055 | 26426 ± 1084 | 0.0018 | 71.2 ± 3 | 89 ± 2.7 | 17.8 | 1.3 |
| I253N | 1319 ± 62 | 8202 ± 357 | 0.0001 | 4.9 ± 0.2 | 30.6 ± 1.3 | 25.7 | 6.2 |
| I253V | 28837 ± 2142 | 37575 ± 3353 | 0.0053 | 83.9 ± 5.7 | 105.4 ± 4.3 | 21.5 | 1.3 |
| V254A | 23186 ± 1352 | 30783 ± 1376 | 0.0006 | 86.2 ± 4.9 | 114.5 ± 5 | 28.3 | 1.3 |
| V254D | 9616 ± 701 | 17536 ± 1256 | 0.0001 | 36.2 ± 2.9 | 65.7 ± 4.9 | 29.5 | 1.8 |
| V254F | 17887 ± 792 | 25725 ± 1079 | 0.0001 | 67 ± 3.5 | 96.5 ± 4.9 | 29.5 | 1.4 |
| V254G | 16438 ± 761 | 23014 ± 1190 | 0.0001 | 63.8 ± 3.3 | 88.3 ± 4 | 24.5 | 1.4 |
| D255A | 25626 ± 616 | 30916 ± 1369 | 0.0020 | 83.5 ± 2.1 | 100.1 ± 3.7 | 16.6 | 1.2 |
| D255E | 23441 ± 971 | 28215 ± 1532 | 0.0077 | 75.6 ± 2.1 | 90 ± 3 | 14.4 | 1.2 |
| D255H | 28982 ± 1416 | 35899 ± 1244 | 0.0005 | 93.8 ± 3.8 | 117 ± 4.2 | 23.1 | 1.2 |
| D255N | 17034 ± 769 | 22522 ± 1285 | 0.0011 | 66.2 ± 3.3 | 86.9 ± 4.8 | 20.7 | 1.3 |
| D255V | 12495 ± 504 | 17974 ± 1031 | 0.0002 | 40.2 ± 0.9 | 57.4 ± 2.2 | 17.2 | 1.4 |
| D255Y | 20319 ± 836 | 25724 ± 1133 | 0.0004 | 65.8 ± 2 | 83.2 ± 2.9 | 17.5 | 1.3 |
| V256D | 22272 ± 1410 | 31742 ± 1047 | 0.0001 | 77.2 ± 4.4 | 110.7 ± 3.2 | 33.5 | 1.4 |
| V256G | 21683 ± 942 | 30389 ± 884 | 0.0001 | 75.2 ± 2.4 | 106.6 ± 3.8 | 31.4 | 1.4 |
| V256L | 24022 ± 935 | 31507 ± 1624 | 0.0028 | 77.3 ± 1.7 | 100.9 ± 3.2 | 23.6 | 1.3 |
| A257S | 23677 ± 1041 | 30608 ± 983 | 0.0001 | 82.7 ± 3.4 | 107.4 ± 4 | 24.7 | 1.3 |
| G258E | 17926 ± 1400 | 26780 ± 1366 | 0.0001 | 62.6 ± 4.8 | 93.7 ± 4.9 | 31.1 | 1.5 |
| P259A | 19721 ± 1213 | 32585 ± 3063 | 0.0001 | 57 ± 2.4 | 91.7 ± 4.4 | 34.7 | 1.7 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| P259T | 10040 ± 780 | 20286 ± 925 | 0.0001 | 34.6 ± 2.3 | 71.2 ± 3.4 | 36.6 | 2.0 |
| G260W | 155 ± 55 | 1188 ± 98 | 0.0001 | 0.4 ± 0.1 | 3.4 ± 0.2 | 3.0 | 7.7 |
| G261A | 27318 ± 2249 | 34233 ± 3145 | 0.0382 | 79.5 ± 5.9 | 96.4 ± 4.5 | 16.9 | 1.3 |
| N263H | 7205 ± 590 | 22283 ± 1252 | 0.0001 | 25.4 ± 2 | 78.9 ± 4.7 | 53.6 | 3.1 |
| N263T | 527 ± 54 | 4649 ± 207 | 0.0001 | 1.8 ± 0.2 | 17.2 ± 1.5 | 15.4 | 8.8 |
| D264H | 407 ± 21 | 4188 ± 439 | 0.0001 | 1.5 ± 0.1 | 15.4 ± 2.2 | 14.0 | 10.3 |
| D264N | 18857 ± 1196 | 31010 ± 1310 | 0.0001 | 66 ± 4.1 | 110.4 ± 5.7 | 44.4 | 1.6 |
| P265A | 35589 ± 1537 | 47153 ± 2302 | 0.0001 | 86.9 ± 7.1 | 114 ± 8.6 | 27.1 | 1.3 |
| P265Q | 8975 ± 521 | 31993 ± 1540 | 0.0001 | 21 ± 1.1 | 76.8 ± 5.2 | 55.8 | 3.6 |
| M267L | 2982 ± 411 | 9684 ± 760 | 0.0001 | 8.4 ± 1.1 | 26.8 ± 1.3 | 18.4 | 3.3 |
| M267V | 13852 ± 1513 | 17656 ± 1363 | 0.0219 | 39 ± 3.8 | 50.2 ± 3.5 | 11.2 | 1.3 |
| L268F | BLD | 3139 ± 435 | 0.0001 | N/A | 8 ± 1.1 | 8.0 | NC |
| L268I | 30462 ± 1925 | 36529 ± 2102 | 0.0411 | 74 ± 4.1 | 90.1 ± 5.3 | 16.1 | 1.2 |
| V269L | 429 ± 36 | 4675 ± 523 | 0.0001 | 1 ± 0.1 | 11.7 ± 1.3 | 10.6 | 10.9 |
| I270L | 36361 ± 2544 | 46689 ± 3106 | 0.0104 | 87.4 ± 3.4 | 113.7 ± 5.2 | 26.2 | 1.3 |
| I270S | 274 ± 39 | 7634 ± 573 | 0.0001 | 0.7 ± 0.1 | 21.3 ± 1.8 | 20.6 | 27.9 |
| I270V | 30682 ± 2319 | 37467 ± 2651 | 0.0301 | 73.6 ± 3.5 | 90.3 ± 3.6 | 16.8 | 1.2 |
| N272D | 28459 ± 2692 | 39327 ± 2685 | 0.0024 | 68.5 ± 4.5 | 95.9 ± 4.5 | 27.4 | 1.4 |
| F273Y | 35815 ± 3175 | 45321 ± 3511 | 0.0319 | 82.3 ± 5.6 | 105.8 ± 6.6 | 23.5 | 1.3 |
| L275I | 5669 ± 420 | 22341 ± 1943 | 0.0001 | 13.1 ± 0.6 | 52.8 ± 3.9 | 39.6 | 3.9 |
| W277L | 28295 ± 2855 | 37190 ± 3059 | 0.0234 | 62 ± 5.8 | 86.8 ± 10.3 | 24.9 | 1.3 |
| N278I | 471 ± 67 | 7024 ± 774 | 0.0001 | 1.1 ± 0.1 | 16.7 ± 1.7 | 15.6 | 14.9 |
| Q280L | 454 ± 64 | 8041 ± 943 | 0.0001 | 1 ± 0.1 | 19.2 ± 2.2 | 18.1 | 17.7 |
| Q280R | 1165 ± 139 | 10482 ± 1406 | 0.0001 | 2.7 ± 0.2 | 24.8 ± 3.3 | 22.2 | 9.0 |
| V281A | 27793 ± 1110 | 45870 ± 2186 | 0.0001 | 58.6 ± 3.1 | 97.1 ± 5.7 | 38.4 | 1.7 |
| V281E | 23351 ± 783 | 37701 ± 1194 | 0.0001 | 53.1 ± 1.3 | 85.8 ± 1.9 | 32.6 | 1.6 |
| V281G | 8729 ± 380 | 17662 ± 959 | 0.0001 | 18.3 ± 0.9 | 37.4 ± 2.4 | 19.2 | 2.0 |
| V281L | 30655 ± 1494 | 38560 ± 1647 | 0.0007 | 64.1 ± 3.3 | 81 ± 4.2 | 16.9 | 1.3 |
| T282S | 16612 ± 753 | 25105 ± 1005 | 0.0001 | 37.7 ± 1.3 | 57 ± 1.5 | 19.3 | 1.5 |
| Q283E | 366 ± 31 | 6195 ± 415 | 0.0001 | 0.8 ± 0.1 | 13.4 ± 1.2 | 12.6 | 16.9 |
| Q283H | 32420 ± 1104 | 44815 ± 1903 | 0.0001 | 74.1 ± 2.4 | 101.7 ± 3.1 | 27.6 | 1.4 |
| Q283L | 160 ± 25 | 7906 ± 977 | 0.0001 | 0.4 ± 0.1 | 21.3 ± 1.9 | 20.9 | 49.5 |
| M284I | 24698 ± 1943 | 35578 ± 2125 | 0.0011 | 58.6 ± 3.7 | 85.3 ± 3.7 | 26.7 | 1.4 |
| M284L | 28797 ± 1915 | 36282 ± 1676 | 0.0008 | 65.4 ± 3.7 | 83.8 ± 4.1 | 18.4 | 1.3 |
| A285G | 21580 ± 1326 | 29210 ± 1510 | 0.0006 | 51.9 ± 2.5 | 70.1 ± 2.4 | 18.2 | 1.4 |
| A285T | 20186 ± 1322 | 32504 ± 2023 | 0.0001 | 45.5 ± 2.4 | 73.5 ± 3.7 | 28.0 | 1.6 |
| A285V | 23407 ± 861 | 32500 ± 1568 | 0.0001 | 55.1 ± 2.1 | 76.5 ± 3.6 | 21.4 | 1.4 |
| L286F | 29390 ± 1225 | 39732 ± 2859 | 0.0004 | 64.5 ± 2.8 | 87.7 ± 7.3 | 23.2 | 1.4 |
| L286H | 359 ± 52 | 7960 ± 1511 | 0.0001 | 0.8 ± 0.1 | 16.2 ± 2.5 | 15.4 | 22.2 |
| L286V | 28713 ± 3734 | 41335 ± 3422 | 0.0030 | 66 ± 5.1 | 98.9 ± 4.3 | 32.9 | 1.4 |
| A288G | 22208 ± 1755 | 30458 ± 2381 | 0.0057 | 56.8 ± 6.3 | 76.7 ± 7.4 | 19.9 | 1.4 |
| A288S | 45790 ± 3395 | 55988 ± 2609 | 0.0206 | 114.6 ± 10.6 | 140.4 ± 10.5 | 25.8 | 1.2 |
| A288V | 32777 ± 3168 | 45501 ± 4634 | 0.0193 | 82.5 ± 9 | 114.2 ± 12.4 | 31.7 | 1.4 |
| I289L | 37941 ± 3208 | 49640 ± 3368 | 0.0077 | 96.9 ± 10.5 | 124.4 ± 11.3 | 27.5 | 1.3 |
| I289T | 15033 ± 1450 | 29673 ± 2480 | 0.0001 | 38.6 ± 4.8 | 75.3 ± 7.9 | 36.7 | 2.0 |
| I289V | 25845 ± 1706 | 31489 ± 1397 | 0.0039 | 61.2 ± 3.2 | 74.8 ± 2.7 | 13.6 | 1.2 |
| A291G | 6953 ± 474 | 16073 ± 954 | 0.0001 | 26.6 ± 1.5 | 61.5 ± 2.6 | 34.9 | 2.3 |
| A292G | 12091 ± 652 | 19406 ± 1361 | 0.0001 | 41.1 ± 2.2 | 65.3 ± 4 | 24.3 | 1.6 |
| A292S | 18002 ± 1127 | 23779 ± 1584 | 0.0077 | 68.6 ± 2.9 | 89.9 ± 3.4 | 21.3 | 1.3 |
| L294F | 10147 ± 971 | 23486 ± 2100 | 0.0001 | 29.6 ± 3 | 68.4 ± 6.5 | 38.8 | 2.3 |
| L294I | 8345 ± 717 | 26761 ± 1915 | 0.0001 | 24.8 ± 2.4 | 78.4 ± 6 | 53.6 | 3.2 |
| L294V | 1452 ± 71 | 13038 ± 880 | 0.0001 | 4.4 ± 0.3 | 38.2 ± 2.7 | 33.8 | 9.0 |
| F295I | 26687 ± 1470 | 35634 ± 2203 | 0.0013 | 78.3 ± 4.5 | 104.1 ± 6.6 | 25.7 | 1.3 |
| F295S | 230 ± 45 | 3847 ± 309 | 0.0001 | 0.6 ± 0.1 | 11.1 ± 0.9 | 10.5 | 16.8 |
| F295V | 24973 ± 1752 | 41782 ± 2877 | 0.0001 | 73.4 ± 5.7 | 121.5 ± 7.7 | 48.0 | 1.7 |
| F295Y | 21452 ± 1929 | 34502 ± 2504 | 0.0003 | 62.9 ± 6.1 | 99.2 ± 6.5 | 36.3 | 1.6 |
| S297T | BLD | 3178 ± 327 | 0.0001 | N/A | 9.7 ± 0.8 | 9.7 | NC |
| N298D | 795 ± 56 | 7645 ± 388 | 0.0001 | 2.5 ± 0.2 | 24.2 ± 1.2 | 21.7 | 9.6 |
| N298I | 2942 ± 262 | 13906 ± 535 | 0.0001 | 9.2 ± 0.7 | 44.1 ± 1.8 | 34.9 | 4.7 |
| N298T | 20581 ± 1736 | 25249 ± 1705 | 0.0033 | 61.2 ± 4.7 | 75.4 ± 4.3 | 14.2 | 1.2 |
| D299H | 358 ± 36 | 8424 ± 875 | 0.0001 | 1 ± 0.1 | 23.1 ± 2.4 | 22.1 | 23.5 |
| D299N | 11973 ± 1961 | 14668 ± 809 | 0.0005 | 29.2 ± 4.7 | 37.1 ± 2.9 | 7.8 | 1.2 |
| L300I | 7328 ± 448 | 19317 ± 757 | 0.0001 | 20.7 ± 0.9 | 55.1 ± 2 | 34.4 | 2.6 |
| L300V | 406 ± 48 | 5354 ± 203 | 0.0001 | 1.3 ± 0.2 | 15.3 ± 0.6 | 14.0 | 13.2 |
| H302D | 32677 ± 1437 | 41716 ± 1847 | 0.0008 | 95.1 ± 5.8 | 120.8 ± 6.6 | 25.8 | 1.3 |
| H302L | 24188 ± 1797 | 34251 ± 1760 | 0.0001 | 60.7 ± 5.1 | 85.3 ± 4.7 | 24.6 | 1.4 |
| H302N | 31958 ± 1777 | 42296 ± 2028 | 0.0003 | 91.2 ± 4.3 | 121.4 ± 6.2 | 30.2 | 1.3 |
| H302Y | 22554 ± 1372 | 31688 ± 1241 | 0.0001 | 59 ± 3.5 | 84.2 ± 5.2 | 25.3 | 1.4 |
| I303S | BLD | 1496 ± 117 | 0.0001 | N/A | 3.8 ± 0.3 | 3.8 | NC |
| S304I | 11675 ± 939 | 17257 ± 1837 | 0.0072 | 30.6 ± 1.4 | 44.6 ± 2.4 | 13.9 | 1.5 |
| Q306E | 31745 ± 2212 | 39019 ± 2405 | 0.0169 | 82 ± 2.8 | 101.7 ± 4.2 | 19.7 | 1.2 |
| Q306L | 19792 ± 1899 | 26515 ± 1960 | 0.0147 | 56.9 ± 4 | 76.4 ± 3.4 | 19.6 | 1.3 |
| Q306P | 19933 ± 1648 | 29495 ± 1671 | 0.0004 | 57.4 ± 2.8 | 87.5 ± 4.8 | 30.0 | 1.5 |
| A307D | 42522 ± 2430 | 54502 ± 3031 | 0.0026 | 126 ± 5.7 | 161.9 ± 8.6 | 35.9 | 1.3 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| A307G | 17871 ± 1029 | 26053 ± 1631 | 0.0006 | 52.9 ± 2.5 | 76.3 ± 3.1 | 23.4 | 1.5 |
| A307P | 11388 ± 905 | 15572 ± 1124 | 0.0072 | 32.8 ± 1.7 | 45.2 ± 2.1 | 12.3 | 1.4 |
| A307S | 29300 ± 2037 | 38558 ± 2274 | 0.0026 | 85.9 ± 4.5 | 113.6 ± 5.2 | 27.7 | 1.3 |
| A307V | 11478 ± 1200 | 25989 ± 2015 | 0.0001 | 27.5 ± 2 | 62.2 ± 3.3 | 34.7 | 2.3 |
| K308I | 19195 ± 1555 | 29251 ± 2026 | 0.0005 | 48.6 ± 3.9 | 72.7 ± 3.6 | 24.2 | 1.5 |
| K308Q | 24208 ± 1996 | 35663 ± 2680 | 0.0022 | 59.1 ± 3.8 | 89.1 ± 5.5 | 30.0 | 1.5 |
| K308R | 27103 ± 1767 | 35824 ± 2438 | 0.0057 | 68.9 ± 4.3 | 89.1 ± 4.5 | 20.3 | 1.3 |
| A309D | 31696 ± 3036 | 38325 ± 2376 | 0.0077 | 78.3 ± 5.2 | 95.8 ± 3.7 | 17.6 | 1.2 |
| A309T | 29214 ± 1907 | 36228 ± 1841 | 0.0067 | 74.1 ± 4.6 | 92.7 ± 4.8 | 18.6 | 1.2 |
| L310I | 31871 ± 2599 | 40310 ± 3345 | 0.0266 | 72.8 ± 3.6 | 92.4 ± 5.1 | 19.6 | 1.3 |
| L311I | 4020 ± 235 | 11558 ± 781 | 0.0001 | 12.1 ± 0.8 | 35.3 ± 3.1 | 23.2 | 2.9 |
| Q312E | 1365 ± 57 | 6331 ± 466 | 0.0001 | 4.1 ± 0.2 | 19.2 ± 1.7 | 15.1 | 4.6 |
| Q312K | 6733 ± 510 | 11934 ± 624 | 0.0001 | 19.7 ± 1.4 | 35.2 ± 1.8 | 15.5 | 1.8 |
| Q312L | 16986 ± 1428 | 23967 ± 1400 | 0.0011 | 50.1 ± 4.1 | 71.5 ± 4.6 | 21.3 | 1.4 |
| D313E | 14321 ± 1579 | 18273 ± 1330 | 0.0014 | 42.5 ± 2.3 | 55.7 ± 1.9 | 13.2 | 1.3 |
| D313V | 894 ± 33 | 3480 ± 580 | 0.0001 | 2.9 ± 0.2 | 9.6 ± 0.9 | 6.7 | 3.9 |
| K314E | 13026 ± 1767 | 16765 ± 2098 | 0.0033 | 37.7 ± 2.5 | 48.7 ± 2.8 | 11.0 | 1.3 |
| K314M | 18231 ± 2878 | 23043 ± 2838 | 0.0014 | 50.9 ± 3.8 | 66.8 ± 3.8 | 15.9 | 1.3 |
| K314N | 14205 ± 2418 | 17364 ± 2225 | 0.0022 | 39.1 ± 3.4 | 49.9 ± 2.6 | 10.8 | 1.2 |
| K314T | 25162 ± 2701 | 30501 ± 2332 | 0.0036 | 75.9 ± 4.4 | 93.8 ± 4.5 | 17.9 | 1.2 |
| D315A | 18519 ± 1370 | 24758 ± 1512 | 0.0036 | 68.3 ± 4.8 | 93.4 ± 7 | 25.1 | 1.3 |
| D315G | 13326 ± 859 | 19115 ± 1697 | 0.0042 | 49.7 ± 3.7 | 73.3 ± 8 | 23.6 | 1.4 |
| D315H | 9791 ± 1077 | 14136 ± 1573 | 0.0030 | 35.7 ± 2.8 | 53.2 ± 5.5 | 17.4 | 1.4 |
| D315N | 8553 ± 425 | 13037 ± 869 | 0.0001 | 34.1 ± 1.7 | 52.1 ± 3.7 | 17.9 | 1.5 |
| D315V | 8191 ± 717 | 14580 ± 1235 | 0.0001 | 31.2 ± 3.6 | 56 ± 6 | 24.8 | 1.8 |
| D315Y | 9198 ± 1179 | 12674 ± 1008 | 0.0206 | 34.5 ± 3.5 | 48.7 ± 2.4 | 14.2 | 1.4 |
| V316A | 13166 ± 1029 | 18908 ± 1577 | 0.0033 | 48.8 ± 4.1 | 71.5 ± 7.1 | 22.7 | 1.4 |
| V316L | 12854 ± 958 | 21812 ± 1450 | 0.0001 | 47.4 ± 3.9 | 81.3 ± 6.3 | 33.9 | 1.7 |
| I317L | 14780 ± 1222 | 18770 ± 1141 | 0.0199 | 54.4 ± 4.9 | 70.9 ± 5.6 | 16.5 | 1.3 |
| I317M | 340 ± 29 | 3988 ± 177 | 0.0001 | 1 ± 0.1 | 11.2 ± 0.8 | 10.2 | 11.7 |
| I317V | 14885 ± 1495 | 19927 ± 1565 | 0.0147 | 55 ± 6.1 | 73.6 ± 5.5 | 18.6 | 1.3 |
| A318D | 15357 ± 1499 | 20838 ± 1817 | 0.0012 | 42.5 ± 3.6 | 59.4 ± 5.3 | 16.9 | 1.4 |
| A318P | 526 ± 42 | 2799 ± 174 | 0.0001 | 1.5 ± 0.2 | 8 ± 0.8 | 6.5 | 5.3 |
| A318T | 16954 ± 1483 | 22296 ± 1232 | 0.0009 | 45.2 ± 2.8 | 62.9 ± 4.6 | 17.7 | 1.3 |
| A318V | 14603 ± 1377 | 19658 ± 1108 | 0.0022 | 37.9 ± 2.1 | 54.4 ± 3.5 | 16.5 | 1.4 |
| I319M | 12191 ± 433 | 14802 ± 727 | 0.0047 | 47.4 ± 2.2 | 56.8 ± 2.3 | 9.4 | 1.2 |
| N320S | 21562 ± 1285 | 28097 ± 1522 | 0.0022 | 82.9 ± 4.5 | 106.7 ± 3.9 | 23.9 | 1.3 |
| N320T | 5597 ± 442 | 11276 ± 658 | 0.0001 | 21.6 ± 1.5 | 43.3 ± 1.9 | 21.8 | 2.0 |
| Q321K | 7590 ± 520 | 16046 ± 870 | 0.0001 | 29.2 ± 2 | 61.2 ± 2.4 | 32.0 | 2.1 |
| D322A | 1908 ± 139 | 6170 ± 310 | 0.0001 | 6.8 ± 0.4 | 22.2 ± 1 | 15.3 | 3.2 |
| D322V | 714 ± 53 | 3989 ± 217 | 0.0001 | 2.6 ± 0.2 | 14.3 ± 0.6 | 11.7 | 5.6 |
| L324V | 17027 ± 1167 | 20866 ± 1331 | 0.0090 | 57.2 ± 2.1 | 70.2 ± 2 | 13.0 | 1.2 |
| L324W | 20623 ± 721 | 25772 ± 1045 | 0.0004 | 73.5 ± 1.8 | 93.3 ± 4.5 | 19.8 | 1.3 |
| G325A | 18183 ± 1254 | 27523 ± 1456 | 0.0001 | 64.9 ± 3.8 | 99.2 ± 5.4 | 34.4 | 1.5 |
| G325C | 14482 ± 695 | 23873 ± 1021 | 0.0001 | 51.4 ± 1.7 | 85.9 ± 4 | 34.5 | 1.7 |
| G325V | 572 ± 30 | 5333 ± 294 | 0.0001 | 2.2 ± 0.2 | 19.3 ± 1.1 | 17.1 | 9.3 |
| K326E | 15541 ± 832 | 22340 ± 828 | 0.0001 | 55.6 ± 2.6 | 80.9 ± 3.9 | 25.3 | 1.4 |
| K326M | 8482 ± 500 | 31204 ± 1979 | 0.0001 | 24.4 ± 1.6 | 87.6 ± 3.5 | 63.2 | 3.7 |
| K326Q | 22075 ± 1209 | 29168 ± 1869 | 0.0010 | 78 ± 3 | 104.1 ± 5.7 | 26.1 | 1.3 |
| K326R | 17744 ± 923 | 31690 ± 1112 | 0.0001 | 61.7 ± 3.4 | 109.7 ± 2.9 | 48.0 | 1.8 |
| K326T | 19442 ± 739 | 26653 ± 877 | 0.0001 | 69.6 ± 2.4 | 96 ± 3.7 | 26.4 | 1.4 |
| Q327H | BLD | 2197 ± 226 | 0.0001 | N/A | 7.4 ± 0.7 | 7.4 | NC |
| Q327P | 7775 ± 561 | 18612 ± 1075 | 0.0001 | 26.2 ± 1.8 | 62.6 ± 3.1 | 36.4 | 2.4 |
| Y329C | 9148 ± 414 | 11442 ± 480 | 0.0011 | 31.2 ± 1.5 | 38.9 ± 1.6 | 7.8 | 1.3 |
| Y329D | 1249 ± 66 | 4917 ± 181 | 0.0001 | 4.2 ± 0.2 | 16.7 ± 0.6 | 12.5 | 3.9 |
| Y329F | 10368 ± 646 | 15566 ± 603 | 0.0001 | 30.6 ± 1.5 | 47.1 ± 2.8 | 16.6 | 1.5 |
| Y329H | 13757 ± 963 | 18672 ± 772 | 0.0002 | 47.2 ± 3.8 | 63.4 ± 2.6 | 16.2 | 1.4 |
| Y329N | 6448 ± 436 | 11035 ± 429 | 0.0001 | 21.8 ± 1.5 | 37.4 ± 1.2 | 15.6 | 1.7 |
| Q330E | 7500 ± 345 | 13086 ± 589 | 0.0001 | 26.4 ± 1.5 | 46.4 ± 2.6 | 19.9 | 1.7 |
| Q330H | 9296 ± 649 | 20752 ± 592 | 0.0001 | 33.1 ± 2.8 | 73.9 ± 3.6 | 40.8 | 2.2 |
| Q330K | 20289 ± 720 | 26149 ± 1074 | 0.0001 | 71 ± 2.7 | 92.1 ± 4.2 | 21.1 | 1.3 |
| L331H | 11743 ± 634 | 19003 ± 791 | 0.0001 | 42 ± 3.2 | 67.9 ± 4.3 | 25.9 | 1.6 |
| L331P | 157 ± 20 | 1029 ± 32 | 0.0001 | 0.6 ± 0.1 | 3.7 ± 0.2 | 3.1 | 6.5 |
| L331R | 9725 ± 634 | 15841 ± 639 | 0.0001 | 33.2 ± 1.5 | 56.5 ± 3.2 | 23.3 | 1.6 |
| L331V | 25163 ± 801 | 33050 ± 967 | 0.0001 | 89.4 ± 4.5 | 117.4 ± 5.6 | 28.0 | 1.3 |
| R332G | 33043 ± 1431 | 42737 ± 1959 | 0.0002 | 78.8 ± 2.7 | 102.3 ± 4.6 | 23.4 | 1.3 |
| R332I | 24614 ± 1678 | 41550 ± 2461 | 0.0001 | 63.3 ± 4.5 | 106.6 ± 6.4 | 43.2 | 1.7 |
| R332S | 33936 ± 2528 | 41700 ± 2778 | 0.0193 | 87.6 ± 6.6 | 108.1 ± 8.4 | 20.5 | 1.2 |
| R332T | 26141 ± 1254 | 39363 ± 2176 | 0.0001 | 73.3 ± 2.9 | 109.5 ± 4.7 | 36.2 | 1.5 |
| Q333E | 30291 ± 2094 | 38709 ± 2428 | 0.0067 | 77.8 ± 5.3 | 101.3 ± 7.6 | 23.5 | 1.3 |
| Q333L | 25450 ± 2094 | 33727 ± 1965 | 0.0042 | 68.6 ± 2.9 | 93.3 ± 4.1 | 24.7 | 1.3 |
| Q333P | 11819 ± 1039 | 22746 ± 1255 | 0.0001 | 30.3 ± 1.7 | 61.3 ± 3.9 | 31.0 | 1.9 |
| G334R | 25886 ± 3237 | 31174 ± 2016 | 0.0429 | 58.9 ± 4.6 | 76.4 ± 2.7 | 17.5 | 1.2 |
| G334V | 31991 ± 2390 | 38301 ± 2744 | 0.0219 | 68.4 ± 3.2 | 82.1 ± 3.8 | 13.7 | 1.2 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| D335A | 21055 ± 1662 | 33829 ± 4641 | 0.0120 | 57.9 ± 3 | 85.6 ± 6.9 | 27.7 | 1.6 |
| D335E | 30532 ± 1962 | 39124 ± 2722 | 0.0053 | 68.7 ± 4.8 | 86.5 ± 4.5 | 17.7 | 1.3 |
| D335G | 22766 ± 1355 | 30341 ± 3325 | 0.0234 | 51.3 ± 2.8 | 67 ± 5.6 | 15.7 | 1.3 |
| D335V | 7938 ± 336 | 16557 ± 929 | 0.0001 | 18.1 ± 0.6 | 37.5 ± 1.6 | 19.4 | 2.1 |
| D335Y | 19469 ± 982 | 24732 ± 2214 | 0.0147 | 43 ± 1.7 | 54.1 ± 3.5 | 11.0 | 1.3 |
| N336D | 23869 ± 1072 | 39534 ± 2519 | 0.0001 | 53.7 ± 2.8 | 88.1 ± 4.9 | 34.3 | 1.7 |
| N336I | 8544 ± 1083 | 18303 ± 1404 | 0.0001 | 20.7 ± 2.7 | 43.8 ± 1.6 | 23.0 | 2.1 |
| N336S | 32974 ± 2396 | 40651 ± 2487 | 0.0169 | 79.7 ± 3.8 | 98.4 ± 3.1 | 18.7 | 1.2 |
| N336T | 12743 ± 709 | 25898 ± 1374 | 0.0001 | 28.9 ± 1.3 | 58.6 ± 2.3 | 29.7 | 2.0 |
| N336Y | 29615 ± 1640 | 37475 ± 2540 | 0.0045 | 66.3 ± 3.7 | 83 ± 4.4 | 16.6 | 1.3 |
| F337C | 9557 ± 452 | 17991 ± 960 | 0.0001 | 21.7 ± 0.8 | 40.7 ± 1.6 | 19.0 | 1.9 |
| F337L | 23197 ± 2254 | 31963 ± 2641 | 0.0022 | 57.8 ± 4.8 | 78.6 ± 3.1 | 20.8 | 1.4 |
| F337V | 29582 ± 2747 | 42718 ± 2776 | 0.0007 | 65.9 ± 4.1 | 97 ± 4.6 | 31.1 | 1.4 |
| F337Y | 21577 ± 1930 | 30991 ± 2695 | 0.0023 | 52.3 ± 4.2 | 73.9 ± 3.2 | 21.6 | 1.4 |
| E338A | 15626 ± 769 | 25719 ± 1376 | 0.0001 | 39.5 ± 2.3 | 64.3 ± 3 | 24.8 | 1.7 |
| E338D | 25700 ± 1958 | 31632 ± 1825 | 0.0033 | 65.7 ± 4.9 | 80.9 ± 4.6 | 15.2 | 1.2 |
| E338G | 6415 ± 391 | 12588 ± 538 | 0.0001 | 17.1 ± 1.1 | 33.9 ± 1.8 | 16.8 | 2.0 |
| V339M | 26113 ± 1116 | 33867 ± 2526 | 0.0030 | 63.5 ± 2.9 | 81.7 ± 5 | 18.2 | 1.3 |
| E341A | 1444 ± 159 | 5855 ± 690 | 0.0001 | 3.8 ± 0.4 | 15.4 ± 1.3 | 11.6 | 4.1 |
| E341Q | 20802 ± 2164 | 28411 ± 2891 | 0.0294 | 55.5 ± 3.7 | 75.2 ± 4.1 | 19.7 | 1.4 |
| P343A | 25254 ± 2385 | 32890 ± 2292 | 0.0062 | 69.5 ± 4.9 | 90.7 ± 3.7 | 21.2 | 1.3 |
| P343S | 22132 ± 1243 | 29289 ± 2351 | 0.0147 | 62.1 ± 2.7 | 81.1 ± 4.6 | 19.0 | 1.3 |
| L344F | 217 ± 25 | 3629 ± 614 | 0.0001 | 0.6 ± 0.1 | 9.6 ± 1.4 | 9.0 | 16.7 |
| L344R | 4983 ± 848 | 11592 ± 1593 | 0.0006 | 10.9 ± 1.4 | 26.2 ± 2.6 | 15.3 | 2.3 |
| L344V | 13586 ± 1026 | 19262 ± 903 | 0.0002 | 40.6 ± 3.2 | 57.5 ± 2.5 | 16.8 | 1.4 |
| G346A | 23263 ± 1479 | 31948 ± 1306 | 0.0001 | 58.3 ± 3.3 | 80.4 ± 2.8 | 22.0 | 1.4 |
| G346C | 18258 ± 1054 | 22856 ± 1772 | 0.0206 | 39.5 ± 1.9 | 49.2 ± 2.9 | 9.7 | 1.3 |
| G346D | 31327 ± 3822 | 46560 ± 3904 | 0.0053 | 67.5 ± 6.4 | 103.3 ± 6 | 35.8 | 1.5 |
| G346V | 11683 ± 1406 | 20902 ± 2356 | 0.0012 | 28.8 ± 2.4 | 51.4 ± 3.9 | 22.7 | 1.8 |
| L347I | 26815 ± 2533 | 33517 ± 2802 | 0.0429 | 65 ± 3.8 | 82.4 ± 5 | 17.4 | 1.3 |
| A348D | 21682 ± 817 | 26025 ± 1129 | 0.0030 | 41.6 ± 1.5 | 50 ± 2.2 | 8.4 | 1.2 |
| W349C | 17800 ± 1182 | 23210 ± 1299 | 0.0009 | 41.5 ± 2.6 | 53.7 ± 2.5 | 12.3 | 1.3 |
| W349L | 18128 ± 742 | 24184 ± 1517 | 0.0013 | 35 ± 1.6 | 46.8 ± 3.2 | 11.8 | 1.3 |
| A350G | 21459 ± 695 | 26360 ± 1002 | 0.0012 | 41 ± 0.9 | 50.5 ± 1.7 | 9.5 | 1.2 |
| A350S | 26493 ± 1291 | 34474 ± 1484 | 0.0004 | 62.9 ± 4.2 | 80.5 ± 3.6 | 17.6 | 1.3 |
| A350T | 20227 ± 1499 | 26484 ± 1189 | 0.0013 | 47.4 ± 3.7 | 61.7 ± 2.7 | 14.4 | 1.3 |
| A350V | 12786 ± 654 | 22855 ± 1012 | 0.0001 | 27.9 ± 0.9 | 50.2 ± 1.6 | 22.3 | 1.8 |
| V351A | 24009 ± 1662 | 30218 ± 1531 | 0.0053 | 56.9 ± 4.7 | 71.1 ± 4.1 | 14.2 | 1.3 |
| V351E | 4760 ± 281 | 7910 ± 348 | 0.0001 | 10.5 ± 0.5 | 17.7 ± 1 | 7.2 | 1.7 |
| A352S | 23476 ± 1901 | 28397 ± 1310 | 0.0169 | 52.8 ± 3.7 | 64.9 ± 2.5 | 12.1 | 1.2 |
| A352T | 15803 ± 777 | 29351 ± 1532 | 0.0001 | 37.2 ± 2.1 | 68.2 ± 3.2 | 31.0 | 1.9 |
| M353K | 13638 ± 804 | 19335 ± 946 | 0.0003 | 30.3 ± 1.8 | 43.4 ± 2.6 | 13.0 | 1.4 |
| M353L | 30347 ± 1572 | 36987 ± 1768 | 0.0083 | 66.6 ± 2.7 | 81.2 ± 2.7 | 14.6 | 1.2 |
| M353T | 15631 ± 1026 | 21953 ± 937 | 0.0001 | 46.4 ± 2.8 | 65.6 ± 3 | 19.2 | 1.4 |
| I354R | 9157 ± 633 | 21854 ± 1398 | 0.0001 | 20.1 ± 1.2 | 47.9 ± 2.6 | 27.8 | 2.4 |
| N355D | 3366 ± 241 | 11004 ± 832 | 0.0001 | 7.3 ± 0.4 | 24 ± 1.6 | 16.7 | 3.3 |
| N355H | 1822 ± 81 | 6399 ± 338 | 0.0001 | 4 ± 0.2 | 13.9 ± 0.6 | 9.9 | 3.5 |
| N355S | 11397 ± 817 | 24820 ± 1396 | 0.0001 | 25.9 ± 1.6 | 56.7 ± 2.8 | 30.8 | 2.2 |
| N355Y | 5994 ± 461 | 16930 ± 1745 | 0.0001 | 15.2 ± 1 | 41.8 ± 3.3 | 26.6 | 2.8 |
| R356L | 10680 ± 518 | 29548 ± 2017 | 0.0001 | 24.4 ± 1 | 68.1 ± 4.6 | 43.7 | 2.8 |
| Q357E | 15264 ± 877 | 28922 ± 1194 | 0.0001 | 42.8 ± 2.1 | 84.3 ± 6.3 | 41.5 | 1.9 |
| I359F | 6138 ± 568 | 13144 ± 1091 | 0.0001 | 13 ± 1 | 27 ± 1.6 | 14.1 | 2.1 |
| I359L | 16254 ± 909 | 26791 ± 1713 | 0.0001 | 39.1 ± 1.8 | 64.7 ± 3.9 | 25.6 | 1.7 |
| I359N | 10862 ± 655 | 17332 ± 879 | 0.0001 | 20.8 ± 1.2 | 33.3 ± 1.8 | 12.5 | 1.6 |
| I359S | 37737 ± 2594 | 48055 ± 2727 | 0.0067 | 101.6 ± 6.3 | 131.2 ± 8.4 | 29.6 | 1.3 |
| I359V | 20990 ± 1174 | 34265 ± 1528 | 0.0001 | 51.5 ± 3.4 | 83.1 ± 3.3 | 31.6 | 1.6 |
| P362A | 35322 ± 3087 | 49809 ± 2721 | 0.0007 | 100.8 ± 9.5 | 140.9 ± 8.5 | 40.1 | 1.4 |
| P362H | 3713 ± 377 | 14620 ± 531 | 0.0001 | 11.2 ± 1 | 44.6 ± 1.9 | 33.4 | 3.9 |
| P362R | 8745 ± 1176 | 15971 ± 1019 | 0.0001 | 25 ± 3.1 | 48.9 ± 4.1 | 23.9 | 1.8 |
| P362S | 25234 ± 2794 | 45209 ± 4138 | 0.0003 | 71.2 ± 7.7 | 125 ± 9 | 53.8 | 1.8 |
| R363G | 13990 ± 1613 | 37837 ± 2998 | 0.0001 | 41.8 ± 5.1 | 114.4 ± 10.7 | 72.6 | 2.7 |
| R363L | 8123 ± 869 | 27997 ± 2485 | 0.0001 | 23.2 ± 1.9 | 85.4 ± 9.5 | 62.2 | 3.5 |
| R363S | 16400 ± 1695 | 44621 ± 3266 | 0.0001 | 50.1 ± 5.9 | 136.7 ± 12.4 | 86.6 | 2.7 |
| S364C | 41263 ± 2389 | 53912 ± 3067 | 0.0020 | 127 ± 10.6 | 167 ± 14.8 | 40.0 | 1.3 |
| S364P | 48193 ± 4573 | 66731 ± 4698 | 0.0062 | 143.2 ± 13.7 | 206.4 ± 20 | 63.1 | 1.4 |
| Y365D | 9119 ± 1027 | 14664 ± 1311 | 0.0013 | 31.3 ± 2.7 | 51 ± 3.5 | 19.7 | 1.6 |
| Y365F | 19631 ± 2010 | 25395 ± 2160 | 0.0266 | 67.7 ± 5.1 | 88.8 ± 5.3 | 21.1 | 1.3 |
| Y365N | 19111 ± 869 | 26514 ± 1978 | 0.0002 | 59.7 ± 1.7 | 82.2 ± 4.5 | 22.5 | 1.4 |
| Y365S | 14346 ± 1563 | 19484 ± 1899 | 0.0180 | 49.4 ± 4.1 | 67.8 ± 4.9 | 18.4 | 1.4 |
| T366I | 18539 ± 1165 | 24814 ± 1897 | 0.0045 | 57.8 ± 2.5 | 77.8 ± 5.3 | 20.0 | 1.3 |
| T366N | 24650 ± 1756 | 30947 ± 1867 | 0.0137 | 78.1 ± 5.3 | 98.5 ± 5.4 | 20.4 | 1.3 |
| T366P | 13407 ± 1462 | 16910 ± 1608 | 0.0455 | 46.2 ± 4 | 59.5 ± 5.1 | 13.4 | 1.3 |
| T366S | 20731 ± 2170 | 24885 ± 1760 | 0.0301 | 70.6 ± 4.9 | 86.7 ± 3.6 | 16.2 | 1.2 |
| I367F | 15728 ± 1680 | 22178 ± 1794 | 0.0020 | 48.3 ± 3.7 | 69.9 ± 5.7 | 21.6 | 1.4 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| I367L | 25211 ± 1640 | 31257 ± 2256 | 0.0339 | 79 ± 4 | 101 ± 9.3 | 21.9 | 1.2 |
| I367M | 28430 ± 1769 | 36008 ± 2249 | 0.0104 | 76.7 ± 3.9 | 99 ± 6.7 | 22.3 | 1.3 |
| A368G | 31616 ± 2552 | 42198 ± 2923 | 0.0111 | 83.9 ± 4.7 | 114.8 ± 7.8 | 30.9 | 1.3 |
| A368P | 26402 ± 926 | 33525 ± 1803 | 0.0001 | 91.7 ± 4.6 | 117.4 ± 8.7 | 25.7 | 1.3 |
| V369A | 23968 ± 1797 | 35925 ± 2462 | 0.0006 | 77.6 ± 5 | 116.2 ± 6.3 | 38.6 | 1.5 |
| V369F | 11912 ± 1197 | 18282 ± 1960 | 0.0137 | 37.7 ± 2.8 | 57.3 ± 4.8 | 19.6 | 1.5 |
| V369G | 803 ± 59 | 2628 ± 291 | 0.0001 | 2.6 ± 0.2 | 8.1 ± 0.7 | 5.5 | 3.3 |
| V369I | 30094 ± 3211 | 36630 ± 2373 | 0.0206 | 79.7 ± 6.8 | 99.3 ± 5.5 | 19.6 | 1.2 |
| V369L | 27680 ± 1912 | 38458 ± 2367 | 0.0014 | 74.2 ± 3.7 | 104.5 ± 5.6 | 30.3 | 1.4 |
| A370D | 27098 ± 2504 | 33279 ± 2473 | 0.0405 | 87.5 ± 6.1 | 109.8 ± 6.8 | 22.4 | 1.2 |
| A370G | 24835 ± 2637 | 31805 ± 3001 | 0.0382 | 78.1 ± 4.4 | 101 ± 5.4 | 22.9 | 1.3 |
| A370P | 10431 ± 975 | 15618 ± 1776 | 0.0020 | 33.9 ± 2.8 | 50.7 ± 5.4 | 16.9 | 1.5 |
| A370T | 25024 ± 1951 | 30276 ± 2364 | 0.0481 | 79.9 ± 4.3 | 97.5 ± 6.1 | 17.6 | 1.2 |
| A370V | 15754 ± 1222 | 24151 ± 1591 | 0.0003 | 40.1 ± 3.1 | 60.7 ± 3.5 | 20.6 | 1.5 |
| S371C | 10189 ± 1078 | 14546 ± 1141 | 0.0022 | 23.5 ± 1.3 | 34.7 ± 1.6 | 11.1 | 1.4 |
| S371T | 27962 ± 2785 | 37065 ± 2351 | 0.0028 | 65 ± 3.3 | 91.1 ± 5 | 26.1 | 1.3 |
| G373A | 14426 ± 630 | 18622 ± 1289 | 0.0011 | 40.8 ± 1.5 | 53.2 ± 3.7 | 12.4 | 1.3 |
| G373C | 1744 ± 92 | 5543 ± 547 | 0.0001 | 4.3 ± 0.2 | 13 ± 0.9 | 8.7 | 3.2 |
| K374E | 19699 ± 1718 | 24879 ± 2423 | 0.0429 | 49.9 ± 3.6 | 64 ± 5.7 | 14.1 | 1.3 |
| K374I | 8194 ± 506 | 16076 ± 936 | 0.0001 | 22.3 ± 1.3 | 44.2 ± 2.9 | 21.9 | 2.0 |
| K374R | 27984 ± 2321 | 34403 ± 2426 | 0.0147 | 74.3 ± 4.8 | 92.2 ± 4.9 | 17.9 | 1.2 |
| K374T | 16418 ± 1050 | 26614 ± 1659 | 0.0001 | 46.1 ± 2.8 | 76.2 ± 5.7 | 30.2 | 1.6 |
| G375R | 15302 ± 1157 | 22033 ± 1442 | 0.0015 | 41.7 ± 1.9 | 60.4 ± 2.1 | 18.7 | 1.4 |
| V376E | 22992 ± 924 | 30929 ± 1635 | 0.0003 | 74 ± 4.6 | 95.9 ± 3.8 | 21.9 | 1.4 |
| V376G | 33903 ± 2255 | 44774 ± 2982 | 0.0036 | 93.9 ± 4.6 | 122.9 ± 5.6 | 28.9 | 1.3 |
| V376L | 27275 ± 1181 | 34152 ± 1845 | 0.0062 | 82.4 ± 3.4 | 102.3 ± 4.2 | 19.9 | 1.3 |
| V376M | 27547 ± 1431 | 34563 ± 1762 | 0.0024 | 79.3 ± 2.7 | 99.4 ± 3.2 | 20.1 | 1.3 |
| A377G | 26583 ± 1072 | 32517 ± 981 | 0.0006 | 71.6 ± 2.5 | 87.7 ± 2.3 | 16.1 | 1.2 |
| A377P | 21842 ± 930 | 28189 ± 1292 | 0.0004 | 59.4 ± 2.6 | 76.6 ± 3.5 | 17.2 | 1.3 |
| A377S | 17737 ± 860 | 22793 ± 999 | 0.0004 | 48.1 ± 2.3 | 61.8 ± 2.7 | 13.7 | 1.3 |
| A377T | 15839 ± 802 | 20817 ± 838 | 0.0003 | 42.5 ± 1.9 | 56.1 ± 2 | 13.5 | 1.3 |
| N379D | 4128 ± 1118 | 5604 ± 979 | 0.0339 | 9.4 ± 2.2 | 13.1 ± 1.9 | 3.8 | 1.4 |
| N379I | 13128 ± 1712 | 17862 ± 1825 | 0.0057 | 28.7 ± 2.7 | 40 ± 2.8 | 11.4 | 1.4 |
| N379K | 31962 ± 2268 | 40568 ± 2417 | 0.0083 | 74.6 ± 3.3 | 95 ± 2.7 | 20.4 | 1.3 |
| N379T | 18827 ± 1525 | 23023 ± 1524 | 0.0266 | 43.2 ± 2.7 | 52.9 ± 2.7 | 9.8 | 1.2 |
| P380A | 9820 ± 705 | 17454 ± 1133 | 0.0001 | 23.2 ± 1.7 | 40.7 ± 2.3 | 17.5 | 1.8 |
| P380H | 10463 ± 941 | 17759 ± 1310 | 0.0001 | 23.7 ± 1.4 | 41.1 ± 2.2 | 17.4 | 1.7 |
| P380R | 14432 ± 1315 | 21330 ± 1744 | 0.0083 | 37.8 ± 5 | 52.4 ± 3.4 | 14.6 | 1.5 |
| P380T | 10544 ± 669 | 13919 ± 666 | 0.0013 | 24.2 ± 1.1 | 32.2 ± 1 | 8.0 | 1.3 |
| A381D | 20587 ± 1974 | 30666 ± 2629 | 0.0015 | 46.7 ± 3 | 71.4 ± 5 | 24.7 | 1.5 |
| F383C | 22779 ± 2557 | 29945 ± 3409 | 0.0339 | 59.6 ± 4.6 | 79 ± 6.8 | 19.3 | 1.3 |
| F383I | 31554 ± 2813 | 39170 ± 2761 | 0.0169 | 81.7 ± 5.6 | 104.2 ± 8 | 22.6 | 1.2 |
| F383Y | 28986 ± 2572 | 39286 ± 2306 | 0.0057 | 73.7 ± 3.8 | 105.1 ± 6 | 31.4 | 1.4 |
| I384F | 4673 ± 750 | 7946 ± 807 | 0.0012 | 11.1 ± 1.3 | 19.7 ± 1.6 | 8.6 | 1.7 |
| I384M | 15481 ± 1665 | 20745 ± 1623 | 0.0036 | 39.7 ± 3 | 54.5 ± 3.7 | 14.8 | 1.3 |
| I384T | 4755 ± 673 | 8160 ± 1059 | 0.0062 | 12.3 ± 1.6 | 20.5 ± 2.4 | 8.2 | 1.7 |
| T385I | 18236 ± 2074 | 23597 ± 1843 | 0.0018 | 43.4 ± 3.3 | 56.1 ± 2.4 | 12.7 | 1.3 |
| Q386H | 1148 ± 70 | 2424 ± 353 | 0.0002 | 4.1 ± 0.3 | 8.1 ± 0.9 | 3.9 | 2.1 |
| Q386K | 7135 ± 749 | 9850 ± 1061 | 0.0219 | 17.2 ± 1.6 | 23.1 ± 1.8 | 5.9 | 1.4 |
| Q386L | 7326 ± 646 | 9698 ± 839 | 0.0219 | 17.8 ± 1.4 | 23.1 ± 1.5 | 5.3 | 1.3 |
| L387F | 17188 ± 1822 | 21003 ± 1547 | 0.0234 | 59.1 ± 4.9 | 72.6 ± 4.5 | 13.5 | 1.2 |
| L387H | 16827 ± 1557 | 23648 ± 1827 | 0.0030 | 58.8 ± 4.7 | 81.3 ± 4.6 | 22.5 | 1.4 |
| L387I | 28707 ± 3510 | 36657 ± 3056 | 0.0062 | 95.8 ± 6.8 | 123.7 ± 5.1 | 28.0 | 1.3 |
| L387R | 11133 ± 1516 | 15211 ± 1727 | 0.0249 | 28.2 ± 3.6 | 39.4 ± 4.4 | 11.2 | 1.4 |
| L388F | 12563 ± 1654 | 17583 ± 1509 | 0.0030 | 32.1 ± 4.2 | 45 ± 3.4 | 12.9 | 1.4 |
| L388H | 1354 ± 89 | 7341 ± 518 | 0.0001 | 3.2 ± 0.2 | 17.2 ± 1 | 13.9 | 5.4 |
| L388I | 18562 ± 2245 | 24746 ± 2326 | 0.0249 | 46.6 ± 5.2 | 64.2 ± 6 | 17.6 | 1.3 |
| L388R | 1833 ± 101 | 5072 ± 627 | 0.0001 | 4.4 ± 0.3 | 12.2 ± 1.5 | 7.8 | 2.8 |
| L388V | 15962 ± 1927 | 25028 ± 2179 | 0.0018 | 39.3 ± 3.6 | 65 ± 5.6 | 25.7 | 1.6 |
| K391I | 1544 ± 98 | 5343 ± 587 | 0.0001 | 4.3 ± 0.3 | 14.1 ± 1.4 | 9.9 | 3.5 |
| K391N | 23114 ± 1999 | 30489 ± 2411 | 0.0111 | 60.5 ± 5.2 | 78.3 ± 5.4 | 17.9 | 1.3 |
| K391Q | 20154 ± 2061 | 30714 ± 2783 | 0.0028 | 51.5 ± 4.6 | 76.6 ± 4.7 | 25.2 | 1.5 |
| K391R | 26395 ± 2258 | 33349 ± 2491 | 0.0158 | 69.1 ± 6 | 85.9 ± 4.8 | 16.8 | 1.3 |
| R392G | 21151 ± 1706 | 26480 ± 2033 | 0.0249 | 59.1 ± 5.3 | 72.1 ± 5 | 13.0 | 1.3 |
| R392K | 33729 ± 2386 | 42707 ± 2665 | 0.0057 | 98.7 ± 6.6 | 125.9 ± 8.5 | 27.2 | 1.3 |
| R392M | 32856 ± 2534 | 41635 ± 1964 | 0.0042 | 97.2 ± 6.1 | 125.2 ± 5.2 | 27.9 | 1.3 |
| R392W | 17580 ± 1671 | 22596 ± 1839 | 0.0219 | 46.9 ± 4.8 | 58.2 ± 4.1 | 11.4 | 1.3 |
| K393E | 16648 ± 1284 | 32275 ± 1905 | 0.0001 | 50.5 ± 3.8 | 98.3 ± 6.2 | 47.9 | 1.9 |
| K393N | 23262 ± 1719 | 30064 ± 1959 | 0.0007 | 68.3 ± 7.8 | 86.6 ± 8.7 | 18.3 | 1.3 |
| K393Q | 19722 ± 1445 | 32686 ± 1866 | 0.0001 | 60.3 ± 4.6 | 99.9 ± 6.6 | 39.6 | 1.7 |
| K393T | 18084 ± 1183 | 23886 ± 1214 | 0.0009 | 55.7 ± 4.1 | 73.6 ± 4.8 | 17.9 | 1.3 |
| L394I | 30400 ± 2425 | 41644 ± 3334 | 0.0067 | 98.5 ± 13 | 135.5 ± 17.6 | 37.0 | 1.4 |
| L394Q | 11635 ± 1091 | 17701 ± 1268 | 0.0006 | 36.5 ± 5.1 | 57 ± 6.8 | 20.5 | 1.5 |
| L394R | 16836 ± 1562 | 25594 ± 1826 | 0.0005 | 53.6 ± 6.9 | 83 ± 10.3 | 29.4 | 1.5 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| G395R | 2850 ± 220 | 5995 ± 589 | 0.0001 | 8 ± 0.8 | 17.4 ± 2.4 | 9.4 | 2.1 |
| F396C | 11516 ± 725 | 15447 ± 607 | 0.0001 | 45.5 ± 2.6 | 61.5 ± 2.3 | 16.0 | 1.3 |
| F396I | 12835 ± 938 | 20028 ± 1684 | 0.0001 | 51.3 ± 4 | 80.2 ± 7.2 | 28.9 | 1.6 |
| F396L | 16519 ± 1148 | 29921 ± 1158 | 0.0001 | 65 ± 3.8 | 119.2 ± 4.7 | 54.3 | 1.8 |
| F396V | 20066 ± 1220 | 24860 ± 1682 | 0.0193 | 79.5 ± 4.6 | 99.3 ± 7.1 | 19.7 | 1.2 |
| Y397C | 4930 ± 944 | 11372 ± 1534 | 0.0001 | 18.4 ± 4.2 | 41.1 ± 7.1 | 22.7 | 2.3 |
| Y397F | 20498 ± 833 | 26411 ± 932 | 0.0001 | 71.3 ± 2.5 | 92.6 ± 3.8 | 21.3 | 1.3 |
| Y397H | 14821 ± 1007 | 21935 ± 1308 | 0.0002 | 51.1 ± 2.4 | 76.7 ± 3.8 | 25.5 | 1.5 |
| Y397N | 3438 ± 291 | 6232 ± 402 | 0.0001 | 13.5 ± 1 | 24.8 ± 1.7 | 11.4 | 1.8 |
| Y397S | 4624 ± 362 | 9056 ± 406 | 0.0001 | 16 ± 1 | 31.6 ± 1.4 | 15.7 | 2.0 |
| E398G | 12507 ± 771 | 15528 ± 885 | 0.0057 | 43.4 ± 2.3 | 54.9 ± 3.8 | 11.5 | 1.2 |
| E398Q | 22163 ± 1206 | 26967 ± 1243 | 0.0018 | 76.7 ± 3.2 | 94.4 ± 4.7 | 17.6 | 1.2 |
| W399G | 21476 ± 1276 | 28481 ± 1315 | 0.0007 | 74.8 ± 4.2 | 99.2 ± 4.3 | 24.3 | 1.3 |
| W399R | 15451 ± 1268 | 23299 ± 1725 | 0.0002 | 53.6 ± 3.9 | 81.2 ± 5.4 | 27.6 | 1.5 |
| T400A | 12742 ± 1056 | 26604 ± 1720 | 0.0001 | 41.8 ± 3.5 | 86.2 ± 5 | 44.4 | 2.1 |
| T400I | 8922 ± 851 | 14017 ± 1295 | 0.0001 | 28.3 ± 1.6 | 44 ± 2.2 | 15.7 | 1.6 |
| T400N | 21166 ± 1602 | 31312 ± 1522 | 0.0001 | 68.6 ± 4 | 103.1 ± 5.7 | 34.5 | 1.5 |
| T400P | 8423 ± 755 | 28286 ± 2670 | 0.0001 | 27.5 ± 2.1 | 89 ± 6.1 | 61.4 | 3.4 |
| T400S | 17855 ± 1480 | 27106 ± 1992 | 0.0004 | 59 ± 5.6 | 86.8 ± 5 | 27.8 | 1.5 |
| S401A | 18412 ± 2150 | 23425 ± 1714 | 0.0045 | 56.4 ± 3.2 | 74.9 ± 3.9 | 18.5 | 1.3 |
| S401L | 8799 ± 918 | 15148 ± 1020 | 0.0002 | 33.1 ± 3.6 | 57.3 ± 3.5 | 24.2 | 1.7 |
| S401T | 13582 ± 1242 | 23965 ± 1621 | 0.0001 | 43.3 ± 2.8 | 75.7 ± 3.9 | 32.4 | 1.8 |
| R402G | 19518 ± 1866 | 31224 ± 2455 | 0.0004 | 74.8 ± 8.3 | 121.1 ± 11.4 | 46.3 | 1.6 |
| R402M | 23649 ± 2051 | 33639 ± 1954 | 0.0013 | 87.4 ± 6.3 | 131.8 ± 10.8 | 44.4 | 1.4 |
| R402S | 25974 ± 2272 | 32424 ± 2592 | 0.0266 | 96.9 ± 8.1 | 128.7 ± 13.4 | 31.7 | 1.3 |
| R402T | 22606 ± 1743 | 30958 ± 2697 | 0.0083 | 81.4 ± 6.4 | 106.4 ± 4.9 | 25.0 | 1.4 |
| R402W | 14605 ± 1371 | 21501 ± 1053 | 0.0004 | 56.7 ± 6.4 | 83 ± 4.8 | 26.3 | 1.5 |
| L403F | 30710 ± 1843 | 37991 ± 1546 | 0.0004 | 91.4 ± 3.2 | 115 ± 4.6 | 23.6 | 1.2 |
| L403V | 26390 ± 767 | 32130 ± 807 | 0.0001 | 80.3 ± 3.2 | 98.8 ± 4.6 | 18.5 | 1.2 |
| R404G | 22301 ± 810 | 32168 ± 1138 | 0.0001 | 68.4 ± 3.3 | 98.7 ± 4.8 | 30.3 | 1.4 |
| R404I | 33222 ± 1740 | 44883 ± 3650 | 0.0015 | 99.7 ± 4.3 | 134.4 ± 9.5 | 34.7 | 1.4 |
| R404K | 30197 ± 1649 | 39268 ± 2115 | 0.0002 | 90.1 ± 3.4 | 118.5 ± 5.8 | 28.4 | 1.3 |
| R404S | 33060 ± 1443 | 42020 ± 2092 | 0.0002 | 100.3 ± 4.5 | 128 ± 6.9 | 27.7 | 1.3 |
| R404T | 28304 ± 1734 | 37173 ± 1791 | 0.0001 | 85 ± 4.5 | 112.7 ± 5.4 | 27.8 | 1.3 |
| S405G | 17071 ± 2013 | 21938 ± 1964 | 0.0158 | 49.4 ± 4.6 | 64.7 ± 4.6 | 15.3 | 1.3 |
| H406D | 36477 ± 2031 | 46168 ± 3080 | 0.0072 | 94.2 ± 3.9 | 118 ± 5.6 | 23.8 | 1.3 |
| H406L | 19135 ± 1127 | 23089 ± 1299 | 0.0283 | 81.5 ± 3.6 | 99.4 ± 5.2 | 17.9 | 1.2 |
| H406Q | 23925 ± 1238 | 30984 ± 1471 | 0.0007 | 99.3 ± 3.5 | 130.4 ± 6.2 | 31.1 | 1.3 |
| I407L | 9275 ± 775 | 14136 ± 1118 | 0.0009 | 37.8 ± 2.6 | 58.9 ± 4.7 | 21.1 | 1.5 |
| I407M | 6020 ± 370 | 12673 ± 641 | 0.0001 | 24.9 ± 1.2 | 53 ± 2.5 | 28.1 | 2.1 |
| I407T | 5565 ± 419 | 9751 ± 458 | 0.0001 | 23.1 ± 1.5 | 40.8 ± 1.7 | 17.7 | 1.8 |
| N408D | 15729 ± 571 | 23783 ± 870 | 0.0001 | 65.8 ± 1.8 | 99.8 ± 3.3 | 34.0 | 1.5 |
| N408H | 4294 ± 289 | 5224 ± 232 | 0.0042 | 17.8 ± 0.9 | 22 ± 1 | 4.2 | 1.2 |
| N408T | 25401 ± 1693 | 33264 ± 1531 | 0.0007 | 97.2 ± 6 | 129 ± 6.2 | 31.8 | 1.3 |
| P409L | 5691 ± 1184 | 11404 ± 1867 | 0.0007 | 19.9 ± 3.5 | 41.1 ± 5.2 | 21.2 | 2.0 |
| T410S | 13723 ± 1986 | 28944 ± 3416 | 0.0001 | 47.1 ± 6 | 99.1 ± 9.6 | 52.0 | 2.1 |
| G411A | 9911 ± 610 | 15641 ± 698 | 0.0001 | 34.3 ± 2.1 | 54.1 ± 2.3 | 19.8 | 1.6 |
| G411C | 9940 ± 492 | 13530 ± 529 | 0.0001 | 34 ± 1.3 | 46.6 ± 1.4 | 12.5 | 1.4 |
| G411V | 428 ± 38 | 4594 ± 128 | 0.0001 | 1.6 ± 0.2 | 16.2 ± 0.8 | 14.6 | 10.7 |
| T412A | 11226 ± 412 | 20104 ± 484 | 0.0001 | 39.5 ± 2.3 | 70.5 ± 3.1 | 31.0 | 1.8 |
| T412I | 4553 ± 335 | 13268 ± 538 | 0.0001 | 15 ± 0.9 | 44 ± 1.4 | 29.0 | 2.9 |
| T412S | 14822 ± 1059 | 20447 ± 906 | 0.0003 | 51.5 ± 4 | 70.4 ± 2.7 | 18.9 | 1.4 |
| V413F | 6626 ± 534 | 9755 ± 657 | 0.0013 | 21.6 ± 1.4 | 32 ± 1.6 | 10.3 | 1.5 |
| V413G | 1065 ± 60 | 2930 ± 303 | 0.0001 | 3.6 ± 0.2 | 9.5 ± 0.9 | 5.9 | 2.8 |
| V413I | 26821 ± 1450 | 33410 ± 2091 | 0.0014 | 93.8 ± 6.9 | 117.2 ± 9.7 | 23.3 | 1.3 |
| L414F | 16323 ± 958 | 25092 ± 844 | 0.0001 | 56.7 ± 3.5 | 87 ± 2.6 | 30.3 | 1.5 |
| L414V | 9522 ± 515 | 14805 ± 636 | 0.0001 | 31.4 ± 1.3 | 49.1 ± 1.7 | 17.7 | 1.6 |
| L415H | 11323 ± 474 | 14204 ± 528 | 0.0001 | 39.1 ± 1.3 | 49.2 ± 1.5 | 10.0 | 1.3 |
| L415I | 26954 ± 887 | 32699 ± 1144 | 0.0004 | 93.6 ± 3.1 | 113.1 ± 3 | 19.4 | 1.2 |
| Q416E | 22022 ± 886 | 27625 ± 1201 | 0.0009 | 76.4 ± 2.9 | 95.7 ± 3.9 | 19.3 | 1.3 |
| Q416H | 29518 ± 1787 | 41306 ± 2269 | 0.0001 | 96.6 ± 3.7 | 136.2 ± 6.1 | 39.7 | 1.4 |
| Q416L | 31088 ± 1385 | 38168 ± 1637 | 0.0024 | 107.5 ± 4.2 | 132.2 ± 5.4 | 24.7 | 1.2 |
| L417I | 29869 ± 2186 | 36566 ± 1460 | 0.0013 | 98.1 ± 5.4 | 122 ± 5 | 24.0 | 1.2 |
| E418A | 25155 ± 910 | 33780 ± 1103 | 0.0001 | 84.1 ± 3.2 | 112.8 ± 3.9 | 28.7 | 1.3 |
| E418D | 26797 ± 1152 | 32116 ± 1602 | 0.0096 | 79.6 ± 3.5 | 97.2 ± 6.5 | 17.5 | 1.2 |
| E418K | 10503 ± 452 | 16154 ± 633 | 0.0001 | 35.2 ± 1.7 | 54 ± 2.3 | 18.8 | 1.5 |
| E418Q | 25651 ± 1049 | 31249 ± 1099 | 0.0009 | 85.8 ± 3.6 | 103.9 ± 3.3 | 18.1 | 1.2 |
| N419I | 12161 ± 966 | 16825 ± 757 | 0.0001 | 36.1 ± 2.8 | 51 ± 3.3 | 14.9 | 1.4 |
| N419S | 26543 ± 1425 | 35911 ± 2777 | 0.0013 | 69.5 ± 3.6 | 93.3 ± 5.8 | 23.9 | 1.4 |
| N419T | 24406 ± 1544 | 35654 ± 2884 | 0.0001 | 64.6 ± 4.4 | 92.7 ± 6.3 | 28.2 | 1.5 |
| N419Y | 12788 ± 858 | 19160 ± 838 | 0.0001 | 37.9 ± 2.4 | 57.8 ± 3.3 | 19.9 | 1.5 |
| T420K | 20374 ± 1876 | 27866 ± 1129 | 0.0007 | 60.6 ± 3.8 | 86.6 ± 4.1 | 26.1 | 1.4 |
| T420P | 17155 ± 1546 | 26139 ± 851 | 0.0001 | 51.6 ± 3.4 | 82.1 ± 4.3 | 30.5 | 1.5 |
| T420R | 15732 ± 1356 | 26243 ± 771 | 0.0001 | 48.1 ± 3.4 | 82.4 ± 4.3 | 34.3 | 1.7 |

TABLE 7-continued

| α-Gal A Mutant Form | Baseline α-Gal A activity (nmol/mg/hr) | 10 μM migalastat α-Gal A activity (nmol/mg/hr) | Mann-Whitney U p-value | Baseline α-Gal A activity (% WT) | 10 μM migalastat α-Gal A activity (% WT) | Absolute increase (% WT) | Relative increase |
|---|---|---|---|---|---|---|---|
| T420S | 23505 ± 1306 | 32465 ± 897 | 0.0001 | 71.4 ± 2.6 | 101.5 ± 4.6 | 30.1 | 1.4 |
| M421I | 19000 ± 943 | 33949 ± 1412 | 0.0001 | 65.7 ± 2.5 | 118.9 ± 6 | 53.2 | 1.8 |
| M421K | 36942 ± 3086 | 45754 ± 1808 | 0.0004 | 123.9 ± 4.9 | 159.6 ± 6.2 | 35.7 | 1.2 |
| M421L | 21513 ± 1479 | 28263 ± 1128 | 0.0001 | 65.6 ± 3.4 | 87.5 ± 3.7 | 21.9 | 1.3 |
| M421R | 27913 ± 817 | 36429 ± 989 | 0.0001 | 87.1 ± 3.8 | 114.2 ± 5.5 | 27.1 | 1.3 |
| M421T | 14666 ± 828 | 21185 ± 707 | 0.0001 | 44.6 ± 1.8 | 66.2 ± 3.1 | 21.6 | 1.4 |
| Q422P | 27059 ± 2022 | 45170 ± 1440 | 0.0001 | 93.5 ± 5.9 | 157.3 ± 4.4 | 63.8 | 1.7 |
| M423I | 20857 ± 918 | 25268 ± 1106 | 0.0036 | 70.3 ± 3.6 | 85.8 ± 5.3 | 15.4 | 1.2 |
| M423K | 18352 ± 1047 | 24240 ± 993 | 0.0002 | 61.8 ± 3.8 | 81.4 ± 3.8 | 19.7 | 1.3 |
| M423L | 16037 ± 874 | 22114 ± 1324 | 0.0011 | 53.6 ± 2.8 | 73.3 ± 3.8 | 19.7 | 1.4 |
| M423T | 19669 ± 956 | 26392 ± 1093 | 0.0001 | 66.1 ± 3.5 | 88.6 ± 4.2 | 22.5 | 1.3 |
| S424L | 27072 ± 1966 | 33333 ± 1634 | 0.0120 | 69.2 ± 4.7 | 88.1 ± 6.7 | 18.9 | 1.2 |
| L425F | 26370 ± 948 | 36447 ± 3394 | 0.0001 | 91.5 ± 4.6 | 125.1 ± 11.1 | 33.6 | 1.4 |
| D427N | 33454 ± 4593 | 49103 ± 5890 | 0.0249 | 82.4 ± 7.8 | 116.6 ± 7.7 | 34.2 | 1.5 |
| L429R | 29098 ± 1230 | 35876 ± 1241 | 0.0004 | 99.6 ± 5.3 | 123.3 ± 6 | 23.7 | 1.2 |

In Table 7, values for the mean±standard error of the mean (SEM) were calculated. nmol/mg/hr indicates "nmoles of free 4-MU released per mg of protein per hour". WT indicates "wild-type". NC indicates "not calculable". N/A indicates "not applicable".

Baseline and 10 μM migalastat α-Gal A activity: Differences in the α-Gal A activity between lysates incubated in the absence and presence of 10 μM migalastat were determined using a one-tailed, Mann Whitney U test; an increase at 10 μM migalastat with a $p<0.05$ was considered significant. "BLD" indicates that the mean α-Gal A activity was below the limit of detection (<142 nmol/mg/hr).

Baseline α-Gal A activity (% WT)=(α-Gal A activity in mutant transfected cell lysates without migalastat÷α-Gal A activity in wild-type transfected cell lysates without migalastat)*100.

10 μM migalastat α-Gal A activity (% WT)=(α-Gal A activity in mutant transfected cell lysates incubated with 10 μM migalastat÷α-Gal A activity in wild-type transfected cell lysates without migalastat)*100.

Absolute increase (% WT)=is the 10 μM migalastat α-Gal A activity (% WT) minus the baseline α-Gal A activity (% WT).

Relative increase is the 10 μM migalastat α-Gal A activity in mutant transfected cell lysates÷baseline α-Gal A activity in mutant transfected cell lysates incubated without migalastat.

As can be seen from Table 7, the novel α-Gal A mutations listed in Table 2 demonstrated an in vitro response to incubation with migalastat that met amenability criteria. Accordingly, patients with these mutations are expected to be treatable with migalastat therapy as described herein.

In some instances, a set of electronic components may communicate to determine a predicted result of using migalastat or a migalastat salt based on mutation data representing one or more mutations. The predicted result may be based on, for example, whether a mutation represented in the mutation data is identified in a data store and/or which data value(s) are associated with the identification in the data store.

Figure 4B:
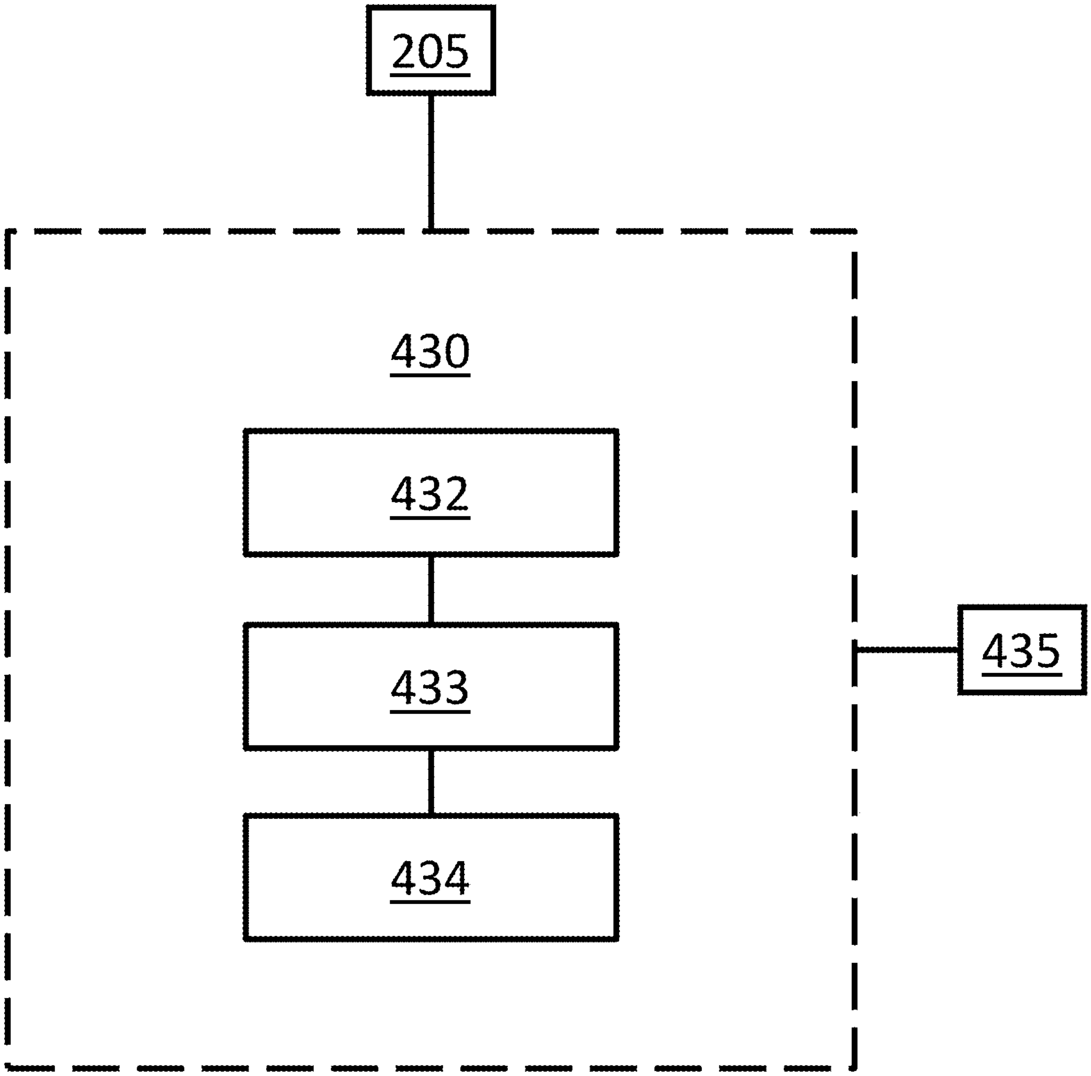
FIG. 4B shows a schematic view of an exemplary mutation classifier system.

FIG. 4 shows an exemplary interaction system 400 to generate treatment classifications based on mutation data. Depicted components (e.g. systems) may communicate with each other over one or more networks (e.g., the Internet, a wide-area network, a local-area network, the Internet or a short-range connection).

Interaction system 400 can include a provider system 405, which can be associated with a provider providing care to a subject. The provider may include (for example) a physician, nurse, health clinic, hospital, etc. The subject may include a person (e.g., male or female) diagnosed with or tentatively diagnosed with Fabry disease and/or diagnosed with or tentatively diagnosed with a disorder pertaining to α-Gal A activity. Provider system 405 may collect subject data corresponding to the data from a variety of sources. For example, some subject data may be locally collected as a result of information provided directly from the subject to the provider, such as demographic information, symptom profiles and/or treatment history. Some subject data may have been initially collected and/or detected at a laboratory system 410, such as urine-culture data (e.g., indicating whether any of proteinuria, albuminuria or accumulation of lyso-Gb3 were detected in a urine sample from the subject) and/or blood-test data (e.g., characterizing an activity of the α-galactosidase A enzyme and/or indicating whether an accumulation of Lyso-Gb3 was detected in a blood sample from the subject). Some subject data may have been collected by a sequencing system 415, which may sequence one or more genes and/or detect one or more mutations. For example, the GLA gene may be sequenced, and a mutation-detection analysis may be performed to identify any mutation in the GLA gene (e.g., any single nucleotide polymorphism or structural mutation). Sequencing system 415 may identify and/or represent a mutation as a nucleotide mutation, protein sequence mutation, etc.

In some instances, provider system 405 sends subject-data requests (e.g., with an identifier of the subject) directly to laboratory system 410 and/or sequencing system 415, potentially along with an indication that the subject has authorized availing data to the provider (e.g., the authorization being provided via a signature). In some instances, one or both of laboratory system 410 and sequencing system 415 transmit the subject data to a coordinating access control system 420, which controls a manages a central (e.g., remote and/or cloud-based) subject data store 425. Access control system 420 may perform data-aggregation, synchronization and authorization processes. For example, access control system 420 may use a white-list, black-list, cryptographic and/or account-verification technique to determine whether to update subject data store 425 based on data from a given system and/or whether to transmit requested data from subject data store 425 to a given system. To illustrate, access control system 420 may require use of a private information link (supported by a shared secret) between a provider system and the access control system in order to transmit any subject data to the provider system. As another example, a data synchronization process may—upon detecting inconsistent data—delete the older data value and use the newer data value, store each of the older and newer data values, assign a confidence to one or both of the older and newer data values (e.g., based on a reliability of a data source, degree to which the a data value is represented in a patient group), etc.

Provider system 405 can send a request to a mutation classification system 430 to generate a predictive metric or predictive output for the subject. The request can include or can be accompanied by at least some of the subject data, such as the sequence data (e.g., corresponding to one or more genes) and/or mutation data (e.g., corresponding to one or more genes).

The predictive metric and/or the predictive output may be predictive of whether and/or an extent to which a given treatment would be effective in treating, delaying and/or preventing a particular condition. For example, the predictive metric and/or predictive output may be predictive of whether and/or an extent to which administering migalastat or a migalastat salt (e.g., generally, in a particular dosage and/or via a particular route of administration) is effective at treating Fabry disease.

Mutation classifier system 430 can, in some instances, include a web server 432, at least one data processor 433 and a non-transitory computer readable storage medium 434. The web server 432 serves a webpage that accepts input that identifies mutation data. The webpage need not require entry of subject-identifying data. In some instances, the webpage may be configured such that the only input fields for accepting subject-associated data are to accept sequence data and/or mutation data. In some instances, the webpage is configured such that a file that identifies a sequence can be uploaded. In some instances, the webpage is configured to include an input component that accepts text inputs that identify a mutation. The webpage may identify a format in which mutation identifications are to be represented and/or a file type to be used for sequence-data uploads.

Upon receiving a communication that corresponds to a request for a predictive metric and/or predictive output, mutation classifier system 430 can determine if an identification of a mutation (and/or if an uploaded sequence file) is of a correct format. In some embodiments, the determination of the proper format is made by data processor 433. For example, a format may require that a nucleotide mutation include a prefix letter ("c"), followed by a period (or these may be optional components). The format may further require that the mutation identify a wild-type nucleotide, the nucleotide number and a mutant nucleotide. The format may require (or permit) the ">" symbol and/or a particular order. For example, a permitted or required format may include the following components in the following order: (optionally "c.") nucleotide number, wild-type nucleotide, ">", and mutant nucleotide. As another example, a permitted or required forma may include the following components in the following order: (optionally "c."), wild-type nucleotide, nucleotide number and mutant nucleotide.

In some instances, if a mutation identification is not of a required or permitted format, mutation classifier system 430 may return an error indication by web server 432. In some instances, if a mutation identification provided in a first format is not of a required or permitted format, mutation classifier system 430 may generate one or more proposed identifications in a second format based on the input and transmit the proposed identification(s) to be availed at provider system 205 (e.g., presented at a webpage), such that one of the proposed identifications in the second format can be selected or such that the proposed identification(s) can guide subsequent input. The proposed identification(s) in the second format may be generated by data processor 433 by detecting numbers and/or letters in the initial input of the first format and reorganizing them in a manner that accords with a permitted or required format (e.g., and by adding or removing one or more characters, such as "." or ">"). In instances in which sequence data is received, mutation classifier system 430 can identify one or more mutations by comparing the sequence to a reference sequence.

Mutation classifier system 430 and data processor 433 can query an amenable mutation data store medium 435 using a representation of one or more mutations to retrieve data that corresponds to a predicted outcome of using each of one or more treatments by a subject having the one or more mutations. The outcome may relate to (for example) an efficacy and/or low incidence of adverse effects. The one or more treatments may include migalastat or a migalastat salt. The outcome can include or can be based on an observed outcome, such as one generated based on a human trial or animal experiment in which subjects having the mutation were administered the treatment, and their condition (e.g., state of a condition, such as state of Fabry disease) was monitored. The outcome can alternatively or additional include or can be based on a theoretical outcome, which may be based on in vitro experiments that indicate whether and/or an extent to which administering an agent corresponding to the treatment to cells having the mutation(s) has a target effect (e.g., increased α-Gal activity). In some instances, amenable mutation data store medium 435 indicates whether in vivo experiments/trials have been performed and analyzed (e.g., versus having only in vitro data or no data). In some instances, both in vivo and in vitro data is available for at least some of the mutations, and this paired data may be used to derive a scaling factor and/or transformation function to normalize data and/or transform in-vitro-based data to a different scale.

The data processor 433 can detect the query result from amenable mutation data store medium 435 and determine whether the query result indicates that the one or more mutations is amenable to a given treatment.

A result of a given query can include one or more of: an indication as to whether retrieved data corresponds to in vivo data or theoretical data (e.g., in-vitro-based data); an indication as to whether a treatment is predicted to be effective given an occurrence of an input-identified mutation; and/or a predicted magnitude (e.g., of efficacy, time course or adverse-event occurrence) of administering the treatment given an occurrence of an input-identified mutation. The indication as to whether a treatment is predicted to be effective may include a binary indicator. The binary indicator may be determined based on whether a magnitude of a desirable effect (as observed in an in vivo or in vitro study) exceeds a predefined magnitude threshold (e.g., such that median or mean values of treated and untreated data sets differ by at least 80%, 50%, 30%, 10% or 5%), whether a p value corresponding to the desirable effect is below a predefined p-value threshold (e.g. 0.1, 0.05, 0.02, 0.01 or 0.005) and/or whether a confidence value corresponding to the desirable effect is below a predefined confidence threshold (e.g., 70%, 80%, 90%, 95%, 98%, or 99%). The binary indicator may be determined based on whether a magnitude of an undesirable effect (as observed in an in vivo or in vitro study) is below a predefined magnitude threshold (e.g., such that median or mean values of treated and untreated data sets differ by less than 80%, 50%, 30%, 10% or 5%), whether a p value corresponding to the undesirable effect is above a predefined p-value threshold (e.g. 0.1, 0.05, 0.02, 0.01 or 0.005) and/or whether a confidence value corresponding to the undesirable effect is above a predefined confidence threshold (e.g., 70%, 80%, 90%, 95%, 98%, or 99%). The predicted magnitude may correspond to subtractive or multiplicative differences between means or medians of the untreated and treated groups.

Further, the data processor 433 can generate output indicative of the amenability of the one more mutations to a given treatment. The output may be transmitted to and provided by the webserver 432 and/or the provider system 205.

In some instances, a request corresponds to multiple mutations. Amenable mutation data store medium 435 need not reliably include data corresponding to each possible mutation combination. Thus, mutation classifier system 430 and data processor 433 may separately retrieve data corresponding to each individual mutation. In some instances, mutation classifier system 430 and data processor 433 then selects data corresponding to a single mutation. The single mutation may correspond to (for example) a mutation from amongst the multiple mutations for which results were most positive (e.g., corresponding with metrics indicative of highest predicted efficacy and/or lowest predicted adverse-effect occurrence or magnitude), most negative, or at a midpoint. In some instances, rankings are assigned to individual mutations in amenable mutation data store medium 435, such that the single mutation is identified the mutation, and the single mutation is selected as that being of the lowest relative rank (with low ranks being superior to high ranks). Rankings may represent how predominant a mutation is in influencing a disease-treatment outcome.

In some instances, one or more classifications are assigned to each of one or more mutations and or to a collective mutation set (e.g., if multiple are identified in an input). For example, in some instances, amenable mutation data set 435 may identify one or more classifications for each represented mutation. A classification may correspond to (for example) a predicted efficacy magnitude, a prediction as to whether a treatment will result in any efficacy, a time scale of any efficacy, a predicted adverse-event magnitude and/or a prediction as to whether a treatment will result in any adverse events. In some instances, a classification corresponds to transforming a numeric value of a single variable to a category of the same variable (using one or more thresholds). In some instances, a classification transforms values of multiple variables (e.g., corresponding to two or more of: predicted efficacy magnitude, predicted efficacy occurrence, predicted adverse-event magnitude and predicted adverse-event occurrence) to a single variable. Clustering-transformation functions may be defined based on (for example) clustering algorithms, component analyses (e.g., principal component analysis or independent component analysis), a neural network and/or user input. The classifications may be represented at amenable mutation data store medium 435 and/or determined by mutation classifier system 430. For example, amenable mutation data store medium 435 may associate each mutation with one or more classifications, or amenable mutation data store medium 435 may associate each mutation with one or more values (e.g., numeric values, binary values or even categorical values), which mutation classifier system 430 may process to identify the classification(s).

A data-store controller system 450 can control what data is included in amenable mutation data store medium 435. For example, data-store controller system 450 may authorize, receive and evaluate communications indicative of experimental results and/or study results from an in vivo study system 455 and/or in vitro testing system 460. The authorization process may include (for example) ensuring that the system is white-listed and/or has provided requisite authenticating information. In vivo study system 455 may be configured to (for example) assess data corresponding to a clinical trial (e.g., a Phase I, Phase II or Phase III trial) or corresponding to an experiment performed on a (human or non-human) animal. In some instances, authorization information may further be used to resolve any data conflict. For example, if multiple in vivo study systems 455 submit conflicting results as to whether a given treatment is effective (or an extent to which the given treatment is effective) when a particular mutation is detected, data-store controller system 450 may use a prioritization list to determine which of the in vivo study systems 455 is to control. Data conflicts may also be resolved so as to prioritize (for example) study data performed in accordance with clinical-trial procedures, performed on humans, performed on mammals and/or performed recently. In vitro testing system 460 may be configured to (for example) assess data corresponding to cell-culture experiments.

Upon receiving a result, provider system 405 may (but need not) further process the result in view of additional subject data (e.g., that is not related to genetic sequence data). Based on the result (and any additional data), provider system 405 can identify an appropriate treatment strategy for the subject. The treatment may be selected as a treatment associated with a highest predicted (e.g., average, median or probability of) efficacy, lowest predicted (e.g., average, median or probability of) adverse-event incidence or combination thereof. In some instances, provider system 405 sends an order for a given treatment (e.g., prescription) to a pharmacy system 465. The subject or another entity may administer the treatment to the patient.

Figure 5:
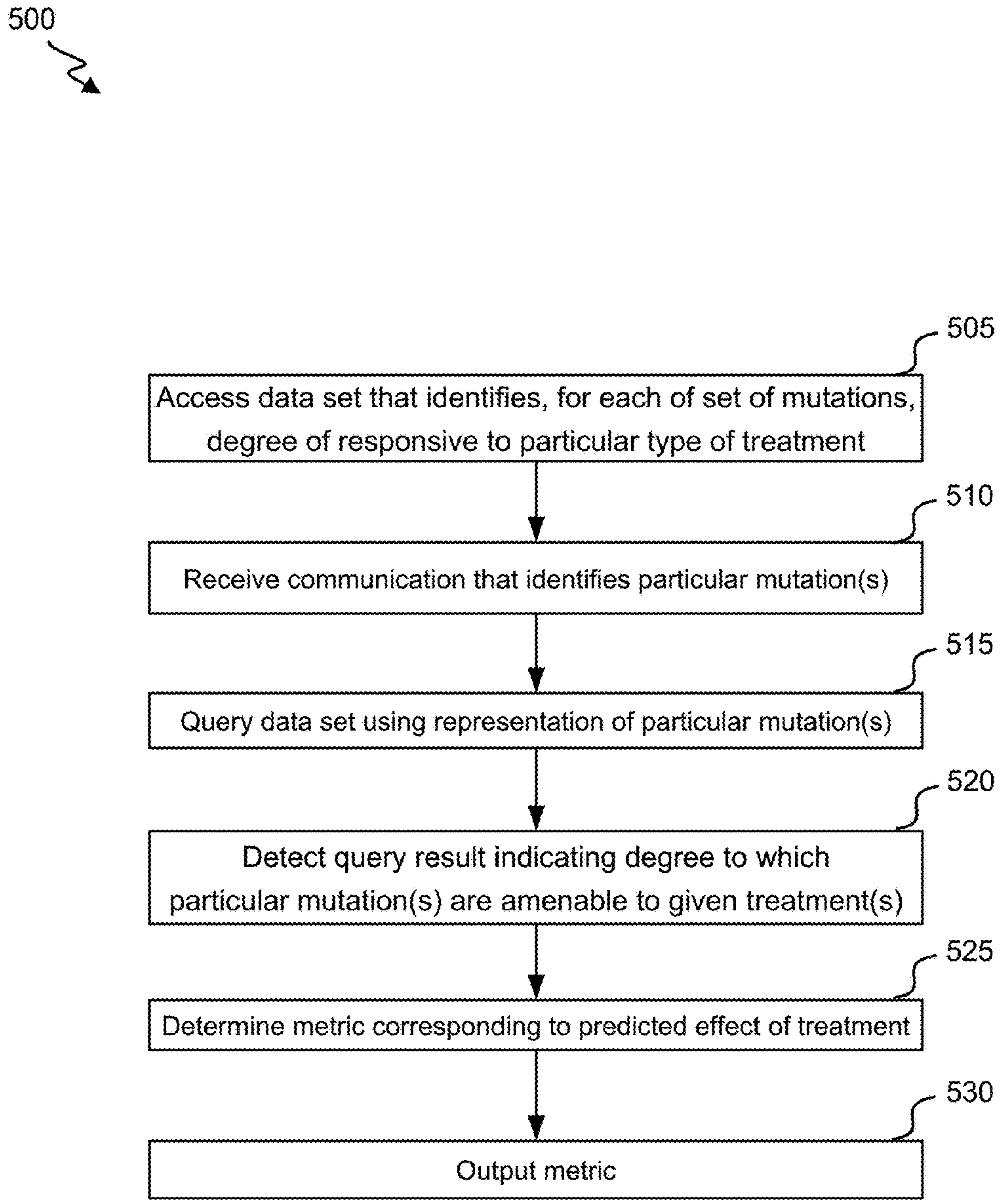
FIG. 5 illustrates an exemplary process for using mutation data to generate predictive metrics.

FIG. 5 illustrates an exemplary process for using mutation data to generate predictive metrics. Process 500 may be performed by (for example) mutation classifier system 430. Process 500 begins at block 505, at which a data set unit storing a data set is accessed that identifies, for each mutation of a set of mutations, a degree of responsiveness to a particular type of treatment. The degree of responsiveness may indicate (for example) a predicted efficacy magnitude, a predicted efficacy occurrence, a predicted adverse-event magnitude, and/or a predicted adverse-event occurrence. The type of treatment may include (for example) treatment with migalastat or migalastat salt. The degree of responsiveness may be constrained to a particular subject group (e.g., having a given condition and/or a mutation in a particular gene). The data set may have been derived from in vivo (e.g., human and/or non-human; primate and/or non-primate; mammal and/or non-mammal) studies and/or in vitro studies. The data set may be accessed from one or more local or remote data stores.

At block 510, a communication is received that identifies one or more particular mutations. For example, the particular mutations(s) may include one or more nucleotide mutations and/or one or more protein mutations. The particular mutation(s) may correspond to one or more genes. The communication may be received over a network and may have been generated in response to provision of input at a webpage. The particular mutation(s) may correspond to a particular subject and may have been identified based on (for example) input from the subject, from a provider and/or from a sequencing system.

At block 515, a data set is queried using a representation of the one or more particular mutations. The data set may be local or remote to a computer system performing the query. The query may correspond to a request for data indicating an effect of administration of a particular treatment to a subject having (one, some or all) of the particular mutation(s). The query may (but need not specify) the particular treatment.

The data set may include or may be based on experimental data that indicates whether or an extent to which the particular treatment increases α-Gal A activity. More specifically, α-Gal A activity (e.g., a mean or median activity) may be determined for wild-type cells; each of a set of mutant cells, and each of a set of treated mutant cells (having been treated with the particular treatment). The data set may include each of these values. The data set may include, for each of a set of mutations, a fraction or percentage that compares the α-Gal activity of mutant cells (having the mutation) to the α-Gal activity of the wild-type cells and/or a fraction or percentage that compares the α-Gal activity of treated mutant cells to the α-Gal activity of the wild-type cells.

The data set may include, for each of the set of mutations, an absolute difference between the α-Gal activity of the treated mutant cells and the α-Gal activity of untreated mutant cells and/or an absolute difference between the relative α-Gal activity of the treated mutant cells (as compared to wild-type instances) and the relative α-Gal activity of the untreated mutant cells. The data set may include, for each of the set of mutations, a relative difference calculated by subtracting the α-Gal activity of untreated mutant cells from the α-Gal activity of treated mutant cells or by subtracting the relative α-Gal activity of untreated mutant cells (relative to wild-hype instances) from the relative α-Gal activity of treated mutant cells.

The data set may include, for each of the set of mutations, a category or binary indicator determined based on one of the aforementioned activity values, For example, an activity-change variable Δ may be defined as: $activity_{treated,mutant}/activity_{WT}-activity_{untreated,mutant}/activity_{WT}$, where activity is α-Gal activity. Categories may be defined as: $\Delta\leq1$, $1<\Delta\leq5$, $5<\Delta\leq10$, $10<\Delta\leq20$, and $20<\Delta$. As another example, a binary indicator can be set to "Amenable" when Δ>thresh and "Unamenable" when Δ≤thresh (e.g., where thresh is set to 1.0, 2.0, 5.0, or 10.0).

As another example, an activity-change variable 4 may be defined as: $100\%*activity_{treated,mutant}/activity_{untreated,mutan}$. Categories may be defined as: $\Delta\leq100\%$, $100\%<\Delta\leq105\%$, $105\%<\Delta\leq110\%$, $110\%<\Delta\leq150\%$, and $150\%<\Delta$. As another example, a binary indicator can be set to "Amenable" when Δ>thresh and "Unamenable" when Δ≤thresh (e.g., where thresh is set to 100%, 101%, 105% or 110%.

At block 520, one or more results for the query may be detected. The query result(s) may indicate a degree to which a subject having the particular mutation is amenable to each of one or more treatments (e.g., migalastat and/or a migalastat salt). The query result(s) may indicate a predicted occurrence of and/or magnitude of an efficacy and/or adverse-event incidence of administering the treatment. The query result(s) may include a binary indication (e.g., indicating whether each of the particular mutation(s) is amenable to the particular treatment(s)) and/or a numeric or categorical value that more specifically indicates a degree to which each of the particular mutation(s) is amenable to the particular treatment(s).

In some instances, the query result identifies an α-Gal A activity metric associated with mutant, treated cells; mutant, untreated cells; and/or wild-type cells and/or absolute or relative differences between two or more of such cell types.

At block 525, a metric is determined corresponds to a predicted effect of administering a treatment (e.g., an identified particular treatment) to a subject having the particular mutation(s). The metric may include one or more query results and/or processed version(s) thereof. For example, a relative or absolute difference can be calculated between α-Gal A activity in treated mutant cells as compared to as in untreated mutant cells (e.g., with the activity being an absolute value or relative to wild-type activity). Further, a numeric result (or processed version thereof) can be converted into a categorical or binary metric. Further, if multiple particular mutations are identified, the metric may be a maximum, minimum, average or median of mutation-specific results. The metric may include a predicted occurrence of and/or magnitude of an efficacy and/or adverse-event incidence of administering the treatment.

At block 530, the metric is output. Outputting the metric may include (for example) transmitting the metric to a provider system or subject device, such that it is displayed via an interface at the provider system or subject device. Alternatively or additionally, outputting the metric can include locally presenting and/or storing the metric (e.g., in association with an identifier of the subject and/or of the particular mutation(s).

In some instances, the metric itself indicates and/or is accompanied by an indication as to whether the metric was based on theoretical and/or in vitro data. For example, a metric generated based on in vivo human data that indicates that a treatment is effective for treating a given condition in relation to a given mutation may be differentially represented from a metric generated based only on in vitro or simulation data that indicates a similar efficacy in a similar context. Thus, in some instances, four potential metrics are available: Amenable for treatment based on in vivo data; unamenable for treatment based on in vivo data; amenable for treatment based on in vitro data; and unamenable for treatment based on in vitro data. In some instances, a variable type differs between instances supported by in vivo data and other instances. For example, the metric may be a binary indicator when supported by in vivo data but may be a categorical or numeric value in other instances.

Figure 6:
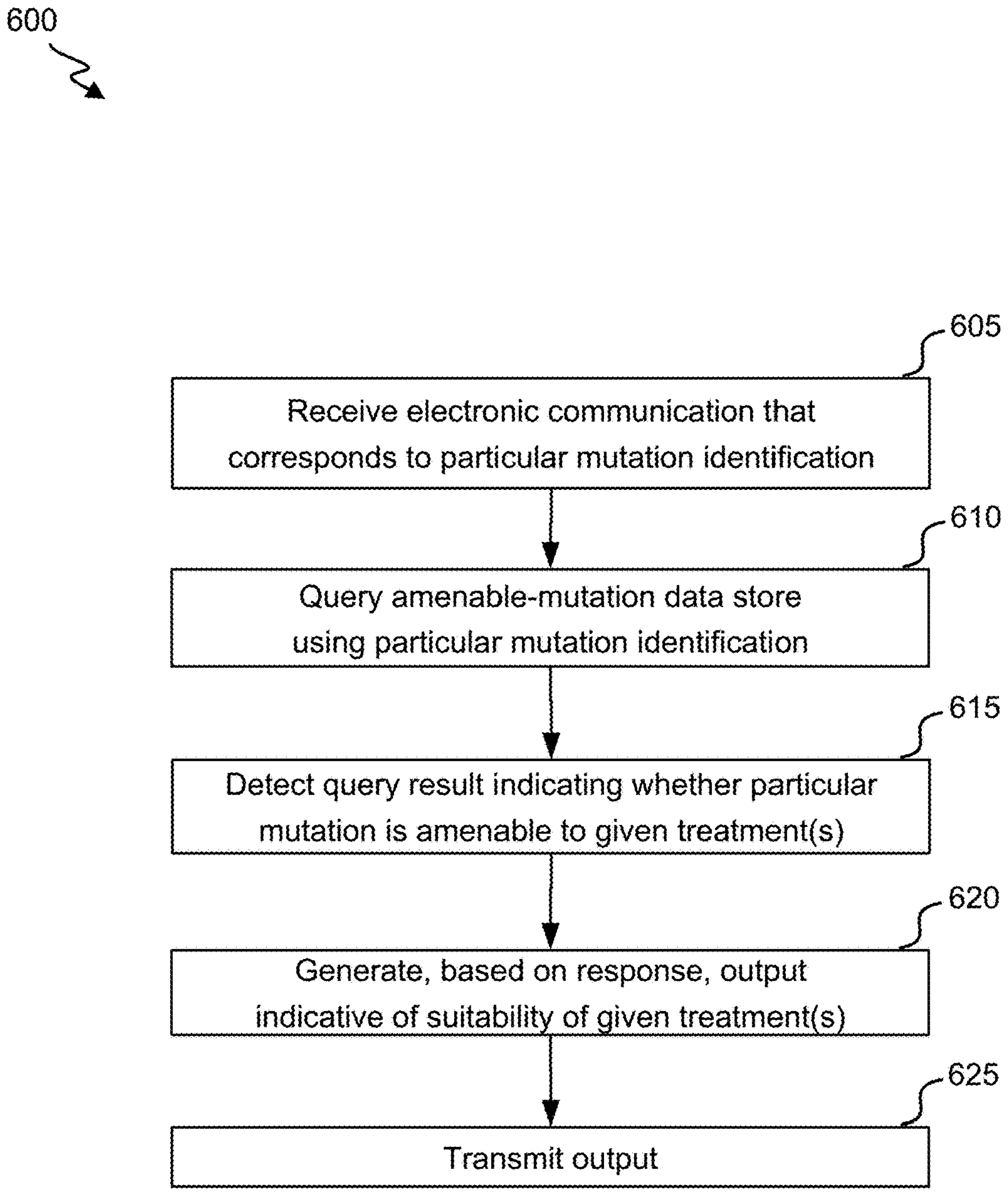
FIG. 6 illustrates an exemplary process for using mutation data to generate predictive outputs.

FIG. 6 illustrates an exemplary process for using mutation data to generate predictive outputs. Process 600 may be performed by (for example) mutation classifier system 430, including webserver 432, data processor 433 and storage medium 434. Process 600 begins at block 605, at which an electronic communication is received by the webserver 432 that corresponds to an identification of one or more particular mutations. The communication may be received as (for example) an HTTP request received in correspondence with a webpage. The particular mutation(s) may (but need not) correspond to one or more particular genes.

At block 610, an amenable-mutation data store is queried by the data processor 433 using the particular mutation identification(s). The amenable mutation data store may local or remote relative to a computer system transmitting the query. The query may correspond to a request for data indicating an effect of administration of a particular treatment to a subject having (one, some or all) of the particular mutation(s). The query may (but need not specify) the particular treatment. The amenable-mutation data store medium 435 may include one or more types of data and/or characteristics as described in relation to the data set queried at block 500 in process 500.

In some instances, the amenable-mutation data store medium 435 selectively lists and/or stores data for mutations determined to be amenable for a given treatment (e.g., migalastat or a migalastat salt). For example, mutations may be selectively identified for inclusion in the amenable-mutation data store when in vivo data indicates that the treatment is effective when the mutation is present and/or when in vitro data indicates that administering the treatment to cells having the mutation results in a desired effect (e.g., increasing absolute α-Gal A activity by at least a threshold amount as compared to untreated instances or increasing α-Gal A activity, relative to wild-type instances, by at least a threshold amount as compared to untreated mutant instances).

At block 615, one or more results for the query may be detected by the data processor 433. The query result(s) may indicate whether the particular mutation (or each of multiple identifier particular mutations) is amenable to the particular treatment. The query result may indicate whether the particular mutation was represented in the amenable-mutation data store, and/or the query result may include one or more values associated with an identifier of the particular mutation in the amenable-mutation data store (e.g., indicating an effect of the treatment when the particular treatment is administered and/or indicating a type of experiment or study used to identify such effect).

At block 620, one or more outputs indicative of a suitability of one or more treatments, with respect to a subject having the particular mutation(s), are generated by the data processor 433. The output(s) can include or can be generated based on the query result(s). For example, if multiple particular mutations are being assessed, the output(s) may include a query result for each of the particular mutations or a maximum, average, median or minimum result. To illustrate, the output may indicate that multiple particular mutations are collectively amenable to a treatment if query results indicate that at least one of the particular mutations is individually amenable to the treatment. The output may be numeric, binary, and/or categorical. The output(s) may be numeric, categorical or binary. In some instances, a numeric and/or categorical input represents increased suitability as a predicted occurrence and/or predicted magnitude of an effect increases and/or as a predicted occurrence and/or predicted magnitude of an adverse event increases.

At block 625, the output is transmitted by the data processor 433 to the webserver 432 or the provider system 205. For example, the output can be transmitted to a provider system or subject device, such that it is displayed via an interface at the provider system or subject device.

Figure 7:
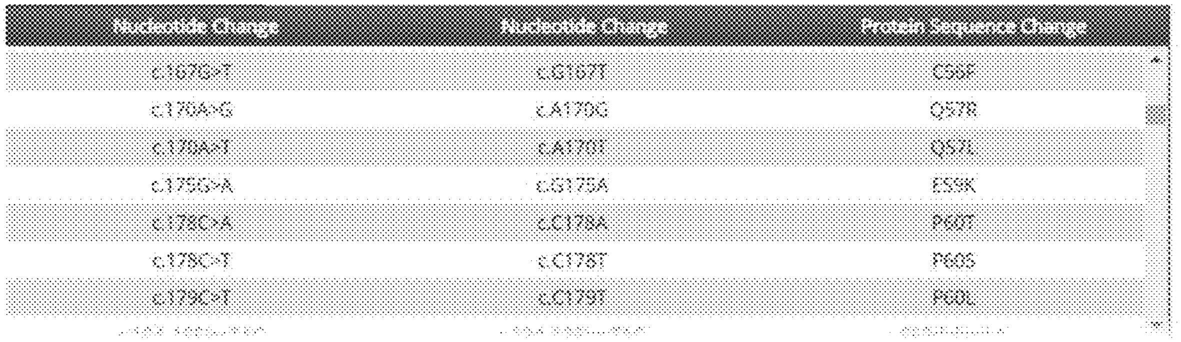
FIG. 7 illustrates exemplary mutation representations for to be used to facilitate assessments of mutation-based effects.
Figure 8:
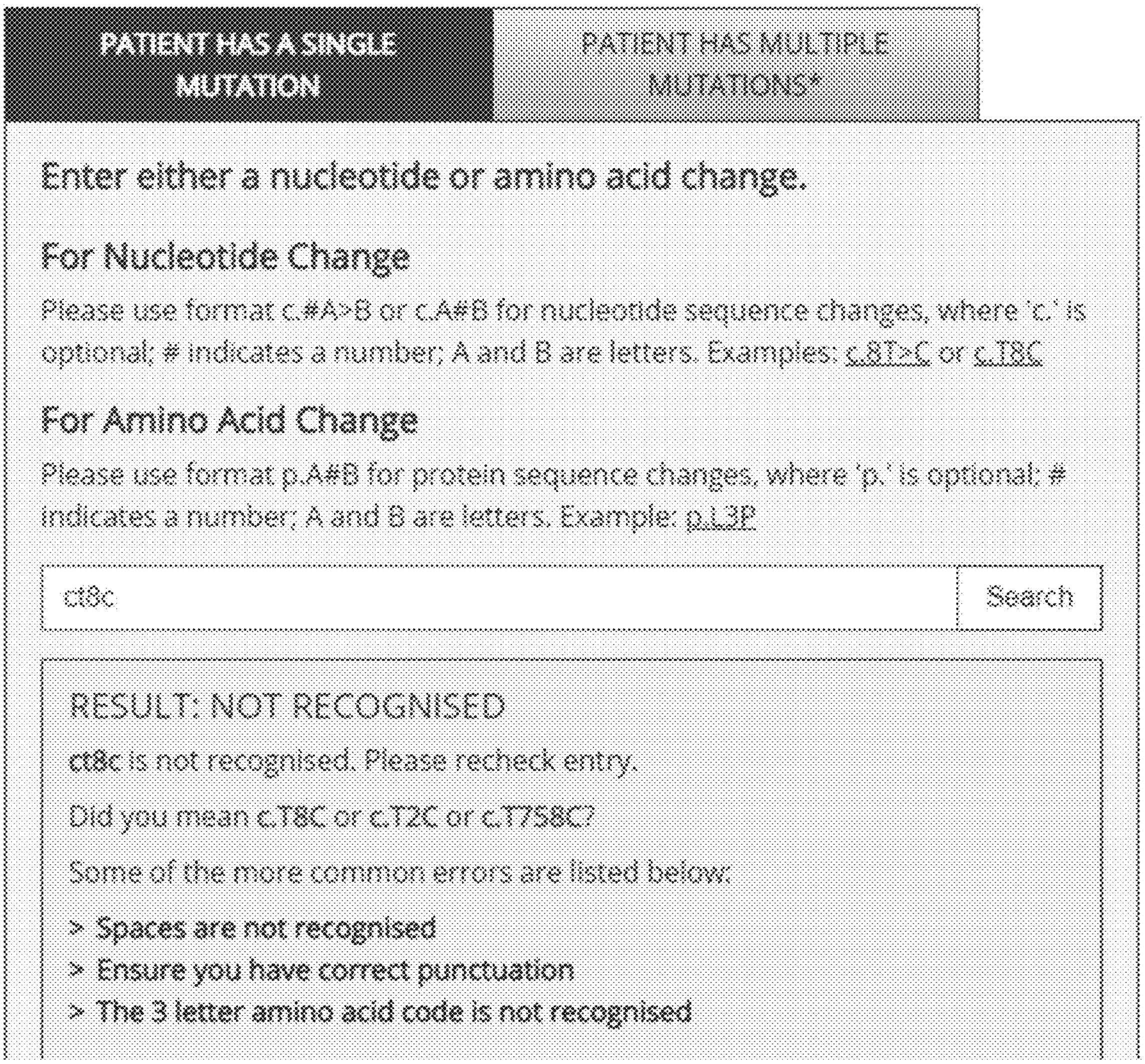
FIG. 8 illustrates an exemplary interface to facilitate mutation-based treatment classifications.

FIG. 7 illustrates exemplary mutation representations for to be used to facilitate assessments of mutation-based effects. For example, two different formats for representing nucleotide mutations are represented. Each includes the wild-type amino acid (first amino acid) and mutant amino acid (second amino acid), as well as the amino acid position. Thus, detecting whether a given character or character string corresponds to a letter, number, multi-digit number, etc. can indicate which (if any) of the above fields are represented by the character or character string. This determination can facilitate automated or suggested transformation of mutation format. The third column represents a representation of various protein sequence mutations, which further convey wild-type and mutant proteins and positio FIG. 8 illustrates an exemplary interface to facilitate mutation-based treatment classifications. The depicted interface provides information that indicates formats in which mutations are to be identified. In the depicted instance, the searched mutation does not comply with the format. A returned result suggests multiple mutation representations that may correspond to the input. The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional operations not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of operations may be undertaken before, during, or after the above elements are considered. Accordingly, the above description does not bind the scope of the claims.

As used herein and in the appended claims, the singular forms “a”, “an”, and “the” include plural references unless the context clearly dictates otherwise. Thus, for example, reference to “a user” includes a plurality of such users, and reference to “the processor” includes reference to one or more processors and equivalents thereof known to those skilled in the art, and so forth.

Also, the words “comprise”, “comprising”, “contains”, “containing”, “include”, “including”, and “includes”, when used in this specification and in the following claims, are intended to specify the presence of stated features, integers, components, or operations, but they do not preclude the presence or addition of one or more other features, integers, components, operations, acts, or groups.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method of treating Fabry disease in a subject comprising:

accessing mutation information corresponding to the subject, the mutation information identifying one or more α-galactosidase A mutations;

determining, based on the mutation information, that the subject has at least one mutation selected from a first group consisting of: N5D, N5K, P6L, P6Q, P6R, P6S, P6T, E7D, E7K, E7V, L81, L8P, L8Q, H9L, H9Q, H9R, H9Y, L10M, L10P, L10Q, L10R, L10V, G11C, G11D, G11R, GUS, G11y, C12G, C12R, C12S, C12Y, A13E, A13G, L14F, L14H, L14V, R17C, R17G, R17H, R17P, R17S, F181, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, S65C, S65G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G80S, W81L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, I91S, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G104S, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, 1117M, 1117T, A121V, Y123D, Y123F, Y123N, Y123S, V124I, H125D, H125N, H125R, K127E, G128A, L129V, K130M, K130N, K130Q, L131V, I133L, I133T, I133V, A135E, A135G, A135S, A135T, D136A, D136N, D136V, V137A, V137D, V137G, V137I, V137L, G138A, N139H, N139I, N139K, N139Y, K140E, K140I, K140N, K140Q, K140R, T141S, A143E, A143G, G144A, G144C, G144R, G1445, F145C, F145L, F145V, F145Y, P146A, P146H, P146L, P146T, G147A, S148C, S148G, S148T, F149C, G150E, G150V, Y151C, Y151D, Y151S, Y152F, Y152S, D153A, D153H, D153N, D153V, D153Y, A156G, Q157E, Q157K, Q157L, Q157P, T158A, T158I, T158N, T158S, F159I, F159L, F159V, F159Y, A160G, A160S, A160T, A160V, D161H, D161N, D161V, D161Y, W162S, V164A, V164I, V164L, D165A, D165E, L166M, L166Q, L167I, F169C, F169L, F169V, F169Y, G171A, G171V, Y173C, Y173F, Y173H, Y173S, D175G, D175H, D175V, D175Y, S176C, S176R, L177F, L177M, L177S, L177V, L177W, E178A, E178G, E178K, E178Q, L180M, L180S, A181P, A181T, A181V, D182A, D182E, D182V, D182Y, Y184F, Y184H, Y184S, K185M, K185N, K185Q, K185T, H186D, H186L, H186N, H186Q, H186Y, M187L, S188A, S188C, S188F, S188P, S188T, S188Y, L189S, L189V, A190D, A190G, A190S, A190T, A190V, L191M, L191V, N192D, N192H, N192K, N192S, N192T, R193G, R193M, R193T, R193W, T194N, T194P, T194S, G195C, G195R, G195S, R196I, R196K, S197C, S197G, S197I, S197N, S197T, I198M, I198S, V199E, V199L, Y200N, Y200S, S201A, S201C, S201T, E203A, E203G, E203Q, W204S, L206F, L206H, L2061, L206R, L206V, Y207F, M208K, W209C, W209G, P210H, P210T, F211C, F211L, F211S, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T217S, E218A, E218D, E218G, E218K, E218Q, E218V, 1219F, 1219M, 1219S, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, P265A, P265Q, M267L, M267V, L268F, L268I, V269L, 1270L, 1270S, 1270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, 1317L, 1317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, 1407L, 1407M, 1407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N and L429R; and administering migalastat or a salt thereof to the subject determined to have at least one mutation selected from the first group.

2. The method of claim 1, wherein determining that the subject has at least one mutation selected from the first group includes:

initiating a query of a data store that identifies two or more mutations from a set of mutations identified in the first group; and receiving a query result that identifies the at least one mutation is represented in the mutations identified in the data store.

3. The method of claim 2, wherein the data store further identifies two or more mutations from another set of mutations selected from a second group consisting of: L3V, L3P, R4M/Y207S, A13T, A13P, A15T, A15G, F18C, A20P, A20D, V22G, W24R, W24G, W24C, L32P, D33H, D33Y, D33G, N34D, N34H, N34T, N34S, N34K, G35R, G35E, G35A, G35V, L36S, L36W, L36F, A37T, A37V, T41I, M42L, M42V, M42K, M42T, M42R, M42I, H46P, E48Q, M51K, M51I, N53K, N53D, N53L, L54F, L54P, D55G, D55V, D55V/Q57L, C56F, C56Y, Q57R, Q57L, E59K, P60T, P60S, P60L, S62delinsLA, E66K, E66G, F69L, M72V, M72I, A73V, M76T, G80D, G80V, D83N, G85S, G85D, G85N, G85M, E87D, Y88S, L89F, I91T, M96I, M96V, A97P, A97V, S102L, G104V, L106F, Q107R, A108T, D109G, R112G, R112H, R112L, F1131, F113L, R118C, A121T, Y123C, H125Y, H125L, S126G, G128E, I133M, A135V, D136E, N139S, K140T, A143T, G144D, G144V, F145S, P146S, P146R, Y152D, Y152H, Y152C, D155E, A156S, A156T, A156V, Q157H, W162G, D165H, D165G, L166G, L166V, L166S, L167V, F169S, G171S, C174R, C174G, D175E, L180W, L180F, G183A, G183D, Y184N, Y184C, K185E, M187V, p.M187 S188dup, M187T, M1871, L189F, L191Q, T194A, T1941, G195V, R196G, I198T, V199M, V199A, V199G, Y200C, S201F, S201Y, E203V, E203D, W204G, W204L, P205T, P205S, P205L, Y207H, Y207S, M208R, P210S, P210L, K213R, K213M, P214S, P214L, N215D, N215S, N215I, N215S/D313Y, Y216D, Y216S, Y216C, 1219L, 1219N, I219T, R220Q, R220P, Q221P, N224T, N224S, H225D, N228D, N228S, F229L, I232T, S238G, S238N, I239T, I239M, K240N, I242V, I242F, I242N, I242T, L243W, L243F, D244N, D244H, W245G, S247C, N249K, Q250K, Q250P, Q250R, Q250H, I253T, I253S, p.V254del, A257P, A257V, A257G, G258R, G258V, P259Q, P259R, P259L, G260E, G260A, G261S, G261R, G261C, N263S, D264Y, P265L, M267T, V269M, V269A, 1270T, 1270M, G271S, G271S/D313Y, G271D, L275V, S276N, W277G, W277C, N278Y, Q279E, Q280K, Q280H, T282A, T282I, M284V, M284T, W287L, A288P, I289S, M290L, M290T, M290I, A291T, P293T, L294S, F295C, M296V, M296L, M296T, M296I, N298S, D299E, L300F, L300P, R301G, R301P, R301Q, R301L, 1303F, 1303N, S304N, S304T, A307T, K308E, K308N, A309P, A309V, L310F, L311V, Q312R, Q312H, D313Y, D313Y/G411D, D313G, V316I, V316G, I317T, 1319F, I319T, N320H, N320I, Q321R, Q321L, Q321H, D322N, D322H, D322E, P323T, P323R, G325S, G325R, K326N, Q327E, Q327L, G328A, Q330P, Q330R, G334E, F337S, E338K, E338V, V339A, V339E, P343T, P343L, S345P, W349S, A352G, A352V, I354K, R356G, R356W, R356Q, R356P, E358Q, E358A, E358G, E358D, I359T, G360S, G360C, G360D, G361E, G361A, P362T, P362L, R363C, R363H, A368T, G373S, G375E, P380L, T385A, V390M, K391E, K391T, R392T, G395E, G395A, E398K, p.T400 S401dup, L403S, N408Y, P409A, P409S, P409T, T410A, T410I, G411D, T412P, T412N, E418G, M421V.

4. The method of claim 2, wherein the data store includes at least 50% of the set of mutations identified in the first group.

5. The method of claim 2, wherein the query is initiated by accessing a particular webpage hosted by a web server that controls a data store identifying at least some of the mutations in the first group.

6. The method of claim 2, wherein the query is initiated by:

accessing a particular webpage on a website;

providing input at the particular webpage that identifies at least part of the mutation information; and selecting an option at the webpage to submit, to a web server, an electronic request to perform the query, the electronic request including a representation of the input;

wherein the query result is received from the web server in response to the query and is displayed at the particular webpage or another webpage on the website.

7. The method of claim 2, wherein the at least one mutation includes one or more mutations of Δ-galactosidase A at amino acid residues 5-14, 17-18, 20-30, 32-33, 36-39, 41, 43, 45-46, 48, 50-51, 53-56, 58-62, 64-89, 91, 96-99, 101-102, 104-110, 113-117, 121, 123-131, 133, 135-141, 143-153, 156-162, 164-167, 169, 171, 173, 175-178, 180-182, 184-201, 203, 204, 206-222, 224, 227-230, 232-233, 235, 237-261, 263-265, 267-270, 272-273, 275, 277-278, 280-286, 288-289, 291-292, 294-295, 297-300, 302-304, 306-322, 324-327, 329-339, 341, 343-344, 346-357, 359, 362-371, 373-377, 379-381, 383-388, 391-425, 427, 429, or any combination thereof, wherein the residues are numbered relative to SEQ ID NO:2.

8. The method of claim 2, wherein the at least one mutation includes a mutation:

at amino acid residue 5 that comprises N5D or N5K;

at amino acid residue 6 that comprises P6L, P6Q, P6R, P6S, or P6T;

at amino acid residue 7 that comprises E7D, E7K, E7V;

at amino acid residue 8 that comprises, L8I, L8P, L8Q;

at amino acid residue 9 that comprises H9L, H9Q, H9R, or H9Y;

at amino acid residue 10 that comprises, L10M, L10P, L10QL10R, or L10V;

at amino acid residue 11 that comprises G11C, G11D, G11R, G115, or Glly;

at amino acid residue 12 that comprises C12G, C12R, C125, or C12Y;

at amino acid residue 13 that comprises A13E or A13G;

at amino acid residue 14 that comprises L14F, L14H, or L14V at amino acid residue 17 that comprises R17C, R17G, R17H, R17P, or R175;

at amino acid residue 18 that comprises, F18I or F18L;

at amino acid residue 20 that comprises A20G;

at amino acid residue 21 that comprises L21H;

at amino acid residue 22 that comprises V22A, V22F, V22I, or V22L;

at amino acid residue 23 that comprises S23P orS23T;

at amino acid residue 24 that comprises W24S;

at amino acid residue 25 that comprises D25H;

at amino acid residue 184 that comprises Y184S;

at amino acid residue 228 that comprises N228H; or at amino acid residue 412 that comprises T412I;

wherein the residues are numbered relative to SEQ ID NO:2.

9. A method for treatment of Fabry disease in a human patient in need thereof, the method comprising administering to the patient a therapeutically effective dose of migalastat or a salt thereof, wherein the patient has an Δ-galactosidase A mutation selected from a first group consisting of: NSD, NSK, P6L, P6Q, P6R, P6S, P6T, E7D, E7K, E7V, L8I, L8P, L8Q, H9L, H9Q, H9R, H9Y, L10M, L10P, L10Q, L10R, L10V, G11C, G11D, G11R, G11S, Glly, C12G, C12R, C12S, C12Y, A13E, A13G, L14F, L14H, L14V, R17C, R17G, R17H, R17P, R17S, F181, F18L, A20G, L21H, V22A, V22F, V22I, V22L, S23P, S23T, W24S, D25H, I26N, P27A, P27L, P27S, P27T, G28E, G28R, G28W, A29G, A29P, A29V, R30G, L32M, L32Q, L32R, L32V, D33A, D33E, D33V, L36M, L36V, A37E, A37G, A37S, R38G, R38M, R38W, T39A, T39K, T39M, T39R, T39S, T41A, T41N, T41S, G43A, L45M, L45V, H46D, H46N, H46Q, E48A, F50Y, M51R, M51T, M51V, N53H, N53I, N53S, N53T, L54H, L54R, L54V, D55A, D55E, D55H, D55Y, C56W, E58K, E59A, E59D, E59G, E59Q, E59V, P60A, P60Q, P60R, D61E, D61V, S62A, S62C, S62F, S62P, S62Y, I64L, I64V, S65C, S65G, S65R, E66D, E66V, K67E, K67M, K67N, K67Q, K67T, L68I, F69I, F69Y, M70I, M70K, M70L, M70R, E71A, E71D, E71G, E71Q, E71V, M72L, M72T, A73S, A73T, E74D, E74G, E74K, E74V, L75F, L75P, M76V, V77I, V77L, S78L, S78P, E79A, E79D, E79G, E79K, E79Q, E79V, G80A, G80C, G805, W81L, K82E, K82M, K82N, K82R, K82T, D83A, D83E, D83G, D83V, A84E, A84G, A84P, A84S, A84T, A84V, G85A, G85C, G85R, Y86F, E87G, Y88H, Y88N, L89V, I91F, I91L, I91M, 1915, M96L, M96T, A97D, A97S, A97T, P98H, P98L, P98R, Q99E, Q99L, Q99P, Q99R, D101A, D101E, D101G, D101H, D101V, S102A, S102P, S102T, G104A, G104D, G1045, R105G, R105I, R105K, R105T, L106H, L106I, L106P, L106V, Q107E, Q107H, Q107K, A108E, A108V, D109A, D109E, D109H, D109N, D109Y, P110T, F113V, F113Y, P114L, H115D, H115N, G116R, 1117M, 1117T, A121V, Y123D, Y123F, Y123N, Y1235, V124I, H125D, H125N, H125R, K127E, G128A, L129V, K130M, K130N, K130Q, L131V, I133L, I133T, I133V, A135E, A135G, A1355, A135T, D136A, D136N, D136V, V137A, V137D, V137G, V137I, V137L, G138A, N139H, N139I, N139K, N139Y, K140E, K140I, K140N, K140Q, K140R, T1415, A143E, A143G, G144A, G144C, G144R, G1445, F145C, F145L, F145V, F145Y, P146A, P146H, P146L, P146T, G147A, S148C, S148G, S148T, F149C, G150E, G150V, Y151C, Y151D, Y1515, Y152F, Y1525, D153A, D153H, D153N, D153V, D153Y, A156G, Q157E, Q157K, Q157L, Q157P, T158A, T158I, T158N, T1585, F159I, F159L, F159V, F159Y, A160G, A1605, A160T, A160V, D161H, D161N, D161V, D161Y, W1625, V164A, V164I, V164L, D165A, D165E, L166M, L166Q, L167I, F169C, F169L, F169V, F169Y, G171A, G171V, Y173C, Y173F, Y173H, Y1735, D175G, D175H, D175V, D175Y, S176C, S176R, L177F, L177M, L1775, L177V, L177W, E178A, E178G, E178K, E178Q, L180M, L1805, A181P, A181T, A181V, D182A, D182E, D182V, D182Y, Y184F, Y184H, Y1845, K185M, K185N, K185Q, K185T, H186D, H186L, H186N, H186Q, H186Y, M187L, S188A, S188C, S188F, S188P, S188T, S188Y, L1895, L189V, A190D, A190G, A1905, A190T, A190V, L191M, L191V, N192D, N192H, N192K, N192S, N192T, R193G, R193M, R193T, R193W, T194N, T194P, T1945, G195C, G195R, G1955, R196I, R196K, S197C, S197G, 51971, S197N, S197T, I198M, 11985, V199E, V199L, Y200N, Y200S, S201A, S201C, S201T, E203A, E203G, E203Q, W2045, L206F, L206H, L2061, L206R, L206V, Y207F, M208K, W209C, W209G, P210H, P210T, F211C, F211L, F2115, F211V, F211Y, Q212H, Q212P, K213E, K213Q, P214A, P214H, P214R, P214T, N215H, N215K, N215T, N215Y, Y216F, Y216H, Y216N, T217A, T217I, T217K, T217P, T217R, T2175, E218A, E218D, E218G, E218K, E218Q, E218V, 1219F, 1219M, 12195, R220L, Q221E, Q221H, Q221K, Q221L, Q221R, Y222C, Y222D, Y222H, Y222N, Y222S, N224H, R227G, N228H, N228I, N228T, F229I, F229S, F229Y, A230D, A230G, A230P, A230V, I232L, I232M, I232V, D233A, D233E, D233G, D233V, S235A, S235T, K237I, S238C, S238I, S238T, I239L, K240E, K240M, K240R, S241C, S241I, S241T, I242L, I242M, I242S, L243M, L243S, L243V, D244A, D244E, D244G, D244V, D244Y, W245C, T246A, T246I, T246K, T246R, S247A, S247F, S247T, S247Y, F248C, F248L, F248V, F248Y, N249D, N249H, N249I, N249S, N249T, N249Y, Q250E, Q250L, E251G, E251K, E251Q, E251V, R252G, I253F, I253N, I253V, V254A, V254D, V254F, V254G, D255A, D255E, D255H, D255N, D255V, D255Y, V256D, V256G, V256L, A257S, G258E, P259A, P259T, G260W, G261A, N263H, N263T, P265A, P265Q, M267L, M267V, L268F, L268I, V269L, 1270L, 1270S, 1270V, N272D, F273Y, L275I, W277L, N278I, Q280L, Q280R, V281A, V281E, V281G, V281L, T282S, Q283E, Q283H, Q283L, M284I, M284L, A285G, A285T, A285V, L286F, L286H, L286V, A288G, A288S, A288V, I289L, I289T, I289V, A291G, A292G, A292S, L294F, L294I, L294V, F295I, F295S, F295V, F295Y, S297T, N298D, N298I, N298T, D299H, D299N, L300I, L300V, H302D, H302L, H302N, H302Y, 1303S, S304I, Q306E, Q306L, Q306P, A307D, A307G, A307P, A307S, A307V, K3081, K308Q, K308R, A309D, A309T, L310I, L311I, Q312E, Q312K, Q312L, D313E, D313V, K314E, K314M, K314N, K314T, D315A, D315G, D315H, D315N, D315V, D315Y, V316A, V316L, 1317L, 1317M, I317V, A318D, A318P, A318T, A318V, 1319M, N320S, N320T, Q321K, D322A, D322V, L324V, L324W, G325A, G325C, G325V, K326E, K326M, K326Q, K326R, K326T, Q327H, Q327P, Y329C, Y329D, Y329F, Y329H, Y329N, Q330E, Q330H, Q330K, L331H, L331P, L331R, L331V, R332G, R332I, R332S, R332T, Q333E, Q333L, Q333P, G334R, G334V, D335A, D335E, D335G, D335V, D335Y, N336D, N336I, N336S, N336T, N336Y, F337C, F337L, F337V, F337Y, E338A, E338D, E338G, V339M, E341A, E341Q, P343A, P343S, L344F, L344R, L344V, G346A, G346C, G346D, G346V, L347I, A348D, W349C, W349L, A350G, A350S, A350T, A350V, V351A, V351E, A352S, A352T, M353K, M353L, M353T, I354R, N355D, N355H, N355S, N355Y, R356L, Q357E, I359F, I359L, I359N, I359S, I359V, P362A, P362H, P362R, P362S, R363G, R363L, R363S, S364C, S364P, Y365D, Y365F, Y365N, Y365S, T366I, T366N, T366P, T366S, I367F, I367L, I367M, A368G, A368P, V369A, V369F, V369G, V369I, V369L, A370D, A370G, A370P, A370T, A370V, S371C, S371T, G373A, G373C, K374E, K374I, K374R, K374T, G375R, V376E, V376G, V376L, V376M, A377G, A377P, A377S, A377T, N379D, N379I, N379K, N379T, P380A, P380H, P380R, P380T, A381D, F383C, F383I, F383Y, I384F, I384M, I384T, T385I, Q386H, Q386K, Q386L, L387F, L387H, L387I, L387R, L388F, L388H, L388I, L388R, L388V, K391I, K391N, K391Q, K391R, R392G, R392K, R392M, R392W, K393E, K393N, K393Q, K393T, L394I, L394Q, L394R, G395R, F396C, F396I, F396L, F396V, Y397C, Y397F, Y397H, Y397N, Y397S, E398G, E398Q, W399G, W399R, T400A, T400I, T400N, T400P, T400S, S401A, S401L, S401T, R402G, R402M, R402S, R402T, R402W, L403F, L403V, R404G, R4041, R404K, R404S, R404T, S405G, H406D, H406L, H406Q, 1407L, 1407M, 1407T, N408D, N408H, N408T, P409L, T410S, G411A, G411C, G411V, T412A, T412I, T412S, V413F, V413G, V413I, L414F, L414V, L415H, L415I, Q416E, Q416H, Q416L, L417I, E418A, E418D, E418K, E418Q, N419I, N419S, N419T, N419Y, T420K, T420P, T420R, T420S, M421I, M421K, M421L, M421R, M421T, Q422P, M423I, M423K, M423L, M423T, S424L, L425F, D427N and L429R.

10. The method of claim 9, wherein the mutation is selected from the group consisting of: N5D, N5K, P6L, P6Q, P6R, P6S, P6T, E7D, E7K, E7V, L8I, L8P, L8Q, H9L, H9Q, H9R, H9Y, L10M, L10P, L10Q, Y184S, N228H, and T412I.

11. The method of claim 9, wherein the migalastat or salt thereof is administered to the patient every other day.

12. The method of claim 9, wherein the patient is administered about 100 to about 150 mg free base equivalent of the migalastat or salt thereof every other day.

13. The method of claim 9, wherein the patient is administered about 123 mg free base equivalent of the migalastat or the salt thereof every other day.

14. The method of claim 9, wherein the migalastat or salt thereof enhances Δ-galactosidase A activity.

15. The method of claim 1, wherein the subject has at least one mutation selected from the group consisting of: Y184S, N228H, or T412I.

16. The method of claim 1, wherein the subject has the mutation Y184S.

17. The method of claim 1, wherein the subject has the mutation N228H.

18. The method of claim 1, wherein the subject has the mutation T412I.

19. The method of claim 9, wherein the patient has a mutation selected from the group consisting of: Y184S, N228H, or T412I.

20. The method of claim 9, wherein the patient has the mutation Y184S.

21. The method of claim 9, wherein the patient has the mutation N228H.

22. The method of claim 9, wherein the patient has the mutation T412I.

23. A method for treatment of Fabry disease in a human patient in need thereof, the method comprising orally administering to the patient about 123 mg free base equivalent of migalastat or a salt thereof every other day, wherein the patient has an α-galactosidase A mutation selected from the group consisting of: Y184S, N228H, or T412I.

24. The method of claim 23, wherein the patient is administered about 150 mg of migalastat hydrochloride every other day.

25. The method of claim 23, wherein the patient has the mutation Y184S.

26. The method of claim 23, wherein the patient has the mutation N228H.

27. The method of claim 23, wherein the patient has the mutation T412I.

28. The method of claim 23, wherein the administration reduces the patient's plasma lyso-Gb3.

29. The method of claim 23, wherein the administration reduces GL-3 accumulation in the patient.

30. The method of claim 23, wherein the administration reduces left ventricular hypertrophy in the patient.

31. The method of claim 23, wherein: (1) the administration reduces the patient's plasma lyso-Gb3; (2) the administration reduces GL-3 accumulation in the patient; or (3) the administration reduces left ventricular hypertrophy in the patient.

32. The method of claim 23, wherein the administration improves renal function in the patient.

33. The method of claim 23, wherein: (1) the administration reduces the patient's plasma lyso-Gb3; (2) the administration reduces GL-3 accumulation in the patient; (3) the administration reduces left ventricular hypertrophy in the patient; or (4) the administration improves renal function in the patient.

* * * * *

SEQUENCE LISTING

```
<160> NUMBER OF SEQ ID NOS: 3

<210> SEQ ID NO 1
<211> LENGTH: 12436
<212> TYPE: DNA
<213> ORGANISM: Homo sapiens

<400> SEQUENCE: 1

cccttctgta ggggcagaga ggttctactt cattactgcg tctcctggga aggccatcag     60

gactgctggc taaagtggga accaggactc tttgtgagtt aagaatttgt gtatttatat    120

gtgtgttata cacatttttt aaaaaactgt aacgacatca ggttgagcag tcgtctccgg    180

gtggtgaatt atgtgtattt ttaaatttta tactatattg ttatttttca aatgttcgaa    240

attgaatatg tagattgttg ttatcagcag aaaaataaac attattcaaa tactctattc    300

agtaaagtaa tttattgggc gcctttgtca agcacgcatt tgcctagatg tgactctaca    360

gataaaattc acttggggcc tccccttaca gacaatcagg cagtggagac tgagtgcctg    420

aatggataga ccagcactca gaccactatt ttcagtatct gtttttctta actcagggcc    480

gtggttttca aacgtttttc gccttacggt caccccttagg gtcccccgag accggcccag    540

acagacagat atacaaaaac acatacacag tcatgagcgt ccaccatttc cccaccaggc    600

gcagcacagg cggcttcccg gcactgagat ggggggggagg agggagagag cgcgaggggg    660

gaggggaaag cagagaacga aagaggcgga ggcggccccc gaaccccgct ctggtcttca    720

tcatcaccac ccctgggtcc ccagttccca cccacacacc aacctctaac gataccgggt    780

aattttcctc cttcttccct caaacggcta tagcgagacg gtagacgacg accagaacta    840

cttctgctca cgtaagcgag taatcacgtg agcgcctacg tcatgtgaga tctcggtcac    900

gtgagcaact ctcggcttaa actcgggatc actaaggtgc cgcacttcct tctggtatgg    960

aaatagggcg ggtcaatatc aagaaaggaa gagggtgatt ggttagcgga acgtcttacg   1020

tgactgatta ttggtctacc tctggggata accgtcccag ttgccagaga aacaataacg   1080

tcattattta ataagtcatc ggtgattggt ccgcccctga ggttaatctt aaaagcccag   1140

gttacccgcg gaaatttatg ctgtccggtc accgtgacaa tgcagctgag gaacccagaa   1200

ctacatctgg gctgcgcgct tgcgcttcgc ttcctggccc tcgtttcctg ggacatccct   1260

ggggctagag cactggacaa tggattggca aggacgccta ccatgggctg gctgcactgg   1320

gagcgcttca tgtgcaacct tgactgccag gaagagccag attcctgcat caggtatcag   1380

atattgggta ctcccttccc tttgcttttc catgtgtttg ggtgtgtttg gggaactgga   1440

gagtctcaac gggaacagtt gagcccgagg gagagctccc ccacccgact ctgctgctgc   1500

ttttttatcc ccagcaaact gtcccgaatc aggactagcc ctaaactttc tctgtgtgac   1560

ctttcctggg atgggagtcc ggccagcggc ccctgtttct ttctctctct ctctctctct   1620

cgttctcctt ctctttctct ttctcttctt tcctctctct ttctctctct ccctgcccgg   1680
```

-continued

```
ttctcttttt tcactgctcc ttgcagagca gggccacccc ataggcagtg tgcccaaagt   1740
agccctgccc ggttctattc agacccttct tgtgaacttc tgctcttcct ctgccgggtg   1800
ctaaccgtta gaacatctag ggtgggtagg aggaatgggg aactaagatt cgtgccattt   1860
tttctccttt tggggtcgtg gatttctcgg cagtatctcg agggagttag agagaccata   1920
aggtcgctga gatctctccc acctcgccca tgagcgtggc atcaggctgg aaggttgaca   1980
tggaggaact ttatacattt acacctttgc gtgagggttg aggctggatt agataggtat   2040
tgaacatatc tgaccctcac aatccttatc tgtaaattgg gattacaacc ttttaatttc   2100
agggagctga caaaaaaaat ctgaaaaata gttcttatct cacacaggtg agttttcaag   2160
gagataacct atttaaagta catagcacag cgcttgacca ttcaactgcg cttacagagc   2220
aaatgttcaa tgggaaaatg aatgtaaatc tacaaatctg aatgaatatg tgtatttttc   2280
tggagagagg atatttacct ttcttcaaat tctcaaaggg ctctgtgatt taaaaaaggt   2340
taggaatcac tgatagatgt tggtaaaagg tggcagtcac agtacatttc tgtgtccata   2400
agttattcct atgaatatct ttatagataa agtcaggatg ttggtcagac atcacagaag   2460
aaattggcct tgtaagtttc atgtgaccct gtggtacagt atgtgtggca attttgccca   2520
tcacggattt tttttattg gtatttgcat ctgattataa aactaatgca tgatcattgc   2580
aaaaaatgta gataaagaag agcaaaatga aaataaagat ttccccccac cgttccacca   2640
cccagaaata atcatggttt aaatgttaat atacaacctt acaattgttt tctatataaa   2700
tgaaaacata gatttcttta tttcattatt ttccataaaa aatggatcat gtttatgtca   2760
tgtttggcta atggcaagac cctggcaccc agtctgggct caaattctgc ctcattgtta   2820
cttagccctg tgacattggg taaattacac tttttttttt tttttttttt tgagacgggg   2880
tctcgctctg tcgcccaggc tggagtgcag tggcacgatc tcggctcact gcaagtccgc   2940
ctcctgggtt cacgccattc ttctgcctca gcctcccgag tagctgggac tacaggcgcc   3000
tgccaccacg cctggctctt tttttttttt tttttttttt tagtacagac ggggtttcac   3060
catgttagcc agggtggtct caatctcctg acctcgtgat tcgcccgcct cagcctccca   3120
aagtgctggt gtgagccacc gtgcccagcc ttactttttt ttttgagagg gggtctcact   3180
ctgtcaccca ggttggagtg cagtggcgcg atctctgctc agtgcaaact ccacctcccg   3240
ggtttaagca gttctcctgt cgtagtctcc tgagtagctg ggattacagg cacaccacca   3300
cggccagcta atttttgtat tttcagtaga gacgggtttc accatgttgc ccaagctggt   3360
ctcgaactcc tggcctcaag tgatctgccc gccttggcct cccagagtgc tgggattaca   3420
ggtgtgagcc accgcacccg gcctcttttt tctttttag tctatcatac cttgcaaata   3480
cagtggttct tcctatgtgt tggttttgat atttatgtaa tcaaacacat cagtttttcc   3540
tttctgattt ctgactttgg ggtcatgctg agaaagtcct ttcctacctg aagataatac   3600
agtatatacg tttcttacta gtatttttgt ggatttttaa aatatttaaa tctttagtcc   3660
atctgaactt gttcttctat cagaaatgcc acatttaata aataataagt cccatggtat   3720
cagatggctg gaaggacctc tttcgaaact ttgtttaatt ccattaatct gtgtattctt   3780
attctaatgc taatagttcc acactagctt cctttatctt ttttttcttt tttttttttt   3840
ttttgagctg gagtttcgct cttgttgccc aggctggagt acaatgtcac gatctcggtt   3900
caccgcaacc tccgcctccc aggttcaagc aattctcctg cctcatcctc gcgagtagct   3960
ggaattacag gcatgcgcca ccacgcctag ctattttgta tttttagtag agatggggtt   4020
tctccatgtt ggtcaggctg gtctcaaact cccagcctca ggtgatctgc ctgcctcggc   4080
```

-continued ctcccaaaat gctgttatta caggcgtgag ccaccacgcc cagccttcat cttttaatga 4140
atgtacatgt atgtaatctt ttaggtgaac tttttgtaat gttgtgccaa gttccttaaa 4200
aagccctttt ggaagctggg caggtggcca cgcctgtaat cccagcattt tgggagtctg 4260
aggcaggtgg atcacttgag gccaggagtt caagactagc ctagccaaaa tgcaaaaccc 4320
tgtctctact aaagatacaa aaattagccg gatgcgatgg cacatgcctg taatctcagc 4380
tactcgggag gctgaggtag aagaatcgct tgaaccgggg aggcagaggt tgcagtgagc 4440
aagatggcgc cactgcactc cagcctgggt gacagaggga gactccatct caaaaaaaaa 4500
aaaaaaaaaa aagataaaaa ggaaacctaa gtactcttgg gctttgttaa ggattttgtt 4560
aaatatacaa aggattgcag ggaaaattaa cttattttta atattgagta tgcttatcca 4620
agagcaaaat aatatttctc catttattca aatcatttag gagcatcata gttttaacat 4680
atgggccttg cacgtatctt aaatttatct ctaggcattt taggttgttc agttgttctt 4740
gtgaatggga tctttttctc caaataggat tattgttgat atctgttgat tatgttaact 4800
ttgtagtttc tgactttact gaactgtctt cttagatcta atactctttt caatttcatc 4860
atatatttct cattcctatt ttgtttgggg tttttagggc gggaatatta acgggataag 4920
agagacaaaa gaaaatctgg aaaaacaatt cattttacct tacattgctt gtgattacta 4980
ccacactatt actgggttgg aaaaaattgt gaaatcccaa ggtgcctaat aaatgggagg 5040
tacctaagtg ttcatttaat gaattgtaat gattattgga atttctcttt cagtgagaag 5100
ctcttcatgg agatggcaga gctcatggtc tcagaaggct ggaaggatgc aggttatgag 5160
tacctctgca ttgatgactg ttggatggct ccccaaagag attcagaagg cagacttcag 5220
gcagaccctc agcgctttcc tcatgggatt cgccagctag ctaattatgt gagtttatag 5280
ataatgttct tgttcattca gaggactgta agcacttctg tacagaagct tgtttagaaa 5340
cagccctcat ggccgggcgt ggtggctcac gctgtaatcc caacactttg ggaggccgag 5400
gcgggtggat cacctgaggt caagagttca agaccagcct ggccaacatg gtgaaacccc 5460
aactctatta aaagtacaaa aaattagctg ggcatggtgg tgaacgcctg taaccccagc 5520
tacttgggag gctgaggcag gagaatcgct tgaacccagg aggtggaagt ttcagtgagc 5580
tgagatcacg ccattgcact ctagcctggg caacaaaaga gaaactccat ctcaaaaaaa 5640
aaaacaagga aaaaaagaaa cagccctcat gacacttaga aagtagaata gctggctgtt 5700
atctgaacat tgaattgtaa ggcttatcag gtggactttg cattccatca gcagacaatt 5760 ttttttttt tttttttg agatggagtc tcattctgtc tcccaggctg gagggcagtg 5820
gtgcgatctc ggctcactgc aagctccacc tcctgggttc atgccattct cctgcctcag 5880
cctcccaagt agctgggacc acaggcaccc gccaccatgc ccagttaatt ttttgtattt 5940
ttagtagaga cggggtttca ccatgttagc caagatggtc tcgatctcct gacctcgtga 6000
tccgcccacc tcggcctccc aaagtgctgg gattacaggc atgagccacc gcgcctagcc 6060
tacaaatgtt ttgtaatagc tcttgaggcc catcttggag ttctcctttt gctaaaacca 6120
ctgaactctc taggaggaaa aaggaacttg gttcttgaca tatgtgtgca tgtatttcca 6180
tataaccttt aggaagctat tgcaatggta ctataaacta gaattttaga agatagaagg 6240
aaaatattct ggagatcatt gaagagaaat ggagtccaac actagttaaa gatgatgaag 6300
acagattttt tttttgacg gagtctcgct ctgtcgccca ggctggagtg cagtggcaca 6360
atctcagctc actgcaaccc tccacctctt gggttcaagt gattctcctg cctcagcctc 6420

-continued

```
ccaagtagct gggactacag gcgcacacca ccacgcccgg ctaattttg tatttttagt   6480
agagacaagg tttcaccata ttcgccaggc tggtctcgaa ctcctgacct tgtaatccgc   6540
ccaccttggc ctcccaaagt gctgggatta caggcatgag ccaccacgcc cggccgatga   6600
agacagattt tattcagtac taccacagta gaggaaagag ccaagttcaa ttccaaatac   6660
aacaaagaca ggtggagatt tatagccaat gagcagattg agggggtcag tggatggaat   6720
atttaagaag acatcaaggg tagggagctt cttgctaaag cttcatgtac ttaaacaaga   6780
agggtggggg atgagggaaa ttgatcagat atcaatggtg gcagtattga cttagcagga   6840
ttcttgctaa gaggtcttgc taggacagac ataggaagcc aaggtggagg tctagtcgaa   6900
aagaaggctc atcagagaag tctaactaaa gtttggtcaa gaagagtctt tgtcaaggta   6960
aatctatcat ttccctcaaa aggtaatttt caggatccca tcaggaagat tagcatggct   7020
gctagctttc tcctcagttc tgggctatag ctcacatgcc tagtttgaac tagctcagca   7080
gaactggggg atttattctt tgtcttccaa caaactcatc tggatgattt tgggggtttg   7140
tggggaaaag cccccaatac ctggtgaagt aaccttgtct cttcccccag cctggaatgg   7200
ttctctcttt ctgctacctc acgattgtgc ttctacaatg gtgactcttt tcctccctct   7260
catttcaggt tcacagcaaa ggactgaagc tagggattta tgcagatgtt ggaaataaaa   7320
cctgcgcagg cttccctggg agttttggat actacgacat tgatgcccag acctttgctg   7380
actggggagt agatctgcta aaatttgatg gttgttactg tgacagtttg gaaaatttgg   7440
cagatggtaa tgtttcattc cagagattta gccacaaagg aaagaacttt gaggccatgg   7500
tagctgagcc aaagaaccaa tcttcagaat tttaaatacc ctgtcacaat actggaaata   7560
attattctcc atgtgccaga gctcccatct cttctctttc agttcattaa ttaattaatt   7620
aattcatgta aaatccatgc atacctaacc atagctaata ttgtgcactt ataattcaag   7680
agggctctaa gagttaatta gtaattgtaa ctctctataa catcatttag gggagtccag   7740
gttgtcaatc ggtcacagag aaagaagcat cttcattcct gcctttcctc aatatacaca   7800
ccatctctgc actacttcct cagaacaatc ccagcagtct gggaggtact ttacacaatt   7860
taagcacaga gcaactgcct gtccctgctg ctagtttaaa catgaacctt ccaggtagcc   7920
tcttcttaaa atatacagcc ccagctgggc atgatggctc atgcctgtaa tcctagcact   7980
ttgggaggct gaggcgggtg gattacttga ggtcaggagt tcgagaccac cctggccaac   8040
atggtgaaac cccatctcta gtaaaaatac aaaaattagc tgactttggt ggcacatgcc   8100
tgtaatccca gctacttggg aagctgagac agaagagtca cttgaacctg ggaaacagag   8160
gttgcagtga gccaagatcg caccactgca ctccaccctg gatgacagac tgaaccccat   8220
ctcaaaaaat taaaataaaa taaaataaaa taactatata tatagcccca gctggaaatt   8280
catttctttc ccttatttta cccattgttt tctcatacag gttataagca catgtccttg   8340
gccctgaata ggactggcag aagcattgtg tactcctgtg agtggcctct ttatatgtgg   8400
ccctttcaaa aggtgagata gtgagcccag aatccaatag aactgtactg atagatagaa   8460
cttgacaaca aaggaaacca aggtctcctt caaagtccaa cgttacttac tatcatccta   8520
ccatctctcc caggttccaa ccacttctca ccatccccac tgctgtaatt atagcctaag   8580
ctaccatcac ctggaaagtc atccttgtgt cttccccttt atttcaccat tcatgtcctg   8640
tctatcaaca gtccttccac cagtatctct aaaatatctc ctgaatcagc ccacttcctt   8700
ccatcttcac tacatgcacc ctggccttcc aagctactat cggctctcaa ccagactgct   8760
gggaccacct gatctctctg cttccactct gtctcaaccc ccatctattt tccaagcagc   8820
```

actagagtta tcatattaaa atgtaaatat cagttttttt tttaaagaaa aaaaccctga 8880
gacttaacag agttataaaa aatataaatg tcatcatcag ttccctgctt aaaaccctta 8940
actcgcttcc aattgcactt ggaatgaaac caaactgcac tgatccagcc cttgcctgcc 9000
tccccaaagt ccaaggggtc atggctcttt ccctggctac actggttttc tttctgtccc 9060
tcaacactgc aagcctattg ctgccccagg gcctttacac ttgctttttt tctgcctaga 9120
acagttcttc cccaaagatt tttaaagggc cgggctcctt aacattgaag tcgcagacca 9180
aacgccacat atgcagacag ttcttctcta actactttaa aatagccctc tgtccattca 9240
ttcttcatca cattaacctg tttaattttc ttctcagagc tccacactat ttggaagtat 9300
ttgttgactt gttaccatgt ctccccacta gagtgtaagt ttcatgaggg cagggacctt 9360
gtctgacttt gactgtatct ctcgcatatg gttaagtgtt aaatagttat ttatggaatg 9420
aatccctatt attccctcat tatctctgca aaatagtctt ttttctcaac atcttaaacc 9480
tgatatccca cctgcctatc tacaaacttt ttttttgcga cagagtctca ctgtcaccca 9540
ggctagagtg cagtggcgcc atctcggctc actgcaacct ccgcctcccg ggtttaagcg 9600
attctcttgc ctcagcctcc cagtagctgg gattataggc gtgcgctacc acatctggct 9660
aatttttgta tttttagtag agatggtttc accatgttgg ccaggcttgt ctcgaactcc 9720
tgacctcaga tgatccacct gcctcggcct cccaaagtgc tgggattaca ggcatgagcc 9780
accgtgccca gcctctacaa actttttatt ccattaacaa actatatgct gggatttaag 9840
ttttcttaat acttgatgga gtcctatgta attttcgagc ttttaatttt actaagacca 9900
ttttagttct gattatagaa gtaaattaac tttaagggat ttcaagttat atggcctact 9960
tctgaagcaa acttcttaca gtgaaaattc attataaggg tttagacctc cttatggaga 10020
cgttcaatct gtaaactcaa gagaaggcta caagtgcctc ctttaaactg ttttcatctc 10080
acaaggatgt tagtagaaag taaacagaag agtcatatct gttttcacag cccaattata 10140
cagaaatccg acagtactgc aatcactggc gaaattttgc tgacattgat gattcctgga 10200
aaagtataaa gagtatcttg gactggacat cttttaacca ggagagaatt gttgatgttg 10260
ctggaccagg gggttggaat gacccagata tggtaaaaac ttgagccctc cttgttcaag 10320
accctgcggt aggcttgttt cctattttga cattcaaggt aaatacaggt aaagttcctg 10380
ggaggaggct ttatgtgaga gtacttagag caggatgctg tggaaagtgg tttctccata 10440
tgggtcatct aggtaacttt aagaatgttt cctcctctct tgtttgaatt atttcattct 10500
ttttctcagt tagtgattgg caactttggc ctcagctgga atcagcaagt aactcagatg 10560
gccctctggg ctatcatggc tgctccttta ttcatgtcta atgacctccg acacatcagc 10620
cctcaagcca aagctctcct tcaggataag gacgtaattg ccatcaatca ggaccccttg 10680
ggcaagcaag ggtaccagct tagacaggta aataagagta tatattttaa gatggcttta 10740
tatacccaat accaactttg tcttgggcct aaatctattt ttttcccttg ctcttgatgt 10800
tactatcagt aataaagctt cttgctagaa acattacttt atttccaaaa taatgctaca 10860
ggatcatttt aatttttcct acaagtgctt gatagttctg acattaagaa tgaatgccaa 10920
actaacaggg ccacttatca ctagttgcta agcaaccaca ctttcttggt ttttcaggga 10980
gacaactttg aagtgtggga acgacctctc tcaggcttag cctgggctgt agctatgata 11040
aaccggcagg agattggtgg acctcgctct tataccatcg cagttgcttc cctgggtaaa 11100
ggagtggcct gtaatcctgc ctgcttcatc acacagctcc tccctgtgaa aaggaagcta 11160

-continued

```
gggttctatg aatggacttc aaggttaaga agtcacataa atcccacagg cactgttttg  11220

cttcagctag aaaatacaat gcagatgtca ttaaaagact tactttaaaa tgtttatttt  11280

attgccaact actacttcct gtccaccttt ttctccattc actttaaaag ctcaaggcta  11340

ggtggctcat gcctgtaatc ccagcacttt gggaggctga ggcgggcaga tcacctgagg  11400

tcgggacttt gagacccgcc tggacaacat ggtgaaaccc catttctaat aaaaatataa  11460

aaattagcca ggtgtggtgg cgcacctgtg gtcccagcta ctctgggggc tgaggcatga  11520

gaatcgcttg aacccgggag tggaggttgc attgagctga gatcatgcca cctcactcca  11580

gcctgggcaa caaagattcc atctcaaaaa aaaaaaaaaa gccaggcaca gtggctcatg  11640

cctggaatcc cagcactttt ggaagctgag gcaggcagat cacttgaggt taggatttca  11700

agaccagcct ggctaacata gtaaagccct gtctctacta aaaatacaaa aattagccag  11760

gtatggtggc gagcttctgt agccccagct actcaggaga ctgaggcagg agaatcactt  11820

gaacccggga agtggggggg tgcagtgacc caagatcacg ccactgcatt ccagcctggg  11880

caacagagca agactccatc tcaaaaaaaa aagttctatt tccttgaata aaattttccg  11940

aagtttaaac tttaggaata aaactattaa acccgtattt actcatccag atacccaccc  12000

cccttgttga gattctctcc caattatcaa aatgtgtagc atatttaact accaagagct  12060

aaacatcatt aagactgaaa tgtattaaga aggatgtata ggccaggcac ggtgtctcac  12120

gcctgtaatc ccaacacttt gggaggccaa gtcgggcgga tcacgaggtc aggagatgga  12180

gaccatcctg gccaacatgg tgaaaccccc tctctactaa aaatacaaaa attagccagg  12240

caggtggcag gcacctgtaa tcccagctac tccagaggct gaggcaggac aatcacttga  12300

acctgggagg cagaggctgc agtgagctga ggttgtacca attgcactcc agcctaggta  12360

acgagcaaca ctccatctca aaaaaagaaa aaaaaaaaga tgtataattt ggaactgtta  12420

agaggcattt taaaga                                                  12436
```

<210> SEQ ID NO 2
<211> LENGTH: 429
<212> TYPE: PRT
<213> ORGANISM: Homo sapiens

<400> SEQUENCE: 2

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140
```

-continued

```
Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425
```

<210> SEQ ID NO 3
<211> LENGTH: 1290
<212> TYPE: DNA
<213> ORGANISM: Homo sapiens

<400> SEQUENCE: 3

```
atgcagctga ggaatcccga gctccacctg ggctgtgctc tggctctgcg gttcctggcc     60

ctcgtgtcct gggacatccc tggcgctagg gccctcgata acggactggc ccggaccccc    120

acaatgggat ggctccactg ggaaaggttc atgtgcaatc tggactgtca ggaggaaccc    180

gactcctgca tcagcgaaaa gctcttcatg gagatggccg agctgatggt gagcgagggc    240

tggaaggacg ccggctacga gtatctgtgc atcgatgact gctggatggc ccctcaaagg    300

gactccgaag gcaggctgca ggctgatccc caaaggtttc cccacggaat ccggcagctc    360

gccaactacg tgcattccaa gggcctcaag ctcggcatct acgccgacgt gggcaacaaa    420

acatgcgccg gattccccgg cagcttcggc tactacgaca tcgacgccca gacattcgct    480

gattggggag tggacctgct gaagttcgac ggctgttact gcgattccct ggaaaacctg    540
```

-continued

```
gccgacggct acaaacacat gtccctcgcc ctgaaccgga caggcaggtc catcgtgtac    600
agctgcgagt ggcccctgta catgtggcct ttccagaagc ccaactacac agagatcagg    660
cagtactgca accactggag gaacttcgct gacatcgacg actcctggaa gagcatcaag    720
agcatcctgg actggaccag cttcaaccag gagaggatcg tggacgtggc tggacccgga    780
ggctggaacg accccgatat gctggtgatt ggcaacttcg gactgagctg gaaccagcag    840
gtgacccaga tggccctgtg ggccattatg gccgctcccc tgttcatgtc caacgacctg    900
aggcacatca gcccccaggc caaggctctg ctgcaggaca aggatgtgat cgccatcaac    960
caggaccccc tgggcaagca gggctaccag ctgaggcaag gagataactt cgaggtgtgg   1020
gagaggcccc tgtccggact ggcttgggcc gtggccatga tcaatcggca ggagatcggc   1080
ggaccccggt cctacaccat tgctgtggcc agcctgggaa aaggagtcgc ctgcaacccc   1140
gcctgcttca ttacccagct gctccccgtg aagcggaagc tgggcttcta tgagtggacc   1200
agcaggctga ggtcccatat caatcctacc ggcaccgtcc tcctccagct cgagaatacc   1260
atgcagatga gcctcaagga tctgctgtga                                    1290
```